US011466060B2

(12) United States Patent
Sun et al.

(10) Patent No.: US 11,466,060 B2
(45) Date of Patent: Oct. 11, 2022

(54) CARBOHYDRATE PRODUCING PLANT MATERIAL

(71) Applicant: GREEN RICE SWEDEN AB, Uppsala (SE)

(72) Inventors: Chuanxin Sun, Uppsala (SE); Roger Andersson, Uppsala (SE); Christer Jansson, Pasco, WA (US); Per Åman, Uppsala (SE)

( * ) Notice: Subject to any disclaimer, the term of this patent is extended or adjusted under 35 U.S.C. 154(b) by 263 days.

(21) Appl. No.: 16/497,989

(22) PCT Filed: Mar. 28, 2018

(86) PCT No.: PCT/SE2018/050335
§ 371 (c)(1),
(2) Date: Sep. 26, 2019

(87) PCT Pub. No.: WO2018/182493
PCT Pub. Date: Oct. 4, 2018

(65) Prior Publication Data
US 2020/0040045 A1    Feb. 6, 2020

Related U.S. Application Data

(60) Provisional application No. 62/479,374, filed on Mar. 31, 2017.

(30) Foreign Application Priority Data

Mar. 31, 2017   (CA) ................. CA 2962852

(51) Int. Cl.
*C12N 15/82* (2006.01)
*C07K 14/415* (2006.01)

(52) U.S. Cl.
CPC ........ *C07K 14/415* (2013.01); *C12N 15/8246* (2013.01)

(58) Field of Classification Search
CPC .................. C12N 15/8246; C12N 15/8245
See application file for complete search history.

(56) References Cited

U.S. PATENT DOCUMENTS 7,538,259 B2   5/2009   Rodriguez-Franco et al.
7,834,167 B2   11/2010  Rodriguez-Franco et al.
(Continued)

FOREIGN PATENT DOCUMENTS

WO    2004/050881 A2    6/2004

OTHER PUBLICATIONS

Sun, Chuanxin et al., Expression of barley SUSIBA2 transcription factor yields high-starch low-methane rice, Antisense oligodeoxynucleotide inhibition as a potent strategy in plant biology: identification of SUSIBA2 as a transcriptional activator in plant sugar signalling, The Plant Journal, vol. 44, pp. 128-138 (2005).

(Continued)

*Primary Examiner* — Weihua Fan
(74) *Attorney, Agent, or Firm* — Porter Wright Morris & Arthur LLP

(57) ABSTRACT

A plant material comprises a genomic nucleotide sequence encoding a SUSIBA2 or SUSIBA2-like transcription factor under transcriptional control of a promoter active in the plant material. The genomic nucleotide sequence encoding the SUSIBA2 or SUSIBA2-like transcription factor lacks at least a portion of an activation region of a SUSIBA1 or SUSIBA1-like promote represent in an intron of a wild-type version of the genomic nucleotide sequence encoding the SUSIBA2 or SUSIBA2-like transcription factor. The plant material has a controlled production of carbohydrates, in particular starch or starch and fructan. In particular, the plant (Continued)

material can be designed to produce carbohydrates at enhanced levels.

10 Claims, 76 Drawing Sheets

Specification includes a Sequence Listing.

(56) References Cited

U.S. PATENT DOCUMENTS

| | | |
|---|---|---|
| 7,985,833 B2 | 7/2011 | Wakamiya et al. |
| 8,604,162 B2 | 12/2013 | Wakamiya et al. |
| 9,062,316 B2 | 6/2015 | Flasinski |
| 9,771,595 B2 | 9/2017 | Flasinski |
| 9,834,777 B2 | 12/2017 | Flasinski |
| 10,208,314 B2 | 2/2019 | Flasinski |
| 10,538,776 B2 | 1/2020 | Flasinski |
| 10,731,170 B2 | 8/2020 | Flasinski |
| 10,752,910 B2 | 8/2020 | Flasinski |
| 2003/0158382 A1 | 8/2003 | Wakamiya et al. |
| 2006/0191037 A1* | 8/2006 | Jansson .............. C12N 15/8245 800/278 |
| 2009/0106861 A1 | 4/2009 | Frankard |
| 2017/0006815 A1 | 1/2017 | Giroux |
| 2020/0370061 A1 | 11/2020 | Flasinski |

OTHER PUBLICATIONS

Su, J. et al., Expression of barley SUSIBA2 transcription factor yields high-starch low-methane rice, Nature, vol. 523, pp. 602-620 (Jul. 30, 2015).

Sun, Chuanxin et al., A Novel WRKY Transcription Factor, SUSIBA2, Participates in Sugar Signaling in Barley by Binding to the Sugar-Responsive Elements of the iso1 Promoter, The Plant Cell, vol. 15, pp. 2076-2092 (Sep. 2003).

Jin, Yunkai et al., A Dual-Promoter Gene Orchestrates the Sucrose-Coordinated Synthesis of Starch and Fructan in Barley, Molecular Plant 10, pp. 1556-1570 (Dec. 2017).

Rosenquist, Sara, Plant Sugar Signaling: Regulation of Starch and Fructan Metabolism, Faculty of Natural Resources and Agricultural Sciences Department of Plant Biology and Forest Genetics Uppsala, Doctoral Thesis, pp.1-40 (2007).

* cited by examiner

Figure 1B

```
agatcatgcatcgttgagccgcttggtgggcgagacggctcgatgggctcccgagcgggcacgcggctcgatgaagtactcccgtgcttcacttctgcgcacg
gtgatctccttgggtcggtccaagccgaaacctagctccggggaccctccccgcgccgggagctcgcccgagagccctaccccgccgggatcgacgcgtcggg
cgctcgccggcgcgcggcgaggtacaaggccatgtccccgccgcgatctgccgatcgcgcgagtcctgcctcaccatcccgccggcttcagccctcagcgctc
ctcgactccccgtgctcctcaccaacttcaaggttgaaccttcaccaacaactgtagtctgggcatgctgcgattctgcacaagagcgctcatccagacatgct
gccttcgcacgggataaatctgttcgtaatgccatgaagataggggttctagggatttgaattcaagctcatctgaattcgtcttctcaatcactgctcctg
ctatgagtgatctaaaaaacatgagcattctatgcaaatcagagtatgaatccagctcatcatctagacaatatgtgaatgaaaacagacctccctgttcacgt
gagtcgagtcttacagtgaatgtaagtgctcagaaccaacctgttggaatgttggtttgactgacagcatgcctgctgaagttggtacatctgagcgcagagat
gaatagctctgacaatgccatgcacaagaccgcagtctgaaatgttgctgacaactcggagatgatggctacaactgggaaatacgggcagaagcatgtcaagg
gaagtgaaaacctagaagttactacaagtgcacacatcctaattgtggagcgtgcagttgaagcgtgcagttgtctgatcacgaagttgtctataag
→Band3
ggacgccacaatcatcctagcccagccagtgcccaataggaggttagctgtcagttccttcaaaccaggtgaagaacgatatgacggcgctcagctgctgatga
taaatcttccaatgctcttagcaacctgtaatccggtacattcgcctgtagtcctgttccagctgttgagcctgtcagttagtgatgacatcgatgctgagg
gaagacctaccctggggatgatgctactgaggaggaggaggattagatctgggagtctgctggtattgatgctgctctgatgggtaaacctaac
cgtgagcccgtgtcgtcgttcaaacatgtgagtgaggttgacatcttggatgatggcctatcgttggcggaaatatggacagaaagttgtcaaggaaccccatcc
acggagttactacaaatgcacaagcacaggatgcccctgtgaggaagcatgttgagagagcatgttgagaacgatccttaaatcagtgataacaacgtatgaaggaaaacata
accatgaagtccctgctgcgaggaatgcaaccatgagatgtccgcgcctccatgagaacgtcgtgcatcagatttaacagcatcgtccagcagcattgtggc
atgagagggcatgtgaagcaggaatgcagtcttcaggtcctgaccagtcctgacagtcaaatgcaaaccatgggttcgatgtacggcaacatgagacatcatcatgcag
cgacgcgacaaaccaaatgcagtgtcttcaggtcttcaggtatcaaatgcaaaccatgggttcgatgtacggcaacatgagacatcatcatgcag
cgccagcggtacaaggaaactctgctgcccgcatgtatgttcgagagaagagaaggttaacgaaggtttacttcagagccacaccgatgaccattcagctaac
ctatgctatagcagtgctgggaactggtctggtcaatgctctcatagcctcatgaatgctcatagcctcatgaatgctgaaatgctcatagctcatagtatttaccaacatgctttg
taatgacaatctcttcagcaagattctcaattgtctcaattgtctatgttacaagtcagttcgtatcgttatgtagcatcgtagctagtataagctatacgtggggcac
tgcagcaaatacgcatgtgtcttttaagtgcggaaaaggcccttgctgtatgcgcagcatcgttgtacagcgaacctaatatgattaattaatt
agattatgagaatttggtttcgtgaactgtctaatcttctgtactgaatattgatagaaatattgtaattttctttaaaaaaaaaaaaaaaaa
```

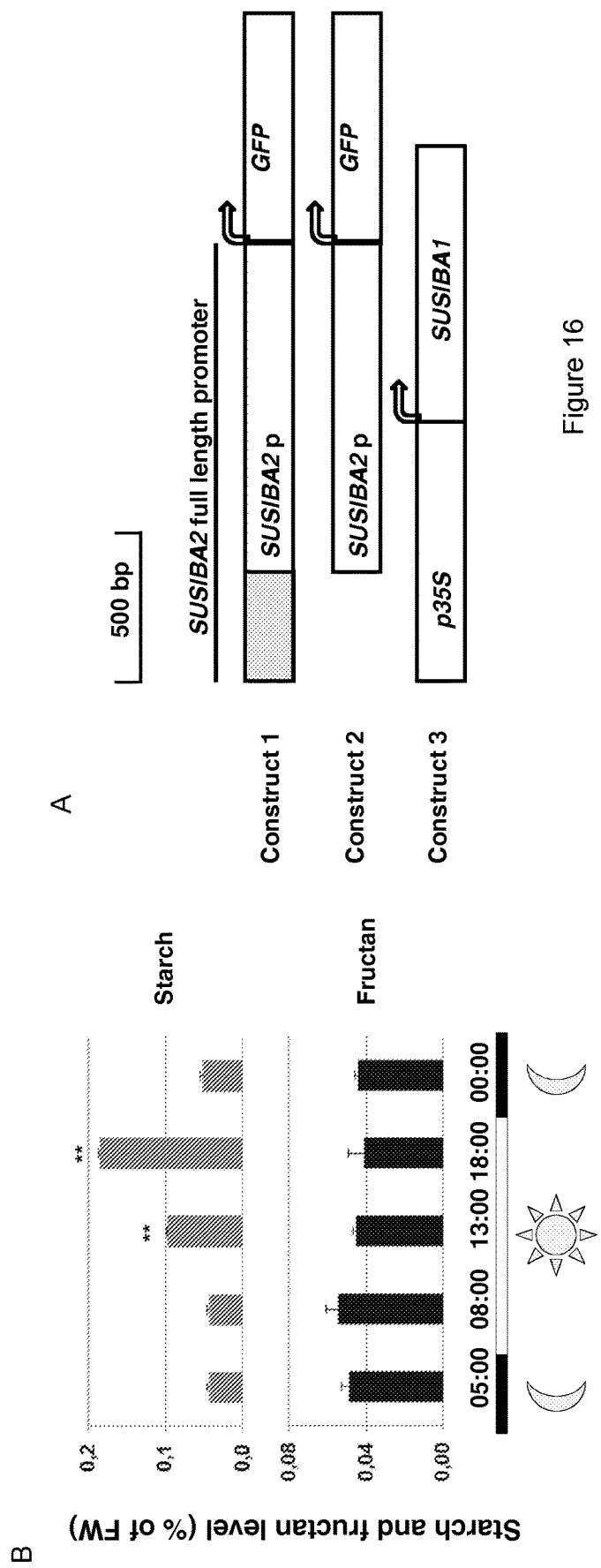

SEQUENCE LISTING

```
<160> NUMBER OF SEQ ID NOS: 119

<210> SEQ ID NO 1
<211> LENGTH: 26
<212> TYPE: DNA
<213> ORGANISM: Hordeum vulgare

<400> SEQUENCE: 1
aagcttgctc ctgctatgag tgatct                                          26

<210> SEQ ID NO 2
<211> LENGTH: 28
<212> TYPE: DNA
<213> ORGANISM: Hordeum vulgare

<400> SEQUENCE: 2
gtcgacttca caattaggat gtgtgcac                                        28

<210> SEQ ID NO 3
<211> LENGTH: 28
<212> TYPE: DNA
<213> ORGANISM: Hordeum vulgare

<400> SEQUENCE: 3
aagcttgtac acaaccttta attttctt                                        28

<210> SEQ ID NO 4
<211> LENGTH: 26
<212> TYPE: DNA
<213> ORGANISM: Aequorea victoria

<400> SEQUENCE: 4
```

-continued

```
gtcgacatgg tgagcaaggg cgagga                                           26

<210> SEQ ID NO 5
<211> LENGTH: 28
<212> TYPE: DNA
<213> ORGANISM: Aequorea victoria

<400> SEQUENCE: 5
gagctcttac ttgtacagct cgtccatg                                         28

<210> SEQ ID NO 6
<211> LENGTH: 28
<212> TYPE: DNA
<213> ORGANISM: Escherichia coli

<400> SEQUENCE: 6
aagcttaact gcatcagccg attatcat                                         28

<210> SEQ ID NO 7
<211> LENGTH: 26
<212> TYPE: DNA
<213> ORGANISM: Escherichia coli

<400> SEQUENCE: 7
gtcgacgtgg tggctagctt gtttgc                                           26

<210> SEQ ID NO 8
<211> LENGTH: 29
<212> TYPE: DNA
<213> ORGANISM: Cauliflower mosaic virus

<400> SEQUENCE: 8
gagctccatg gagtcaaaga ttcaaatag                                        29

<210> SEQ ID NO 9
<211> LENGTH: 25
<212> TYPE: DNA
<213> ORGANISM: Cauliflower mosaic virus

<400> SEQUENCE: 9
gtcgacagtc cccgtgttc tctcc                                             25

<210> SEQ ID NO 10
<211> LENGTH: 29
<212> TYPE: DNA
<213> ORGANISM: Arabidopsis thaliana

<400> SEQUENCE: 10
gtcgactctc agagtttaat gaagaagcg                                        29

<210> SEQ ID NO 11
<211> LENGTH: 26
<212> TYPE: DNA
<213> ORGANISM: Arabidopsis thaliana

<400> SEQUENCE: 11
cacgtgggca aagacattga ttattc                                           26

<210> SEQ ID NO 12
<211> LENGTH: 28
<212> TYPE: DNA
<213> ORGANISM: Hordeum vulgare
```

<400> SEQUENCE: 12
gggagctctc cgtagtaaaa gaaacagg                                28

<210> SEQ ID NO 13
<211> LENGTH: 29
<212> TYPE: DNA
<213> ORGANISM: Hordeum vulgare

<400> SEQUENCE: 13
cggaattctt tgtaggcgta cggtagcgg                               29

<210> SEQ ID NO 14
<211> LENGTH: 28
<212> TYPE: DNA
<213> ORGANISM: Aequorea victoria

<400> SEQUENCE: 14
cggaattcat ggtgagcaag ggcgagga                                28

<210> SEQ ID NO 15
<211> LENGTH: 30
<212> TYPE: DNA
<213> ORGANISM: Aequorea victoria

<400> SEQUENCE: 15
ggcacgtgtt acttgtacag ctcgtccatg                              30

<210> SEQ ID NO 16
<211> LENGTH: 28
<212> TYPE: DNA
<213> ORGANISM: Hordeum vulgare

<400> SEQUENCE: 16
gggtcgacat ggttgagcct gttccagc                                28

<210> SEQ ID NO 17
<211> LENGTH: 28
<212> TYPE: DNA
<213> ORGANISM: Hordeum vulgare

<400> SEQUENCE: 17
aacacgtgtc atggacccat gcccaagt                                28

<210> SEQ ID NO 18
<211> LENGTH: 27
<212> TYPE: DNA
<213> ORGANISM: Hordeum vulgare

<400> SEQUENCE: 18
cggaattctg gacccatgac caagttc                                 27

<210> SEQ ID NO 19
<211> LENGTH: 28
<212> TYPE: DNA
<213> ORGANISM: Hordeum vulgare

<400> SEQUENCE: 19
gggagctcga ggtaaaaccc tacatcct                                28

<210> SEQ ID NO 20
<211> LENGTH: 33
<212> TYPE: DNA
<213> ORGANISM: Hordeum vulgare

```
<400> SEQUENCE: 20
ttaagctttc tcatgtagta atcatacggt ggg                              33

<210> SEQ ID NO 21
<211> LENGTH: 28
<212> TYPE: DNA
<213> ORGANISM: Artificial Sequence
<220> FEATURE:
<223> OTHER INFORMATION: Blue Fluorescent Protein (BFP)

<400> SEQUENCE: 21
ttaagcttat ggtgagcaag ggcgagga                                    28

<210> SEQ ID NO 22
<211> LENGTH: 31
<212> TYPE: DNA
<213> ORGANISM: Artificial Sequence
<220> FEATURE:
<223> OTHER INFORMATION: Blue Fluorescent Protein (BFP)

<400> SEQUENCE: 22
aacacgtgct atttgtacag ctcgtccatg c                                31

<210> SEQ ID NO 23
<211> LENGTH: 28
<212> TYPE: DNA
<213> ORGANISM: Hordeum vulgare

<400> SEQUENCE: 23
gcaagctttg ttgcctctct tttgtaaa                                    28

<210> SEQ ID NO 24
<211> LENGTH: 28
<212> TYPE: DNA
<213> ORGANISM: Hordeum vulgare

<400> SEQUENCE: 24
gcaagcttgg tagagtttga aggaagta                                    28

<210> SEQ ID NO 25
<211> LENGTH: 28
<212> TYPE: DNA
<213> ORGANISM: Hordeum vulgare

<400> SEQUENCE: 25
gcaagcttga ggtaaaaccc tacatcct                                    28

<210> SEQ ID NO 26
<211> LENGTH: 28
<212> TYPE: DNA
<213> ORGANISM: Hordeum vulgare

<400> SEQUENCE: 26
gcaagcttcc cgcgacccga ggacctct                                    28

<210> SEQ ID NO 27
<211> LENGTH: 28
<212> TYPE: DNA
<213> ORGANISM: Hordeum vulgare

<400> SEQUENCE: 27
gcaagctttg gctatctctc tttgttga                                    28
```

<210> SEQ ID NO 28
<211> LENGTH: 28
<212> TYPE: DNA
<213> ORGANISM: Hordeum vulgare

<400> SEQUENCE: 28
aaactagttc tcatgtagta atcatacg                                28

<210> SEQ ID NO 29
<211> LENGTH: 28
<212> TYPE: DNA
<213> ORGANISM: Aequorea victoria

<400> SEQUENCE: 29
aaactagtat ggtgagcaag ggcgagga                                28

<210> SEQ ID NO 30
<211> LENGTH: 28
<212> TYPE: DNA
<213> ORGANISM: Hordeum vulgare

<400> SEQUENCE: 30
aactcgagat gtcccccgcg cggctgcc                                28

<210> SEQ ID NO 31
<211> LENGTH: 28
<212> TYPE: DNA
<213> ORGANISM: Hordeum vulgare

<400> SEQUENCE: 31
aactcgagtc atggacccat gaccaagt                                28

<210> SEQ ID NO 32
<211> LENGTH: 18
<212> TYPE: DNA
<213> ORGANISM: Hordeum vulgare

<400> SEQUENCE: 32
gctattcatc tgctgcgg                                           18

<210> SEQ ID NO 33
<211> LENGTH: 18
<212> TYPE: DNA
<213> ORGANISM: Hordeum vulgare

<400> SEQUENCE: 33
ccgcagcaga tgaatagc                                           18

<210> SEQ ID NO 34
<211> LENGTH: 18
<212> TYPE: DNA
<213> ORGANISM: Hordeum vulgare

<400> SEQUENCE: 34
tcctattggg ctggggct                                           18

<210> SEQ ID NO 35
<211> LENGTH: 18
<212> TYPE: DNA
<213> ORGANISM: Hordeum vulgare

<400> SEQUENCE: 35
gctcaaccat accaggcg                                           18

<210> SEQ ID NO 36
<211> LENGTH: 18
<212> TYPE: DNA
<213> ORGANISM: Hordeum vulgare

<400> SEQUENCE: 36
gtcttccacc tccagcat                                                 18

<210> SEQ ID NO 37
<211> LENGTH: 18
<212> TYPE: DNA
<213> ORGANISM: Hordeum vulgare

<400> SEQUENCE: 37
accagcagac tccatttt                                                 18

<210> SEQ ID NO 38
<211> LENGTH: 18
<212> TYPE: DNA
<213> ORGANISM: Hordeum vulgare

<400> SEQUENCE: 38
cgcgggggac atggcctt                                                 18

<210> SEQ ID NO 39
<211> LENGTH: 18
<212> TYPE: DNA
<213> ORGANISM: Hordeum vulgare

<400> SEQUENCE: 39
aaggccatga cccccgcg                                                 18

<210> SEQ ID NO 40
<211> LENGTH: 20
<212> TYPE: DNA
<213> ORGANISM: Hordeum vulgare

<400> SEQUENCE: 40
tcaacctcac ttacagtttg                                               20

<210> SEQ ID NO 41
<211> LENGTH: 20
<212> TYPE: DNA
<213> ORGANISM: Hordeum vulgare

<400> SEQUENCE: 41
gtgatgctct ctcaacatgc                                               20

<210> SEQ ID NO 42
<211> LENGTH: 21
<212> TYPE: DNA
<213> ORGANISM: Hordeum vulgare

<400> SEQUENCE: 42
ttgatcttgg tgttggaatc a                                             21

<210> SEQ ID NO 43
<211> LENGTH: 20
<212> TYPE: DNA
<213> ORGANISM: Hordeum vulgare

<400> SEQUENCE: 43
cccatggttt gcatttgata                                              20

<210> SEQ ID NO 44
<211> LENGTH: 20
<212> TYPE: DNA
<213> ORGANISM: Hordeum vulgare

<400> SEQUENCE: 44
tgaatgaaaa cagacctccc                                              20

<210> SEQ ID NO 45
<211> LENGTH: 20
<212> TYPE: DNA
<213> ORGANISM: Hordeum vulgare

<400> SEQUENCE: 45
atgtaccaac ttcagcaggc                                              20

<210> SEQ ID NO 46
<211> LENGTH: 20
<212> TYPE: DNA
<213> ORGANISM: Hordeum vulgare

<400> SEQUENCE: 46
gacgaacggc acgactacta                                              20

<210> SEQ ID NO 47
<211> LENGTH: 20
<212> TYPE: DNA
<213> ORGANISM: Hordeum vulgare

<400> SEQUENCE: 47
atagaaggag gtggacgcat                                              20

<210> SEQ ID NO 48
<211> LENGTH: 19
<212> TYPE: DNA
<213> ORGANISM: Arabidopsis thaliana

<400> SEQUENCE: 48
cgtggtggga agagagagc                                               19

<210> SEQ ID NO 49
<211> LENGTH: 24
<212> TYPE: DNA
<213> ORGANISM: Arabidopsis thaliana

<400> SEQUENCE: 49
tgttgatgaa gcagagtcag taga                                         24

<210> SEQ ID NO 50
<211> LENGTH: 20
<212> TYPE: DNA
<213> ORGANISM: Hordeum vulgare

<400> SEQUENCE: 50
agacgaggcg gggtcagttg                                              20

<210> SEQ ID NO 51
<211> LENGTH: 19
<212> TYPE: DNA
<213> ORGANISM: Hordeum vulgare

<400> SEQUENCE: 51
tccccgccgc ggaaactgc                           19

<210> SEQ ID NO 52
<211> LENGTH: 19
<212> TYPE: DNA
<213> ORGANISM: Hordeum vulgare

<400> SEQUENCE: 52
gcggtggaga gcttcggtg                           19

<210> SEQ ID NO 53
<211> LENGTH: 18
<212> TYPE: DNA
<213> ORGANISM: Hordeum vulgare

<400> SEQUENCE: 53
gcgctgagct gtggcacc                            18

<210> SEQ ID NO 54
<211> LENGTH: 18
<212> TYPE: DNA
<213> ORGANISM: Hordeum vulgare

<400> SEQUENCE: 54
tgtaccctga gcacgccg                            18

<210> SEQ ID NO 55
<211> LENGTH: 18
<212> TYPE: DNA
<213> ORGANISM: Hordeum vulgare

<400> SEQUENCE: 55
gccagcctcc atgcttcg                            18

<210> SEQ ID NO 56
<211> LENGTH: 20
<212> TYPE: DNA
<213> ORGANISM: Hordeum vulgare

<400> SEQUENCE: 56
aacggacggg tcagtcatcg                          20

<210> SEQ ID NO 57
<211> LENGTH: 20
<212> TYPE: DNA
<213> ORGANISM: Hordeum vulgare

<400> SEQUENCE: 57
ccaccaggcc cttgctcacg                          20

<210> SEQ ID NO 58
<211> LENGTH: 22
<212> TYPE: DNA
<213> ORGANISM: Hordeum vulgare

<400> SEQUENCE: 58
gccaagaagc gcaagaagaa ga                       22

<210> SEQ ID NO 59
<211> LENGTH: 21
<212> TYPE: DNA
<213> ORGANISM: Hordeum vulgare -continued

```
<400> SEQUENCE: 59
ggtcgaagtg gttggccatg a                                          21

<210> SEQ ID NO 60
<211> LENGTH: 20
<212> TYPE: DNA
<213> ORGANISM: Hordeum vulgare

<400> SEQUENCE: 60
gcgggcgcga ggtacaaggc                                            20

<210> SEQ ID NO 61
<211> LENGTH: 20
<212> TYPE: DNA
<213> ORGANISM: Hordeum vulgare

<400> SEQUENCE: 61
agttggtgag gagcacgggg                                            20

<210> SEQ ID NO 62
<211> LENGTH: 20
<212> TYPE: DNA
<213> ORGANISM: Hordeum vulgare

<400> SEQUENCE: 62
ctgtactgtg tttttagcct                                            20

<210> SEQ ID NO 63
<211> LENGTH: 20
<212> TYPE: DNA
<213> ORGANISM: Hordeum vulgare

<400> SEQUENCE: 63
gacatgacac aaaaatcgga                                            20

<210> SEQ ID NO 64
<211> LENGTH: 20
<212> TYPE: DNA
<213> ORGANISM: Hordeum vulgare

<400> SEQUENCE: 64
cacacatggc acgccaaaac                                            20

<210> SEQ ID NO 65
<211> LENGTH: 20
<212> TYPE: DNA
<213> ORGANISM: Hordeum vulgare

<400> SEQUENCE: 65
gtgtgtaccg tgcggttttg                                            20

<210> SEQ ID NO 66
<211> LENGTH: 20
<212> TYPE: DNA
<213> ORGANISM: Hordeum vulgare

<400> SEQUENCE: 66
ttattttgac catatatacg                                            20

<210> SEQ ID NO 67
<211> LENGTH: 20
<212> TYPE: DNA
<213> ORGANISM: Hordeum vulgare
```

<400> SEQUENCE: 67
aataaaactg gtatatatgc                                                    20

<210> SEQ ID NO 68
<211> LENGTH: 20
<212> TYPE: DNA
<213> ORGANISM: Artificial Sequence
<220> FEATURE:
<223> OTHER INFORMATION: Artificial version of SP8a element in 6-SFT p

<400> SEQUENCE: 68
ctgtaaaaaa aatttagcct                                                    20

<210> SEQ ID NO 69
<211> LENGTH: 20
<212> TYPE: DNA
<213> ORGANISM: Artificial Sequence
<220> FEATURE:
<223> OTHER INFORMATION: Artificial version of SP8a element in 6-SFT p

<400> SEQUENCE: 69
gacatttttt ttaaatcgga                                                    20

<210> SEQ ID NO 70
<211> LENGTH: 20
<212> TYPE: DNA
<213> ORGANISM: Artificial Sequence
<220> FEATURE:
<223> OTHER INFORMATION: Artificial version of W-box element in 6-SFT p

<400> SEQUENCE: 70
ttattaaaaa aatatatacg                                                    20

<210> SEQ ID NO 71
<211> LENGTH: 20
<212> TYPE: DNA
<213> ORGANISM: Artificial Sequence
<220> FEATURE:
<223> OTHER INFORMATION: Artificial version of W-box element in 6-SFT p

<400> SEQUENCE: 71 aataatttttt ttatatatgc                                                   20

<210> SEQ ID NO 72
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 72
caaaaatggc acgccaaaac                                                    20

<210> SEQ ID NO 73
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 73 gtttttccg tgcggttttg                                                     20

<210> SEQ ID NO 74

```
<210> SEQ ID NO 74
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 74
cacacaaaaa acgccaaaac                                                 20

<210> SEQ ID NO 75
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 75
gtgtgttttt tgcggttttg                                                 20

<210> SEQ ID NO 76
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 76
cacacatggc aaaaaaaaac                                                 20

<210> SEQ ID NO 77
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 77
gtgtgtaccg ttttttttg                                                  20

<210> SEQ ID NO 78
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 78
caaaaaaaaa aaaaaaaaac                                                 20

<210> SEQ ID NO 79
<211> LENGTH: 20
<212> TYPE: DNA
<213> ORGANISM: Artificial Sequence
<220> FEATURE:
<223> OTHER INFORMATION: Artificial version of SUREa element in 6-SFT p

<400> SEQUENCE: 79
gttttttttt tttttttttg                                                 20

<210> SEQ ID NO 80
<211> LENGTH: 27
<212> TYPE: DNA
<213> ORGANISM: Hordeum vulgare

<400> SEQUENCE: 80
gtacacaacc tttaattttc ttttctg                                         27
```

<210> SEQ ID NO 81
<211> LENGTH: 27
<212> TYPE: DNA
<213> ORGANISM: Hordeum vulgare

<400> SEQUENCE: 81
catgtgttgg aaattaaaag aaaagac                                27

<210> SEQ ID NO 82
<211> LENGTH: 30
<212> TYPE: DNA
<213> ORGANISM: Hordeum vulgare

<400> SEQUENCE: 82
tgtcctatag agattaatgc actttatctt                             30

<210> SEQ ID NO 83
<211> LENGTH: 30
<212> TYPE: DNA
<213> ORGANISM: Hordeum vulgare

<400> SEQUENCE: 83
acaggatatc tctaattacg tgaaatagaa                             30

<210> SEQ ID NO 84
<211> LENGTH: 30
<212> TYPE: DNA
<213> ORGANISM: Hordeum vulgare

<400> SEQUENCE: 84
gcagaacatt aagatgaaat ttaagcattt                             30

<210> SEQ ID NO 85
<211> LENGTH: 30
<212> TYPE: DNA
<213> ORGANISM: Hordeum vulgare

<400> SEQUENCE: 85
cgtcttgtaa ttctacttta aattcgtaaa                             30

<210> SEQ ID NO 86
<211> LENGTH: 30
<212> TYPE: DNA
<213> ORGANISM: Hordeum vulgare

<400> SEQUENCE: 86
tgtttctaga tgaccctgca acttttttg                              30

<210> SEQ ID NO 87
<211> LENGTH: 30
<212> TYPE: DNA
<213> ORGANISM: Hordeum vulgare

<400> SEQUENCE: 87
acaaagatct actgggacgt tgaaaaaaac                             30

<210> SEQ ID NO 88
<211> LENGTH: 30
<212> TYPE: DNA
<213> ORGANISM: Hordeum vulgare

<400> SEQUENCE: 88

```
gcctttattg tgcatattat ataatttggc                                        30

<210> SEQ ID NO 89
<211> LENGTH: 30
<212> TYPE: DNA
<213> ORGANISM: Hordeum vulgare

<400> SEQUENCE: 89
cggaaataac acgtataata tattaaaccg                                        30

<210> SEQ ID NO 90
<211> LENGTH: 30
<212> TYPE: DNA
<213> ORGANISM: Hordeum vulgare

<400> SEQUENCE: 90
caggttcttg aattgttgca taattcataa                                        30

<210> SEQ ID NO 91
<211> LENGTH: 30
<212> TYPE: DNA
<213> ORGANISM: Hordeum vulgare

<400> SEQUENCE: 91
gtccaagaac ttaacaacgt attaagtatt                                        30

<210> SEQ ID NO 92
<211> LENGTH: 355
<212> TYPE: DNA
<213> ORGANISM: Hordeum vulgare

<400> SEQUENCE: 92
gttgcctctc ttttgtaaat gtatctatga gttacatatt ttattctgat attttttgga       60
tgataggaag gtaacgctat tccagatgca tggcaaatct caatataaaa ctcattaact      120
caatattcat gtgcagcatt acttctttca catgttgtgg agaagtttct ttataaatgg      180
tagagtttga aggaagtatt ttgaatggca gtttggggaa aacctatggt acatatgtag      240
ttagatctat ctgtgcttgc tatattagtc acatcctttc ttaattcgtt gacttgtttt      300
tacatattta gttttgcatt gtgtaacatt tgtgatgtca tattttgtac tgcag           355

<210> SEQ ID NO 93
<211> LENGTH: 398
<212> TYPE: DNA
<213> ORGANISM: Oryza sativa

<400> SEQUENCE: 93
atttccttgc taggtgagac ttgagtggtg ctagtctggc tgcaaattta tagaagtatg       60
tgaaaatttg aggtcagaat acaagtaatt gaatggacca atctaatgag ttctgtagct      120
ttagaataat taatgttaac ataaaaatat gttcatgaaa tcaggtcctt ctgcattttg      180
ttgttaaccg aattccacat tcttctttag ttctcacaag tacagacaag tatcttgtaa      240
tggtggattc ttttttggaa aacaaacttc attacatatt ttgtgtgatc catctatgcc      300
ttgtgccctt gttacctttt tttccctaca ccttgttttc tcttgtactt agttttgcat      360
tgtataacct tttgctgtac tcgtgtcttg tactgtag                              398

<210> SEQ ID NO 94
<211> LENGTH: 178
<212> TYPE: DNA
<213> ORGANISM: Hordeum vulgare
```

<400> SEQUENCE: 94

```
gtacacaacc tttaattttc ttttctgtgt cctatagaga ttaatgcact ttatcttgca    60
gaacattaag atgaaattta agcattttgt ttctagatga ccctgcaact ttttttggcc   120
tttattgtgc atattatata atttggccag gttcttgaat tgttgcataa ttcataat    178
```

<210> SEQ ID NO 95
<211> LENGTH: 605
<212> TYPE: DNA
<213> ORGANISM: Oryza sativa

<400> SEQUENCE: 95

```
gtatggatcc tttctttgag tgattacctg gtatcgtgta attcttcatt tgtgtatact    60
gtatttgaga gtttgaaaaa atttccatag aaataataa catttgttgt ttacaaatgg   120
tcccgccaaa acagtggaat ttatattggg gatgtacata aaaggagtgt aaagttctaa   180
tgtgcttatg ctaacttcct ttccatgatc taaagttgtt accttacggt atgctattta   240
ttggatctat attgcatttt acttggtaaa tctatctgag gttccagctt tgatatttta   300
agttttccta tgtttaattc aaaatattct cacgtgaatc gcaaacctca ccaggagtac   360
aataaattcg ttttattatt attgtaggct gtgttatttc tagtccatgg ttcggtgtct   420
tgaaatttca gtgccaaaat tgggatggat ctggttacat cttcaagtct aataaatgat   480
cacaccgact ttattgtgtg atttgattat agcagggtct gcaacataa atacaagcta   540
ttaattgtga aaggagaaat gagatctttg gtgagatcat gagaataggg tataacagac   600
acaat                                                              605
```

<210> SEQ ID NO 96
<211> LENGTH: 911
<212> TYPE: DNA
<213> ORGANISM: Hordeum vulgare

<400> SEQUENCE: 96

```
gtacacaacc tttaattttc ttttctgtgt cctatagaga ttaatgcact ttatcttgca    60
gaacattaag atgaaattta agcattttgt ttctagatga ccctgcaact ttttttggcc   120
tttattgtgc atattatata atttggccag gttcttgaat tgttgcataa ttcataatgt   180
tgcctctctt ttgtaaatgt atctatgagt tacatatttt attctgatat tttttggatg   240
ataggaaggt aacgctattc cagatgcatg gcaaatctca atataaaact cattaactca   300
atattcatgt gcagcattac ttctttcaca tgttgtggag aagtttcttt ataaatggta   360
gagtttgaag gaagtatttt gaatggcagt ttggggaaaa cctatggtac atatgtagtt   420
agatctatct gtgcttgcta tattagtcac atcctttctt aattcgttga cttgttttta   480
catatttagt tttgcattgt gtaacatttg tgatgtcata ttttgtactg caggctcctg   540
ctatgagtga tctaaaaaaa catgagcatt ctatgcaaaa tcagagtatg aatcccagct   600
catcatctag caatatggtg aatgaaaaca gacctccctg ttcacgtgag tcgagtctta   660
cagtgaatgt aagtgctcag aaccaacctg ttggaatggt tggtttgact gacagcatgc   720
ctgctgaagt tggtacatct gagccgcagc agatgaatag ctctgacaat gccatgcaag   780
agccgcagtc tgaaaatgtt gctgacaagt cggcagatga tggctacaac tggcggaaat   840
acgggcagaa gcatgtcaag ggaagtgaaa accctagaag ttactacaag tgcacacatc   900
ctaattgtga a                                                       911
```

<210> SEQ ID NO 97
<211> LENGTH: 1384
<212> TYPE: DNA
<213> ORGANISM: Oryza sativa

<400> SEQUENCE: 97

```
gtatggatcc tttctttgag tgattacctg gtatcgtgta attcttcatt tgtgtatact      60
gtatttgaga gtttgaaaaa atttccatag aaaataataa catttgttgt ttacaaatgg     120
tcccgccaaa acagtggaat ttatattggg gatgtacata aaaggagtgt aaagttctaa     180
tgtgcttatg ctaacttcct ttccatgatc taaagttgtt accttacggt atgctattta     240
ttggatctat attgcatttt acttggtaaa tctatctgag gttccagctt ttgatattta     300
agttttccta tgtttaattc aaaatattct cacgtgaatc gcaaacctca ccaggagtac     360
aataaattcg ttttattatt attgtaggct gtgttatttc tagtccatgg ttcggtgtct     420
tgaaatttca gtgccaaaat tgggatggat ctggttacat cttcaagtct aataaatgat     480
cacaccgact ttattgtgtg atttgattat agcagggtct tgcaacataa atacaagcta     540
ttaattgtga aggagaaat gagatctttg gtgagatcat gagaataggg tataacagac      600
acaatatttc cttgctaggt gagacttgag tggtgctagt ctggctgcaa atttatagaa     660
gtatgtgaaa atttgaggtc agaatacaag taattgaatg gaccaatcta atgagttctg     720
tagctttaga ataattaatg ttaacataaa atatgttca tgaaatcagg tccttctgca      780
ttttgttgtt aaccgaattc cacattcttc tttagttctc acaagtacag acaagtatct     840
tgtaatggtg gattcttttt tggaaaacaa acttcattac atattttgtg tgatccatct     900
atgccttgtg cccttgttac ctttttttcc ctacaccttg ttttctcttg tacttagttt     960
tgcattgtat aaccttttgc tgtactcgtg tcttgtactg taggcttctg ctatcaatga    1020
tcccaaaaag catgaaactt ctatgaaaaa tgaaagcctg aatactgccc tgtcatctga    1080
cgatatgatg atcgacaata tacctctatg ttctcgtgag tcaactctcg cagtcaatat    1140
ttcaagtgcc ccgagccaac tggttggaat ggttggttta actgacagct cacctgctga    1200
agttggtaca tctgagttgc atcagatgaa tagctctgga aatgctatgc aggagtcaca    1260
gcctgaaagt gtggctgaaa agtctgcaga ggatggttat aactggcgca aatatgggca    1320
aaagcatgtt aagggaagtg agaacccgag aagctattac aagtgcacac atcctaactg    1380
tgat                                                                 1384
```

<210> SEQ ID NO 98
<211> LENGTH: 181
<212> TYPE: DNA
<213> ORGANISM: Hordeum vulgare

<400> SEQUENCE: 98

```
cttccaggtt gaaccttcac caacaactgg tagtctgggc atggctgcga ttctgcacaa      60
gagcgctcat ccagacatgc tgccttcgcc acgggataaa tctgttcgta atgcccatga     120
agatagggt tctagggatt ttgaattcaa gcctcatctg aattcgtctt ctcaatcact      180
g                                                                    181
```

<210> SEQ ID NO 99
<211> LENGTH: 541
<212> TYPE: DNA
<213> ORGANISM: Hordeum vulgare

<400> SEQUENCE: 99

```
gctcctgcta tgagtgatct aaaaaaacat gagcattcta tgcaaaatca gagtatgaat      60
cccagctcat catctagcaa tatggtgaat gaaaacagac ctccctgttc acgtgagtcg     120
agtcttacag tgaatgtaag tgctcagaac caacctgttg gaatggttgg tttgactgac     180
agcatgcctg ctgaagttgg tacatctgag ccgcagcaga tgaatagctc tgacaatgcc     240
atgcaagagc cgcagtctga aaatgttgct gacaagtcgg cagatgatgg ctacaactgg     300
cggaaatacg ggcagaagca tgtcaaggga agtgaaaacc ctagaagtta ctacaagtgc     360
acacatccta attgtgaagt aaaaaagcta ttggagcgtg cagttgatgg tctgatcacg     420
gaagttgtct ataagggacg ccacaatcat cctaagcccc agcccaatag gaggttagct     480
ggtggtgcag ttccttcaaa ccagggtgaa gaacgatatg acggcgcttc agctgctgat     540
g                                                                    541

<210> SEQ ID NO 100
<211> LENGTH: 533
<212> TYPE: DNA
<213> ORGANISM: Hordeum vulgare

<400> SEQUENCE: 100
gtacacaacc tttaattttc ttttctgtgt cctatagaga ttaatgcact ttatcttgca      60
gaacattaag atgaaattta agcattttgt ttcagatgaa ccctgcaact ttttttggcc     120
tttattgtgc atattatata atttggccag gttcttgaat tgttgcataa ttcataatgt     180
tgcctctctt ttgtaaatgt atctatgagt tacatatttt attctgatat tttttggatg     240
ataggaaggt aacgctattc cagatgcatg gcaaatctca atataaaact cattaactca     300
atattcatgt gcagcattac ttcttcaca tgttgtggag aagtttcttt ataaatggta     360
gagtttgaag gaagtatttt gaatggcagt ttggggaaaa cctatggtac atatgtagtt     420
agatctatct gtgcttgcta tattagtcac atcctttctt aattcgttga cttgttttta     480
catatttagt tttgcattgt gtaacatttg tgatgtcata ttttgtactg cag            533

<210> SEQ ID NO 101
<211> LENGTH: 181
<212> TYPE: DNA
<213> ORGANISM: Oryza sativa

<400> SEQUENCE: 101
tgtttaggtt gaaccctctc cgacaactgg tactctgagc atggctgcaa ttatgaacaa      60
gagtgcaaat ccagacatac ttccttcgcc tagggataaa acatctggta gcacccatga     120
agatggtggc tctcgagatt ttgaattcaa gcctcatctg aattcatcct ctcaatcgac     180
g                                                                    181

<210> SEQ ID NO 102
<211> LENGTH: 544
<212> TYPE: DNA
<213> ORGANISM: Oryza sativa

<400> SEQUENCE: 102
gcttctgcta tcaatgatcc caaaaagcat gaaacttcta tgaaaaatga agcctgaat      60 actgccctgt catctgacga tatgatgatc gacaatatac ctctatgttc tcgtgagtca     120
actctcgcag tcaatatttc aagtgcccg agccaactgg ttggaatggt tggtttaact     180
gacagctcac ctgctgaagt tggtacatct gagttgcatc agatgaatag ctctggaaat     240
```

```
gctatgcagg agtcacagcc tgaaagtgtg gctgaaaagt ctgcagagga tggttataac      300
tggcgcaaat atgggcaaaa gcatgttaag ggaagtgaga acccgagaag ctattacaag      360
tgcacacatc ctaactgtga tgtaaaaaag ctattggagc gttcgcttga tggtcagatt      420
actgaagtgg tttataaagg gcgtcacaat caccctaagc cccaacccaa taggaggctg      480
tctgccggtg cagttcctcc aatccagggt gaagaaagat atgatggtgt ggcaactact      540
gatg                                                                  544
```

<210> SEQ ID NO 103
<211> LENGTH: 1003
<212> TYPE: DNA
<213> ORGANISM: Oryza sativa

<400> SEQUENCE: 103

```
gtatggatcc tttctttgag tgattacctg gtatcgtgta attcttcatt tgtgtatact       60
gtatttgaga gtttgaaaaa atttccatag aaaataataa catttgttgt ttacaaatgg      120
tcccgccaaa acagtggaat ttatattggg gatgtacata aaaggagtgt aaagttctaa      180
tgtgcttatg ctaacttcct ttccatgatc taaagttgtt accttacggt atgctattta      240
ttggatctat attgcatttt acttggtaaa tctatctgag gttccagctt ttgatattta      300
agttttccta tgtttaattc aaaatattct cacgtgaatc gcaaacctca ccaggagtac      360
aataaattcg ttttattatt attgtaggct gtgttatttc tagtccatgg ttcggtgtct      420
tgaaatttca gtgccaaaat tgggatggat ctggttacat cttcaagtct aataaatgat      480
cacaccgact ttattgtgtg atttgattat agcagggtct tgcaacataa atacaagcta      540
ttaattgtga aaggagaaat gagatctttg gtgagatcat gagaataggg tataacagac      600
acaatatttc cttgctaggt gagacttgag tggtgctagt ctggctgcaa atttatagaa      660
gtatgtgaaa atttgaggtc agaatacaag taattgaatg gaccaatcta atgagttctg      720
tagctttaga ataattaatg ttaacataaa atatgttca tgaaatcagg tccttctgca       780
ttttgttgtt aaccgaattc cacattcttc tttagttctc acaagtacag acaagtatct      840
tgtaatggtg gattcttttt tggaaaacaa acttcattac atattttgtg tgatccatct      900
atgccttgtg cccttgttac ctttttttcc ctacaccttg ttttctcttg tacttagttt      960
tgcattgtat aaccttttgc tgtactcgtg tcttgtactg tag                       1003
```

<210> SEQ ID NO 104
<211> LENGTH: 573
<212> TYPE: PRT
<213> ORGANISM: Hordeum vulgare

<400> SEQUENCE: 104

```
Met Ser Pro Ala Arg Leu Pro Ile Ser Arg Glu Ser Cys Leu Thr Ile
1               5                   10                  15

Pro Ala Gly Phe Ser Pro Ser Ala Leu Leu Asp Ser Pro Val Leu Leu
            20                  25                  30

Thr Asn Phe Lys Val Glu Pro Ser Pro Thr Thr Gly Ser Leu Gly Met
        35                  40                  45

Ala Ala Ile Leu His Lys Ser Ala His Pro Asp Met Leu Pro Ser Pro
    50                  55                  60

Arg Asp Lys Ser Val Arg Asn Ala His Glu Asp Arg Gly Ser Arg Asp
65                  70                  75                  80

Phe Glu Phe Lys Pro His Leu Asn Ser Ser Ser Gln Ser Leu Ala Pro
                85                  90                  95
```

```
Ala Met Ser Asp Leu Lys Lys His Glu His Ser Met Gln Asn Gln Ser
            100                 105                 110

Met Asn Pro Ser Ser Ser Ser Asn Met Val Asn Glu Asn Arg Pro
        115                 120                 125

Pro Cys Ser Arg Glu Ser Ser Leu Thr Val Asn Val Ser Ala Gln Asn
130                 135                 140

Gln Pro Val Gly Met Val Gly Leu Thr Asp Ser Met Pro Ala Glu Val
145                 150                 155                 160

Gly Thr Ser Glu Pro Gln Gln Met Asn Ser Ser Asp Asn Ala Met Gln
                165                 170                 175

Glu Pro Gln Ser Glu Asn Val Ala Asp Lys Ser Ala Asp Gly Tyr
            180                 185                 190

Asn Trp Arg Lys Tyr Gly Gln Lys His Val Lys Gly Ser Glu Asn Pro
        195                 200                 205

Arg Ser Tyr Tyr Lys Cys Thr His Pro Asn Cys Glu Val Lys Lys Leu
210                 215                 220

Leu Glu Arg Ala Val Asp Gly Leu Ile Thr Glu Val Val Tyr Lys Gly
225                 230                 235                 240

Arg His Asn His Pro Lys Pro Gln Pro Asn Arg Arg Leu Ala Gly Gly
                245                 250                 255

Ala Val Pro Ser Asn Gln Gly Glu Glu Arg Tyr Asp Gly Ala Ser Ala
            260                 265                 270

Ala Asp Asp Lys Ser Ser Asn Ala Leu Ser Asn Leu Ala Asn Pro Val
        275                 280                 285

His Ser Pro Gly Met Val Glu Pro Val Pro Ala Ser Val Ser Asp Asp
290                 295                 300

Asp Ile Asp Ala Gly Gly Gly Arg Pro Tyr Pro Gly Asp Asp Ala Thr
305                 310                 315                 320

Glu Glu Glu Asp Leu Glu Ser Lys Arg Arg Lys Met Glu Ser Ala Gly
                325                 330                 335

Ile Asp Ala Ala Leu Met Gly Lys Pro Asn Arg Glu Pro Arg Val Val
            340                 345                 350

Val Gln Thr Val Ser Glu Val Asp Ile Leu Asp Asp Gly Tyr Arg Trp
        355                 360                 365

Arg Lys Tyr Gly Gln Lys Val Val Lys Gly Asn Pro Asn Pro Arg Ser
370                 375                 380

Tyr Tyr Lys Cys Thr Ser Thr Gly Cys Pro Val Arg Lys His Val Glu
385                 390                 395                 400

Arg Ala Ser His Asp Pro Lys Ser Val Ile Thr Thr Tyr Glu Gly Lys
                405                 410                 415

His Asn His Glu Val Pro Ala Ala Arg Asn Ala Thr His Glu Met Ser
            420                 425                 430

Ala Pro Pro Met Lys Asn Val Val His Gln Ile Asn Ser Asn Met Pro
        435                 440                 445

Ser Ser Ile Gly Gly Met Met Arg Ala Cys Glu Ala Arg Asn Tyr Thr
450                 455                 460

Asn Gln Tyr Ser Gln Ala Ala Glu Thr Asp Thr Val Ser Leu Asp Leu
465                 470                 475                 480

Gly Val Gly Ile Ser Pro Asn His Ser Asp Ala Thr Asn Gln Met Gln
                485                 490                 495

Ser Ser Gly Pro Asp Gln Met Gln Tyr Gln Met Gln Thr Met Gly Ser
            500                 505                 510
```

```
Met Tyr Gly Asn Met Arg His Pro Ser Ser Met Ala Ala Pro Ala Val
            515                 520                 525

Gln Gly Asn Ser Ala Ala Arg Met Tyr Gly Ser Arg Glu Glu Lys Gly
        530                 535                 540

Asn Glu Gly Phe Thr Phe Arg Ala Thr Pro Met Asp His Ser Ala Asn
545                 550                 555                 560

Leu Cys Tyr Ser Ser Ala Gly Asn Leu Val Met Gly Pro
                565                 570

<210> SEQ ID NO 105
<211> LENGTH: 618
<212> TYPE: PRT
<213> ORGANISM: Oryza sativa

<400> SEQUENCE: 105

Met Ala Asp Ser Pro Asn Pro Ser Ser Gly Asp His Pro Ala Gly Val
1               5                   10                  15

Gly Gly Ser Pro Glu Lys Gln Pro Pro Val Asp Arg Arg Val Ala Ala
            20                  25                  30

Leu Ala Gly Ala Ala Gly Ala Gly Ala Arg Tyr Lys Ala Met Ser
        35                  40                  45

Pro Ala Arg Leu Pro Ile Ser Arg Glu Pro Cys Leu Thr Ile Pro Ala
    50                  55                  60

Gly Phe Ser Pro Ser Ala Leu Leu Glu Ser Pro Val Leu Leu Thr Asn
65                  70                  75                  80

Phe Lys Val Glu Pro Ser Pro Thr Thr Gly Thr Leu Ser Met Ala Ala
                85                  90                  95

Ile Met Asn Lys Ser Ala Asn Pro Asp Ile Leu Pro Ser Pro Arg Asp
            100                 105                 110

Lys Thr Ser Gly Ser Thr His Glu Asp Gly Gly Ser Arg Asp Phe Glu
        115                 120                 125

Phe Lys Pro His Leu Asn Ser Ser Ser Gln Ser Thr Ala Ser Ala Ile
    130                 135                 140

Asn Asp Pro Lys Lys His Glu Thr Ser Met Lys Asn Glu Ser Leu Asn
145                 150                 155                 160

Thr Ala Leu Ser Ser Asp Asp Met Met Ile Asp Asn Ile Pro Leu Cys
                165                 170                 175

Ser Arg Glu Ser Thr Leu Ala Val Asn Ile Ser Ser Ala Pro Ser Gln
            180                 185                 190

Leu Val Gly Met Val Gly Leu Thr Asp Ser Ser Pro Ala Glu Val Gly
        195                 200                 205

Thr Ser Glu Leu His Gln Met Asn Ser Ser Gly Asn Ala Met Gln Glu
    210                 215                 220

Ser Gln Pro Glu Ser Val Ala Glu Lys Ser Ala Glu Asp Gly Tyr Asn
225                 230                 235                 240

Trp Arg Lys Tyr Gly Gln Lys His Val Lys Gly Ser Glu Asn Pro Arg
                245                 250                 255

Ser Tyr Tyr Lys Cys Thr His Pro Asn Cys Asp Val Lys Lys Leu Leu
            260                 265                 270

Glu Arg Ser Leu Asp Gly Gln Ile Thr Glu Val Val Tyr Lys Gly Arg
        275                 280                 285

His Asn His Pro Lys Pro Gln Pro Asn Arg Arg Leu Ser Ala Gly Ala
    290                 295                 300

Val Pro Pro Ile Gln Gly Glu Glu Arg Tyr Asp Gly Val Ala Thr Thr
305                 310                 315                 320
```

Asp Asp Lys Ser Ser Asn Val Leu Ser Ile Leu Gly Asn Ala Val His
            325                 330                 335

Thr Ala Gly Met Ile Glu Pro Val Pro Gly Ser Ala Ser Asp Asp Asp
            340                 345                 350

Asn Asp Ala Gly Gly Gly Arg Pro Tyr Pro Gly Asp Asp Ala Val Glu
            355                 360                 365

Asp Asp Asp Leu Glu Ser Lys Arg Arg Lys Met Glu Ser Ala Ala Ile
            370                 375                 380

Asp Ala Ala Leu Met Gly Lys Pro Asn Arg Glu Pro Arg Val Val Val
385                 390                 395                 400

Gln Thr Val Ser Glu Val Asp Ile Leu Asp Asp Gly Tyr Arg Trp Arg
            405                 410                 415

Lys Tyr Gly Gln Lys Val Val Lys Gly Asn Pro Asn Pro Arg Ser Tyr
            420                 425                 430

Tyr Lys Cys Thr Asn Thr Gly Cys Pro Val Arg Lys His Val Glu Arg
            435                 440                 445

Ala Ser His Asp Pro Lys Ser Val Ile Thr Thr Tyr Glu Gly Lys His
            450                 455                 460

Asn His Glu Val Pro Ala Ser Arg Asn Ala Ser His Glu Met Ser Thr
465                 470                 475                 480

Pro Pro Met Lys Pro Val Val His Pro Ile Asn Ser Asn Met Gln Gly
            485                 490                 495

Leu Gly Gly Met Met Arg Ala Cys Glu Pro Arg Thr Phe Pro Asn Gln
            500                 505                 510

Tyr Ser Gln Ala Ala Glu Ser Asp Thr Ile Ser Leu Asp Leu Gly Val
            515                 520                 525

Gly Ile Ser Pro Asn His Ser Asp Ala Thr Asn Gln Leu Gln Ser Ser
            530                 535                 540

Val Ser Asp Gln Met Gln Tyr Gln Met Gln Pro Met Gly Ser Val Tyr
545                 550                 555                 560

Ser Asn Met Gly Leu Pro Ala Met Ala Met Pro Thr Met Ala Gly Asn
            565                 570                 575

Ala Ala Ser Asn Ile Tyr Gly Ser Arg Glu Lys Pro Ser Glu Gly
            580                 585                 590

Phe Thr Phe Lys Ala Thr Pro Met Asp His Ser Ala Asn Leu Cys Tyr
            595                 600                 605

Ser Thr Ala Gly Asn Leu Val Met Gly Pro
            610                 615

<210> SEQ ID NO 106
<211> LENGTH: 281
<212> TYPE: PRT
<213> ORGANISM: Hordeum vulgare

<400> SEQUENCE: 106

Met Val Glu Pro Val Pro Ala Ser Val Ser Asp Asp Ile Asp Ala
1               5                   10                  15

Gly Gly Gly Arg Pro Tyr Pro Gly Asp Asp Ala Thr Glu Glu Glu Asp
            20                  25                  30

Leu Glu Ser Lys Arg Arg Lys Met Glu Ser Ala Gly Ile Asp Ala Ala
            35                  40                  45

Leu Met Gly Lys Pro Asn Arg Glu Pro Arg Val Val Val Gln Thr Val
            50                  55                  60

Ser Glu Val Asp Ile Leu Asp Asp Gly Tyr Arg Trp Arg Lys Tyr Gly

```
            65                  70                  75                  80
        Gln Lys Val Val Lys Gly Asn Pro Asn Pro Arg Ser Tyr Tyr Lys Cys
                        85                  90                  95

Thr Ser Thr Gly Cys Pro Val Arg Lys His Val Glu Arg Ala Ser His
                    100                 105                 110

Asp Pro Lys Ser Val Ile Thr Thr Tyr Glu Gly Lys His Asn His Glu
                    115                 120                 125

Val Pro Ala Ala Arg Asn Ala Thr His Glu Met Ser Ala Pro Pro Met
                130                 135                 140

Lys Asn Val Val His Gln Ile Asn Ser Asn Met Pro Ser Ser Ile Gly
        145                 150                 155                 160

Gly Met Met Arg Ala Cys Glu Ala Arg Asn Tyr Thr Asn Gln Tyr Ser
                        165                 170                 175

Gln Ala Ala Glu Thr Asp Thr Val Ser Leu Asp Leu Gly Val Gly Ile
                    180                 185                 190

Ser Pro Asn His Ser Asp Ala Thr Asn Gln Met Gln Ser Ser Gly Pro
                    195                 200                 205

Asp Gln Met Gln Tyr Gln Met Gln Thr Met Gly Ser Met Tyr Gly Asn
                210                 215                 220

Met Arg His Pro Ser Ser Met Ala Ala Pro Ala Val Gln Gly Asn Ser
        225                 230                 235                 240

Ala Ala Arg Met Tyr Gly Ser Arg Glu Glu Lys Gly Asn Glu Gly Phe
                        245                 250                 255

Thr Phe Arg Ala Thr Pro Met Asp His Ser Ala Asn Leu Cys Tyr Ser
                    260                 265                 270

Ser Ala Gly Asn Leu Val Met Gly Pro
                    275                 280

<210> SEQ ID NO 107
<211> LENGTH: 279
<212> TYPE: PRT
<213> ORGANISM: Oryza sativa

<400> SEQUENCE: 107

Met Ile Glu Pro Val Pro Gly Ser Ala Ser Asp Asp Asn Asp Asn Ala
        1               5                   10                  15

Gly Gly Gly Arg Pro Tyr Pro Gly Asp Asp Ala Val Glu Asp Asp Asp
                        20                  25                  30

Leu Glu Ser Lys Arg Arg Lys Met Glu Ser Ala Ala Ile Asp Ala Ala
                    35                  40                  45

Leu Met Gly Lys Pro Asn Arg Glu Pro Arg Val Val Gln Thr Val
            50                  55                  60

Ser Glu Val Asp Ile Leu Asp Asp Gly Tyr Arg Trp Arg Lys Tyr Gly
        65                  70                  75                  80

Gln Lys Val Val Lys Gly Asn Pro Asn Pro Arg Ser Tyr Tyr Lys Cys
                        85                  90                  95

Thr Asn Thr Gly Cys Pro Val Arg Lys His Val Glu Arg Ala Ser His
                    100                 105                 110

Asp Pro Lys Ser Val Ile Thr Thr Tyr Glu Gly Lys His Asn His Glu
                    115                 120                 125

Val Pro Ala Ser Arg Asn Ala Ser His Glu Met Ser Thr Pro Pro Met
                130                 135                 140

Lys Pro Val Val His Pro Ile Asn Ser Asn Met Gln Gly Leu Gly Gly
        145                 150                 155                 160
```

```
Met Met Arg Ala Cys Glu Pro Arg Thr Phe Pro Asn Gln Tyr Ser Gln
            165                 170                 175

Ala Ala Glu Ser Asp Thr Ile Ser Leu Asp Leu Gly Val Gly Ile Ser
        180                 185                 190

Pro Asn His Ser Asp Ala Thr Asn Gln Leu Gln Ser Ser Val Ser Asp
            195                 200                 205

Gln Met Gln Tyr Gln Met Gln Pro Met Gly Ser Val Tyr Ser Asn Met
    210                 215                 220

Gly Leu Pro Ala Met Ala Met Pro Thr Met Ala Gly Asn Ala Ala Ser
225                 230                 235                 240

Asn Ile Tyr Gly Ser Arg Glu Glu Lys Pro Ser Glu Gly Phe Thr Phe
                245                 250                 255

Lys Ala Thr Pro Met Asp His Ser Ala Asn Leu Cys Tyr Ser Thr Ala
            260                 265                 270

Gly Asn Leu Val Met Gly Pro
            275
```

<210> SEQ ID NO 108
<211> LENGTH: 30
<212> TYPE: DNA
<213> ORGANISM: Hordeum vulgare

<400> SEQUENCE: 108
taggtcgtca atttgactta tataaaatat                              30

<210> SEQ ID NO 109
<211> LENGTH: 30
<212> TYPE: DNA
<213> ORGANISM: Hordeum vulgare

<400> SEQUENCE: 109
atattttata taagtcaaat tgacgaccta                              30

<210> SEQ ID NO 110
<211> LENGTH: 30
<212> TYPE: DNA
<213> ORGANISM: Hordeum vulgare

<400> SEQUENCE: 110
gcttcatcaa cgtatccgca cgttacacgg                              30

<210> SEQ ID NO 111
<211> LENGTH: 30
<212> TYPE: DNA
<213> ORGANISM: Hordeum vulgare

<400> SEQUENCE: 111
ccgtgtaacg tgcggatacg ttgatgaagc                              30

<210> SEQ ID NO 112
<211> LENGTH: 359
<212> TYPE: DNA
<213> ORGANISM: Triticum aestivum

<400> SEQUENCE: 112
cttgcctatc atttgtaaat gcatgtacga acttacctat tttattctga tcttctttgg    60
agggtaggaa ggtaacacta tcccagatgc atggcaaatc tcagtataga actcattaac   120
tcaatatcca tatgtaacat tacttctttc acatgtagcg gagaagtttc tttataaata   180
gtagagtttg aaaaaagcac tttgaatgac agtttgggga aaaactatgg tacatatgta   240

```
gttagatcta tctgtgcttg ctatgttagt cacattcttt cttaattcct gttgacttgt    300
ttttgcatat tttgttttgc atcgtgtaac atttgtaatg ctcatatttt gtactgcag     359

<210> SEQ ID NO 113
<211> LENGTH: 184
<212> TYPE: DNA
<213> ORGANISM: Triticum aestivum

<400> SEQUENCE: 113
gtacacaacc tttaattttc ttttctctgt gtcccataga gattaatgta ctttatcttg     60
cagaacatca aaagaaaatt taagcatttt gtttctatac gaccccacaa atatatctgg    120
cctttattgt gcatattata accataattc ggctaggttc ttgaattgtt gcataattca    180
taat                                                                184

<210> SEQ ID NO 114
<211> LENGTH: 2354
<212> TYPE: DNA
<213> ORGANISM: Hordeum vulgare

<400> SEQUENCE: 114
agatcatgca tcgttgagcc gcttggtggg cgagacggct cgatgggctc cccgagcggg     60
cacgcgggct cgatgaagta ctccccgtgc ttcacttctg cgccacggtg atctccttgg    120
gtcgggtcca agccgaaacc tagctccggg gacctccctt cgcccgccgg gagctcgccc    180
gagaagccct accccgcgga tcgacgcgtc gcggcgctcg ccggcgcggg cgcgaggtac    240
aaggccatgt ccccgcgcg gctgccgatc tcgcgcgagt cctgcctcac catccccgcc     300
ggcttcagcc cctcagcgct cctcgactcc cccgtgctcc tcaccaactt caaggttgaa    360
ccttcaccaa caactggtag tctgggcatg gctgcgattc tgcacaagag cgctcatcca    420
gacatgctgc cttcgccacg ggataaatct gttcgtaatg cccatgaaga taggggttct    480
agggattttg aattcaagcc tcatctgaat tcgtcttctc aatcactggc tcctgctatg    540
agtgatctaa aaaacatga gcattctatg caaaatcaga gtatgaatcc cagctcatca    600
tctagcaata tggtgaatga aaacagacct ccctgttcac gtgagtcgag tcttacagtg    660
aatgtaagtg ctcagaacca acctgttgga atggttggtt tgactgacag catgcctgct    720
gaagttggta catctgagcc gcagcagatg aatagctctg acaatgccat gcaagagccg    780
cagtctgaaa atgttgctga caagtcggca gatgatggct acaactggcg gaaatacggg    840
cagaagcatg tcaagggaag tgaaaaccct agaagttact acaagtgcac acatcctaat    900
tgtgaagtaa aaaagctatt ggagcgtgca gttgatggtc tgatcacgga agttgtctat    960
aagggacgcc acaatcatcc taagccccag cccaatagga ggttagctgg tggtgcagtt   1020
ccttcaaacc agggtgaaga acgatatgac ggcgcttcag ctgctgatga taaatcttcc   1080
aatgctctta gcaaccttgc taatccggta cattcgcctg gtatggttga gcctgttcca   1140
gcttcagtta gtgatgatga catcgatgct ggaggtggaa gaccctaccc tggggatgat   1200
gctactgagg aggaggattt agagtcgaaa cgcaggaaaa tggagtctgc tggtattgat   1260
gctgctctga tgggtaaacc taaccgtgag ccccgtgtcg tcgttcaaac tgtaagtgag   1320
gttgacatct tggatgatgg ctatcgttgg cggaaatatg gacagaaagt tgtcaaagga   1380
aaccccaatc cacggagtta ctacaaatgc acaagcacag gatgccctgt gaggaagcat   1440
gttgagagag catcacacga tcctaaatca gtgataacaa cgtatgaagg aaaacataac   1500
```

| | |
|---|---|
| catgaagtcc ctgctgcgag gaatgcaacc catgagatgt ccgcgcctcc catgaagaac | 1560 |
| gtcgtgcatc agattaacag caatatgccc agcagcattg gtggcatgat gagggcatgt | 1620 |
| gaagccagga actacaccaa ccaatattct caggcggctg aaaccgacac tgtcagtctt | 1680 |
| gatcttggtg ttggaatcag cccaaaccac agcgacgcga caaaccaaat gcagtcttca | 1740 |
| ggtcctgacc agatgcagta tcaaatgcaa accatgggtt cgatgtacgg caacatgaga | 1800 |
| catccatcat caatggcagc gccagcggta caaggaaact ctgctgcccg catgtatggt | 1860 |
| tcgagagaag agaaaggtaa cgaagggttt actttcagag ccacaccgat ggaccattca | 1920 |
| gctaacctat gctatagcag tgctgggaac ttggtcatgg gtccatgaga gggaatgaga | 1980 |
| gtgtctgcaa atgctcatag ctccatgaat catatattac caacaatgct ttgtaatgac | 2040 |
| aatctcttca gcaagattct caattgtctc aattgtgtat cggttacaag tcagttcagc | 2100 |
| cggaggcaag tatgctagta taagctatac gtgggggcac tgcagcaaat acgcatgtgt | 2160 |
| cttttaagt gcggaaaagg cccttgctgt atgtagcatc gcagccctac attcgttgta | 2220 |
| cagcgaacct aatatgatta attaattaga ttatgagaat ttggtttcgt gaactgtcta | 2280 |
| atcttctgta ctggaatatt gatagaaata tagattatgg taattttctt taaaaaaaaa | 2340 |
| aaaaaaaaaa aaaa | 2354 |

<210> SEQ ID NO 115
<211> LENGTH: 1074
<212> TYPE: DNA
<213> ORGANISM: Hordeum vulgare

<400> SEQUENCE: 115

| | |
|---|---|
| gtacacaacc tttaattttc ttttctgtgt cctatagaga ttaatgcact ttatcttgca | 60 |
| gaacattaag atgaaattta agcattttgt ttcagatga ccctgcaact ttttttggcc | 120 |
| tttattgtgc atattatata atttggccag gttcttgaat tgttgcataa ttcataatgt | 180 |
| tgcctctctt ttgtaaatgt atctatgagt tacatatttt attctgatat tttttggatg | 240 |
| ataggaaggt aacgctattc cagatgcatg gcaaatctca atataaaact cattaactca | 300 |
| atattcatgt gcagcattac ttcttttcaca tgttgtggag aagtttcttt ataaatggta | 360 |
| gagtttgaag gaagtatttt gaatggcagt ttggggaaaa cctatggtac atatgtagtt | 420 |
| agatctatct gtgcttgcta tattagtcac atcctttctt aattcgttga cttgttttta | 480 |
| catatttagt tttgcattgt gtaacatttg tgatgtcata ttttgtactg caggctcctg | 540 |
| ctatgagtga tctaaaaaaa catgagcatt ctatgcaaaa tcagagtatg aatcccagct | 600 |
| catcatctag caatatggtg aatgaaaaca gacctccctg ttcacgtgag tcgagtctta | 660 |
| cagtgaatgt aagtgctcag aaccaacctg ttggaatggt tggtttgact dacagcatgc | 720 |
| ctgctgaagt tggtacatct gagccgcagc agatgaatag ctctgacaat gccatgcaag | 780 |
| agccgcagtc tgaaaatgtt gctgacaagt cggcagatga tggctacaac tggcggaaat | 840 |
| acgggcagaa gcatgtcaag ggaagtgaaa accctagaag ttactacaag tgcacacatc | 900 |
| ctaattgtga agtaaaaaag ctattggagc gtgcagttga tggtctgatc acggaagttg | 960 |
| tctataaggg acgccacaat catcctaagc cccagcccaa taggaggtta gctggtggtg | 1020 |
| cagttccttc aaaccagggt gaagaacgat atgacggcgc ttcagctgct gatg | 1074 |

<210> SEQ ID NO 116
<211> LENGTH: 18
<212> TYPE: DNA
<213> ORGANISM: Hordeum vulgare

```
<400> SEQUENCE: 116
agccccagcc caatagga                                                       18

<210> SEQ ID NO 117
<211> LENGTH: 18
<212> TYPE: DNA
<213> ORGANISM: Hordeum vulgare

<400> SEQUENCE: 117
cgcctggtat ggttgagc                                                       18

<210> SEQ ID NO 118
<211> LENGTH: 18
<212> TYPE: DNA
<213> ORGANISM: Hordeum vulgare

<400> SEQUENCE: 118
atgctggagg tggaagac                                                       18

<210> SEQ ID NO 119
<211> LENGTH: 18
<212> TYPE: DNA
<213> ORGANISM: Hordeum vulgare

<400> SEQUENCE: 119
aaaatggagt ctgctggt                                                       18
```

CARBOHYDRATE PRODUCING PLANT MATERIAL

SEQUENCE LISTING

The Sequence Listing submitted herewith, entitled "Sep. 26, 2019-Sequence-Listing-ST25.txt", created Sep. 17, 2019 and having a size of 47,309 bytes, is incorporated herein by reference.

TECHNICAL FIELD

The present embodiments generally relate to plant materials, and in particular to plant materials with controlled carbohydrate production.

BACKGROUND

Sugars are the key energy carriers in transfer of solar energy to chemical energy essential for life on Earth via photosynthesis. In higher plants, sugars are not only basic substrate materials for biomass synthesis, but also signaling molecules for many metabolic pathway. Carbohydrate synthesis is usually mediated by sugars. According to sugar levels and availability, higher plants use different strategies to synthesize different carbohydrates in storage of energy for immediate (minutes), middle-term (hours) and long-term (days to years) energy supply in meeting energy demands from growth, development and reproduction.

Fructan, transient starch and storage starch are examples of the carbohydrates in terms of different energy supply forms. They are produced in a large number of flowering plants including temperate Gramineae, such as barley, wheat, oats, and many forage grasses.

Document [1] discloses the sugar signaling in barley 2 (SUSIBA2) transcription factor (TF), belonging to the WRKY proteins. SUSIBA2 TF binds to sugar responsive (SURE) and W-bow elements but not to the SP8a element in the ISO1 promoter. Transcription of SUSIBA2 is sugar inducible and is a regulatory transcription factor in starch synthesis.

Document [3] discloses expression of barley SUSIBA2 TF in rice, yielding a high-starch and low-methane transgenic rice.

Document [17] discloses a transgenic plant comprising a nucleic acid sequence encoding a sugar-signaling TF, such as SISIBA2 TF, which is capable of activating a promoter of a gene encoding an enzyme involved in the synthesis of starch.

There is still a need for plant material with controlled production of carbohydrates.

SUMMARY

It is a general objective to provide a plant material with controlled production of carbohydrates.

This and other objectives are met by embodiments disclosed herein.

The present invention is defined in the independent claim. Further embodiments are defined in the dependent claims.

A plant material comprises a genomic nucleotide sequence encoding a sugar signaling in barley 2 (SUSIBA2) or SUSIBA2-like transcription factor under transcriptional control of a promoter active in the plant material. The genomic nucleotide sequence encoding the SUSIBA2 or SUSIBA2-like transcription factor lacks at least a portion of an activation region of a SUSIBA1 or SUSIBA1-like promoter (SUSIBA1 or SUSIBA1-like p) present in an intron of a wild-type version of the genomic nucleotide sequence encoding the SUSIBA2 or SUSIBA2-like transcription factor.

A plant material of the present embodiments has a controlled production of carbohydrates, in particular starch or starch and fructan. In particular, the plant material of the present embodiments can be designed to produce carbohydrates at enhanced levels. The plant material of the present embodiments may also reduce emission of methane, and can thereby be a high-starch and low-methane plant material, or a high-starch, high-fructan and low-methane plant material.

BRIEF DESCRIPTION OF THE DRAWINGS

The embodiments, together with further objects and advantages thereof, may best be understood by making reference to the following description taken together with the accompanying drawings, in which:

FIG. 29. The figure compares the nucleotide sequences of the exon 3 (SEQ ID NO: 99) of the SUSIBA2 gene in barley and the exon 3 (SEQ ID NO: 102) of the SUSIBA2-like gene in rice.

DETAILED DESCRIPTION

Figure 1:
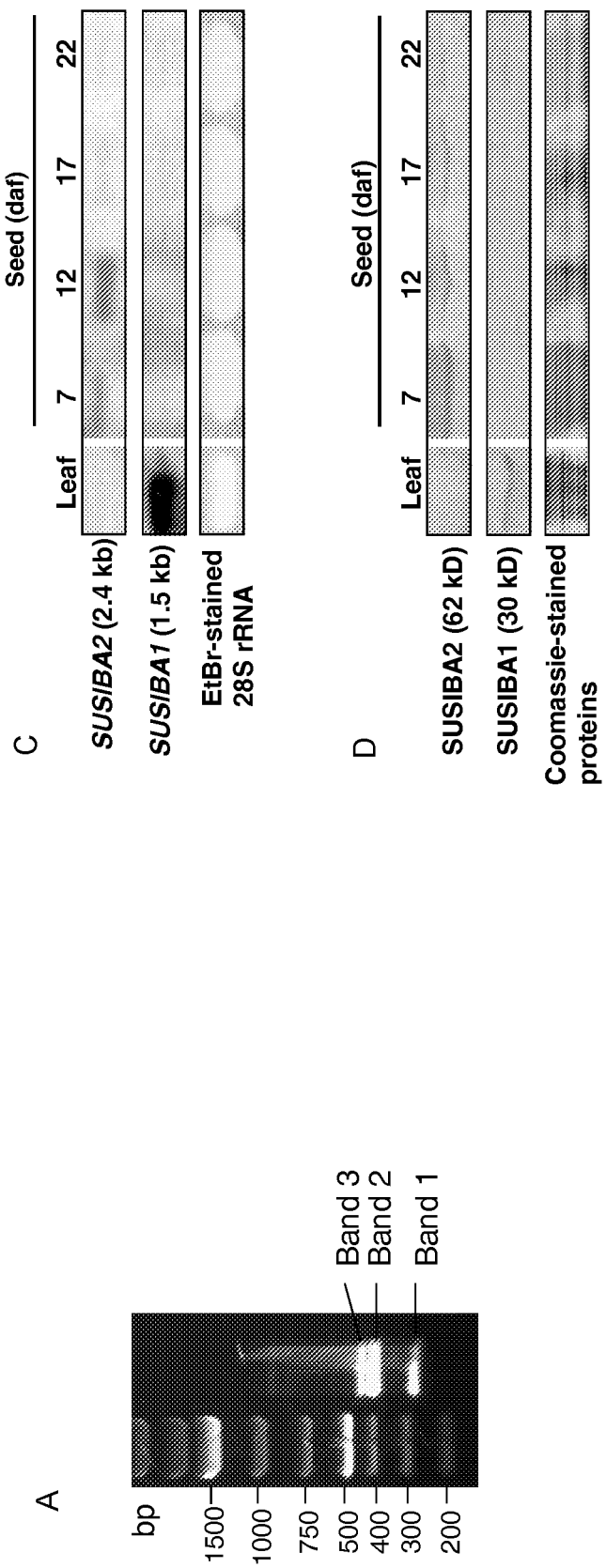
FIG. 1. Identification of the full-length SUSIBA1 cDNA (GenBank accession number KT290558) and detection of transcripts and proteins expressed from SUSIBA1 and SUSIBA2 in barley. (A) Amplification of the 5'-ends of SUSIBA1 cDNAs by 5'-RACE resulted in three amplicons (Band 1-3). (B) Sequencing results (SEQ ID NO: 114) showed that amplicons 1-3 are identical to SUSIBA2 cDNA sequence (GenBank accession number AY323206). The longest band 3 starts from nt 907 as indicated by a black arrow. SUSIBA1 cDNA sequence is in italic. Start and stop codon sequences of SUSIBA2 and SUSIBA1 are underlined. Primers used for 5'-RACE amplification are by arrows (nested-primer). (C) Northern blot analysis of SUSIBA1 and SUSIBA2 transcripts in barley leaf and developing seeds. (D) Western blot analysis of SUSIBA1 and SUSIBA2 in barley leaves and developing seeds. daf, days after flowering.
Figure 2:
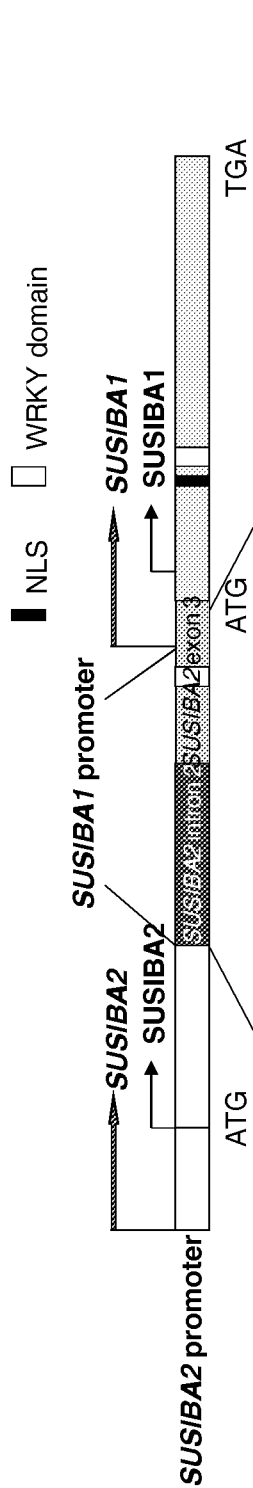
FIG. 2. Schematic representation of the SUSIBA1 and SUSIBA2 promoters (GenBank accession numbers KT290559, KT290560 and AC269483, respectively). The SUSIBA1 promoter includes the SUSIBA2 intron 2 and 5'-exon 3. The SUSIBA1 promoter (SEQ ID NO: 115) is indicated and the sequence including intron 2 (plain text) and the 5'-end of exon 3 (italic and bold) of SUSIBA2 is shown. Transcription (corresponding to SUSIBA1 band 3 cDNA) start is indicated by an arrow. Sequence encoding NLS (nuclear location signal) and sequences encoding amino acid WRKY domains are indicated.

The present embodiments generally relate to plant materials, and in particular to plant materials with controlled carbohydrate production.

The plant material of the embodiments can be designed to have a controlled production of carbohydrates, and in particular designed to produce carbohydrates at elevated or high levels as compared to wild-type plant material.

Sugars are the key energy carriers in transfer of solar energy to chemical energy essential for life on Earth via photosynthesis. In higher plants, sugars are not only basic substrate materials for biomass synthesis, but also signaling molecules for many metabolic pathways. Carbohydrate synthesis is usually mediated by sugars. According to sugar levels and availability, higher plants use different strategies to synthesize different carbohydrates in storage of energy for immediate, i.e., within minutes, middle-term, i.e., within hours, and long-term, i.e., within days to years, energy supply in meeting energy demands from growth, development and reproduction.

Fructan, transient starch and storage starch are examples of the carbohydrates in terms of different energy supply forms. They are produced in a large number of flowing plants including temperature Gramineae, such as barley, wheat, oats, and many forage grasses.

Synthesis of fructan, a fructose polymer, and starch, a glucose polymer, is typically mediated by sugars. However, how plants sense sugar levels and orchestrate different carbohydrate synthesis, such as fructan and/or starch synthesis, is largely unknown.

As is shown herein, synthesis of fructan and starch is well regulated by sugar levels in barley. This sugar-mediated carbohydrate synthesis is tightly controlled by a sophisticated genetic system that employs two alternative promoters to generate two sequence-overlapped but functionally opposed transcription factors, sugar signaling in barley 1 (SUSIBA1) and SUSIBA2, in sensing sugar levels and orchestrating fructan and starch synthesis.

Experimental data presented herein shows that SUSIBA1 has negative or suppressive activity, whereas SUSIBA2 has positive or inducing effect. The sugar-responsive expression of these two transcription factor (TF) genes, with identical sequences but different lengths at 5'-ends from two alternative promoters, SUSIBA1 promoter (SUSIBA1 p) and SUSIBA2 promoter (SUSIBA2 p), creates an opposing, or yin-yang, sugar-sensing system that controls the spatiotemporal synthesis of fructan and starch in barley.

The SUSIBA1 p is, as is further shown herein, an internal promoter within the SUSIBA2 gene in the plant genome that results in expression of a protein, SUSIBA1, with functions distinct from those of the product, SUSIBA2, encoded by the harboring gene SUSIBA2.

At the core of the yin-yang system, competitive binding of the SUSIBA1 and SUSIBA2 TFs to W-boxes in a sugar-responsive region of the SUSIBA2 p serves as an internal adaptive mechanism that shows for autoregulation of SUSIBA1 and SUSIBA2 activities. The SUSIBA1 p comprises a sugar-responsive activation region, to which a trans activation factor binds at low sugar levels, see FIG. 26A. This binding of the trans activation factor or complex activates and induces SUSIBA1 expression. High expression of SUSIBA1 results in high levels of SUSIBA1 that binds to the W-boxes in the SUSIBA2 p in competition with SUSIBA2. This effectively prevents expression of SUSIBA2. Upon increasing sugar levels, the level of the trans activation factor or complex decreases. Without binding of the trans activation factor or complex to the sugar-responsive activation region in the SUSIBA1 p, the expression of SUSIBA1 is low, see FIG. 26B. The low expression of SUSIBA1 leads to SUSIBA2 competing for binding of the W-boxes in the SUSIBA2 p and thereby high expression of SUSIBA2. SUSIBA2 binds to the W-boxes in its own promoter and thereby enhances its on expression.

SUSIBA1 also binds, in barley, to cis elements, such as sugar responsive (SURE), W-box and/or SP8 elements, in fructan gene promoters, such as the sucrose:fructan-6-fructosyltransferase (6-SFT) promoter, sucrose:sucrose 1-fructosyltransferase (1-SST) promoter, and prevents expression of fructan genes, i.e., SUSIBA1 is a repressor in the fructan synthesis in barley. As a consequence, at low sugar levels (FIG. 26A), there is low synthesis and content of fructan, and also of starch.

SUSIBA2 correspondingly acts as an activator of starch synthesis and binds to cis elements, such as sugar responsive (SURE) elements, in starch gene promoters, such as barley isoamylase (ISO1) promoter and starch branching enzyme II (SBEII) promoter. As a consequence, at high sugar levels (FIG. 26B), there is high synthesis and content of starch, and also of fructan.

This means that in order to provide a barley plant material having high production of starch or high production of starch and fructan, the plant material should have high sugar levels and/or lack or silenced expression of SUSIBA1.

Corresponding versions of the SUSIBA2 gene are present in plants other than barley, for instance rice (OsSUSIBA2-like gene), wheat (TaSUSIBA2-like gene), oat (AsSUSIBA2-like gene), maize (ZmSUSIBA2-like gene), rye (ScSUSIBA2-like gene), *Brachypodium* and other grasses. In the following this corresponding versions of SUSIBA2 is denoted SUSIBA2-like gene encoding a SUSIBA2-like transcription factor. A nucleotide sequence encoding a SUSIBA2-like transcription factor, such as a SUSIBA2-like gene, is under transcription control of a promoter, generally denoted SUSIBA2-like promotor (SUSIBA2-like p) herein. The nucleotide sequence encoding the SUSIBA2-like protein comprises a promoter of a nucleotide sequence encoding a SUSIBA1-like transcription factor, denoted SUSIBA1-like p herein. The SUSIBA1-like p is preferably at least partly present in an intron of the SUSIBA2-like gene. In a particular embodiment, the SUSIBA1-like p is an intronic/exonic promoter, i.e., is at least partly present in an intron and at least partly present in an exon of the SUSIBA2-like gene. The SUSIBA1-like p controls transcription of a nucleotide sequence encoding SUSIBA1-like transcription factor, such as a SUSIBA1-like gene.

In an embodiment, a SUSIBA2-like gene preferably has a sequence identity to the barley (*Hordeum vulgare*) SUSIBA2 gene (HvSUSIBA2), with regard to the coding sequence, i.e., exons, of the gene, of at least 50%, preferably of at least 60% and more preferably of at least 70%, such as at least 75% or at least 80%.

In addition, or alternatively, a SUSIBA1-like gene preferably has sequence identity to the barley SUSUBA1 gene (HvSUSIBA1), with regard to the coding sequence, of at least 50%, preferably of at least 60% and more preferably of at least 70%, such as at least 75% or at least 80%.

Barley SUSIBA2 partial genomic sequence is deposited in GenBank with accession number KT290559 and KT290560 and rice SUSIBA2-like partial genomic sequence is identified in GenBank with accession number AP014963.1.

Figure 28:
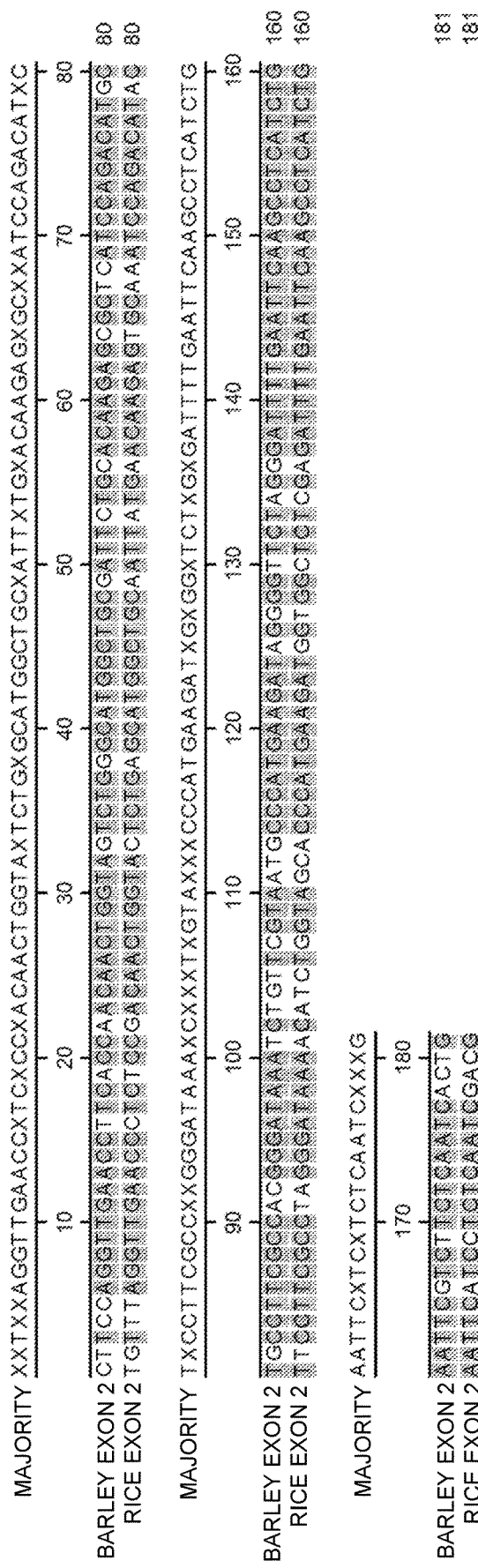
FIG. 28. The figure compares the nucleotide sequences of the exon 2 (SEQ ID NO: 98) of the SUSIBA2 gene in barley and the exon 2 (SEQ ID NO: 101) of the SUSIBA2-like gene in rice.
Figure 29:
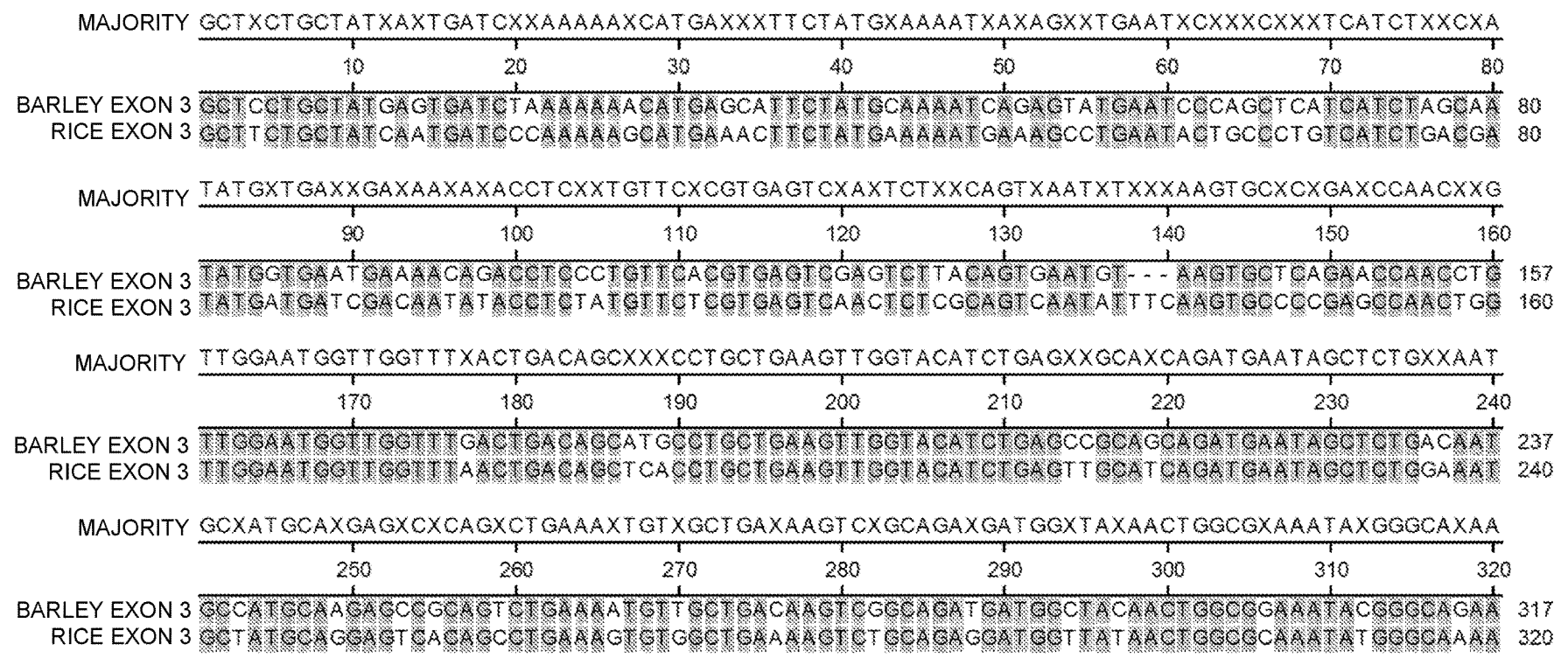
Figure 29:
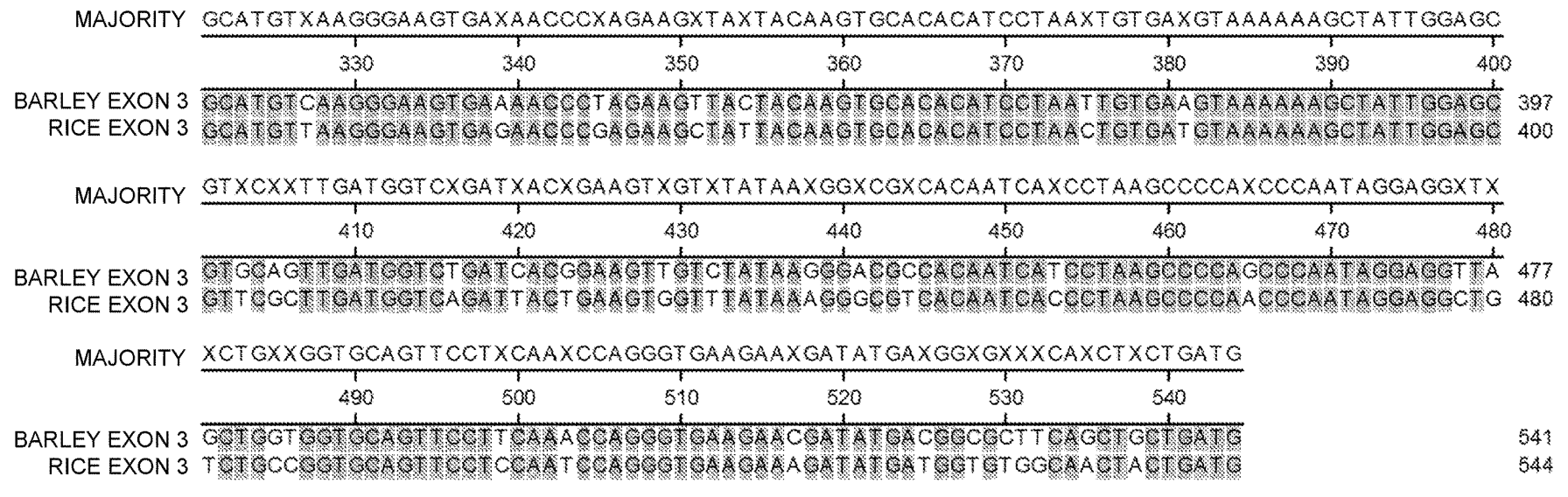

Sequence alignments of exon 2 and exon 3 of SUSIBA2 in barley (HvSUSIBA2) and SUSIBA2-like in rice (OsSUSIBA2-like) are presented in FIGS. 28 and 29. The exonic portion of the HvSUSIBA1 p extends from nucleotide number 1 up to nucleotide number 378 in exon 3 of HvSUSIBA2. Correspondingly, the exonic portion of the OsSUSIBA1-like p extends from nucleotide number 1 up to nucleotide number 381 in exon 3 of OsSUSIBA2-like.

Figure 30:
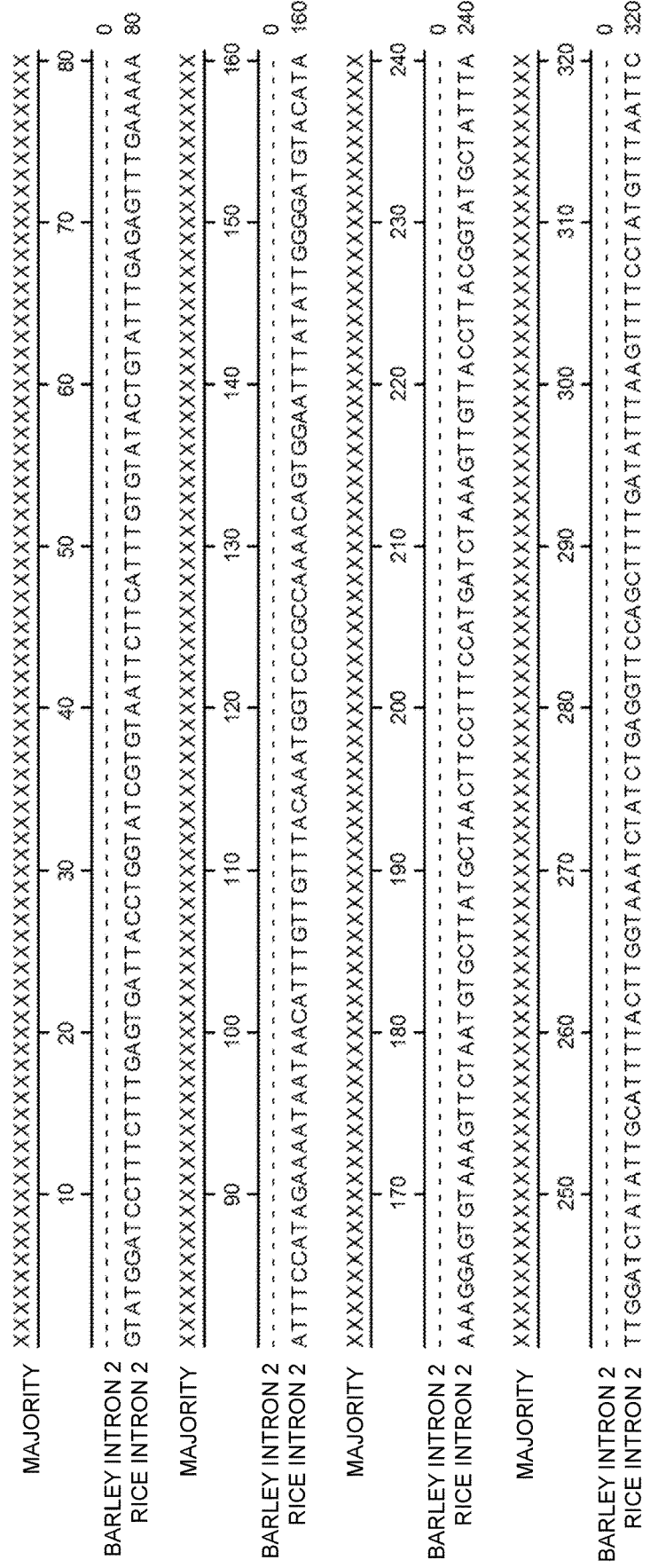
FIG. 30. The figure compares the nucleotide sequences of the intron 2 (SEQ ID NO: 100) of the SUSIBA2 gene in barley and the intron 2 (SEQ ID NO: 103) of the SUSIBA2-like gene in rice.
Figure 30:
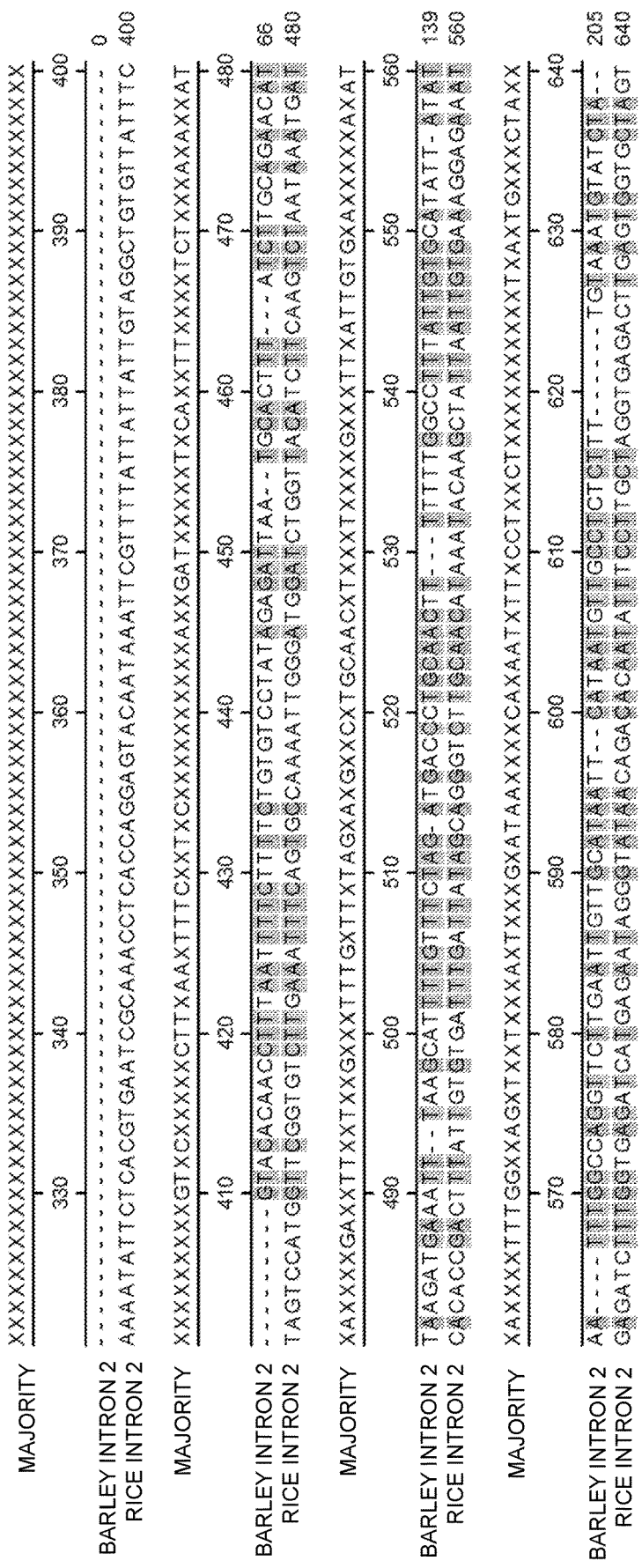

FIG. 30 presents a sequence alignment of intron 2 of HvSUSIBA2 and OsSUSIBA2-like genes. Intron 2 of HvSUSIBA2 comprises the intronic portion of the HvSUSIBA1 p with the sugar repressive region followed by the activation region. Intron 2 of OsSUSIBA2-like correspondingly comprises the intronic portion of the OsSUSIBA1 p with a sugar repressive region followed by an activation region. The sugar repressive region of the OsSUSIBA1 p is longer than the sugar repressive region of the HvSUSIBA1 p or the sugar repressive region of the OsSUSIBA1 p is preceded by a nucleotide sequence (nucleotide number 1 up to 409 in FIG. 30) that is absent in and does not have any correspondence in the intron 2 of the HvSUSIBA2.

Exon 1 of HvSUSIBA2 and OsSUSIBA2-like has a sequence identity of 85% as determined by the web software Clustal Omega. Corresponding sequence identities values for exon 2 and exon 3 of HvSUSIBA2 and OsSUSIBA2-like are 80% and 81%, respectively.

Sequence identity of the activation region and the sugar repressive region of HvSUSIBA1 p and OsSUSIBA1-like p is 52% and 50%, respectively.

The HvSUSIBA2 transcription factor has the following amino acid sequence (SEQ ID NO: 104):

MSPARLPISRESCLTIPAGFSPSALLDSPVLLTNFKVEPSPTTGSLGMAA

ILHKSAHPDMLPSPRDKSVRNAHEDRGSRDFEFKPHLNSSSQSLAPAMSD

LKKHEHSMQNQSMNPSSSSSNMVNENRPPCSRESSLTVNVSAQNQPVGMV

GLTDSMPAEVGTSEPQQMNSSDNAMQEPQSENVADKSADDGYNWRKYGQK

HVKGSENPRSYYKCTHPNCEVKKLLERAVDGLITEVVYKGRHNHPKPQPN

RRLAGGAVPSNQGEERYDGASAADDKSSNALSNLANPVHSPGMVEPVPAS

VSDDDIDAGGGRPYPGDDATEEEDLESKRRKMESAGIDAALMGKPNREPR

VVVQTVSEVDILDDGYRWRKYGQKVVKGNPNPRSYYKCTSTGCPVRKHVE

RASHDPKSVITTYEGKHNHEVPAARNATHEMSAPPMKNVVHQINSNMPSS

IGGMMRACEARNYTNQYSQAAETDTVSLDLGVGISPNHSDATNQMQSSGP

DQMQYQMQTMGSMYGNMRHPSSMAAPAVQGNSAARMYGSREEKGNEGFTF

RATPMDHSANLCYSSAGNLVMGP

The OsSUSIBA2-like transcription factor has the following amino acid sequence (SEQ ID NO: 105):

MADSPNPSSGDHPAGVGGSPEKQPPVDRRVAALAAGAAGAGARYKAMSPA

RLPISREPCLTIPAGFSPSALLESPVLLTNFKVEPSPTTGTLSMAAIMNK

SANPDILPSPRDKTSGSTHEDGGSRDFEFKPHLNSSSQSTASAINDPKKH

ETSMKNESLNTALSSDDMMIDNIPLCSRESTLAVNISSAPSQLVGMVGLT

DSSPAEVGTSELHQMNSSGNAMQESQPESVAEKSAEDGYNWRKYGQHVK

GSENPRSYYKCTHPNCDVKKLLERSLDGQITEVVYKGRHNHPKPQPNRRL

-continued

SAGAVPPIQGEERYDGVATTDDKSSNVLSILGNAVHTAGMIEPVPGSASD

DDNDAGGGRPYPGDDAVEDDDLESKRRKMESAAIDAALMGKPNREPRVVV

QTVSEVDILDDGYRWRKYGQKVVKGNPNPRSYYKCTNTGCPVRKHVERAS

HDPKSVITTYEGKHNHEVPASRNASHEMSTPPMKPVVHPINSNMQGLGGM

MRACEPRTFPNQYSQAAESDTISLDLGVGISPNHSDATNQLQSSVSDQMQ

YQMQPMGSVYSNMGLPAMAMPTMAGNAASNIYGSREEKPSEGFTFKATPM

DHSANLCYSTAGNLVMGP

A sequence alignment of HvSUSIBA2 and OsSUSIBA2-like transcription factors is presented below:

```
  1 ----------------------------------------------MSPA    4
                                                  ||||
  1 MADSPNPSSGDHPAGVGGSPEKQPPVDRRVAALAAGAAGAGARYKAMSPA   50

5 RLPISRESCLTIPAGFSPSALLDSPVLLTNFKVEPSPTTGSLGMAAILHK   54
    |||||||.||||||||||||:||||||||||||||||||:.||||::|
 51 RLPISREPCLTIPAGFSPSALLESPVLLTNFKVEPSPTTGTLSMAAIMNK  100

55 SAHPDMLPSPRDKSVRNAHEDRGSRDFEFKPHLNSSSQSLAPAMSDLKKH  104
    ||:||:|||||||:..:.|||.||||||||||||||||.|.|::|.|||
101 SANPDILPSPRDKTSGSTHEDGGSRDFEFKPHLNSSSQSTASAINDPKKH  150

105 EHSMQNQSMNPSSSSSNMVNENRPPCSRESSLTVNV-SAQNQPVGMVGLT  153
    |.||:|:|:|..:.||.:|::.|.|.||||||:|.||: ||..|.||||||
151 ETSMKNESLNTALSSDDMMIDNIPLCSRESTLAVNISSAPSQLVGMVGLT  200

154 DSMPAEVGTSEPQQMNSSDNAMQEPQSENVADKSADDGYNWRKYGQHVK  203
    ||.|||||||..|||||.|||||.|.:|||:|||:||||||||||||||
201 DSSPAEVGTSELHQMNSSGNAMQESQPESVAEKSAEDGYNWRKYGQHVK  250

204 GSENPRSYYKCTHPNCEVKKLLERAVDGLITEVVYKGRHNHPKPQPNRRL  253
    ||||||||||||||||:|||||||::||.|||||||||||||||||||||
251 GSENPRSYYKCTHPNCDVKKLLERSLDGQITEVVYKGRHNHPKPQPNRL  300

254 AGGAVPSNQGEERYDGASAADDKSSNALSNLANPVHSPGMVEPVPASVSD  303
    :.||||..|||||||||.:..|||||||.||.|.|.||:.||||||.|.||
301 SAGAVPPIQGEERYDGVATTDDKSSNVLSILGNAVHTAGMIEPVPGSASD  350

304 DDIDAGGGRPYPGDDATEEEDLESKRRKMESAGIDAALMGKPNREPRVVV  353
    ||.|||||||||||||.|::|||||||||||.||||||||||||||||||
351 DDNDAGGGRPYPGDDAVEDDDLESKRRKMESAAIDAALMGKPNREPRVVV  400

354 QTVSEVDILDDGYRWRKYGQKVVKGNPNPRSYYKCTSTGCPVRKHVERAS  403
    |||||||||||||||||||||||||||||||||||:||||||||||||||
401 QTVSEVDILDDGYRWRKYGQKVVKGNPNPRSYYKCTNTGCPVRKHVERAS  450

404 HDPKSVITTYEGKHNHEVPAARNATHEMSAPPMKNVVHQINSNMPSSIGG  453
    ||||||||||||||||||||:|||.||||.||||.||||.|||||  ..:||
451 HDPKSVITTYEGKHNHEVPASRNASHEMSTPPMKPVVHPINSNM-QGLGG  499

454 MMRACEARNYTNQYSQAAETDTVSLDLGVGISPNHSDATNQMQSSGPDQM  503
    ||||||.|.:.|||||||:||:||||||||||||||||||:|||..|||
500 MMRACEPRTFPNQYSQAAESDTISLDLGVGISPNHSDATNQLQSSVSDQM  549

504 QYQMQTMGSMYGNMRHPSSMAAPAVQGNSAARMYGSREEKGNEGFTFRAT  553
    |||||.|||:|.||..|  :||.|.:.||:|:.:||||||.:|||||:||
550 QYQMQPMGSVYSNMGLP-AMAMPTMAGNAASNIYGSREEKPSEGFTFKAT  598

554 PMDHSANLCYSSAGNLVMGP                                573
    |||||||||||:||||||||
599 PMDHSANLCYSTAGNLVMGP                                618
```

The HvSUSIBA1 transcription factor has the following amino acid sequence (SEQ ID NO: 106):

MVEPVPASVSDDDIDAGGGRPYPGDDATEEEDLESKRRKMESAGIDAALM
GKPNREPRVVVQTVSEVDILDDGYRWRKYGQKVVKGNPNPRSYYKCTSTG
CPVRKHVERASHDPKSVITTYEGKHNHEVPAARNATHEMSAPPMKNVVHQ
INSNMPSSIGGMMRACEARNYTNQYSQAAETDTVSLDLGVGISPNHSDAT
NQMQSSGPDQMQYQMQTMGSMYGNMRHPSSMAAPAVQGNSAARMYGSREE
KGNEGFTFRATPMDHSANLCYSSAGNLVMGP

The OsSUSIBA1-like transcription factor has the following amino acid sequence (SEQ ID NO: 107):

MIEPVPGSASDDDNDAGGGRPYPGDDAVEDDDLESKRRKMESAAIDAALM
GKPNREPRVVVQTVSEVDILDDGYRWRKYGQKVVKGNPNPRSYYKCTNTG
CPVRKHVERASHDPKSVITTYEGKHNHEVPASRNASHEMSTPPMKPVVHP
INSNMQGLGGMMRACEPRTFPNQYSQAAESDTISLDLGVGISPNHSDATN
QLQSSVSDQMQYQMQPMGSVYSNMGLPAMAMPTMAGNAASNIYGSREEKP
SEGFTFKATPMDHSANLCYSTAGNLVMGP

A sequence alignment of HvSUSIBA1 and OsSUSIBA1-like transcription factors is presented below:

```
  1 MVEPVPASVSDDDIDAGGGRPYPGDDATEEEDLESKRRKMESAGIDAALM   50
    |:||||.|.||||.||||||||||||.|::|||||||||||.||||||
  1 MIEPVPGSASDDDNDAGGGRPYPGDDAVEDDDLESKRRKMESAAIDAALM   50

51 GKPNREPRVVVQTVSEVDILDDGYRWRKYGQKVVKGNPNPRSYYKCTSTG  100
    |||||||||||||||||||||||||||||||||||||||||||||||:||
 51 GKPNREPRVVVQTVSEVDILDDGYRWRKYGQKVVKGNPNPRSYYKCTNTG  100

101 CPVRKHVERASHDPKSVITTYEGKHNHEVPAARNATHEMSAPPMKNVVHQ  150
    |||||||||||||||||||||||||||||||:|||:||||.||||.|||.
101 CPVRKHVERASHDPKSVITTYEGKHNHEVPASRNASHEMSTPPMKPVVHP  150

151 INSNMPSSIGGMMRACEARNYTNQYSQAAETDTVSLDLGVGISPNHSDAT  200
    |||||...:||||||||.|.:.||||||||:||:|||||||||||||||
151 INSNM-QGLGGMMRACEPRTFPNQYSQAAESDTISLDLGVGISPNHSDAT  199

201 NQMQSSGPDQMQYQMQTMGSMYGNMRHPSSMAAPAVQGNSAARMYGSREE  250
    ||:|||..|||||||||.|||:|.||..| :||.|.:.||:|:.:|||||
200 NQLQSSVSDQMQYQMQPMGSVYSNMGLP-AMAMPTMAGNAASNIYGSREE  248

251 KGNEGFTFRATPMDHSANLCYSSAGNLVMGP                     281
    |.:|||||:|||||||||||||:|||||||
249 KPSEGFTFKATPMDHSANLCYSTAGNLVMGP                     279
```

As used herein, the term nucleotide sequence or nucleic acid sequence refers to a polymer or sequence of nucleotides from a 5' to a 3' end of a nucleic acid molecule and includes DNA or RNA molecules, including cDNA, a DNA fragment or portion, genomic DNA, synthetic, e.g., chemically synthesized DNA, plasmid DNA, mRNA, and anti-sense RNA, any of which can be single stranded or double stranded.

A promoter is a nucleotide sequence that controls or regulates the transcription of a nucleotide sequence, i.e., a coding sequence, which is operably associated with the promoter. The coding sequence may encode a polypeptide and/or a functional RNA. Typically, a promoter refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. Promoters can include, for example, constitutive, inducible, temporally regulated, developmentally regulated, chemically regulated, tissue-preferred and/or tissue-specific promoters.

Operably linked or operably associated as used herein means that the indicated elements are functionally related to each other, and are also generally physically related. Thus, the term operably linked or operably associated refers to nucleotide sequences on a single nucleic acid molecule that are functionally associated. Thus, a first nucleotide sequence that is operably linked to a second nucleotide sequence, means a situation where the first nucleotide sequence is placed in a functional relationship with the second nucleotide sequence. For instance, a promoter is operably associated with a nucleotide sequence if the promoter effects the transcription or expression of the nucleotide sequence, i.e., the nucleotide sequence is under transcriptional control of the promoter. Those skilled in the art will appreciate that the control sequences, e.g., promoter, need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the nucleotide sequence can still be operatively linked and under transcriptional control of a promoter.

As used herein, the term endogenous, when used with respect to a nucleotide sequence, refers to a nucleotide sequence that occurs naturally as part of the genome of a plant material where it is present. An endogenous nucleotide sequence is sometimes referred to as a native nucleotide sequence herein.

A genomic nucleotide sequence refers to a nucleotide sequence present in the genome of a plant material, preferably in a chromosome of the plant material.

A wild-type version of a genomic nucleotide sequence refers to a non-modified genomic nucleotide sequence naturally occurring in a plant material. This is compared to a genomic nucleotide sequence that has been modified, such as by removal of part of the wild-type version of the genomic nucleotide sequence from the genome of the plant material.

A plant material is in an embodiment a plant. In another embodiment, a plant material is a plant cell, i.e., a cell of a plant, including multiple such plant cells. A plant material is, in a further embodiment, a plant tissue or organ, including but not limited to, epidermis; ground tissue; vascular tissue, such as xylem or phloem; meristematic tissues, such as apical meristem, lateral meristem or intercalary meristem; permanent tissues, such as simple permanent tissue, including for instance parenchyma, collenchyma, sclerenchyma or epidermis, complex permanent tissue, including for instance xylem, phloem, or special or secretory tissues. A plant material is, in yet another embodiment, a seed of plant.

Sequence identity refers to sequence similarity between two nucleotide sequences or two peptide or protein sequences. The similarity refers to the extent to which two optimally aligned nucleotide, peptide or protein sequences are invariant throughout a window of alignment of nucleotides or amino acids. Identity can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An identity fraction for aligned segments of a test sequence and a reference sequence is the number of identical nucleotides or amino acids which are shared by the two aligned sequences divided by the total number of nucleotides or amino acids in the reference sequence segment, i.e., the entire reference sequence or a smaller defined part of the reference sequence. Percent sequence identity is represented as the identity fraction multiplied by 100.

An aspect of the embodiments relates to a plant material comprising a genomic nucleotide sequence encoding a SUSIBA2 or SUSIBA2-like transcription factor under transcriptional control of a promoter active in the plant material. The genomic nucleotide sequence encoding the SUSIBA2 or SUSIBA2-like transcription factor lacks at least a portion of an activation region of a SUSIBA1 or SUSIBA1-like promoter present in an intron of a wild-type version of the genomic nucleotide sequence encoding the SUSIBA2 or SUSIBA2-like transcription factor.

Thus, according to the embodiments, the genomic nucleotide sequence encoding the SUSIBA2 or SUSIBA2-like transcription factor, such as SUSIBA2 or SUSIBA2-like gene, lacks at least a portion the activation region of the SUSIBA1 p or SUSIBA1-like p that is otherwise present in an intron in the wild-type version of the SUSIBA2 or SUSIBA2-like gene. The absence of at least a portion of the activation region implies that any trans activation factor or complex cannot efficiently bind to the activation region and thereby cannot efficiently activate the SUSIBA1 p or SUSIBA1-like p. As a consequence, no or only low amount of the SUSIBA1 or SUSIBA1-like transcription factor will be produced in the plant material regardless of the sugar level in the plant material. The absence or low amount of SUSIBA1 or SUSIBA1-like transcription factor in the plant material in turn implies that the SUSIBA2 or SUSUBA2-like transcription factor will outcompete the SUSIBA1 or SUSIBA1-like transcription factor for the binding to the SUSIBA2 p or SUSIBA2-like p, and in more detail to the at least one W-box in the SUSIBA2 p or SUSIBA2-like p. This will in turn cause activation of the SUSIBA2 or SUSIBA2-like p and further production of the SUSIBA2 or SUSIBA2-like transcription factor in the plant material. The high levels of the SUSIBA2 or SUSIBA2-like transcription factor and the low levels of the SUSIBA1 or SUSIBA1-like transcription factor in the plant material induces production of starch in the plant material or induces production of starch and fructan in the plant material.

Figure 26:
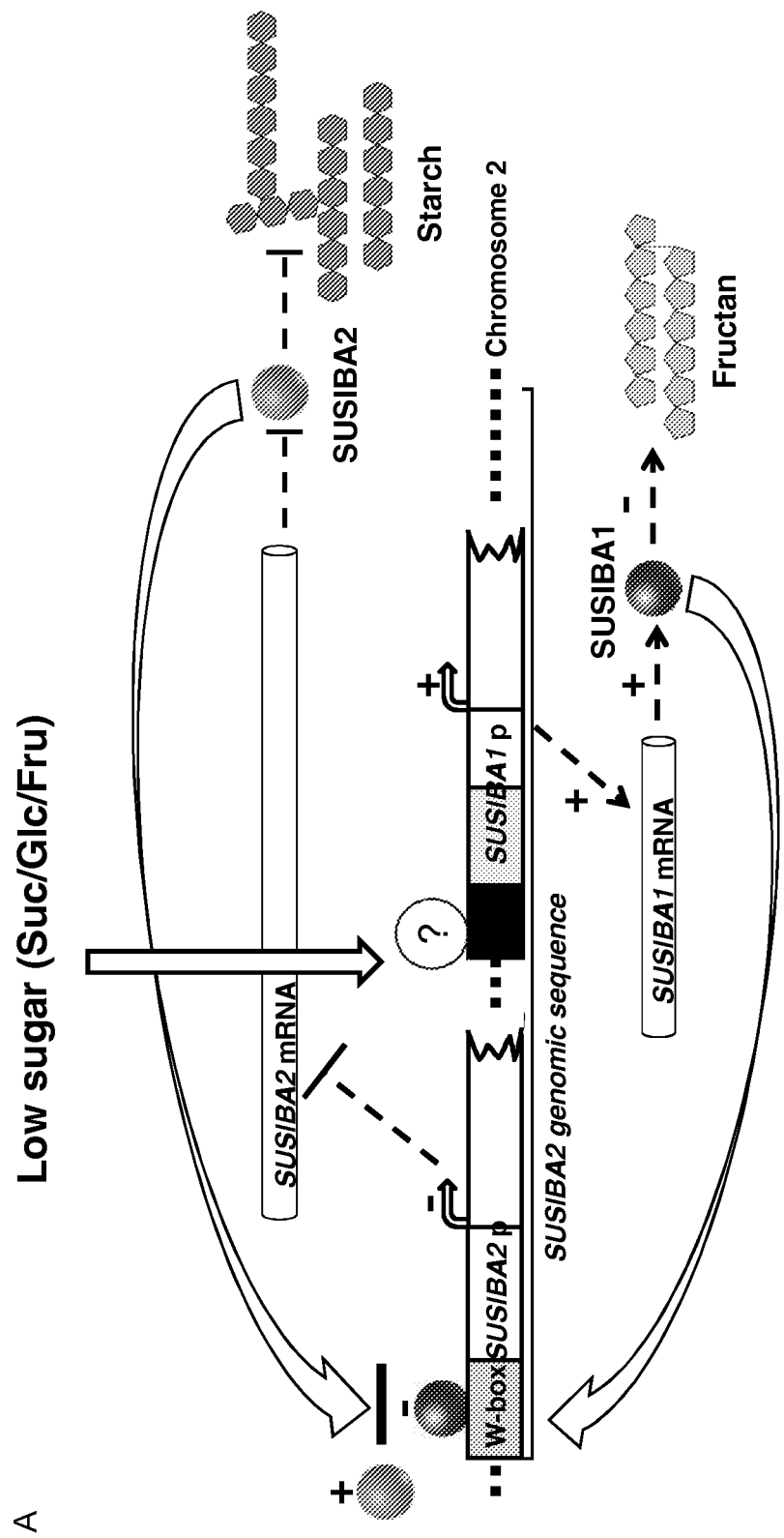
FIG. 26. The sugar-sensing competitive transcription factor binding system controlling the coordinated starch and fructan synthesis in barley. The sugar-responsive activator-repressor SUSIBA2-SUSIBA1 TF duo orchestrates the coordinated starch and fructan in barley via sucrose/glucose/fructose (Suc/Glc/Fru) signaling. When sugar level is low (A), a recruited transcription factor/complex (a ball with a question mark) binds to the sugar-responsive sequence in the SUSIBA1 promoter and activates SUSIBA1 expression. High expression of SUSIBA1 results in a high level of SUSIBA1 that binds to the W-box in the SUSIBA2 promoter preventing SUSIBA2 binding, and to the cis elements in fructan gene promoters (such as the 6-SFT promoter), and represses expression of SUSIBA2 and fructan genes, and as a consequence, low synthesis and content of starch and fructan at a low sugar level. Upon increasing of sugar to a high level (B), the level of the transcription factor/complex decreases and eventually goes to zero when sugar continues to increase. Without binding of the transcription factor/complex to the sugar-responsive sequence in the SUSIBA1 promoter, expression of SUSIBA1 is low. The low expression of SUSIBA1 leads to high expression of fructan genes and a progressive increase of SUSIBA2 expression. SUSIBA2 binds to the W-box in its own promoter and enhances its own expression. More SUSIBA2 binds to the W-box and more SUSIBA2 transcripts are produced. Such positive autoregulation will lead to high expression of SUSIBA2 and high synthesis of starch. Thus, at a high sugar level, high synthesis and content of starch and fructan are generated.
Figure 26:
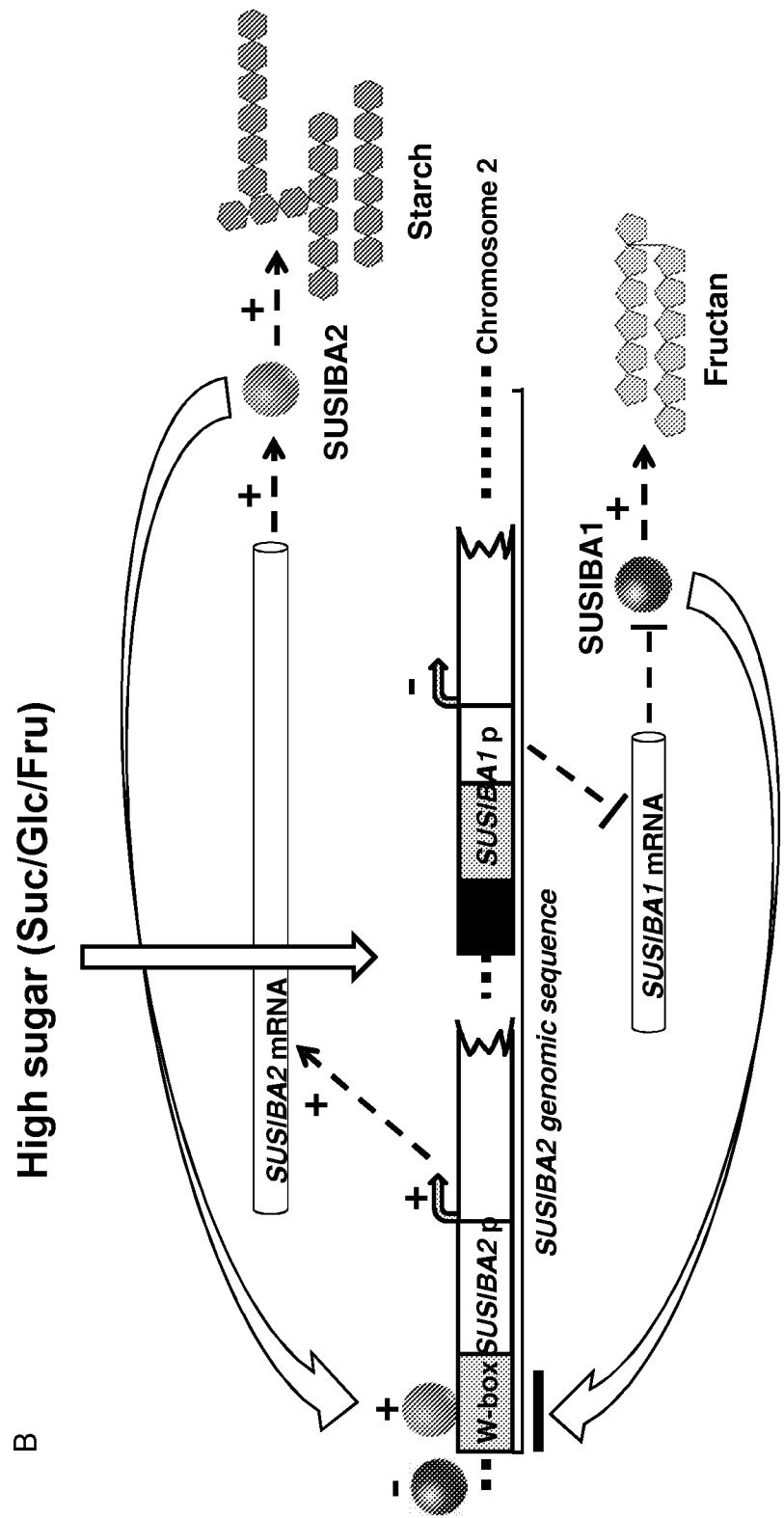

The plant material of the embodiments will thereby be in a situation as illustrated in FIG. 26B regardless of the sugar level in the plant material, i.e., also in low sugar levels.

The suppressed expression of the SUSIBA1 or SUSIBA1-like gene and thereby low levels of the SUSIBA1 or SUSIBA1-like transcription factor, due to the lack or absence of at least a portion of the activation region of the SUSIBA1 p or SUSIBA1-like p, causes enhanced expression of the SUSIBA2 or SUSIBA2-like gene and thereby high levels of the SUSIBA2 or SUSIBA2-like transcription factor. The SUSIBA2 or SUSIBA2-like transcription factor will in turn activate genes involved in the starch synthesis in the plant material. Correspondingly, if the plant material is also capable of fructan synthesis, the low levels of the SUSIBA1 or SUSIBA1-like transcription factor means that the SUSIBA1 or SUSIBA1-like transcription factor will not suppress genes involved in the fructan synthesis in the plant material.

The plant material of the embodiments will thereby be a high-starch plant material or a high-starch and a high-fructan plant material.

The at least a portion of the activation region of the SUSIBA1 p or SUSIBA1-like p is, in an embodiment, deleted from the wild-type version of the genomic nucleotide sequence encoding the SUSIBA2 or SUSIBA2-like transcription factor. As a consequence of this deletion and thereby absence of the at least a portion of the activation region of the SUSIBA1 p or SUSIBA1-like p, the plant material comprises a genomic nucleotide sequence encoding the SUSIBA2 or SUSIBA2-like transcription factor and that lacks the at least a portion of the activation region of the SUSIBA1 p or SUSIBA1-like p. Accordingly, in a preferred embodiment, the plant material does not comprise any such portion of the activation region of the SUSIBA1 p or SUSIBA1-like p.

In a particular embodiment, the at least a portion of the activation region of the SUSIBA1 p or SUSIBA1-like p is deleted by clustered regularly interspaced short palindromic repeat (CRISPR)/CRISPR associated protein 9 (CRISPR/Cas9) mediated deletion from the wild-type version of the genomic sequence encoding the SUSIBA2 or SUSIBA2-like transcription factor.

CRISPR/Cas9 is a DNA cutting method that involves expressing the RNA-guided Cas9 endonuclease along with guide RNAs directing it to a particular sequence to be edited. When Cas9 cuts the target sequence, the plant cell repairs the damage by replacing the original sequence with homologous DNA. By introducing an additional template with appropriate homologies, Cas9 can be used to delete, add, or modify genes in an unprecedentedly simple manner. CRISPR/Cas9 is thereby an efficient technology for deleting at least a portion of the activation region of the SUSIBA1 p or SUSIBA1-like p from the wild-type version of the genomic sequence encoding the SUSIBA2 or SUSIBA2-like transcription factor in the plant material.

Although CRISPR/Cas9 mediated deletion of at least a portion of the activation region of the SUSIBA1 p or SUSIBA1-like p is a preferred technology of producing a plant material with no or suppressed expression of the SUSIBA1 or SUSIBA1-like gene the embodiments are not limited thereto. Other technologies and techniques known in the art and that can be used to remove or delete genomic nucleotide sequences in plant materials can alternatively be used. For instance, promoter deletion could be used to generate or produce a nucleotide sequence encoding the SUSIBA2 or SUSIBA2-like transcription factor but lacks at least a portion of the activation region of the SUSIBA1 p or SUSIBA1-like p that is otherwise present in an intron of the nucleotide sequence (SUSIBA2 or SUSIBA2-like gene). The resulting construct can then be agroinfiltrated into the plant material.

Agroinfiltration is a method used in plant biology to induce expression of genes in a plant material. In the method a suspension of *Agrobacterium tumefaciens* is introduced into the plant material by direct injection or by vacuum infiltration, or brought into association with plant material on a support, where after the bacteria transfer the desired produced nucleotide sequence into the plant material via transfer of T-DNA.

The first step is to introduce the nucleotide sequence to a strain of *Agrobacterium tumefaciens*. Subsequently, the strain is grown in a liquid culture and the resulting bacteria are washed and suspended into a suitable buffer solution. For injection, this solution is then placed in a syringe. The tip of the syringe is pressed against the underside of the plant material, such as a leaf, while simultaneously applying gentle counter pressure to the other side of the leaf. The *Agrobacterium* suspension is then injected into the airspaces inside the leaf through stomata, or sometimes through a tiny incision made to the underside of the leaf.

Vacuum infiltration is another way to introduce *Agrobacterium* deep into plant tissue. In this procedure, leaf disks, leaves, or whole plants are submerged in a beaker containing the solution, and the beaker is placed in a vacuum chamber. The vacuum is then applied, forcing air out of the intercellular spaces within the leaves via the stomata. When the vacuum is released, the pressure difference forces the *Agrobacterium* suspension into the leaves through the stomata into the mesophyll tissue. This can result in nearly all of the cells in any given leaf being in contact with the bacteria.

Once inside the plant material the *Agrobacterium* remains in the intercellular space and transfers the nucleotide sequence as part of the Ti plasmid-derived T-DNA in high copy numbers into the plant cells. In an embodiment, the genomic nucleotide sequence encoding the SUSIBA2 or SUSIBA2-like transcription factor is a genomic endogenous nucleotide sequence. In a particular embodiment, the genomic endogenous nucleotide sequence is present in a chromosome of the plant material. Thus, at least a portion of the activation region of the SUSIBA1 p or SUSIBA1-like p has, according to the embodiments, been deleted, such as by CRISPR/Cas9-mediated deletion, from the genomic endogenous nucleotide sequence, preferably present in a chromosome of the plant material.

In an embodiment, a portion of the activation region of the SUSIBA1 p or SUSIBA1-like p is deleted from the nucleotide sequence encoding the SUSIBA2 or SUSIBA2-like transcription factor. In such a case, the deleted portion is preferably selected to correspond to the sub-region or sequence of the activation region to which the trans activation factor or complex binds. Accordingly, deletion of this sub-region or sequence thereby prevents or at least significantly reduces binding of the trans activation factor or complex to the activation region of the SUSIBA1 p or SUSIBA1-like p.

In another embodiment, the activation region is deleted from the nucleotide sequence. In this embodiment, the genomic nucleotide sequence encoding the SUSIBA2 or SUSIBA2-like transcription factor lacks the activation region of the SUSIBA1 p or SUSIBA1-like p. This total removal of the activation region thereby effectively prevents the trans activation factor or complex from binding to the SUSIBA1 or SUSIBA1-like p.

The activation region of the SUSIBA1 p in barley is shown here below (SEQ ID NO: 92):

GTTGCCTCTCTTTTGTAAATGTATCTATGAGTTACATATTTTATTCTGAT

ATTTTTTGGATGATAGGAAGGTAACGCTATTCCAGATGCATGGCAAATCT

CAATATAAAACTCATTAACTCAATATTCATGTGCAGCATTACTTCTTTCA

CATGTTGTGGAGAAGTTTCTTTATAAATGGTAGAGTTTGAAGGAAGTATT

TTGAATGGCAGTTTGGGGAAAACCTATGGTACATATGTAGTTAGATCTAT

CTGTGCTTGCTATATTAGTCACATCCTTTCTTAATTCGTTGACTTGTTTT

TACATATTTAGTTTTGCATTGTGTAACATTTGTGATGTCATATTTTGTAC

TGCAG

The corresponding activation region of the SUSIBA1-like p in rice is shown here below (SEQ ID NO: 93):

ATTTCCTTGCTAGGTGAGACTTGAGTGGTGCTAGTCTGGCTGCAAATTTA

TAGAAGTATGTGAAAATTTGAGGTCAGAATACAAGTAATTGAATGGACCA

ATCTAATGAGTTCTGTAGCTTTAGAATAATTAATGTTAACATAAAAATAT

GTTCATGAAATCAGGTCCTTCTGCATTTTGTTGTTAACCGAATTCCACAT

TCTTCTTTAGTTCTCACAAGTACAGACAAGTATCTTGTAATGGTGGATTC

TTTTTTGGAAAACAAACTTCATTACATATTTTGTGTGATCCATCTATGCC

TTGTGCCCTTGTTACCTTTTTTTCCCTACACCTTGTTTTCTCTTGTACTT

AGTTTTGCATTGTATAACCTTTTGCTGTACTCGTGTCTTGTACTGTAG

The corresponding activation region of the SUSIBA1-like p in wheat is shown here below (SEQ ID NO: 112):

CTTGCCTATCATTTGTAAATGCATGTACGAACTTACCTATTTTATTCTGA

TCTTCTTTGGAGGGTAGGAAGGTAACACTATCCCAGATGCATGGCAAATC

TCAGTATAGAACTCATTAACTCAATATCCATATGTAACATTACTTCTTTC

ACATGTAGCGGAGAAGTTTCTTTATAAATAGTAGAGTTTGAAAAAAGCAC

```
TTTGAATGACAGTTTGGGGAAAAACTATGGTACATATGTAGTTAGATCTA

TCTGTGCTTGCTATGTTAGTCACATTCTTTCTTAATTCCTGTTGACTTGT

TTTTGCATATTTTGTTTTGCATCGTGTAACATTTGTAATGCTCATATTTT

GTACTGCAG
```

The wild-type SUSIBA1 p or SUSIBA1-like p typically comprises a sugar repressive region in addition to the activation region. In an embodiment, the genomic nucleotide sequence encoding the SUSIBA2 or SUSIBA2-like transcription factor also lacks at least a portion of the sugar repressive region of the SUSIBA1 p or SUSIBA1-like p present in the intron of the wild-type version of the genomic nucleotide sequence encoding the SUSIBA2 or SUSIBA2-like transcription factor.

Thus, the SUSIBA1 p or SUSIBA1-like p comprises, in an embodiment, two control elements: the activation region and the sugar repressive region. These two control elements are present in the portion of the nucleotide sequence encoding the SUSIBA2 or SUSIBA2-like transcription factor corresponding to an intron. These control elements are thereby part of the intronic portion of the SUSIBA1 p or SUSIBA1-like p. As mentioned in the foregoing, the SUSIBA1 p or SUSIBA1-like p also comprises an exonic portion present in an exon of the nucleotide sequence encoding the SUSIBA2 or SUSIBA2-like transcription factor.

In an embodiment, a portion of the sugar repressive region of the SUSIBA1 p or SUSIBA1-like p is deleted from the nucleotide sequence encoding the SUSIBA2 or SUSIBA2-like transcription factor. In another embodiment, the sugar repressive region is deleted from the nucleotide sequence.

The deletion of the sugar repressive region or at least a portion thereof can be performed using, for instance, CRISPR/Cas9 mediated deletion or another technology, such as described in the foregoing for the activation region.

The deletion of a portion of or the complete sugar repressive region of the SUSIBA1 p or SUSIBA1-like p is in addition to the deletion of a portion of or the complete activation region of the SUSIBA1 p or SUSIBA1-like p.

In an embodiment, the genomic nucleotide sequencing encoding the SUSIBA2 or SUSIBA2-like transcription factor lacks i) at least a portion of the activation region, ii) the complete activation region, iii) at least a portion of the activation region and at least a portion of the sugar repressive region, iv) at least a portion of the activation region and the complete sugar repressive region, v) the complete activation region and at least a portion of the sugar repressive region, or vi) the complete activation region and the complete sugar repressive region of the SUSIBA1 p or SUSIBA1-like p.

The sugar repressive region of the SUSIBA1 p in barley is shown here below (SEQ ID NO: 94):

```
GTACACAACCTTTAATTTTCTTTTCTGTGTCCTATAGAGATTAATGCACT

TTATCTTGCAGAACATTAAGATGAAATTTAAGCATTTTGTTTCTAGATGA

CCCTGCAACTTTTTTTGGCCTTTATTGTGCATATTATATAATTTGGCCAG

GTTCTTGAATTGTTGCATAATTCATAAT
```

The corresponding sugar repressive region of the SUSIBA1-like p in rice is shown below (SEQ ID NO: 95):

```
GTATGGATCCTTTCTTTGAGTGATTACCTGGTATCGTGTAATTCTTCATT

TGTGTATACTGTATTTGAGAGTTTGAAAAAATTTCCATAGAAAATAATAA

CATTTGTTGTTTACAAATGGTCCCGCCAAAACAGTGGAATTTATATTGGG

GATGTACATAAAAGGAGTGTAAAGTTCTAATGTGCTTATGCTAACTTCCT

TTCCATGATCTAAAGTTGTTACCTTACGGTATGCTATTTATTGGATCTAT

ATTGCATTTTACTTGGTAAATCTATCTGAGGTTCCAGCTTTTGATATTTA

AGTTTTCCTATGTTTAATTCAAAATATTCTCACGTGAATCGCAAACCTCA

CCAGGAGTACAATAAATTCGTTTTATTATTATTGTAGGCTGTGTTATTTC

TAGTCCATGGTTCGGTGTCTTGAAATTTCAGTGCCAAAATTGGGATGGAT

CTGGTTACATCTTCAAGTCTAATAAATGATCACACCGACTTTATTGTGTG

ATTTGATTATAGCAGGGTCTTGCAACATAAATACAAGCTATTAATTGTGA

AAGGAGAAATGAGATCTTTGGTGAGATCATGAGAATAGGGTATAACAGAC

ACAAT
```

The corresponding sugar repressive region of the SUSIBA1-like p in wheat is shown here below (SEQ ID NO: 113):

```
GTACACAACCTTTAATTTTCTTTTCTCTGTGTCCCATAGAGATTAATGTA

CTTTATCTTGCAGAACATCAAAAGAAAATTTAAGCATTTTGTTTCTATAC

GACCCCACAAATATATCTGGCCTTTATTGTGCATATTATAACCATAATTC

GGCTAGGTTCTTGAATTGTTGCATAATTCATAAT
```

The sugar repressive region in rice comprises a second, following portion having high sequence identity with the corresponding sugar repressive region in barley and a first, preceding portion that is not present in barley.

The activation region and the sugar repressive region of the SUSIBA1 p or SUSIBA1-like p are both present in an intron of the SUSIBA2 or SUSIBA2-like gene. In an embodiment, this intron is deleted from the SUSIBA2 or SUSIBA2-like gene. Thus, in this embodiment, the genomic nucleotide sequence encoding the SUSIBA2 or SUSIBA2-like transcription factor lacks the intron comprising the activation region and the sugar repressive region of the SUSIBA1 p or SUSIBA1-like p. In a particular embodiment, the genomic nucleotide sequence encoding the SUSIBA2 or SUSIBA2-like transcription factor lacks intron 2.

In an embodiment, the genomic nucleotide sequence encoding the SUSIBA2 or SUSIBA2-like transcription factors lacks an intronic portion of the SUSIBA1 p or SUSIBA1-like p. In barley, intron 2 consists of the activation region and the sugar repressive region, i.e., the intronic portion of the HvSUSIBA1 p occupies intron 2. The corresponding intron 2 in, for instance, rice comprises an activation region and a sugar repressive region with high sequence identity to the corresponding regions in barley. Intron 2 in rice, however, also comprises a nucleotide sequence preceding the activation region having high sequence identity to the barley activation region. This preceding nucleotide sequence could be part of a larger activation region in rice, constitute another region within the SUSIBA1-like p in rice or not forming part of the SUSIBA1-like p. Hence, in an embodiment the intron may comprise nucleotide sequence(s) other than the intronic portion of the SUSIBA1-like p. In such an embodiment, the intron consists of the intronic portion of the SUSIBA1-like p, preferably the activation region and the sugar repressive region, and at least one other nucleotide sequence. In the present embodiment, the intronic portion of the SUSIBA1 p or SUSIBA1-like p is deleted from the wild-type version of the genomic nucleotide sequence encoding the SUSIBA2 or SUSIBA2-like transcription factor. This means that following deletion of the intronic portion, the genomic nucleotide sequence encoding the SUSIBA2 or SUSIBA2-like transcription factor may lack intron 2, if the intronic portion occupies the complete sequence of intron 2, or may lack a portion of intron 2, if the intronic portion occupies a portion of the complete sequence of intron 2.

The nucleotide sequence of the SUSIBA1 p in barley is presented below (SEQ ID NO: 96). The underlined portion of the nucleotide sequence corresponds to the part of the SUSIBA1 p present in intron 2 of the SUSIBA2 gene. The underlined and italic portion of the nucleotide sequence corresponds to the activation region, whereas the underlined and bold portion of the nucleotide sequence corresponds to the sugar repressive region. The remaining portion of the nucleotide sequence corresponds to the portion of the SUSIBA1 p present in exon 3 of the SUSIBA2 gene.

<u>gtacacaacctttaattttctttctgtgtcctatagagattaatgcact</u>

<u>ttatcttgcagaacattaagatgaaatttaagcattttgtttctagatga</u>

<u>ccctgcaacttttttggcctttattgtgcatattatataaatttggccag</u>

<u>gttcttgaattgttgcataattcataat</u><u>*gttgcctctcttttgtaaatgt*</u>

<u>*atctatgagttacatattttattctgatattttttggatgataggaaggt*</u>

<u>*aacgctattccagatgcatggcaaatctcaatataaaactcattaactca*</u>

<u>*atattcatgtgcagcattacttctttcacatgttgtggagaagtttcttt*</u>

<u>*ataaatggtagagtttgaaggaagtattttgaatggcagtttgggaaaa*</u>

<u>*cctatggtacatatgtagttagatctatctgtgcttgctatattagtcac*</u>

<u>*atcctttcttaattcgttgacttgtttttacatatttagttttgcattgt*</u>

<u>*gtaacatttgtgatgtcatattttgtactgcag*</u>gctcctgctatgagtga tctaaaaaaacatgagcattctatgcaaaatcagagtatgaatcccagct catcatctagcaatatggtgaatgaaaacagacctccctgttcacgtgag tcgagtcttacagtgaatgtaagtgctcagaaccaacctgttggaatggt tggtttgactgacagcatgcctgctgaagttggtacatctgagccgcagc agatgaatagctctgacaatgccatgcaagagccgcagtctgaaaatgtt gctgacaagtcggcagatgatggctacaactggcggaaatacgggcagaa gcatgtcaagggaagtgaaaaccctagaagttactacaagtgcacacatc ctaattgtgaa The nucleotide sequence of the SUSIBA1-like p in rice is presented below (SEQ ID NO: 97). The underlined portion of the nucleotide sequence corresponds to the part of the SUSIBA1-like p present in intron 2 of the SUSIBA2-like gene. The underlined and italic portion of the nucleotide sequence corresponds to the activation region, whereas the underlined and bold portion of the nucleotide sequence corresponds to the sugar repressive region. The preceding nucleotide sequence is shown in the underlined, bold and italic portion. The remaining portion of the nucleotide sequence corresponds to the portion of the SUSIBA1-like p present in exon 3 of the SUSIBA2-like gene.

<u>gtatggatcctttctttgagtgattacctggtatcgtgtaattc</u>

<u>ttcatttgtgtatactgtatttgagagtttgaaaaaatttc</u>

<u>catagaaaataataacatttgttgtttacaaatggtccc</u>

<u>gccaaaacagtggaatttatattggggatgtacataaaaggagt</u>

<u>gtaaagttctaatgtgcttatgctaacttcctttccatgat</u>

<u>ctaaagttgttaccttacggtatgctatttattggatct</u>

<u>atattgcattttacttggtaaatctatctgaggttccagctttt</u>

<u>gatatttaagttttcctatgtttaattcaaaatattctcacgt</u>

<u>gaatcgcaaacctcaccagga*gtacaataaattcgtt*</u>

<u>*ttattattattgtaggctgtgttattctagtccatggttcg*</u>

<u>*gtgtcttgaaatttcagtgccaaaattgggatggatctggttacatcttc*</u>

<u>*aagtctaataaatgatcacaccgactttattgtgtgatttgattatagca*</u>

<u>*gggtcttgcaacataaatacaagctattaattgtgaaaggagaaatgaga*</u>

<u>*tctttggtgagatcatgagaataggg*tataacagacacaat</u>*atttccttg*

*ctaggtgagacttgagtggtgctagtctggctgcaaatttatagaagtat*

*gtgaaaatttgaggtcagaatacaagtaattgaatggaccaatctaatga*

*gttctgtagctttagaataattaatgttaacataaaaatatgttcatgaa*

*atcaggtccttctgcattttgttgttaaccgaattccacattcttcttta*

*gttctcacaagtacagacaagtatcttgtaatggtggattcttttttgga*

*aaacaaacttcattacatattttgtgtgatccatctatgccttgtgccct*

*tgttacctttttttccctacaccttgttttctcttgtacttagttttgca*

*ttgtataacctttttgctgtactcgtgtcttgtactgtagg*cttctgctat caatgatcccaaaaagcatgaaacttctatgaaaaatgaaagcctgaata ctgccctgtcatctgacgatatgatgatcgacaatatacctctatgttct cgtgagtcaactctcgcagtcaatatttcaagtgccccgagccaactggt tggaatggttggtttaactgacagctcacctgctgaagttggtacatctg agttgcatcagatgaatagctctggaaatgctatgcaggagtcacagcct gaaagtgtggctgaaaagtctgcagaggatggttataactggcgcaaata tgggcaaaagcatgttaagggaagtgagaacccgagaagctattacaagt gcacacatcctaactgtgat In an embodiment, the plant material is a rice (*Oryza sativa* or *Oryza glaberrima*) plant material. Non-limiting examples of such rice plant materials include a rice plant, a rice plant cell, rice tissue and a rice seed. The genomic nucleotide sequence then preferably encodes a SUSIBA2-like transcription factor (OsSUSIBA2-like TF) that lacks at least a portion of the activation region of a SUSIBA1-like p (OsSUSIBA1-like p) present in an intron of a wild-type version of the genomic nucleotide sequence encoding the SUSIBA2-like transcription factor (OsSUSIBA2-like TF).

In another embodiment, the plant material is a *Graminaea* plant material. Non-limiting examples of such Graminaea plant material includes a *Graminaea* plant, a *Graminaea* cell, *Graminaea* tissue and a *Graminaea* seed. Preferred examples of such *Graminaea* plant material comprises barley (*Hordeum vulgare*) plant material, wheat (*Triticum* spp.) plant material, oat (*Avena sativa*) plant material, rye (*Secale cereal*) plant material and maize (*Zea mays*) plant material.

At least some of the plant materials of the embodiments not only have a controlled carbohydrate synthesis, such as elevated starch synthesis or elevated starch and fructan synthesis. The plant material may additionally have other beneficial properties including low methane emission. Expression of HvSUSIBA2 transcription factor in rice has been shown to lead to high starch synthesis but also low methane emissions and decrease in rhizospheric methanogen levels [3]. The rice variety disclosed in [3] is, however, a transgenic rice variety comprising coding sequence of the barley SUSIBA2 transcription factor operatively connected to the barley SBEIIb promoter. The resulting transgenic rice variety thereby comprises a transgenic version of a non-genomic nucleotide sequence encoding the barley SUSIBA2 transcription factor (HvSUSIBA2 TF) and a genomic endogenous nucleotide sequence encoding the rice SUSIBA2-like transcription factor (OsSUSIBA2-like TF). This genomic endogenous nucleotide sequence encoding the rice SUSIBA2-like transcription factor (OsSUSIBA2-like TF) comprises the complete sequence of the rice SUSIBA1-like promoter (OsSUSIBA1-like p) including its activation region and sugar repressive region.

In clear contrast to the transgenic rice variety mentioned above, the plant material of the embodiments preferably does not comprise any transgenic material. In clear contrast, its genomic endogenous nucleotide sequence encoding the SUSIBA2 or SUSIBA2-like transcription factor is modified by deletion of at least a portion of the activation region of the SUSIBA1 p or SUSIBA1-like p. This means, that in clear contrast to the transgenic rice variety in [3], the plant material of the embodiments is preferably not able to produce any SUSIBA1 or SUSIBA1-like transcription factor, or is only capable of producing minute amounts of this transcription factor. The transgenic rice variety [3] comprises endogenous promoter and coding sequence for the rice SUSIBA1-like transcription factor and may therefore produce significant amounts of this transcription factor.

The plant material of the embodiments may produce even higher amount of starch or starch and fructan as compared to prior art transgenic rice due to the lack of any significant production of the SUSIBA1 or SUSIBA1-like transcription factor. In addition, the plant material of the embodiments may have the beneficial properties of low methane emission as mentioned for the transgenic rice variety in [3]. A further advantage of the embodiments, in particular using CRISPR/Cas9 mediated deletion of at least a portion of the activation region of the SUSIBA1 or SUSIBA1-like p, is a plant material that is not regarded as being a genetically modified organism (GMO). Hence, in an embodiment, the plant material is a non-GMO plant material.

Examples

Sequential carbohydrate synthesis is important for plant survival by guaranteeing energy supplies for growth and development during plant ontogeny and reproduction. Starch and fructan are two important carbohydrates in many flowering plants and for human consumptions. Understanding of the coordinated starch and fructan synthesis can not only help unravel how the plants allocate photosynthates and prioritize different carbohydrate synthesis for survival but also benefit cereal improvement in agriculture for food security and quality production. A system is reported herein from a single gene in barley, employing two alternative promoters, one intronic/exonic, to generate two sequence-overlapping but functionally opposing transcription factors, in sensing sugar, via sucrose/glucose/fructose signaling. The system employs an autoregulatory mechanism in perceiving a sugar-controlled trans activity on one promoter and orchestrating, as a whole in the system, the coordinated starch and fructan synthesis by competitive transcription factor binding on the other promoter. This multitasking system can be exploited for breeding traits in grasses with tailored amounts of starch and fructan for diverse applications. The finding of an intron/exon-spanning promoter in a hosting gene, resulting in proteins with distinct functions, contributes to the plant genome complexity.

In plants, sugar is important in mediating plant development and growth. The sugar-mediated plant development involves an important process, sugar mediated sequential carbohydrate synthesis for the strategies of immediate, short-term and long-term supplies of energy and materials. However, how sugar regulates the sequential carbohydrate synthesis for efficient utilization of photosynthates is unclear. Starch and fructan are glucose and fructose polymers, respectively, and are the two important carbohydrates in a large number of flowering plants. Starch is common in the plant kingdom and fructans can be found in more than 36 000 species of plants or over 12% of the angiosperms including both dicots and monocots. In dicots, five principal families produce fructans such as Asteraceae, e.g., dandelion, artichoke and chicory; *Campanulaceae*, e.g., harebell; and *Boraginaceae*, e.g., Early Forget-me-not, and in monocots also five principal families synthesize fructans such as *Liliaceae*, e.g., Madonna lily; *Amaryllidaceae*, e.g. onion; and the important temperate Gramineae including many crops, e.g., barley, wheat, oats, and many forage grasses. During plant development, starch plays as a relatively long-term energy suppling form and fructan as a rapidly available energy resource. Importantly, both of the carbohydrates are in a high demand for human consumptions. Starch is a key factor for present and future food security and, with annual global production of nearly 3 billion tons, most of which comes from cereals, is of immense economic importance. Fructans produced in many grasses during vegetative development and the early stages of reproductive development are essential for grain filling and yield and for drought and cold stress tolerance. Some grass cultivars accumulate high levels of fructans as a reserve carbohydrate in mature seeds. Such seed fructans can be used in a wide range of food and non-food applications, e.g., as a functional low-calorie food ingredient with positive effects on the human gut microbiome. However, current understanding of how plants orchestrate and prioritize carbohydrate synthesis, such as starch and fructan synthesis, to optimize storage and use of photosynthates for development and growth is poor. Here, using starch and fructan synthesis in barley as a model system, in plant sugar signaling networks an autoregulatory mechanism from a single gene whereby sugar-responsive expression of two transcription factor (TF) variants, with identical sequences but different length at 5'-ends from two alternative promoters, creates an opposing sugar-sensing system. The system senses sugar by perceiving a trans activity on the internal promoter and controls, as a whole in the system, the coordinated synthesis of fructan and starch by competitive transcription factor binding on the other promoter.

Sequence-related information that explains the mechanisms behind important crop traits such as yield, carbohydrate compositions, grain filling and abiotic stress tolerance in temperate grasses is critical for efforts to enhance crop productivity by marker-assisted selection and synthetic biology.

Figure 5:
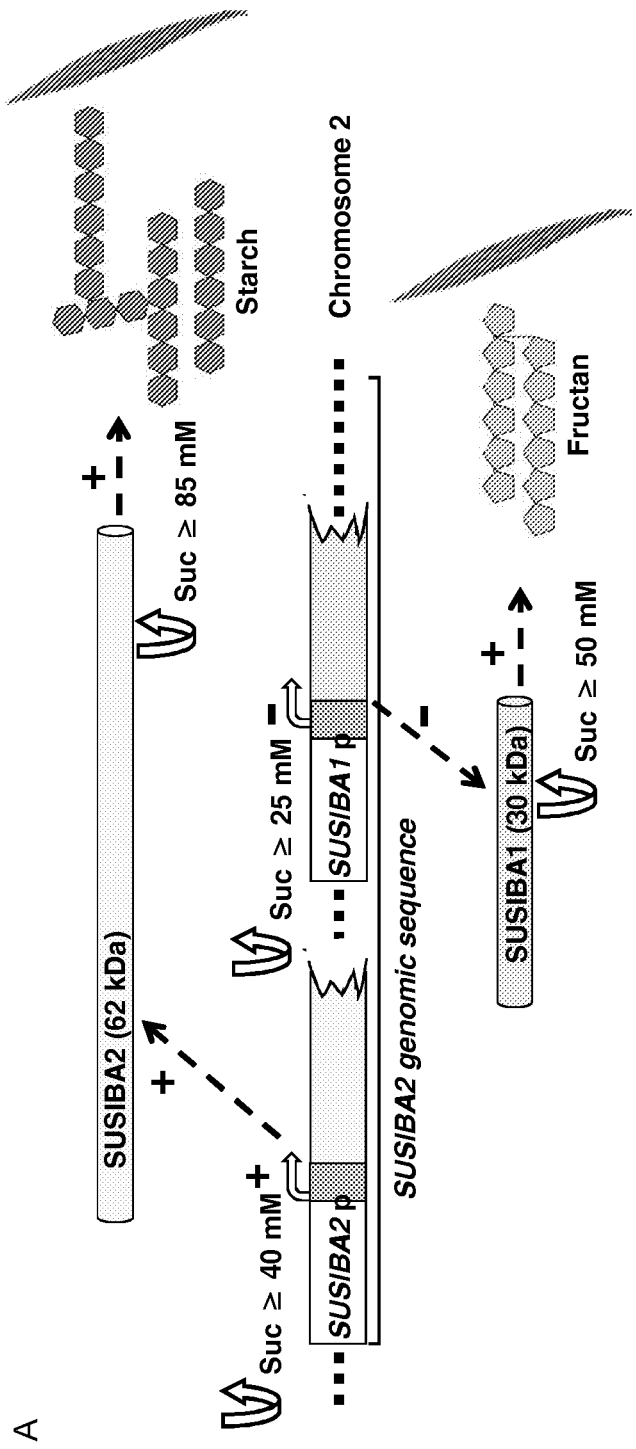
FIG. 5. Sugar-sensing activity of the SUSIBA1 and SUSIBA2 TFs in regulation of starch and fructan synthesis in barley. (A) The two alternative promoters of the SUSIBA sequence, SUSIBA1 promoter (SUSIBA1 p) and SUSIBA2 promoter (SUSIBA2 p) in barley chromosome 2, respond differently to sucrose (Suc) concentrations. With a Suc concentration over 25 mM, reduction of SUSIBA1 p activity occurs and at 40 mM Suc SUSIBA2 p is activated. Expression of SUSIBA1 p and SUSIBA2 p activity eventually results in SUSIBA2 (62 kD) and SUSIBA1 (30 kD) TFs, respectively. SUSIBA1 binds as a repressor to genes involved in fructan synthesis, and SUSIBA2 binds as an activator to genes involved in starch synthesis. Release of SUSIBA1 repression at $\geq 50$ mM Suc initiates fructan synthesis, and binding of SUSIBA2 to the cognate cis-elements at $\geq 85$ mM Suc stimulates starch synthesis. (B) SUSIBA1 p and SUSIBA2 p activity in response to Suc level. The SUSIBA1 p and SUSIBA2 p were fused to the GFP and BFP reporter genes, respectively. Agrobacteria harbouring the constructs were infiltrated into barley leaves, which were then incubated at different Suc concentrations. Fluorescence of SUSIBA1 p:GFP was examined by excitation light at 460-500 nm and that of SUSIBA2 p:BFP at 340-380 nm. A fusion sequence (GUS:GFP) of GUS and GFP was used as negative controls. Bars=100 μm.
Figure 5:
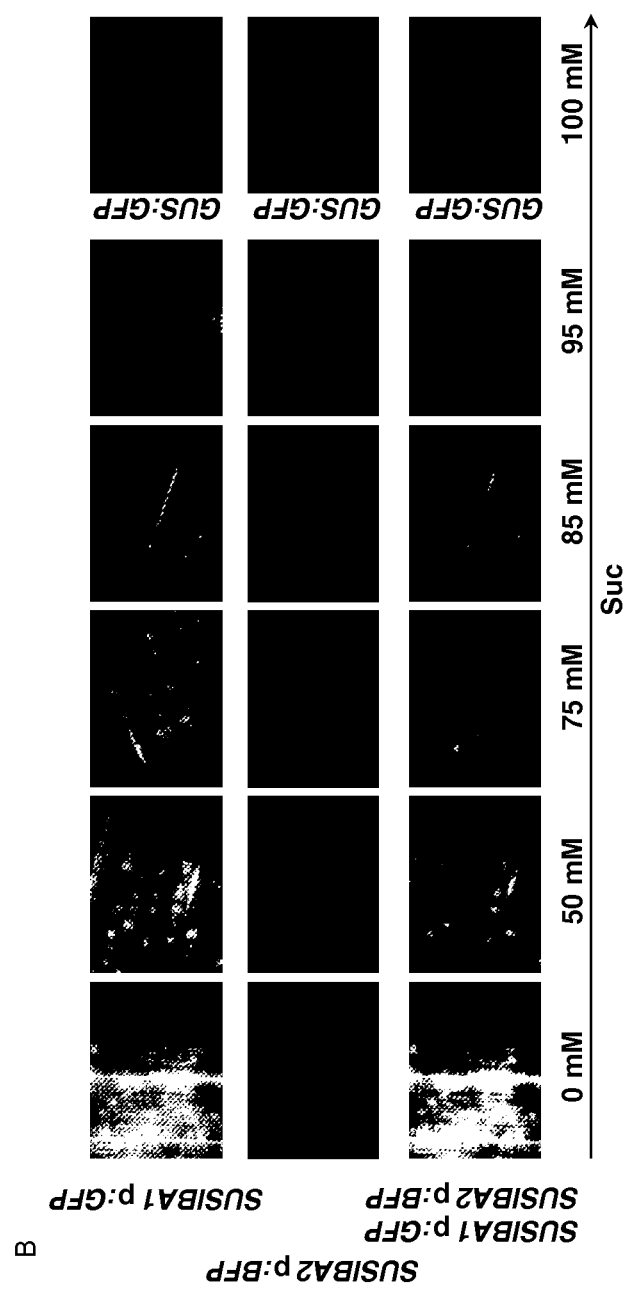

As reported herein, in barley chromosome 2, a single copy sequence encodes two size variants of the sugar signaling in barley (SUSIBA) TFs, SUSIBA1 of 30 kD and SUSIBA2 of 62 kD (FIGS. 1A, 1B, 2, 3A-3C). The promoters of SUSIBA1 and SUSIBA2 (SUSIBA1 p and SUSIBA2 p) respond to different concentrations of sucrose (FIGS. 5A, 5B). SUSIBA1 serves as a repressor that directly suppresses synthesis of fructan, whereas SUSIBA2 is an activator that promotes synthesis of starch. Interestingly, the SUSIBA2 expression is controlled by SUSIBA1/SUSIBA2 competitive binding on the SUSIBA2 promoter, which generates an autoregulatory system for the coordinated synthesis of starch and fructan.

Results

Figure 4:
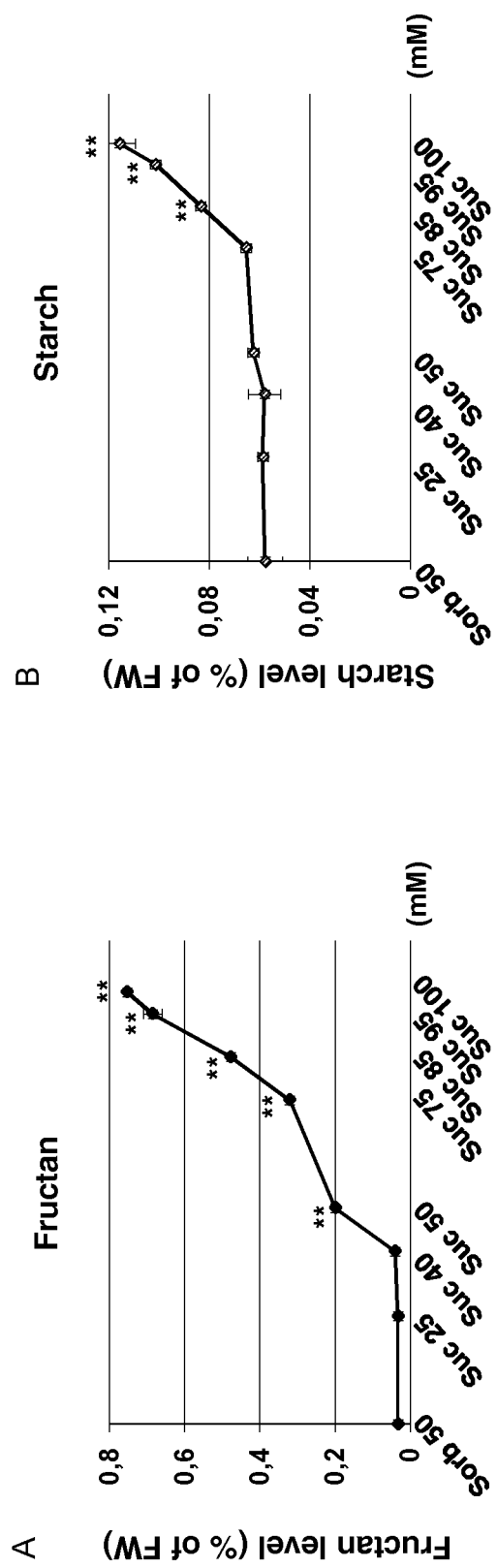
FIG. 4. Fructan and starch content in barley leaves in response to ectopically supplied sucrose (Suc) at different concentrations. Changes in fructan (A) and starch (B) content are presented. Three independent experiments (n=3; two leaves per experiment) were performed and technical duplicates were used for fructan and starch analyses in each experiment. Shifts in fructan and starch levels were detected at 50 mM and 85 mM Suc, respectively. The induction threshold for fructan and starch synthesis in barley leaves was identified as 40-50 mM and 75-85 mM sucrose, respectively. Standard deviation bars were small, as indicated. Significant differences between sucrose-treated samples and the sorbitol (Sorb) controls are indicated by asterisks (**$p \leq 0.01$). One-way ANOVA was used (Error bars show s.d.)

Synthesis of Starch and Fructan Responds to Ectopic Supply of Sucrose at Different Start Set Points Synthesis of starch and fructan in sink leaves is induced when sucrose (Suc) is highly available in vivo or by an ectopic supply of sugars (FIGS. 4A, 4B). The induction of starch and fructan in sucrose-treated barley leaves started at different set points, 50 mM Suc for fructan and 85 mM Suc for starch (FIGS. 4A, 4B). Furthermore, the content of starch and fructan correlated well with supplied sucrose levels (FIGS. 4A, 4B). These observations raise questions as to the nature of the sugar-signaling pathways that mediates the sequential induction of starch and fructan synthesis.

Figure 6:
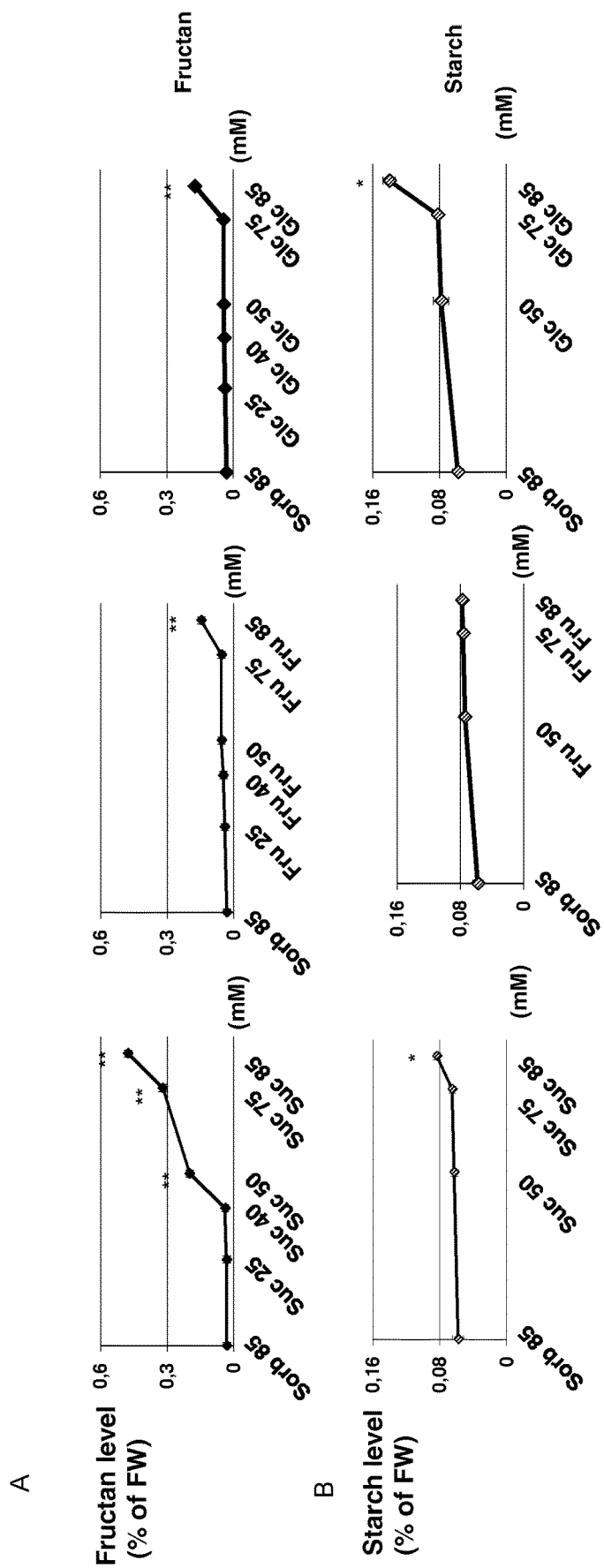
FIG. 6. Fructan and starch content, and transcript and protein levels of SUSIBA1, SUSIBA2, 6-SFT and SBEIIb in barley leaves in response to different concentrations of sucrose (Suc), fructose (Fru) and glucose (Glc). (A) Fructan content. (B) Starch content. (C) qPCR analysis of gene expression levels. (D) Western blot analysis of corresponding protein levels. Three independent experiments (n=3) were performed for analyses of fructan, starch and qPCR and two for Western blot. One-way ANOVA was used (*$p \leq 0.05$ or **$p \leq 0.01$ between sugar-treated samples and the sorbitol controls and error bars show s.d. and are small in (A) and (B)).
Figure 6:
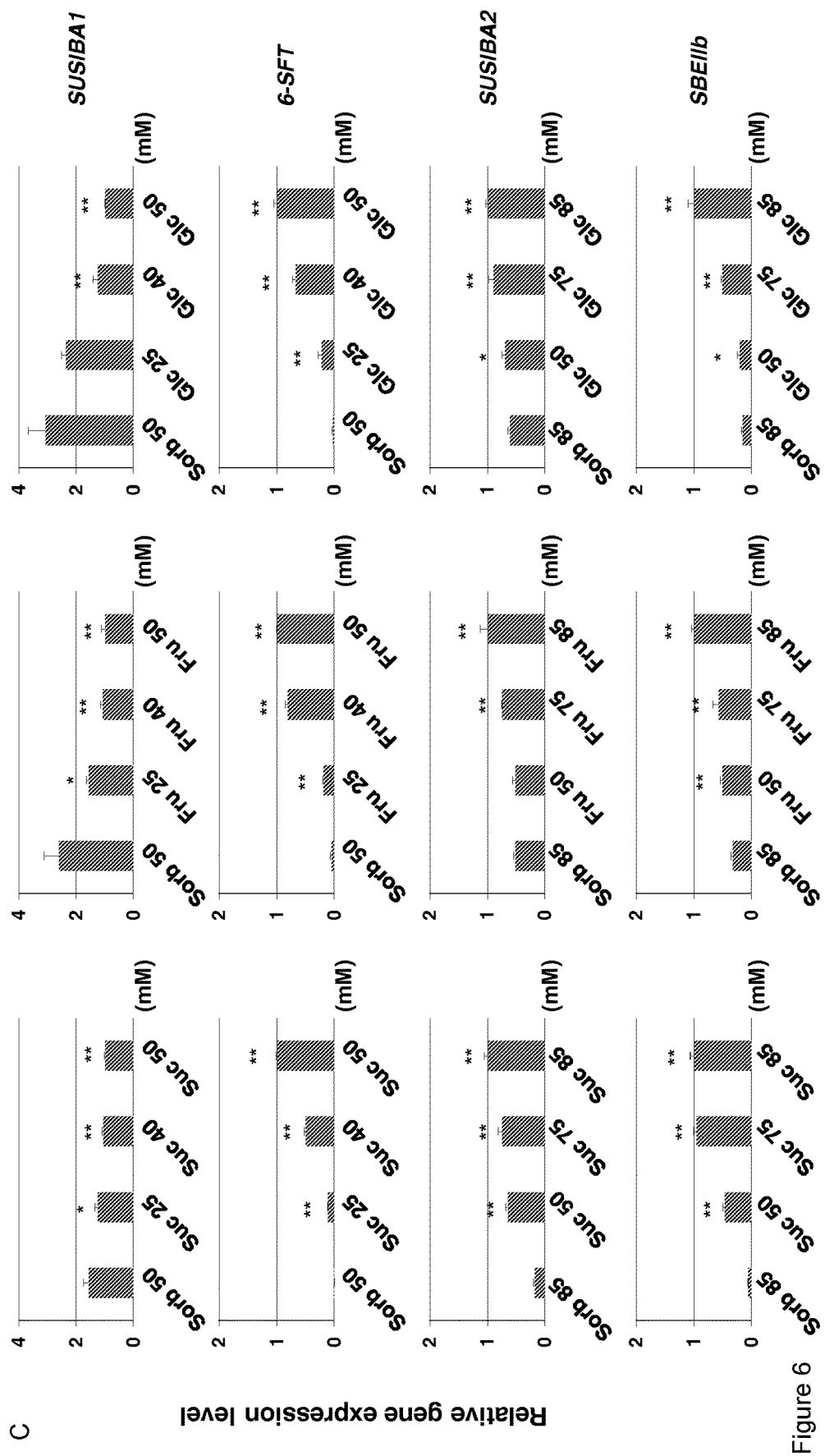
Figure 6:
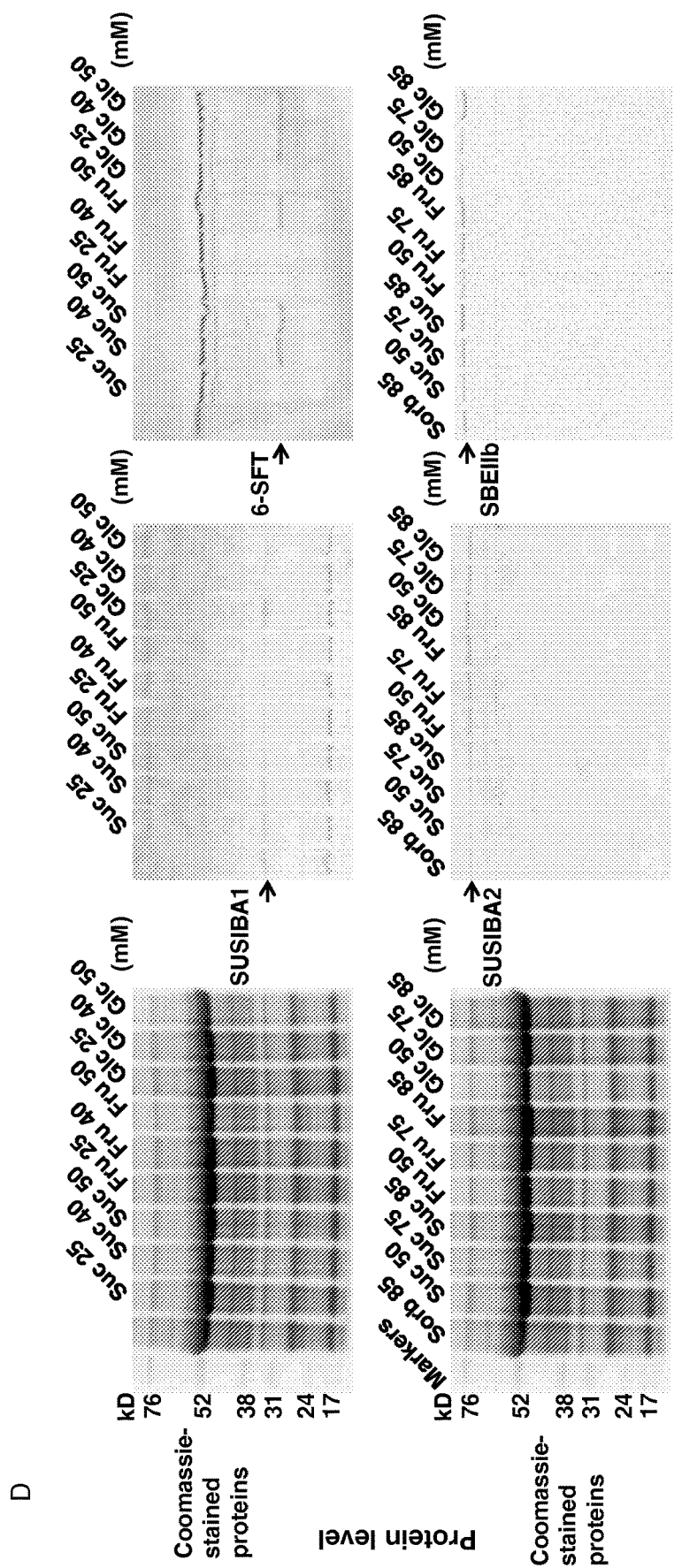
Figure 7:
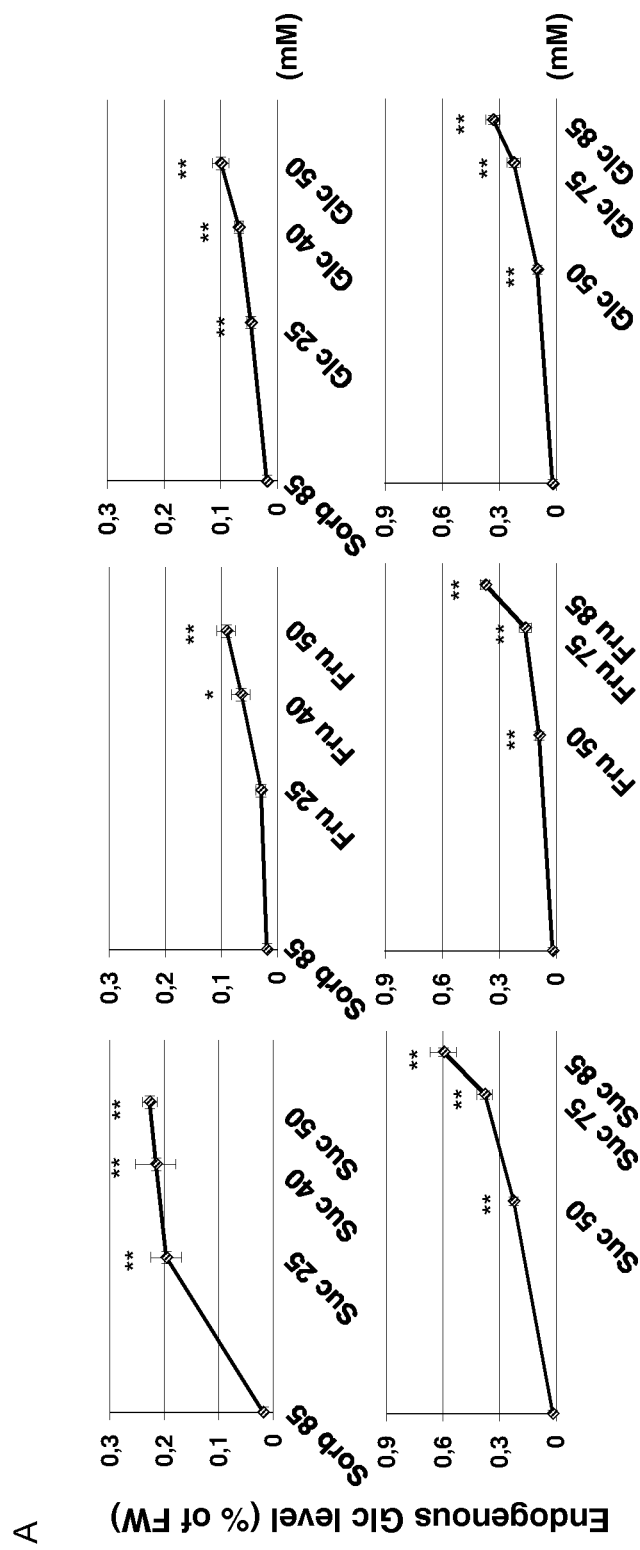
FIG. 7. Changes in endogenous levels of glucose (Glc) and fructose (Fru) and determination of trehalose 6-phophsphate synthase (TPS) activity and TPS-like expression levels in leaves after different sugar treatments. (A) Endogenous Glc. (B) Endogenous Fru. (C) Gene expression levels of barley TPS-like in the corresponding samples. (D) Total activity of TPS. Arabidopsis protein extracts from Suc (85 mM) and light-treated leaf samples were used as a positive control for the enzyme assay. Biological triplicates (A, B, D) and three independent experiments (C) were performed (n=3). One-way ANOVA was used (*$p \leq 0.05$ and **$p \leq 0.01$ for increases of sugar-treated samples compared with the sorbitol (Sorb) controls and error bars show s.d.)
Figure 7:
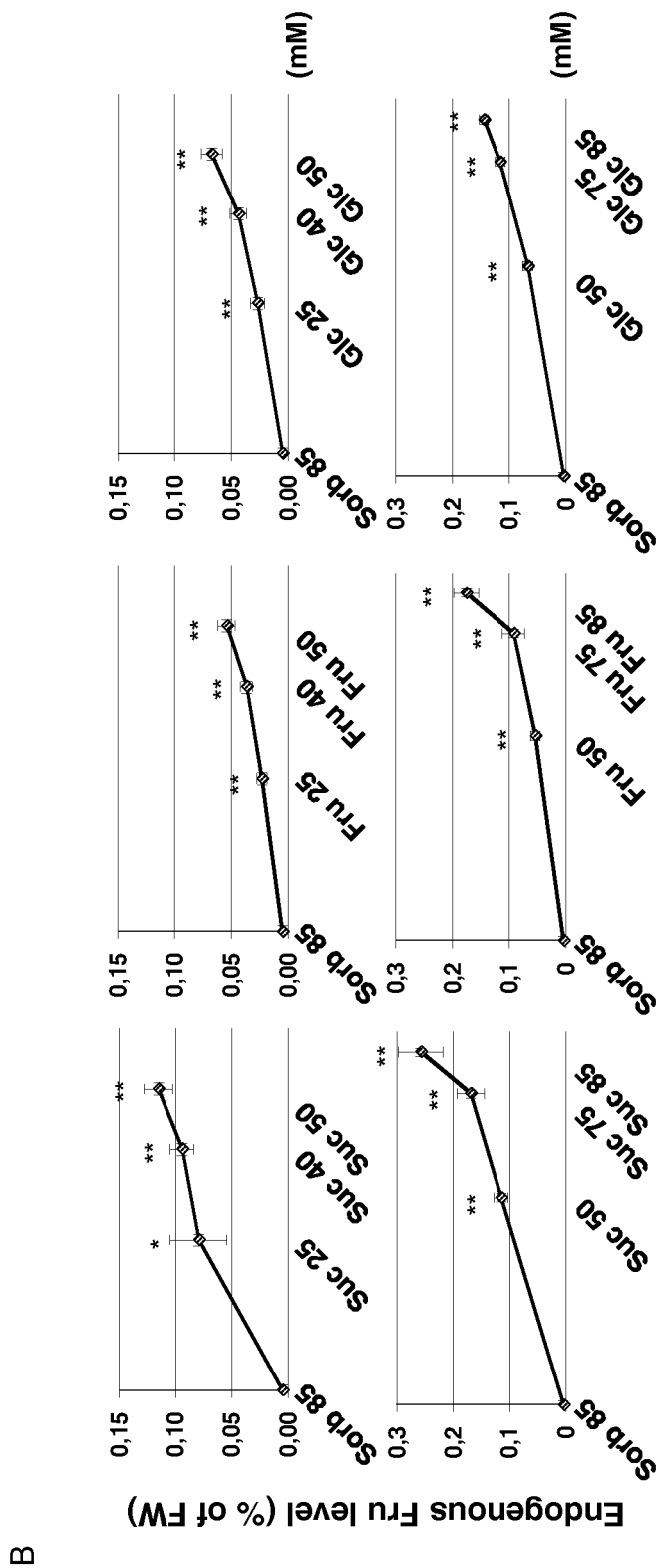
Figure 7:
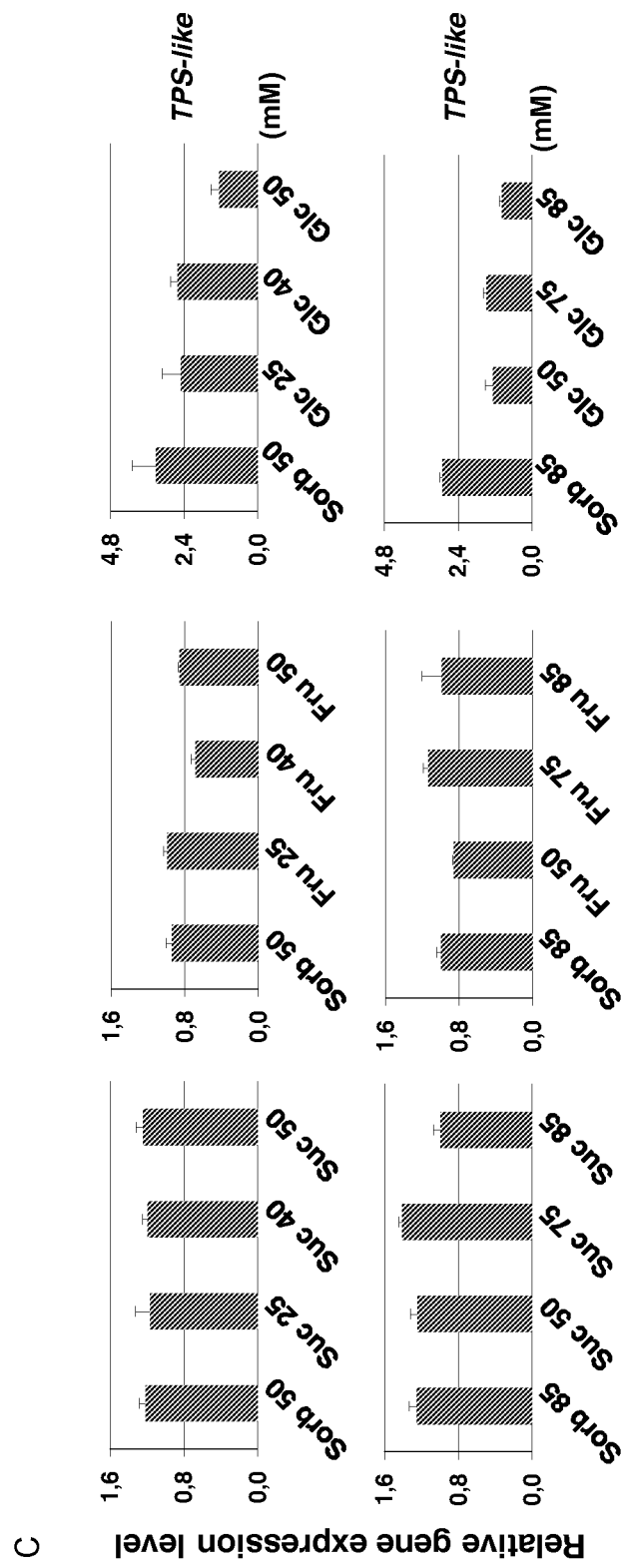
Figure 7:
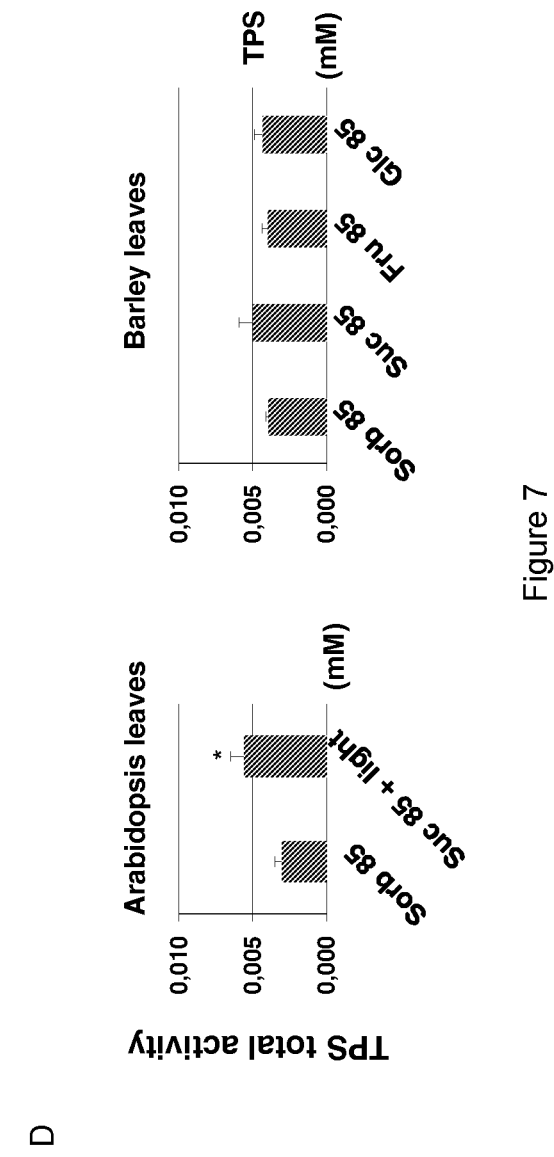

SUSIBA1 and SUSIBA2 Sense Sugar Potentially Via Sucrose/Glucose/Fructose Signaling In many Suc-signaling pathways, it has been found that Glc, Fru, and/or trehalose 6-P (T6P), rather than Suc itself, serve as the primary messenger. It was recently suggested that hexoses can regulate oligofructan synthesis in barley seeds and cell differentiation in cotton, respectively. The same molar concentrations of Suc, Fru and Glc were applied to barley sink leaves and the effect on fructan and starch accumulation was examined (FIGS. 6A and 6B). As is shown, induction of fructan and starch accumulation was observed for Suc concentrations ≥50 and 85 mM, respectively (see also FIGS. 4A, 4B). At 85 mM also Glc but not Fru induced starch accumulation. Neither Glc nor Fru induced fructan accumulation at 50 mM but did so at 85 mM. Examination of transcript and protein levels demonstrated that Fru- and Glc-treated samples displayed the same trend as Suc-treated samples, i.e., with a level decrease for SUSIBA1/SUSIBA1 and an increase for SUSIBA2/SUSIBA2 and transcripts/enzymes for fructan (6-SFT/6-SFT) and starch (SBEIIb/SBEIIb) synthesis (FIGS. 6C and 6D). Levels of endogenous Fru and Glc in Suc-treated samples were higher than in the Fru- and Glc-treated samples (FIGS. 7A and 7B). Levels of endogenous Fru and Glc correlated with fructan and starch accumulation in the sugar-treated samples (FIGS. 6A and 6B and FIGS. 7A and 7B). T6P levels were generally low and could not be positively detected in all samples, whereas a T6P standard of 5 ng (119 pmoles) gave a clear signal in liquid chromatography-mass spectrometry (LC/MS) analysis. The finding was corroborated by the lack of increases in TPS-like transcript levels (FIG. 7C) or total trehalose 6-phosphate synthase (TPS) activity (FIG. 7D) in the Suc, Fru or Glc treatment.

SUSIBA2 Harbors an Intronic/Exonic Promoter for SUSIBA1

Figure 3:
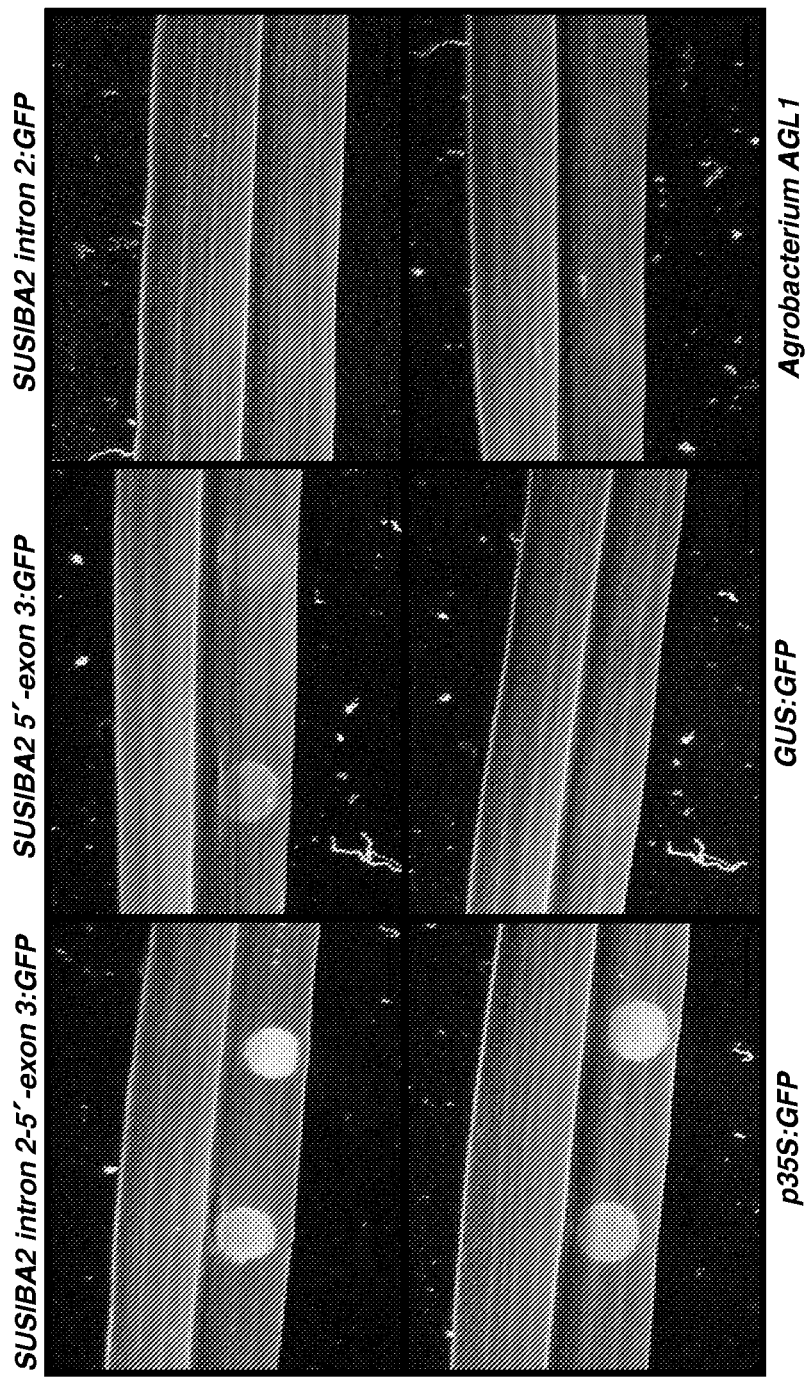
FIG. 3. Analysis of SUSIBA1 promoter activity. Different constructs in agrobacteria were infiltrated. (A) Fluorescence was examined under UV-light. (B) Fluorescent areas of infiltrated leaf triplicates were examined under a microscope. (C) Relative fluorescence intensity quantified from the triplicates. Significant differences of the two truncated SUSIBA2 intron 2-5'-exon 3, p35S:GFP, GUS-GFP and *agrobacterium* AGL1 compared with the full-length of SUSIBA2 intron 2-5'-exon 3, and are indicated by asterisks (**$p \leq 0.01$). One-way ANOVA was used (Error bars show s.d.) Bars in (A)=7 mm and in (B)=100 μm.
Figure 3:
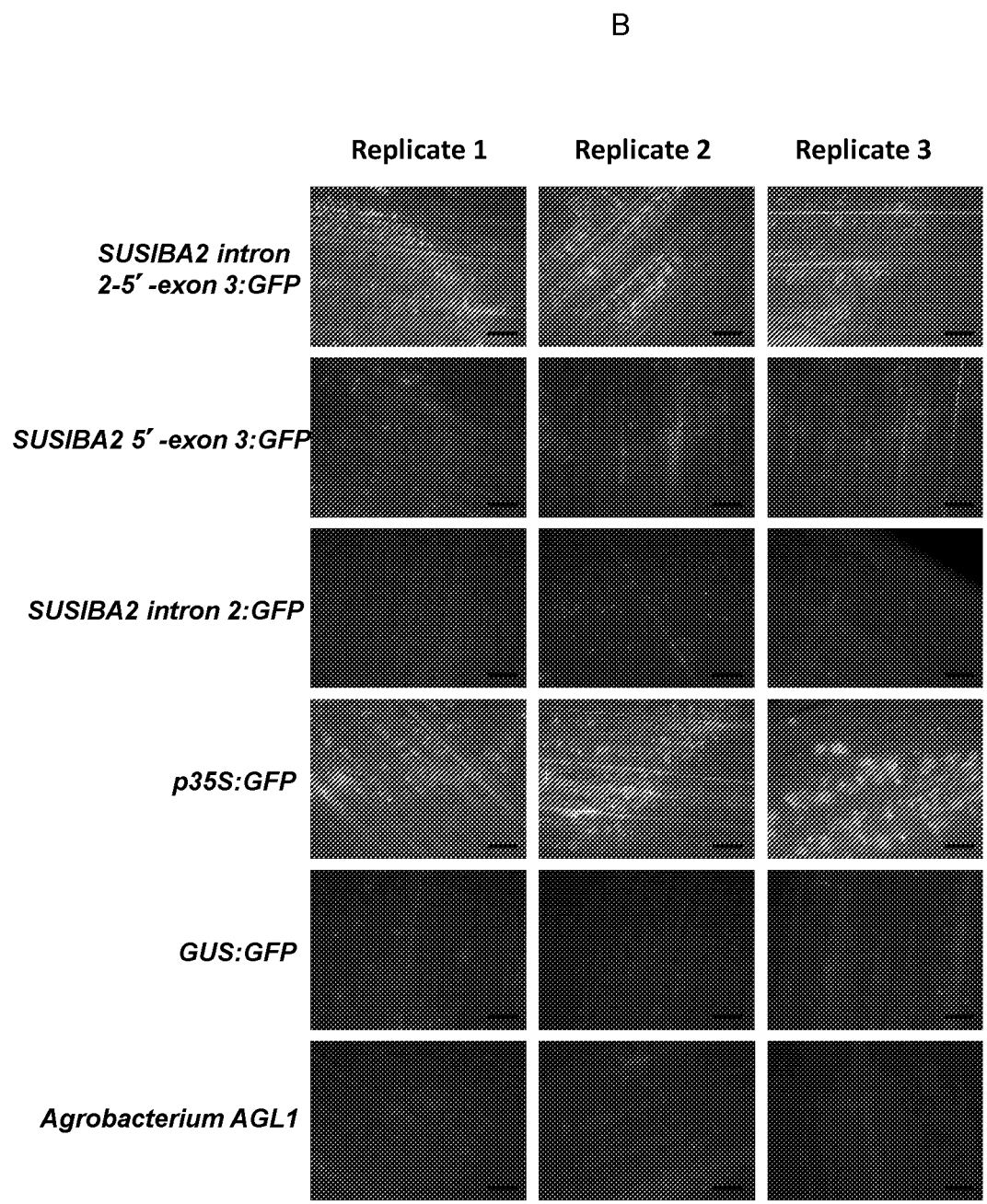
Figure 3:
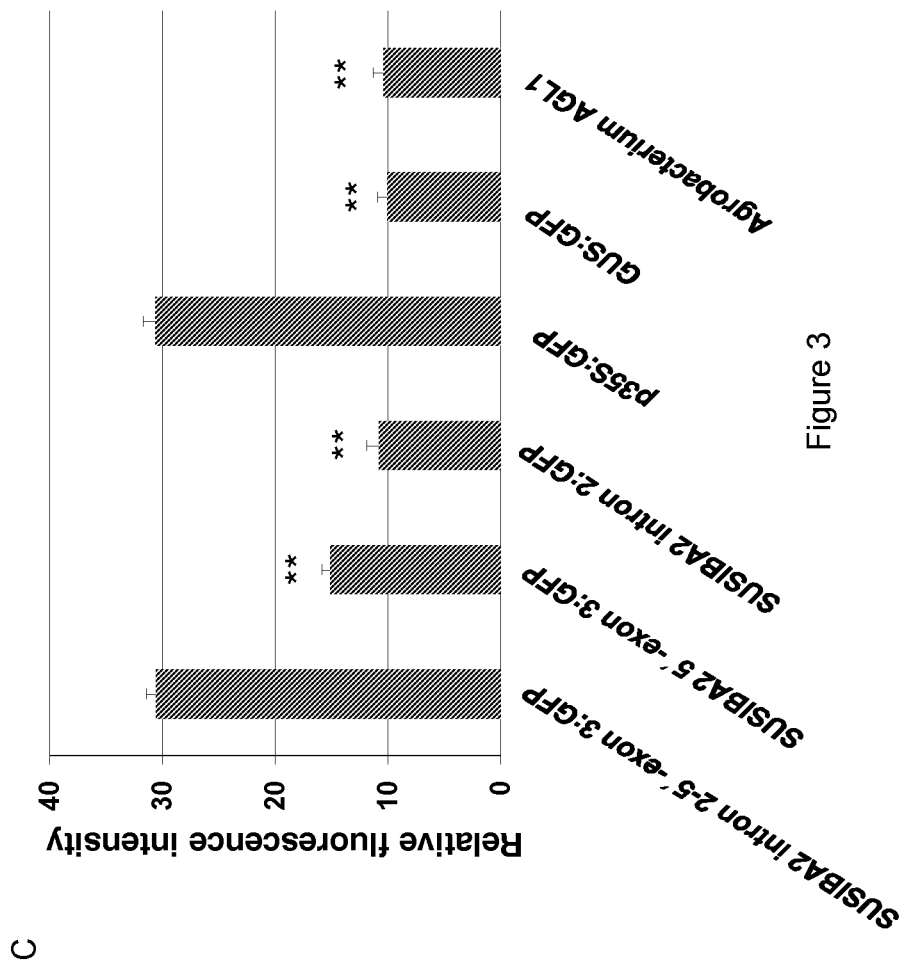
Figure 10:
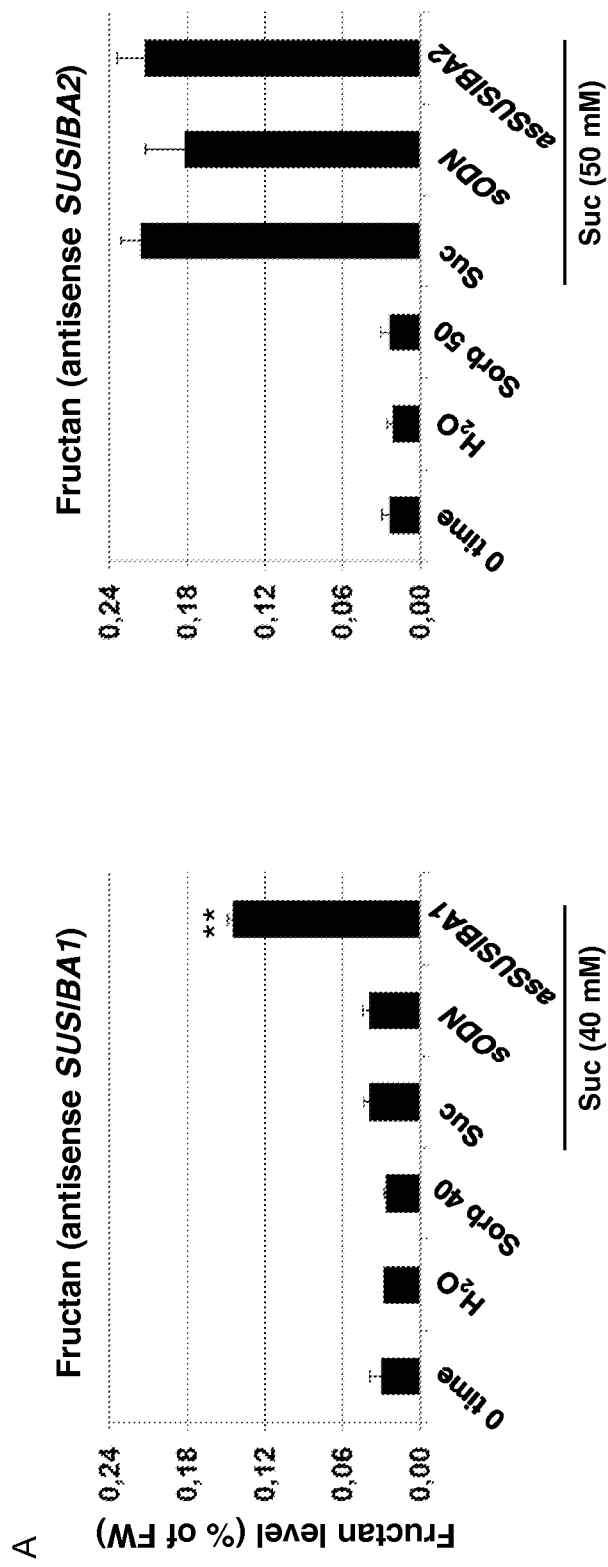
FIG. 10. Changes in fructan and starch content in barley leaves upon antisense oligodeoxynucleotide (asODN) inhibition of SUSIBA1 and SUSIBA2 at the sucrose induction threshold for fructan and starch synthesis. (A) Fructan content in leaves with SUSIBA1 inhibition at 40 mM sucrose (Suc; left panel) and with SUSIBA2 inhibition at 50 mM (right panel). (B) Starch content in leaves with SUSIBA1 inhibition at 75 mM Suc (left panel) and with SUSIBA2 inhibition at 85 mM (right panel). Treatments with the corresponding sense ODNs to SUSIBA1 and SUSIBA2 were used as controls for statistical analyses. Three independent experiments (n=3) were performed. Sorb, sorbitol. One-way ANOVA was used (*$p \leq 0.05$ or **$p \leq 0.01$ and error bars show s.d.)
Figure 10:
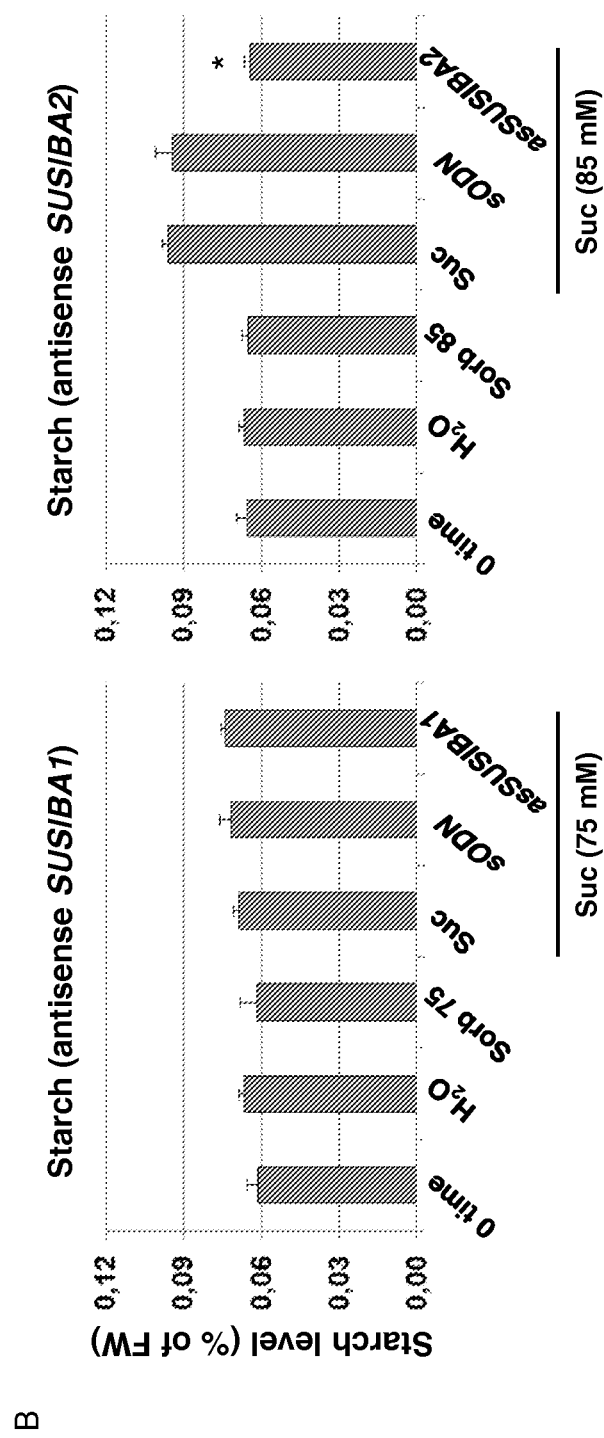
Figure 11:
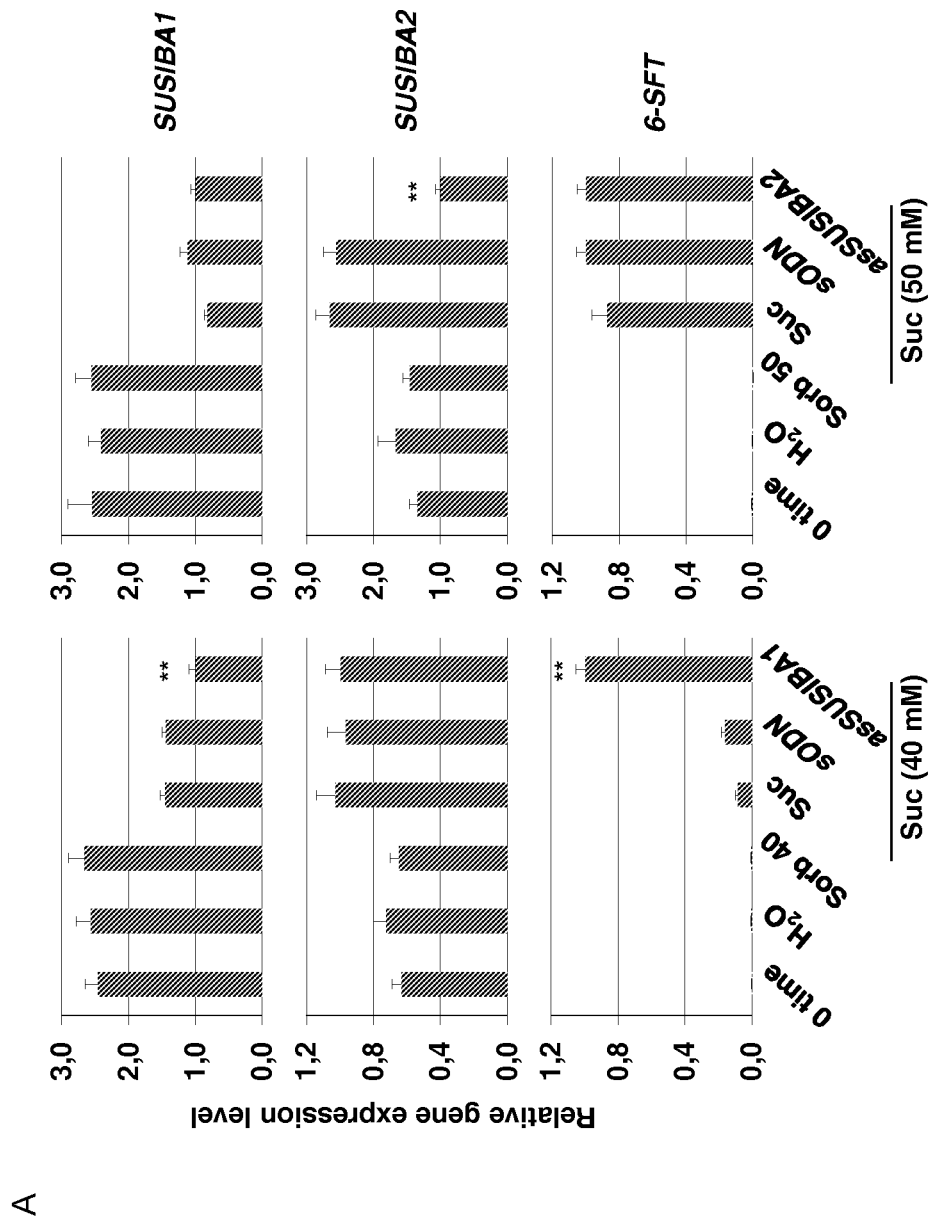
FIG. 11. Changes of transcript and protein levels of SUSIBA1, SUSIBA2 and 6-SFT in barley leaves after inhibition of SUSIBA1 and SUSIBA2 activity by asODNs. (A) qPCR analysis of relative gene expression levels of SUSIBA1, SUSIBA2 and 6-SFT at the indicated sucrose (Suc) concentrations with asODN inhibition of SUSIBA1 (left panels) or SUSIBA2 (right panels). (B) Western blot analysis of corresponding protein levels after asODN inhibition. Significant differences after inhibition are indicated by asterisks compared with controls of sense ODNs (sODNs) in sucrose (Suc). Three independent experiments were performed for asODN inhibition and qPCR analysis (n=3), and two for Western blot analysis. One-way ANOVA was used (Error bars show s.d. and **p≤0.01). Sorb, sorbitol.
Figure 11:
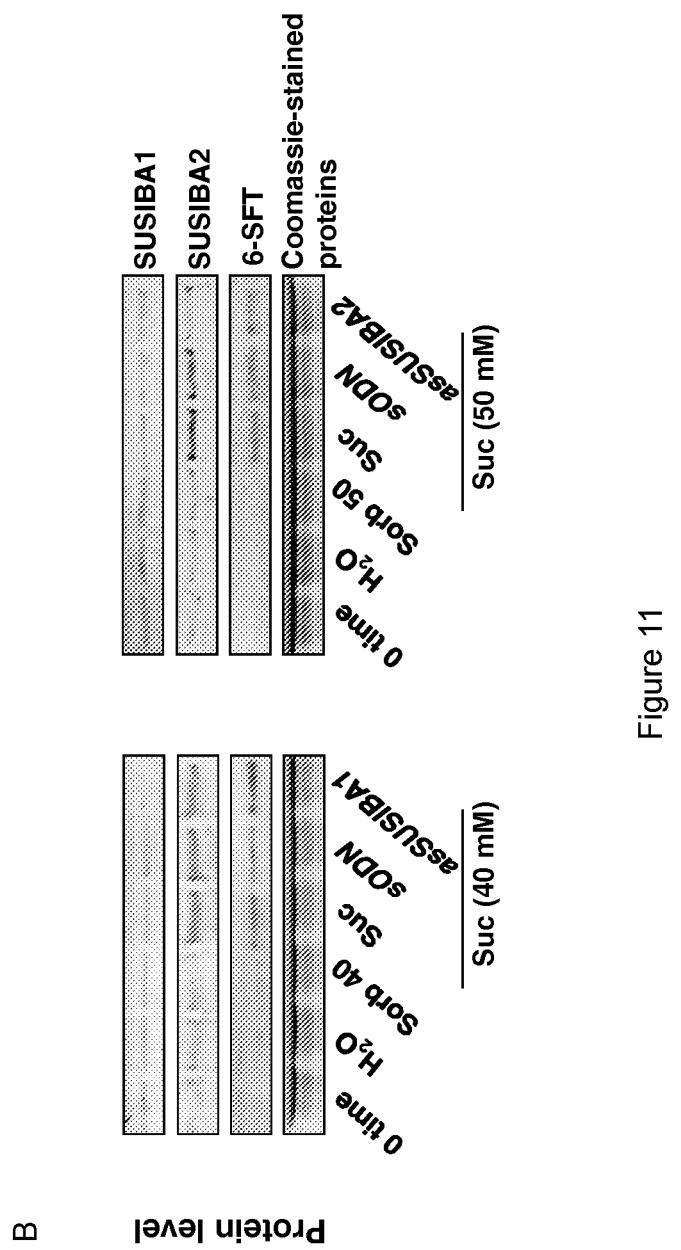
Figure 12:
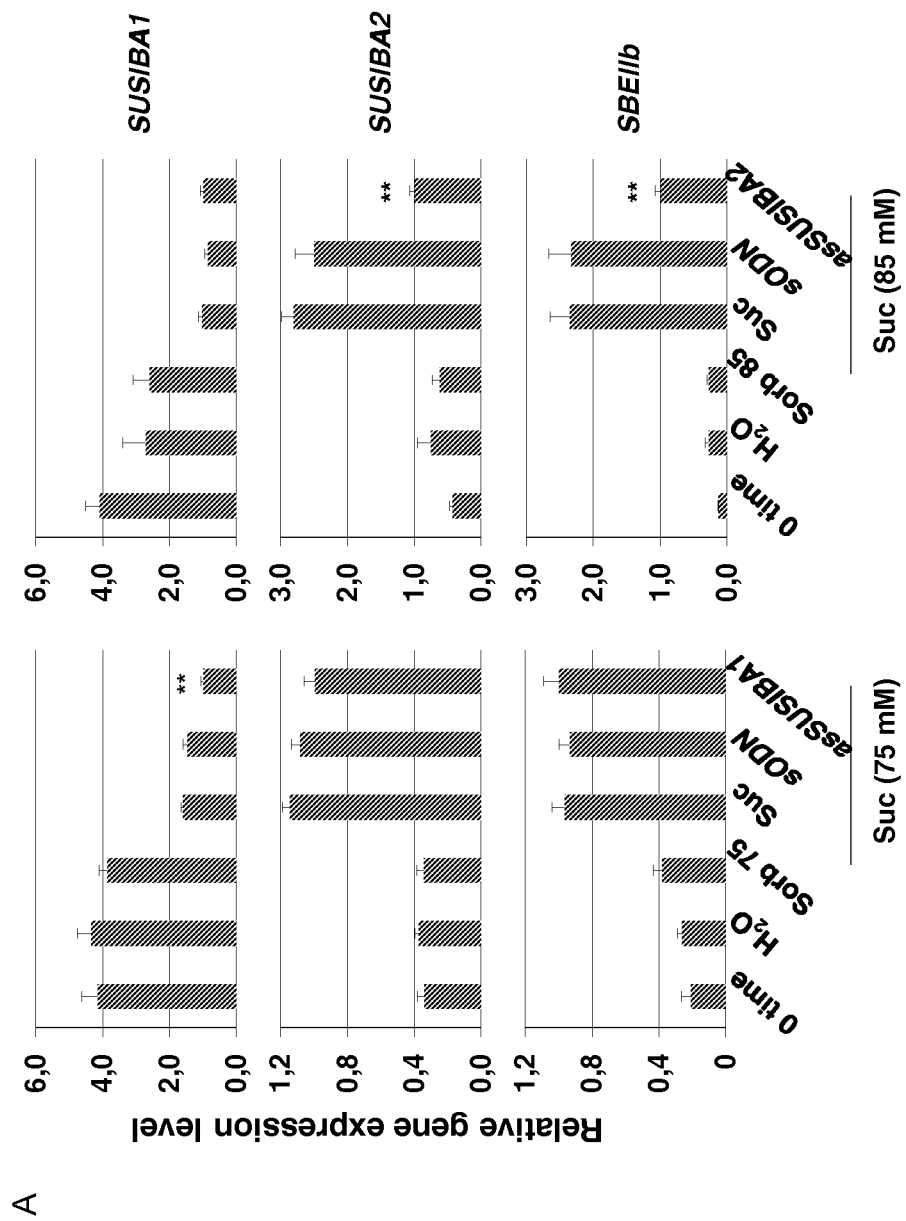
FIG. 12. Changes of transcript and protein levels of SUSIBA1, SUSIBA2 and SBEIIb in barley leaves after inhibition of SUSIBA1 and SUSIBA2 activity by asODNs. (A) qPCR analysis of relative gene expression levels of SUSIBA1, SUSIBA2 and SBEIIb at the indicated sucrose (Suc) concentrations with asODN inhibition of SUSIBA1 (left panels) or SUSIBA2 (right panels). (B) Western blot analysis of corresponding protein levels after asODN inhibition. Significant differences after inhibition are indicated by asterisks compared with controls of sense ODNs (sODNs) in sucrose (Suc). Three independent experiments were performed for asODN inhibition and qPCR analysis (n=3), and two for Western blot analysis. One-way ANOVA was used (Error bars show s.d. and **p≤0.01). Sorb, sorbitol.
Figure 12:
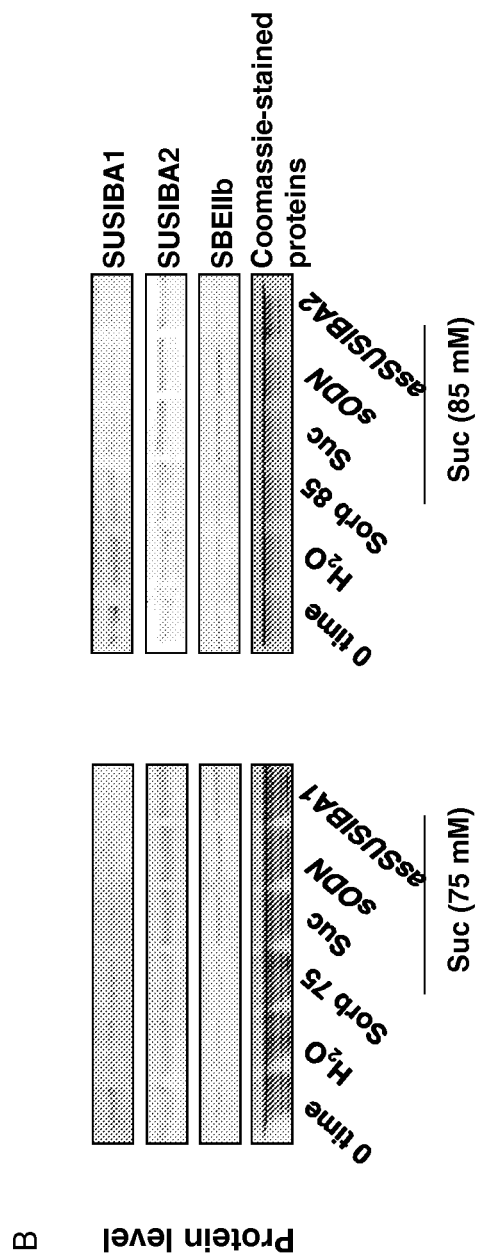

To delineate the functions and interplay of the SUSIBA1 and SUSIBA2 TFs in starch and fructan synthesis, the origin of SUSIBA1 and the identity and sequence of SUSIBA1 p were first investigated. Screening of a barley endosperm cDNA library at 10 days after flowering (daf) with SUSIBA2 cDNA as a probe yielded a few clones identical to the 3'-end of SUSIBA2 cDNAs although expression of SUSIBA1 was low at this stage (FIGS. 10 and 1D). With 5'-RACE (rapid amplification of cDNA ends) using barley leaf total RNA three amplicons were obtained (FIG. 1A). Sequence analysis showed that the amplicons were identical to part of SUSIBA2 cDNAs. The longest cDNA (amplicon 3) of 1448 nt corresponded to a 281-amino acid peptide identical to the C-terminal 281 amino acids of SUSIBA2 and with a deduced molecular weight of around 30 kD (FIG. 1B). Northern and Western blot analyses of barley leaf and endosperm tissues confirmed the presence of a 1.5 kb SUSIBA1 transcript and 30-kD protein product (FIGS. 10 and 1D). To isolate the SUSIBA1 p, intron 2 and the partial 5'-end of exon 3 of SUSIBA2 were PCR amplified from the barley genome. The amplified full-length region, intron 2, or the partial 5'-end of exon 3 was then fused to the GFP reporter gene. Agrobacteria containing the different constructs were used to infiltrate barley leaves. The full-length region gave rise to strong activity, similar to that of the 35S promoter (FIG. 3C), whereas the 5'-end of exon 3 showed weak activity (FIG. 3C). Intron 2, a negative control (GUS:GFP), and agrobacteria without constructs did not result in any reporter gene activity (FIG. 3C). It was concluded that the isolated full-length region represents a functional promoter for SUSIBA1.

To illustrate the differential responses of SUSIBA1 p and SUSIBA2 p to sucrose levels, barley leaves were infiltrated with agrobacteria containing SUSIBA1 p:GFP and SUSIBA2 p:BFP constructs and the leaves were treated with different sucrose concentrations. A direct negative and positive correlation between promoter activity and sucrose concentrations for SUSIBA1 and SUSIBA2, respectively, was clearly evident (FIG. 5B). No florescence was detected from the negative control of GUS:GFP.

Role of SUSIBA1 in Regulation of Fructan Synthesis

Figure 8:
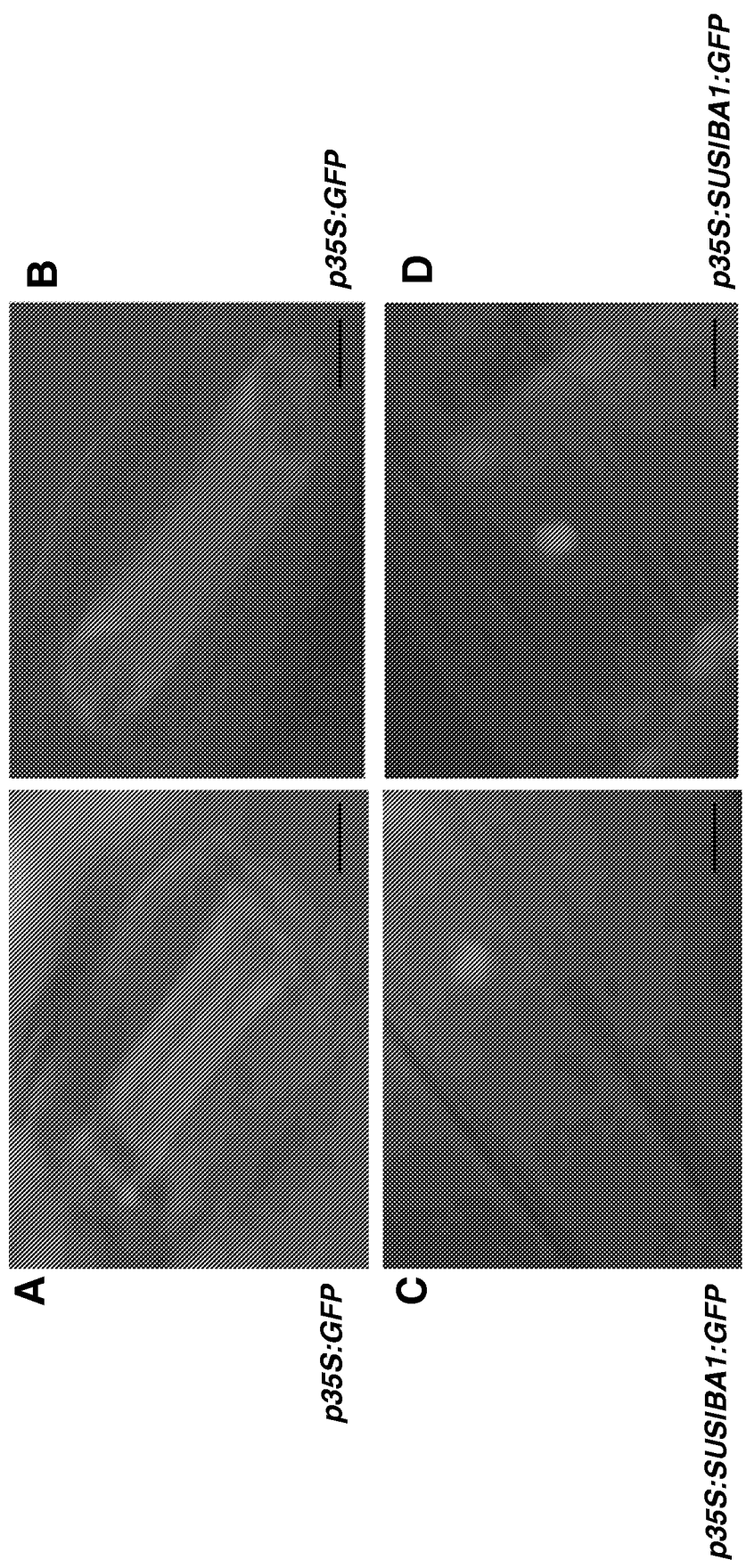
FIG. 8. Repression of the 6-SFT promoter activity by SUSIBA1. (A-D) Nuclear localization of SUSIBA1 in barley cells. SUSIBA1 cDNA was fused to GFP. Agrobacteria with GFP alone (A, B) or SUSIBA1:GFP (C, D) driven by a 35S promoter were infiltrated. (E-J) Binding activity of SUSIBA1 to the SUREa, W-box and SP8a promoter elements of 6-SFT. DNA fragment probes were end-labeled by [$\gamma^{32}$]-ATP with $T_4$ polynucleotide kinase. For oligo probes, one strand was end-labeled by [$\gamma^{32}$]-ATP with $T_4$ polynucleotide kinase and annealed with a complementary strand of oligo. (E) Different elements in the 6-SFT promoter. (F) SUSIBA1 binding activity to the five fragments in (E). SUSIBA1 was overexpressed and purified from E. coli. Binding activity displayed as band shifts is indicated with arrows. (G) Sequences of elements in the 6-SFT promoter (SEQ ID NO: 78, 79, 62-67). Consensus sequences for SP8a and W-Box are given underlined. (H) EMSA of the elements in (G) in presence (+) or absence (-) of SUSIBA1. The position of the free DNA probe is indicated. (I) Sequences of the individual engineered elements (SEQ ID NO: 68-79). An A-stretch (underlined) was designed to replace the consensus sequences. (J) EMSA of the engineered elements in presence (+) or absence (-) of SUSIBA1. (K-O) Co-infiltration of agrobacteria with 6-SFT p:GFP and p35S: SUSIBA1 constructs. (K) Agrobacteria containing 6-SFT p:GFP. (L) A mixture of agrobacteria containing 6-SFT p:GFP and p35S:WRI1. WRI1 is a SUSIBA-unrelated TF gene from Arabidopsis with GenBank accession number NM_202701. (M) A mixture of agrobacteria containing 6-SFT p:GFP and p35S:SUSIBA1. (N) SUSIBA1 transcript and protein levels in the infiltrated area. Insert shows Western blot analysis of protein levels in the area filtrated with living (left lane) agrobacteria or heat-killed background (right lane) agrobacteria. (O) WRI1 transcript levels in the infiltrated area. Three independent experiments (n=3) were performed for qPCR analysis and two for Western blot. Bars in (A-D)=5 μm and in (K-M)=100 μm. One-way ANOVA was used (Error bars show s.d. and **$p \leq 0.01$ between heat-killed background and living agrobacteria).
Figure 8:
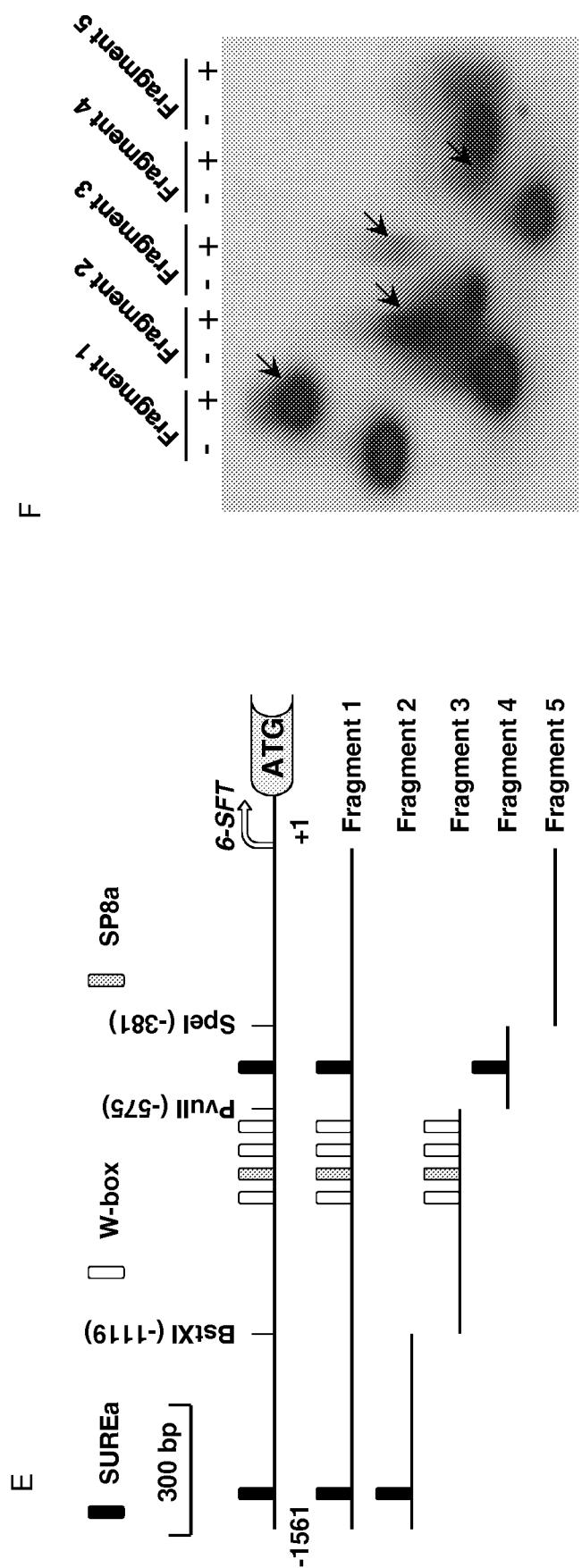
Figure 8:
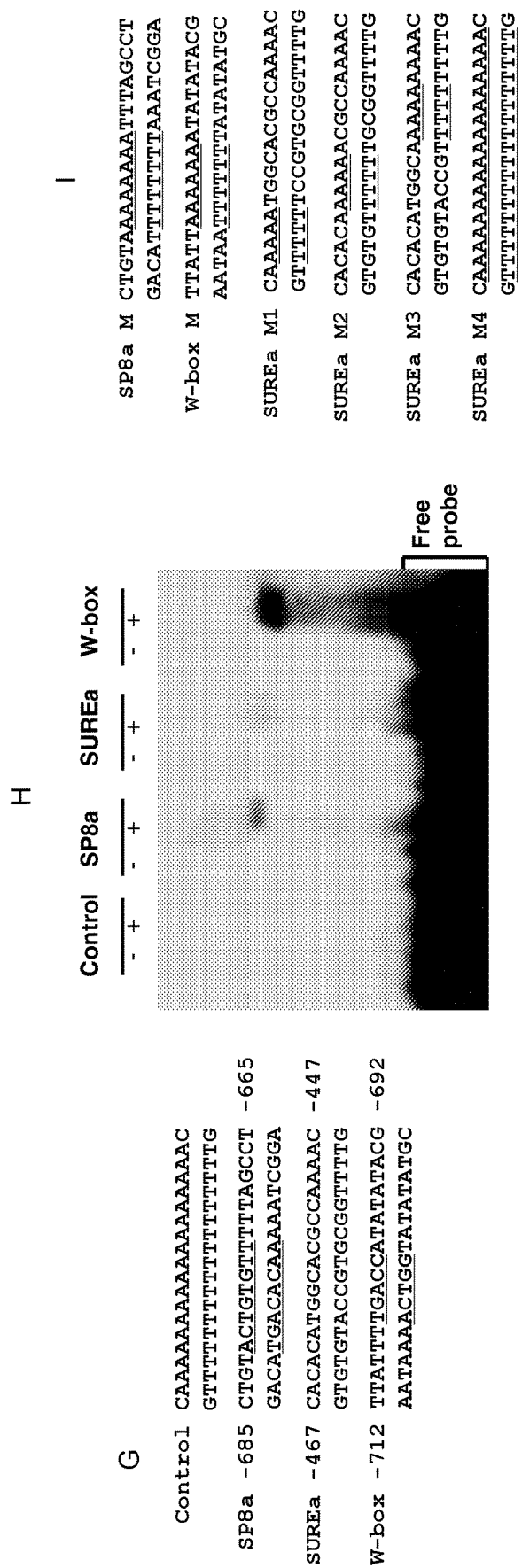
Figure 8:
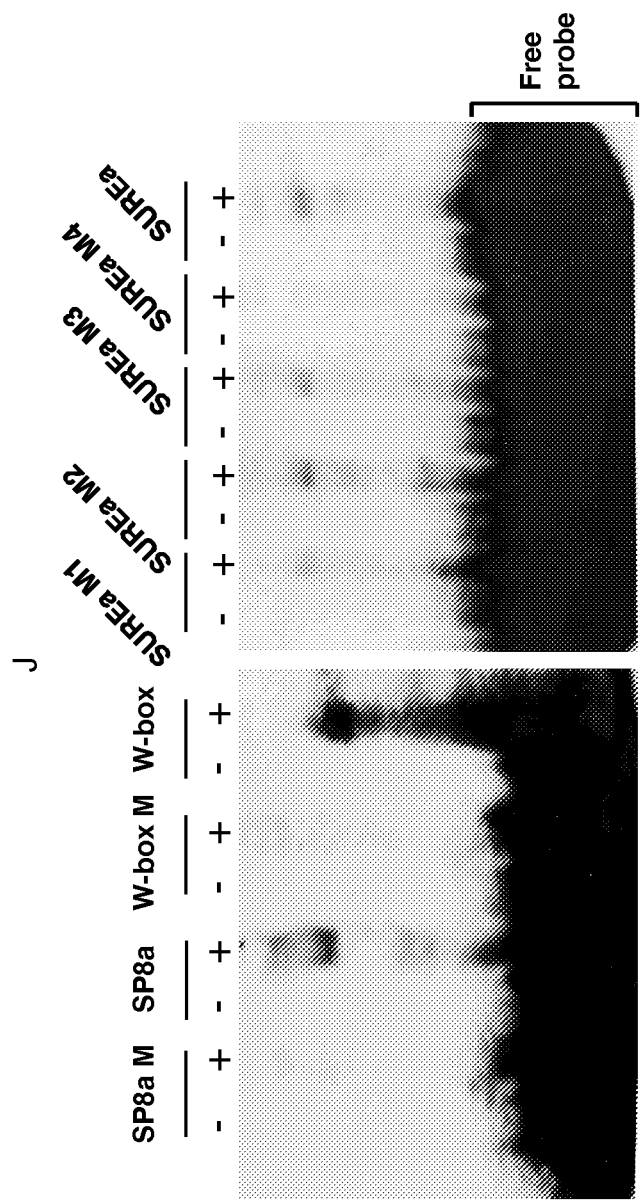
Figure 8:
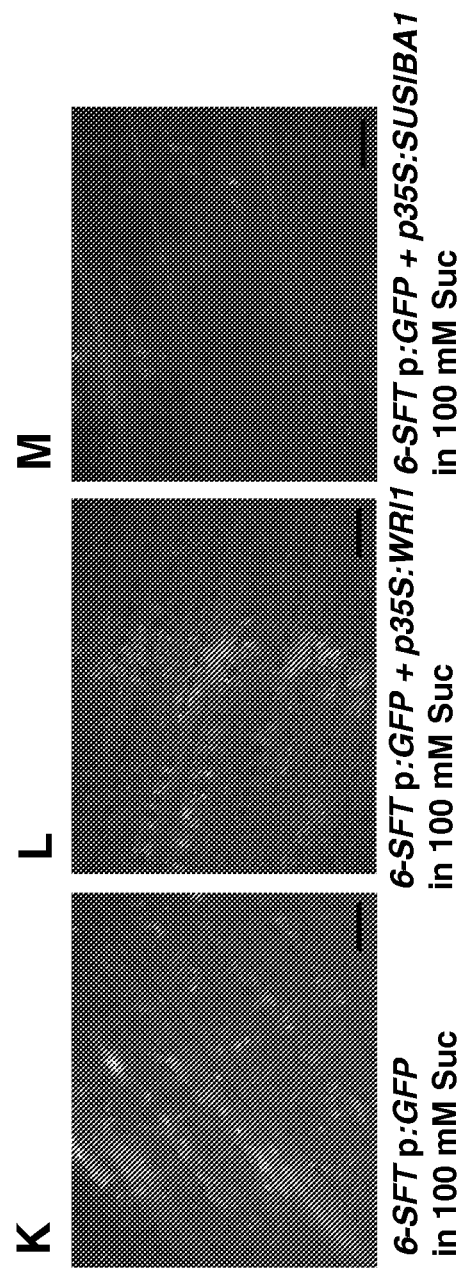
Figure 8:
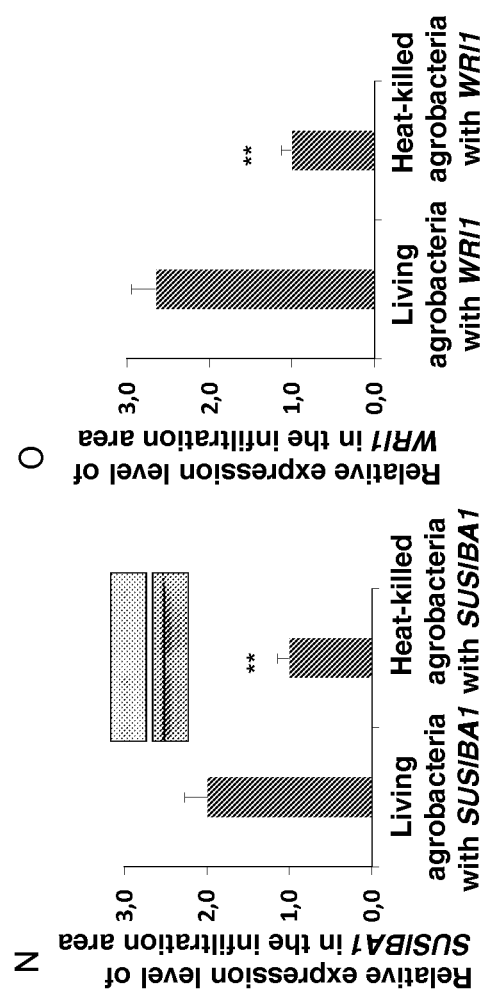

Having identified SUSIBA1 p, the potential involvement of SUSIBA1 in fructan synthesis was investigated. The nuclear location of SUSIBA1 was confirmed by *agrobacterium* infiltration of a SUSIBA1:GFP fusion construct, which demonstrated that SUSIBA1 can successfully target GFP to the nucleus (FIG. 8A to 8D). Electrophoretic mobility shift assay (EMSA) was used to study the in vitro interaction between SUSIBA1 and the promoter of 6-SFT that encodes a key enzyme in synthesis of fructan in barley. EMSA was performed as described previously [1] using overexpressed and purified SUSIBA1 from *E. coli* (FIG. 8E to 8J). In accordance with the hallmark of WRKY proteins, it was shown that the SUSIBA2 TF bound to the W-box DNA cis-element. Further analysis of SUSIBA2 activity revealed that it also bound to the SUREa but not SP8a cis-element. Examination of the 6-SFT promoter led to identification of two SUREa, three W-box and one SP8a element (FIG. 8E). Using different combinations of the restriction enzymes BstXI, PvuII and SpeI, the full-length promoter (fragment 1) was resolved into four fragments (fragments 2-5, FIG. 8E). EMSA showed that SUSIBA1 could bind to fragments 1-4 containing one or more of the cis-elements, but not to fragment 5 lacking any of the elements (FIG. 8F). This indicated that SUSIBA1 might be able to bind SUREa and W-box and/or SP8a. EMSA with constructed oligonucleotide probes for individual elements (FIG. 8G) demonstrated that SUSIBA1 could indeed bind each element (FIG. 8H). To confirm the specificity of the binding activity, the element sequences (FIG. 8I) were engineered and the binding of SUSIBA1 was tested. EMSA showed that when the element sequences were substituted with an A stretch, SUSIBA1 binding activity was abolished (FIG. 8J), indicating that SUSIBA1 can interact with the 6-SFT promoter in vitro by binding to the SUREa, W-box and SP8a elements, with strong binding to the W-box. No binding activity of SUSIBA1 to the engineered element sequences, i.e., SP8a M, W-box M and SUREa M4 also indicated the reliability of EMSA in the assay system (FIG. 8J).

To obtain evidence for the in vivo interaction between SUSIBA1 and the 6-SFT promoter, 6-SFT p:GFP was co-infiltrated with p35S:SUSIBA1 and the influence of SUSIBA1 on 6-SFT promoter activity was monitored (FIG. 8K to 8O). The 6-SFT p:GFP construct alone, or co-infiltrated with an unrelated plant transcription factor (WRI1) in an environment of 100 mM Suc, had no effect on 6-SFT promoter activity (FIGS. 8K and 8L). In contrast, 6-SFT p:GFP co-infiltrated with p35S:SUSIBA1 eliminated the 6-SFT promoter activity (FIG. 8M). To confirm the de novo production of the SUSIBA1 protein in the infiltration area, living and dead agrobacterium cells containing p35S:SUSIBA1 were used and SUSIBA1 transcript and protein levels were compared in the infiltration area using p35S:WRI1 as a control (FIGS. 8N and 8O). As expected, infiltration with living agrobacterium cells gave much higher SUSIBA1 transcript and protein levels compared with the infiltrated dead cell background and the same for the control WRI1 transcript level (FIGS. 8N and 8O).

Figure 9:
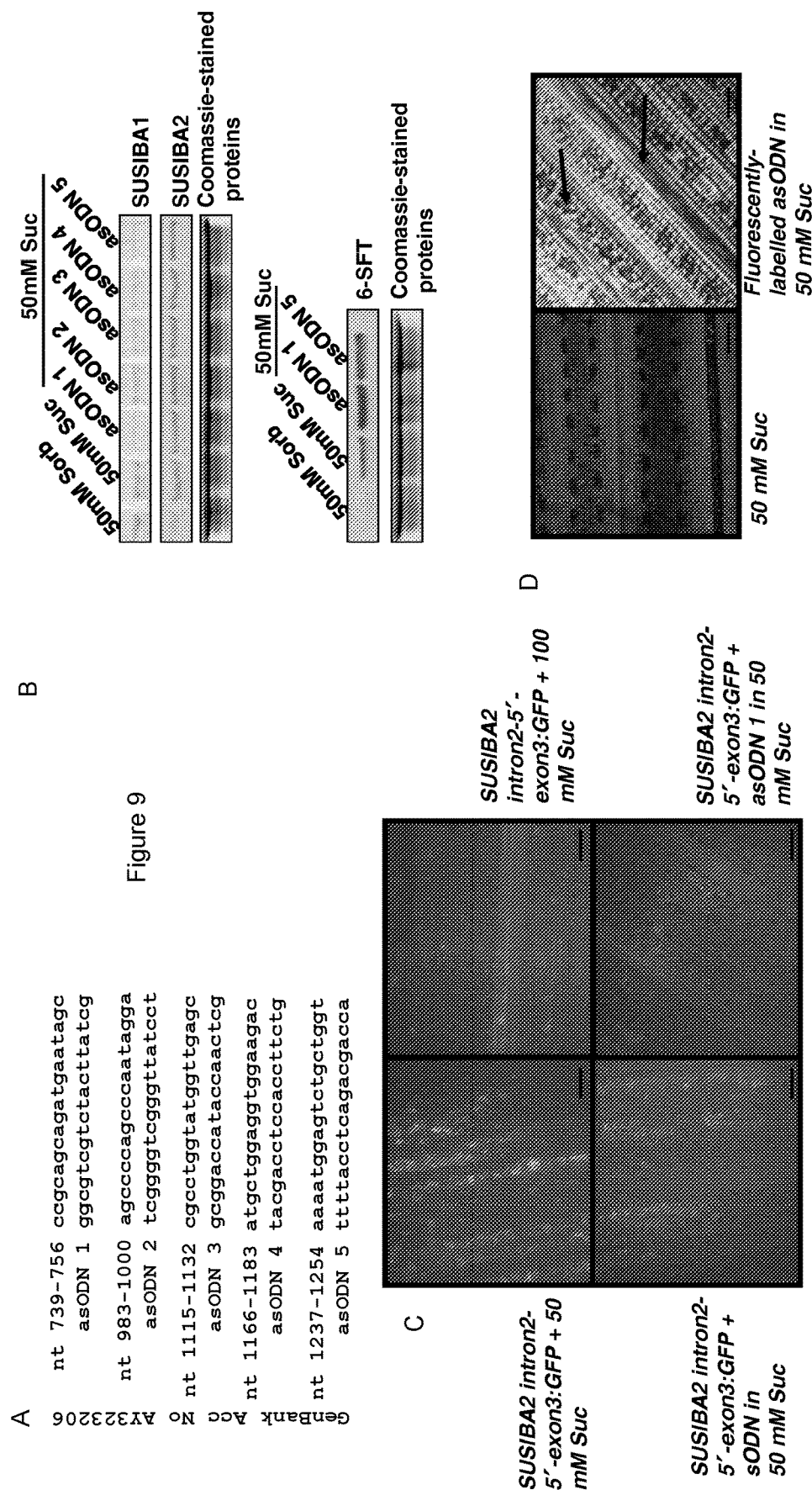
FIG. 9. asODN inhibition of SUSIBA1. (A) Sequence alignment of five selected asODNs, one against a region of SUSIBA2 cDNA overlapping part of the SUSIBA1 promoter (asODN 1), and against regions of SUSIBA1 and SUSIBA2 cDNAs (asODNs 2-5) (SEQ ID NO: 32-37, 116-119). (B) Western blot analysis of SUSIBA1 and SUSIBA2 levels after asODN inhibition with the five selected asODNs (upper panels) and of 6-SFT levels after inhibition of SUSIBA1 with asODNs 1 or 5 (lower panels). (C) Analysis of SUSIBA1 promoter activity after inhibition with asODN 1 against the SUSIBA1 promoter region. Inhibition efficiency with asODN 1 is compared with suppression of SUSIBA1 promoter activity by 100 mM sucrose (Suc; upper and lower panels on right side). Controls with 50 mM Suc and sense ODN (sODN) in 50 mM Suc are included (upper and lower panels on left side). (D) Uptake of a fluorescently labelled ODN in 50 mM Suc into barley leaf cells. Autofluorescence is shown (left panel) and fluorescently labelled ODN (white arrows) is visible in leaf cells (right panel) after 24 hr incubation. Bars in (C)=100 μm, and in (D)=50 μm.

The results so far suggested that SUSIBA1 has the ability to regulate fructan synthesis by repressing 6-SFT activity. To obtain conclusive evidence for this scenario, SUSIBA1 knockdown experiment was performed by antisense oligodeoxynucleotide (asODN) inhibition. The asODN inhibition strategy was selected based on its high reliability as a diagnostic tool for gene function, and its capacity to distinguish between genes of high sequence similarity. Depending on the target sequence, the typical modus operandi for asODN inhibition proceeds via RNase H-directed transcript cleavage, and/or triplet DNA strand formation at an active promoter site. Since the SUSIBA1 sequence overlaps with the 3' portion of the SUSIBA2, inhibiting SUSIBA1 without affecting SUSIBA2 posed a challenge. Therefore, five asODNs (FIG. 9A) were designed and their inhibition efficiency on SUSIBA1 and SUSIBA2 was tested, following the protocol described previously [2]. Two of the asODNs, asODNs 1 and 5, exhibited good inhibition of SUSIBA1 but not SUSIBA2 activity as judged by production of the SUSIBA1 and SUSIBA2 proteins (FIG. 9B, upper panels). The different inhibitory efficiencies of a given ODN at the same sequence regions of SUSIBA1 and SUSIBA2 might be due to different RNA secondary structures, e.g., stems, at the regions that prevent asODN binding. Further comparison between asODN 1 and asODN 5 based on their effect on 6-SFT protein levels identified asODN 1, which maps to the coding region of SUSIBA2 and promoter sequence of SUSIBA1, as the best candidate for the asODN inhibition experiment (FIG. 9B, lower panels). To confirm that asODN 1 interfered with SUSIBA1p activity, sucrose-treated barley leaves were co-infiltrated with SUSIBA1 p:GFP and asODN 1, or sense ODN (sODN). The results demonstrated that SUSIBA1 p activity was effectively inhibited by asODN 1 (FIG. 9C). A fluorescently labeled ODN was used to show efficient uptake of an asODN by barley leaf cells (FIG. 9D). Using asODN 1 against SUSIBA1 and a previously described asODN against SUSIBA2 [2] (named as Su2Antisense 1 in Table 1) at sucrose induction thresholds for fructan and starch synthesis (see FIGS. 4A, 4B for thresholds), the role of SUSIBA1 as a repressor for fructan, and SUSIBA2 is an activator for starch were established (FIGS. 10A, 10B, 11A, 11B, 12A, 12B).

SUSIBA1 and SUSIBA2 Constitute a Molecular Antagonistic System

Figure 13:
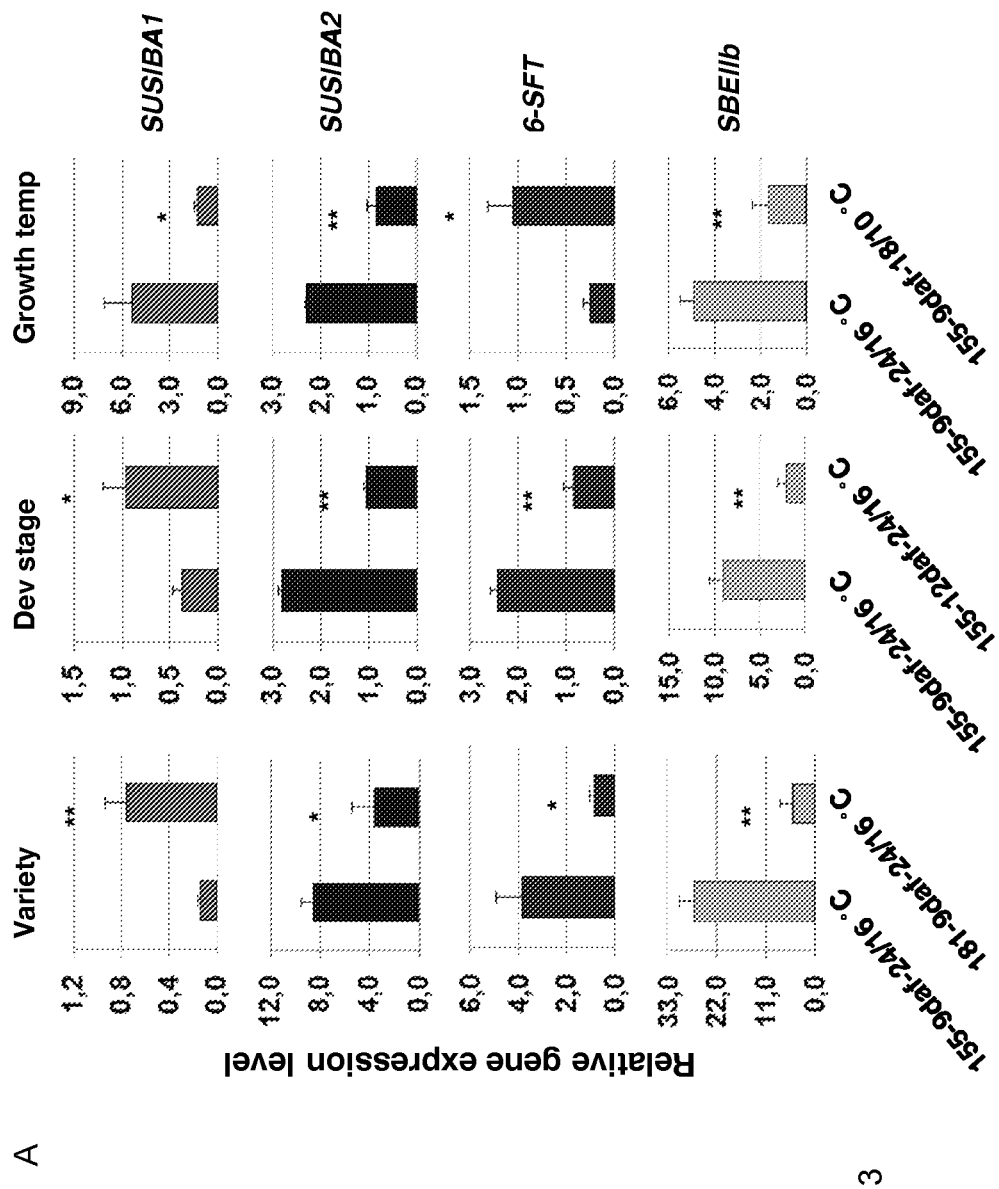
FIG. 13. Analysis of barley varieties with high and low seed fructan content. (A) qPCR analysis of SUSIBA1, SUSIBA2, 6-SFT and SBEIIb gene expression levels in high-fructan (variety 155) and low-fructan (variety 181) varieties at 9 days after flowering (daf; left panels), at different development stages of variety 155 (middle panels), and under different growth temperatures for variety 155 at 24/16° C. (d/n) or 18/10° C. (d/n) (right panels). (B) Western blot analysis of SUSIBA1, SUSIBA2, 6-SFT and SBEIIb protein levels for the corresponding varieties, development stages (Dev stage) and growth temperatures (Growth temp). (C) Analysis of fructan and starch content in the corresponding samples. Significant differences are indicated by asterisks between two samples in each panel. One-way ANOVA was used (Error bars show s.d. and *P≤0.05 or **P≤0.01). d, day; n, night. Dev stages of 9 and 12 days after flowering (9daf; 12daf) correspond to Z73-Z75 on the Zadoks scale in cereal development. Biological triplicates (n=3) with 10 seeds in each biological replicate were used for analyses of fructan and starch content and qPCR. Two independent experiments were performed for Western blot analysis.
Figure 13:
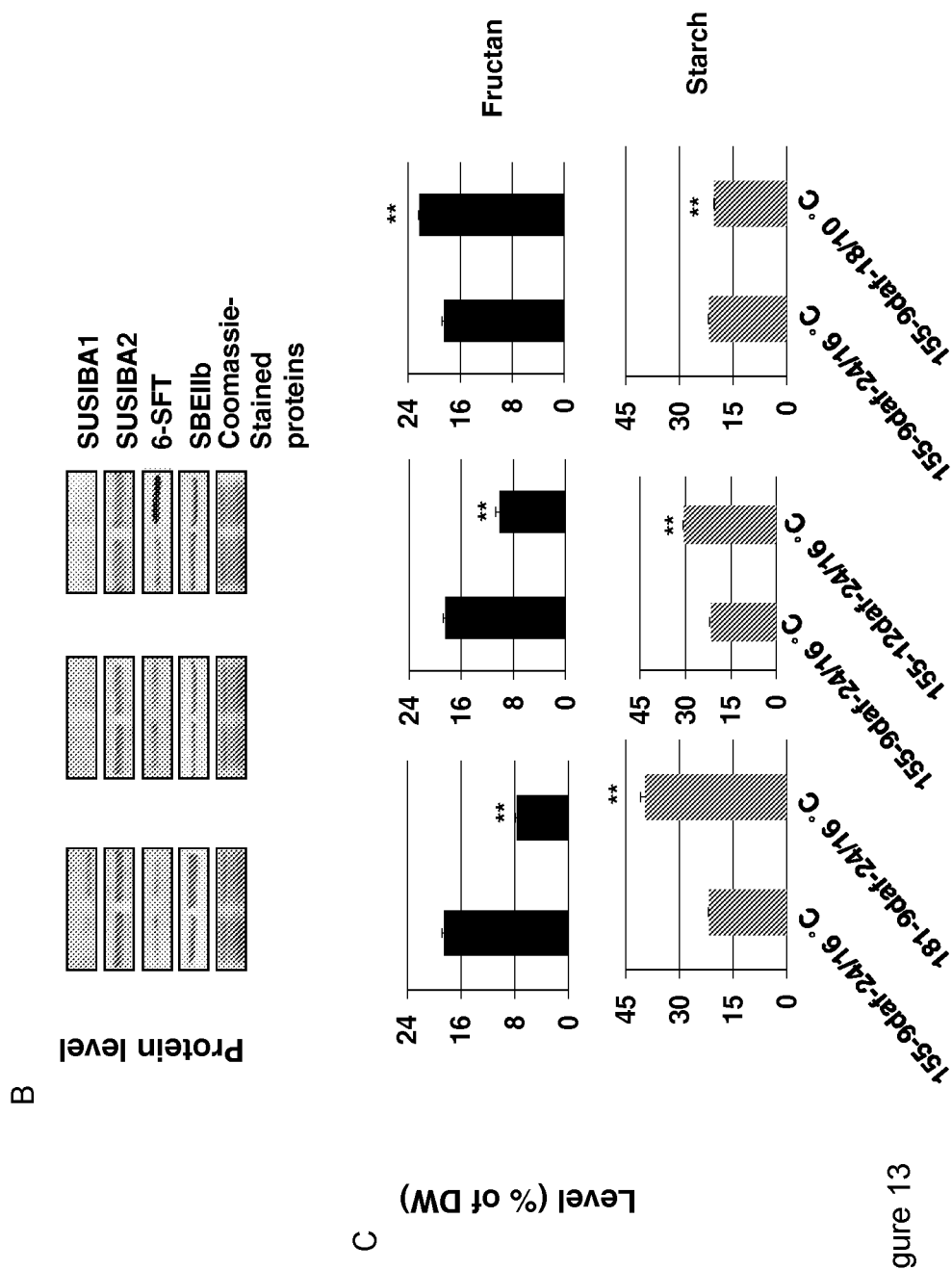
Figure 14:
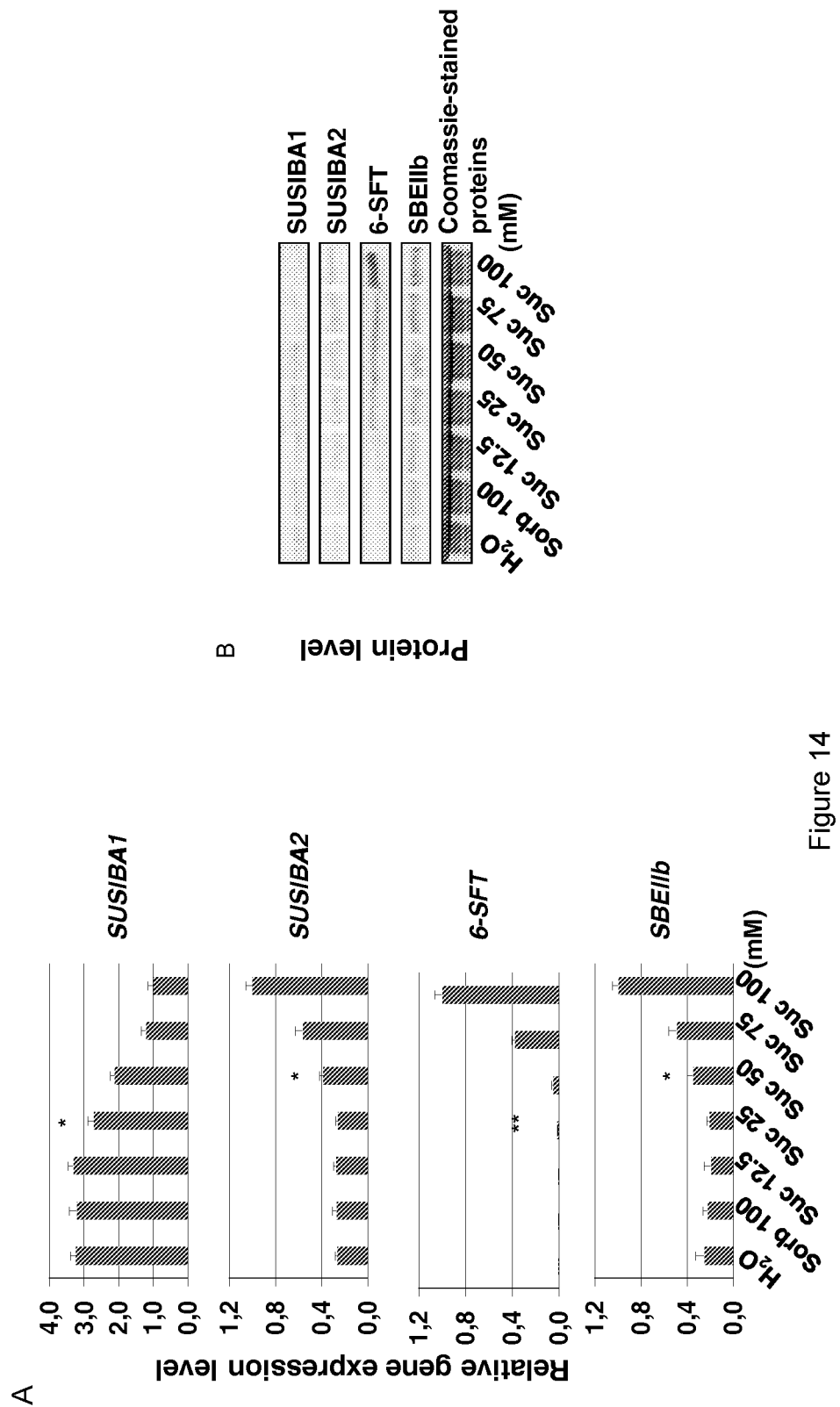
FIG. 14. Response of transcript and protein levels of SUSIBA1, SUSIBA2 and fructan (6-SFT) and starch (SBEIIb) genes to sucrose concentrations. (A) qPCR analysis of relative SUSIBA1, SUSIBA2, 6-SFT and SBEIIb expression levels in response to sucrose (Suc) concentrations. (B) Western blot analysis of SUSIBA1, SUSIBA2, 6-SFT and SBEIIb protein levels in response to sucrose concentrations. Daf, days after flowering; One-way ANOVA was used (Error bars show s.d.) *p≤0.05 and **p≤0.01 are shown when significant differences initiate between sucrose-treated samples and the control of 100 mM sorbitol (Sorb). Three independent experiments were performed for sugar induction and qPCR analysis (n=3), and two for Western blot analysis.
Figure 15:
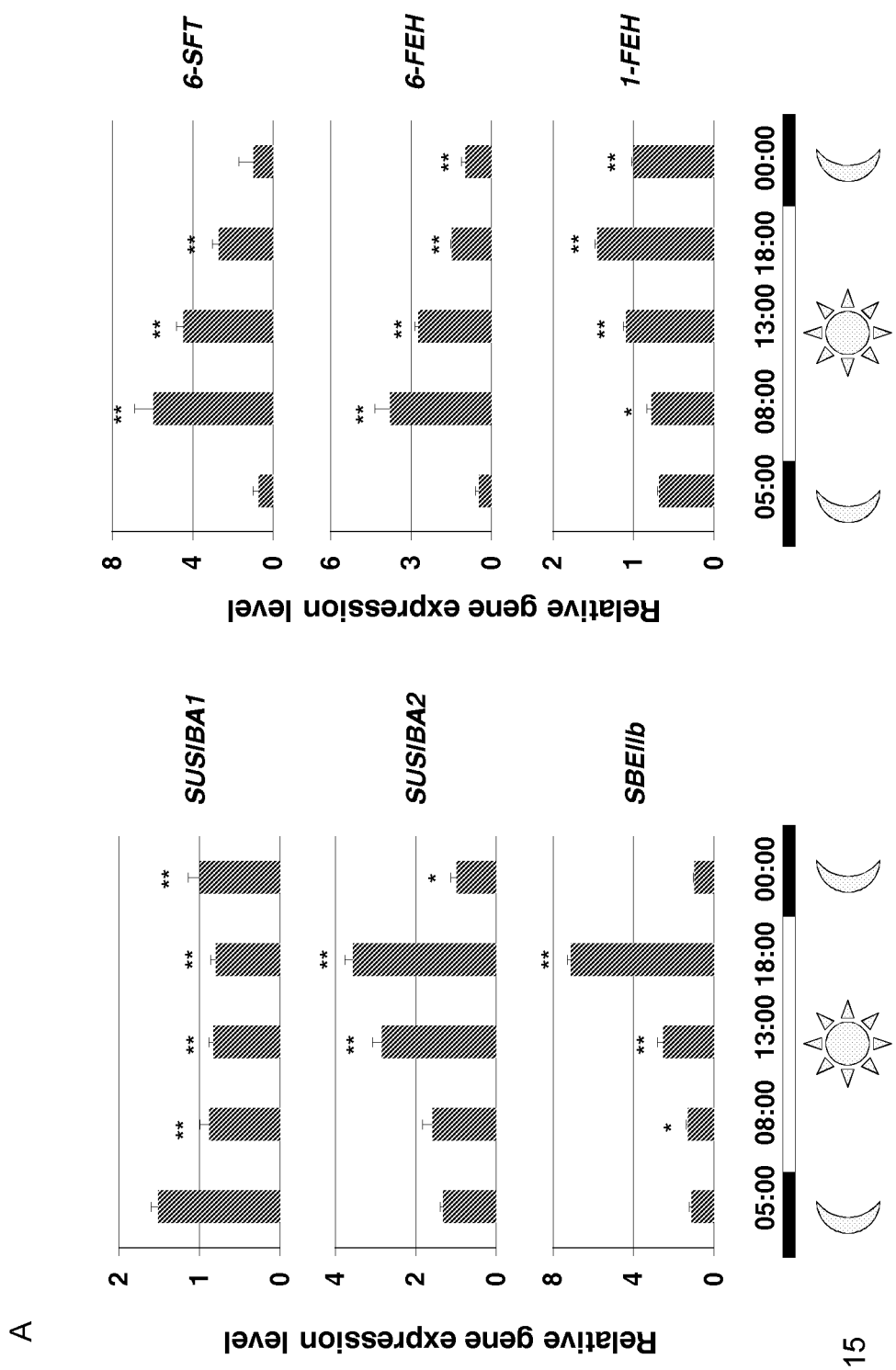
FIG. 15. Starch content and diurnal expression levels of SUSIBA1, SUSIBA2, and starch and fructan metabolic genes in barley sink leaves. (A) qPCR analysis of relative expression levels of SUSIBA1, SUSIBA2, SBEIIb, 6-SFT, 6-FEH and 1-FEH in barley sink leaves. (B) Starch and fructan content in corresponding samples. The time points for sample-harvesting are indicated and dark and light conditions are represented by solid and empty bars with the moon and sun symbols, respectively. One-way ANOVA was used (Error bars show s.d. and *p≤0.05 or **p≤0.01 compared with 05:00 am). Three independent experiments were performed (n=3).

The notion of SUSIBA1 as a repressor of fructan synthesis and SUSIBA2 as an activator of starch synthesis was further probed by evaluating the correlation between SUSIBA1 and SUSIBA2 expression levels and fructan and starch content in more natural conditions, i.e., in different barley varieties with high and low seed fructan content (FIGS. 13A, 13B), in sucrose-induction experiments (FIGS. 14A, 14B), and during diurnal fluctuations of starch and fructan accumulation (FIGS. 15A, 15B). The collective results illustrated a negative correlation between SUSIBA1 activity and fructan content, and a positive correlation between SUSIBA2 activity and starch content. SUSIBA1 and SUSIBA2 thereby constituted a molecular antagonistic system.

To examine how the intricate system that governs the synthesis of starch and fructan correlates with starch and fructan accumulation, the levels of starch and fructan were monitored in barley leaves during a 16 h-8 h day-night cycle (FIGS. 15A, 15B). After the onset of light, expression of SUSIBA2 increased, which stimulated the expression of starch-synthesis genes (e.g., SBEIIb) and resulted in a high accumulation of starch at the end of day (FIG. 15B). Notably, although SUSIBA1 expression was reduced to release and increase 6-SFT expression (FIG. 15A), no fructan accumulation was found during the light phase (FIG. 15B). A plausible explanation would be that the induction of fructan synthesis was being matched by an increased degradation. To probe this hypothesis, the expression levels of genes encoding fructan-degrading enzymes for 1-FEH and 6-FEH were investigated. As is shown in FIG. 15A, activity of 1-FEH and 6-FEH followed that of 6-SFT. This suggested that the dynamics of fructan metabolism is an important component of sink leaf development in barley.

Figure 16:
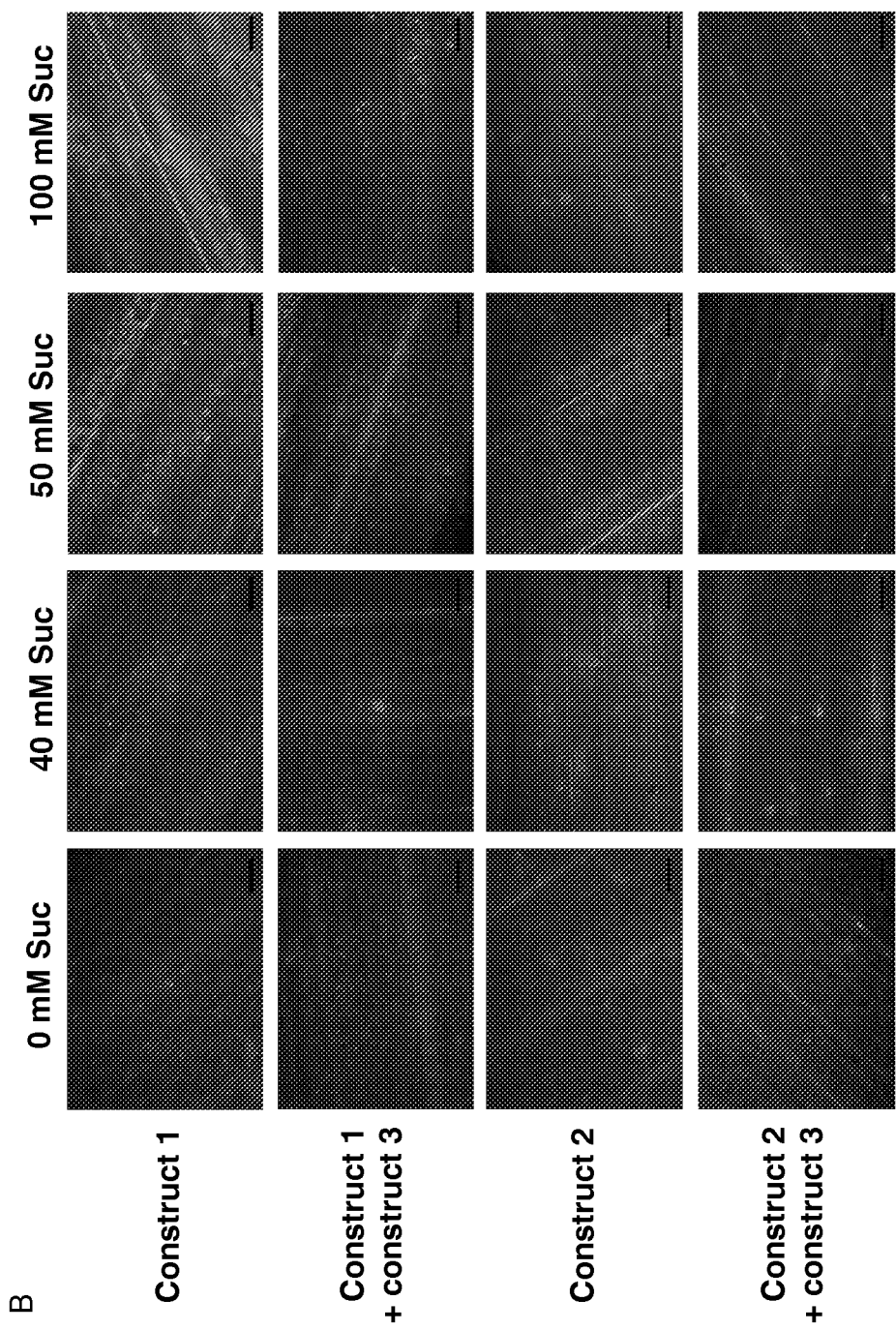
FIG. 16. Identification of a distal 5' region in the SUSIBA2 promoter that links SUSIBA1 repressive activity to SUSIBA2 sugar-responsive activity. (A) Constructs with different lengths of the SUSIBA2 promoter and a construct for SUSIBA1 overexpression were used for agroinfiltration in analysis of SUSIBA2 promoter activity. (B) SUSIBA2 promoter activity. The constructs were transformed into agrobacteria and infiltrated into barley leaves. Infiltrated barley leaves were incubated at different sucrose concentrations. Fluorescence was examined three days after infiltration under a microscope at a wave length of 460-500 nm. (C) Relative fluorescence intensity was quantified from triplicates. Significant differences between construct 1 and construct 1+construct 3 and between construct 2 and construct 2+construct 3 are statistically analyzed and indicated by asterisks (**p≤0.01 or *p≤0.05). One-way ANOVA was used (Error bars show s.d.) Bars=100 μm. Three independent experiments were performed (n=3).
Figure 16:
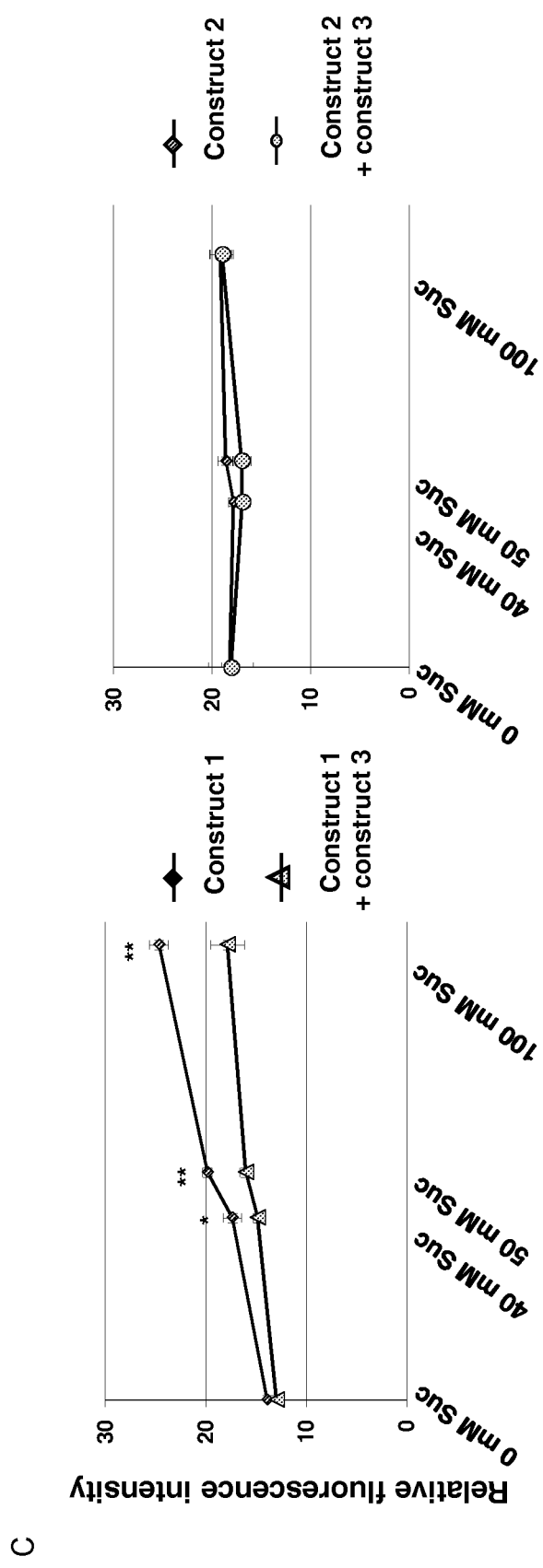
Figure 17:
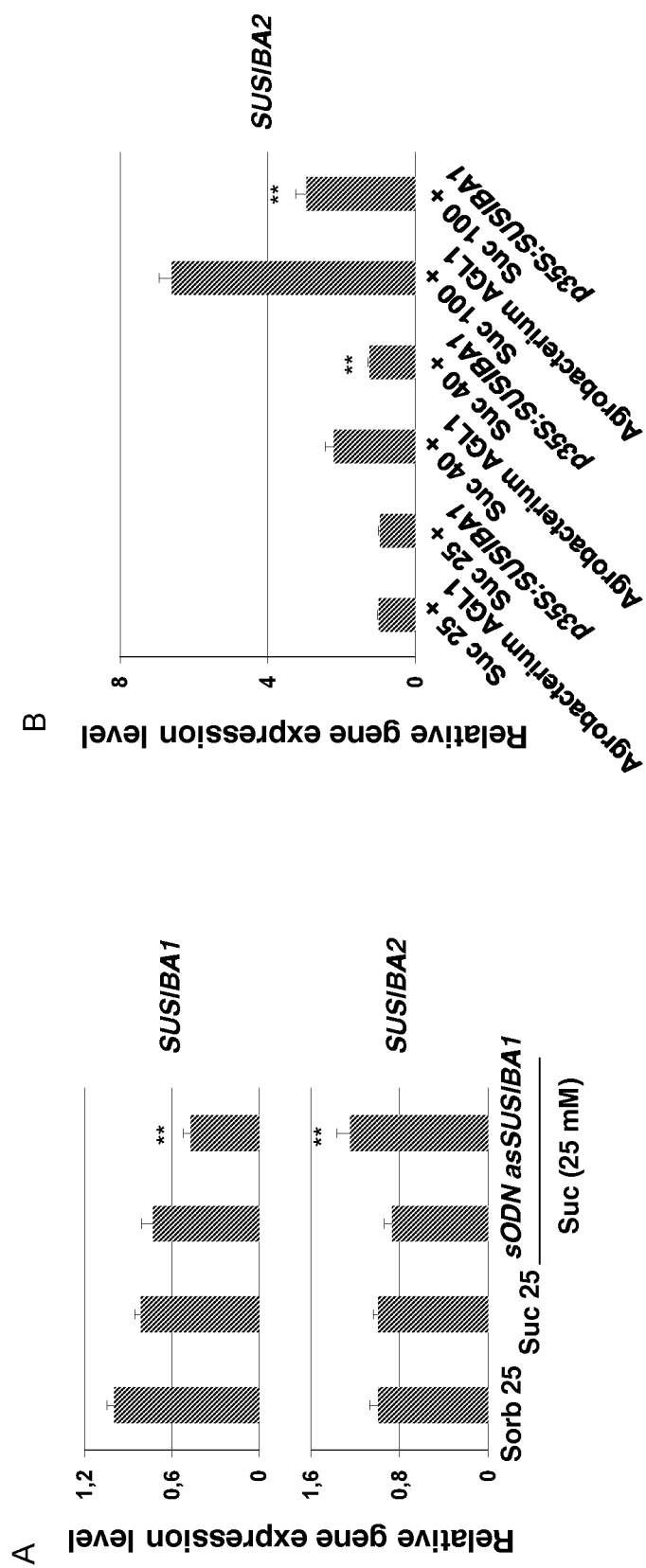
FIG. 17. SUSIBA1 repressive activity on the SUSIBA2 promoter obstructs SUSIBA2 self-promoting activity. (A, B) Antisense ODN inhibition of SUSIBA1 around a sucrose induction threshold level for SUSIBA2 expression (25 mM/40 mM) or overexpression/supply of SUSIBA1 at different Suc concentrations. Changes of SUSIBA2 transcript levels upon asODN inhibition of SUSIBA1 (A) or overexpression of SUSIBA1 (B) were analyzed by qPCR. (C) SUSIBA2 self-promoting activity upon asODN inhibition of SUSIBA1. Changes of SUSIBA2 transcript levels upon overexpression of SUSIBA2 after asODN inhibition of SUSIBA1 were analyzed by qPCR. Significant differences are indicated by asterisks (**p≤0.01) between asSUSIBA1 and sODN in (A), between p35S:SUSIBA1 and corresponding agrobacterial controls at different sucrose concentrations in (B), and between *agrobacterium* AGL1 at 40 mM Suc and the corresponding treatments at 40 mM Suc in (C). One-way ANOVA was used (Error bars show s.d.) Three independent experiments were performed (n=3).
Figures 17, 18:
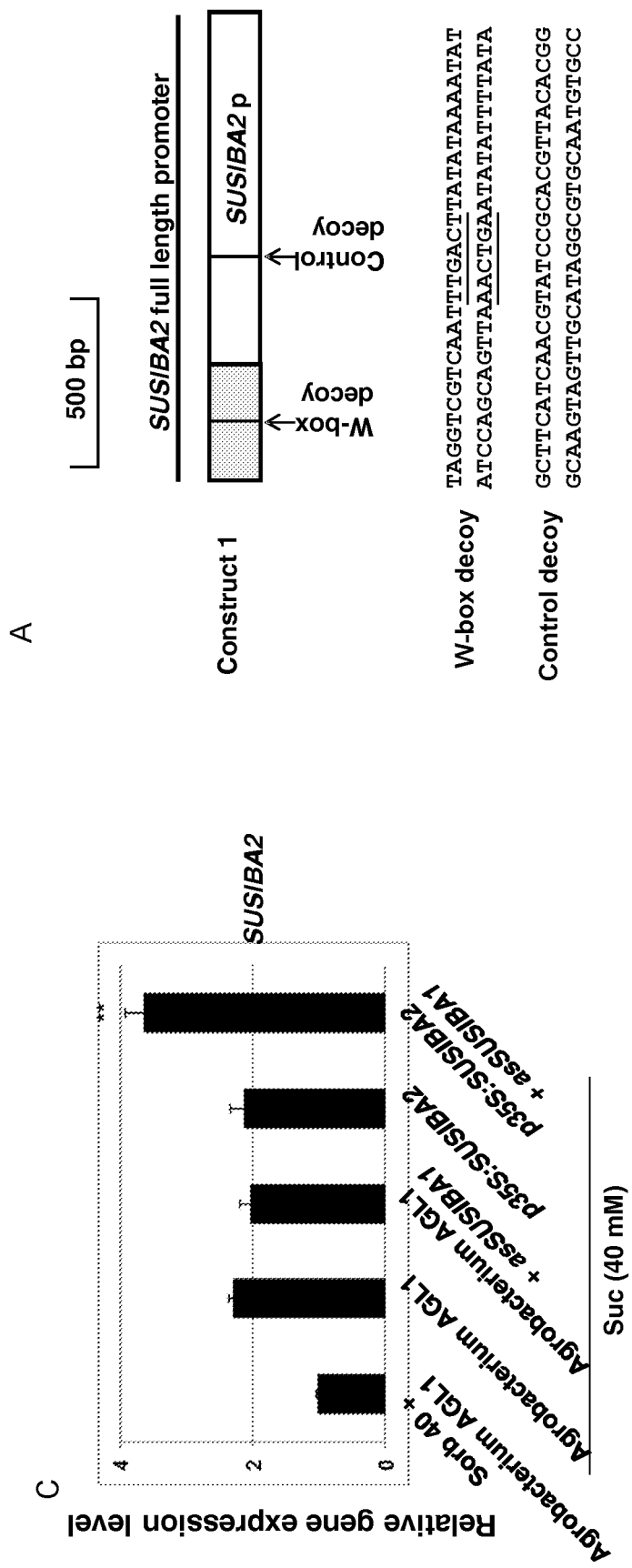
FIG. 18. SUSIBA1/SUSIBA2 competitive binding on a W-box in the SUSIBA2 promoter drives SUSIBA2 expression. (A) A short oligo sequence selected from the distal 5' sugar-responsive region of the SUSIBA2 promoter covering a W-box (underlined) in the region and a control oligo sequence of the same length without any W-box randomly selected from the SUSIBA2 promoter (SEQ ID NO: 108-111). Both oligo sequences are used as double-stranded oligonucleotides for decoy trapping and EMSA experiments. The oligo positions are as indicated in the SUSIBA2 promoter. (B) Transcript levels of SUSIBA2 analyzed by qPCR after co-infiltration of agrobacteria containing p35S:SUSIBA1 with the double-stranded decoy oligoes at 40 mM Suc. The infiltrated leaves were incubated at 40 mM Suc. Two days after infiltration and incubation, qPCR analysis was performed. (C) Transcript levels of SUSIBA2 after co-infiltration of agrobacteria containing p35S:SUSIBA2 with the double-stranded decoy oligoes upon antisense inhibition of SUSIBA1. (D) Transcript levels of SUSIBA2 after infiltration of agrobacteria containing p35S:SUSIBA2 alone or the double-stranded decoy oligoes alone at 100 mM Suc. The infiltrated leaves were incubated at 100 mM Suc for two days before analysis. Significant differences are analyzed statistically between p35S:SUSIBA1 and decoy oligoes, and indicated by asterisks (**p≤0.01) in (B), and between p35:SUSIBA2 and decoy oligoes in (C), and between p35:SUSIBA2 and decoy oligoes in (D). One-way ANOVA was used (Error bars show s.d.) Three independent experiments were performed (n=3). (E) EMSA analysis of competitive activity to the W-box in the SUSIBA2 promoter between SUSIBA2 and SUSIBA1. EMSA of binding activity to the W-box of SUSIBA2 (left panel) and SUSIBA1 (middle panel) and SUSIBA2 and SUSIBA1 in competing (right panel). SUSIBA2 and SUSIBA1 were overexpressed and purified from E. coli and challenged with two oligoes. EMSA was performed in presence (+) or absence (−) of SUSIBA 2 (0.2 μg) and SUSIBA1 (0.2 μg) or in presence of SUSIBA2 (0.2 μg) with an increase of SUSIBA1 (0.0125, 0.025, 0.05, 0.1 and 0.2 μg) for the competitive activity assay. The position of the free DNA probe is indicated.
Figure 18:
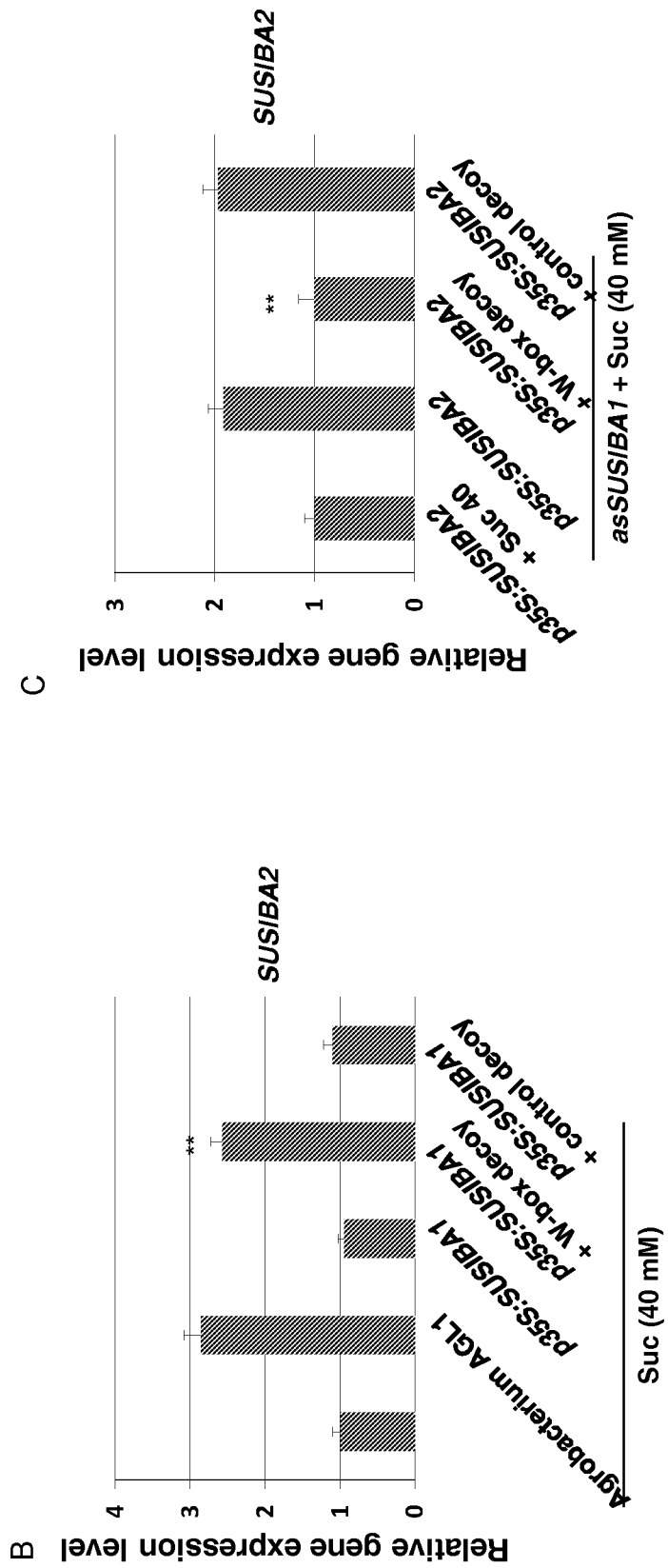
Figure 19:
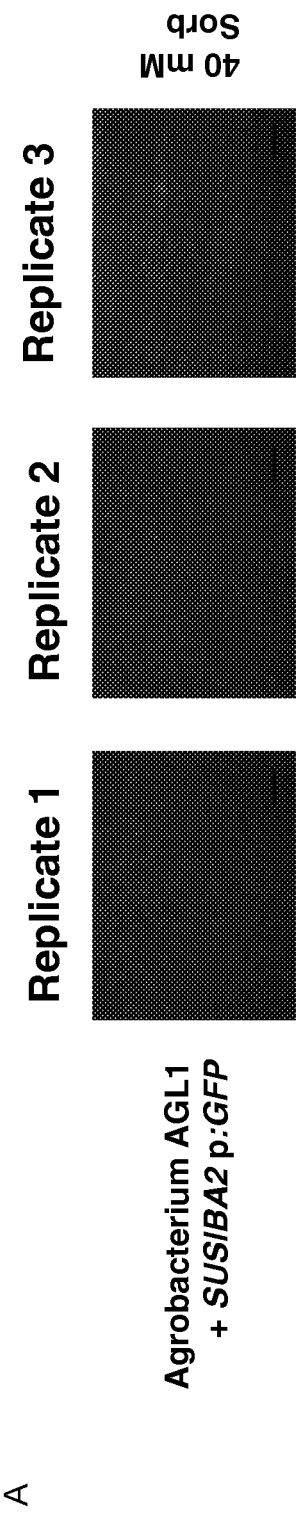
FIG. 19. Fluorescent analysis of SUSIBA2/SUSIBA2 self-promoting activity upon asODN inhibition of SUSIBA1 using the SUSIBA2 p:GFP construct. (A) The SUSIBA2 p:GFP construct was co-infiltrated with the combinations in FIG. 17C to monitor SUSIBA2 promoter activity. Three days after infiltration, fluorescence was examined under a microscope at a wave length of 460-500 nm. (B) Relative fluorescence intensity was quantified. Significant differences are indicated by asterisks (*p≤0.05) between agrobacterium AGL1 at 40 mM Suc and the corresponding treatments at 40 mM Suc. One-way ANOVA was used (Error bars show s.d.) Three independent experiments were performed (n=3). Bars=100 μm.
Figure 19:
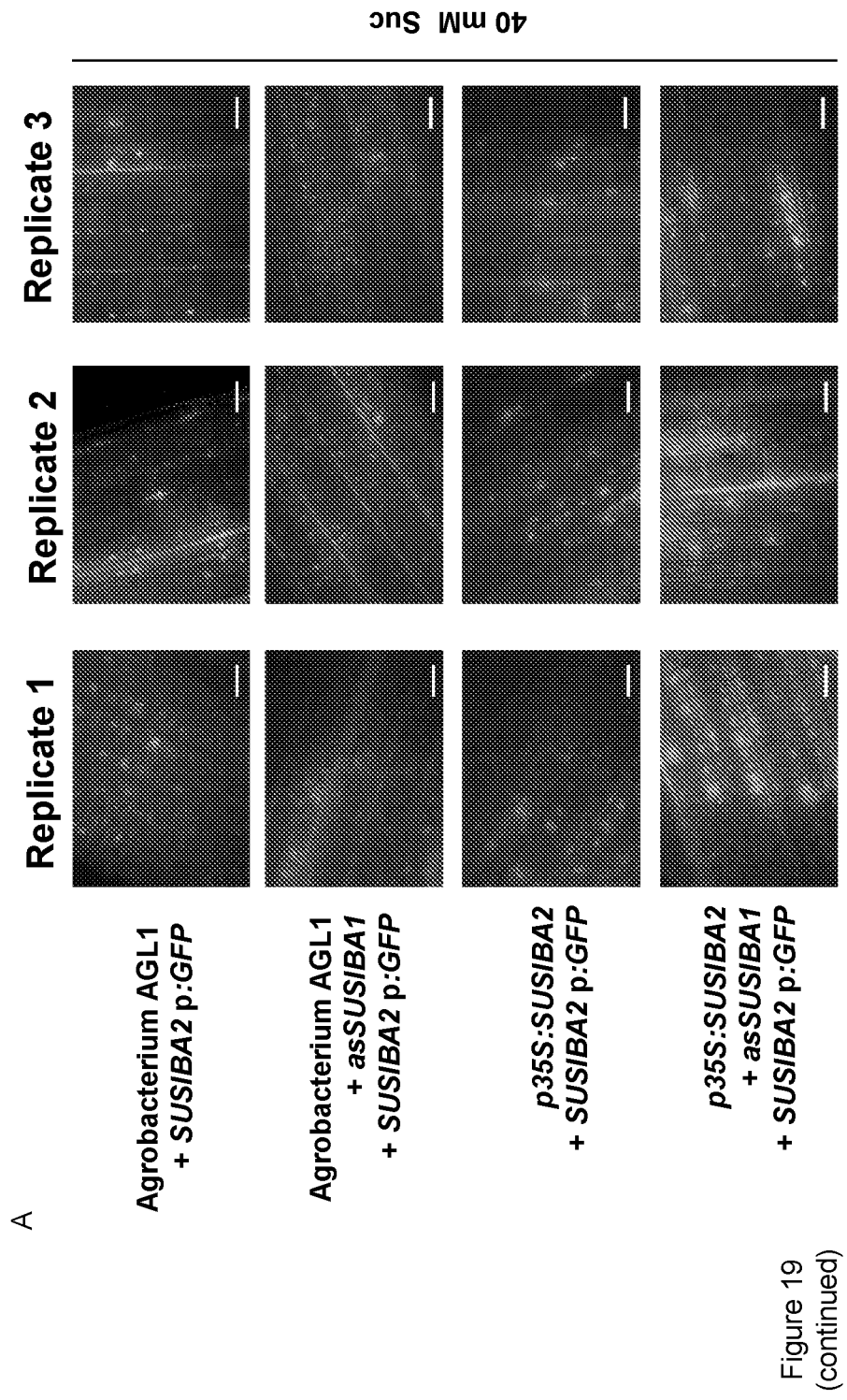
Figure 19:
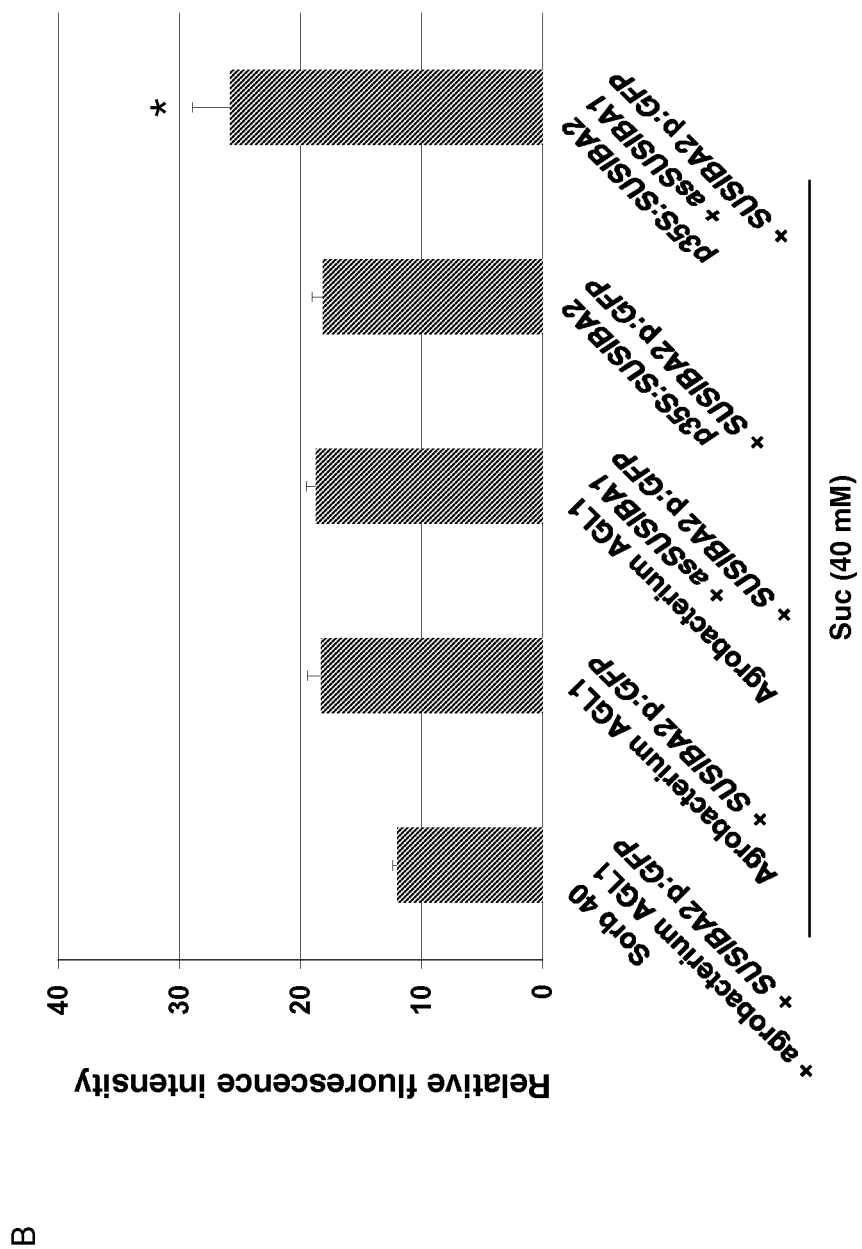
Figure 20:
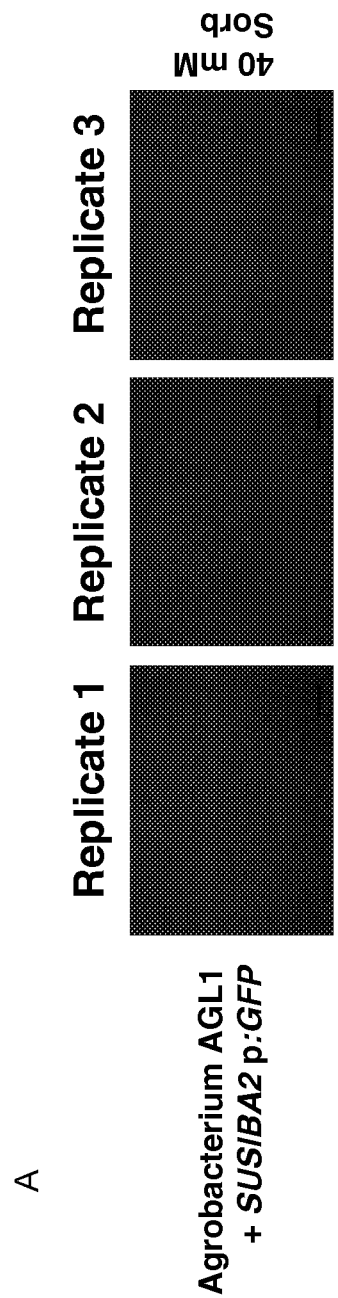
FIG. 20. Fluorescent analysis of the W-box role in SUSIBA1 repressive activity on the SUSIBA2 promoter activity using the SUSIBA2 p:GFP construct. (A) The SUSIBA2 p:GFP construct was co-infiltrated with the combinations in FIG. 18B to monitor SUSIBA2 promoter activity. Three days after infiltration, fluorescence was examined under a microscope at a wave length of 460-500 nm. (B) Relative fluorescence intensity was quantified. Significant differences are analyzed statistically between p35S:SUSIBA1 and decoy oligoes, and indicated by asterisks (**p≤0.01). One-way ANOVA was used (Error bars show s.d.) Three independent experiments were performed (n=3). Bars=100 μm.
Figure 20:
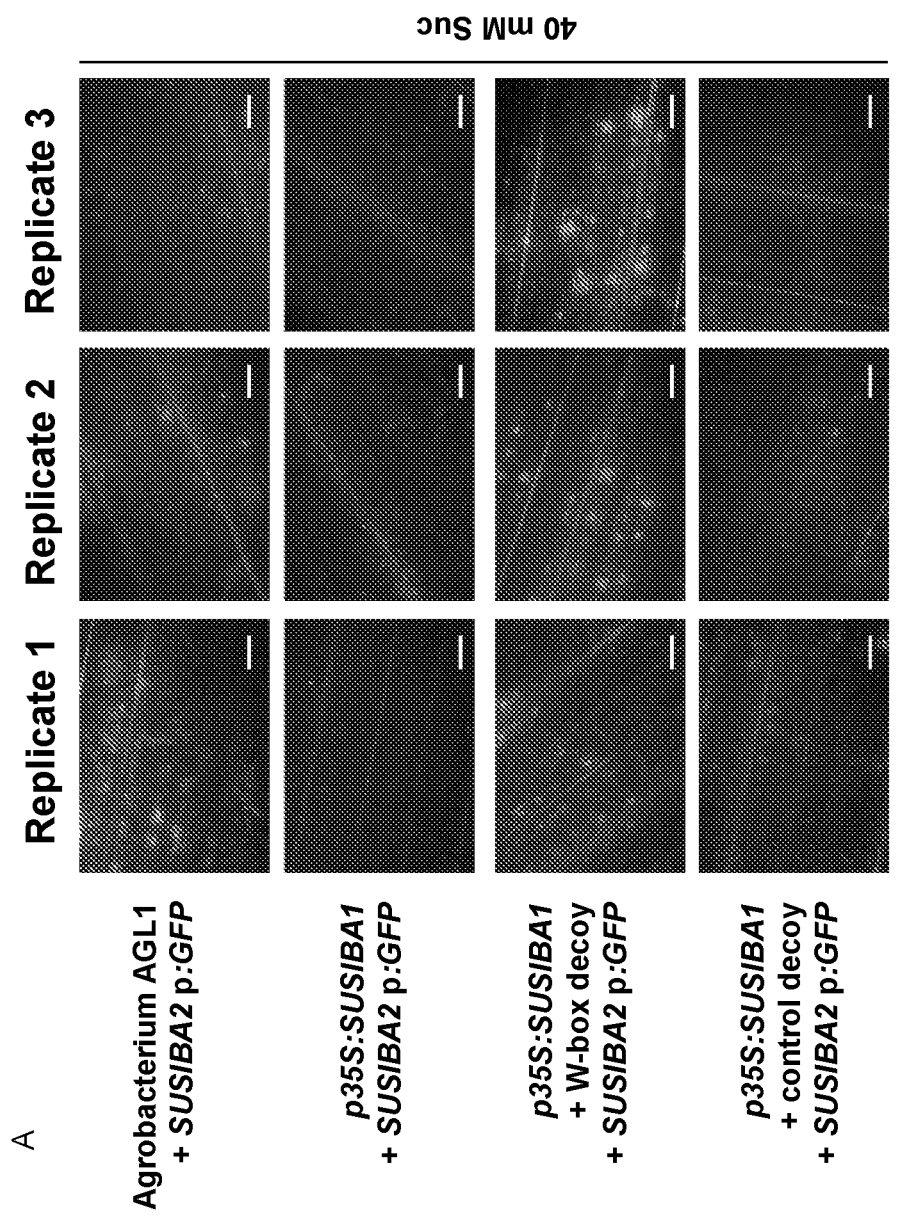
Figure 20:
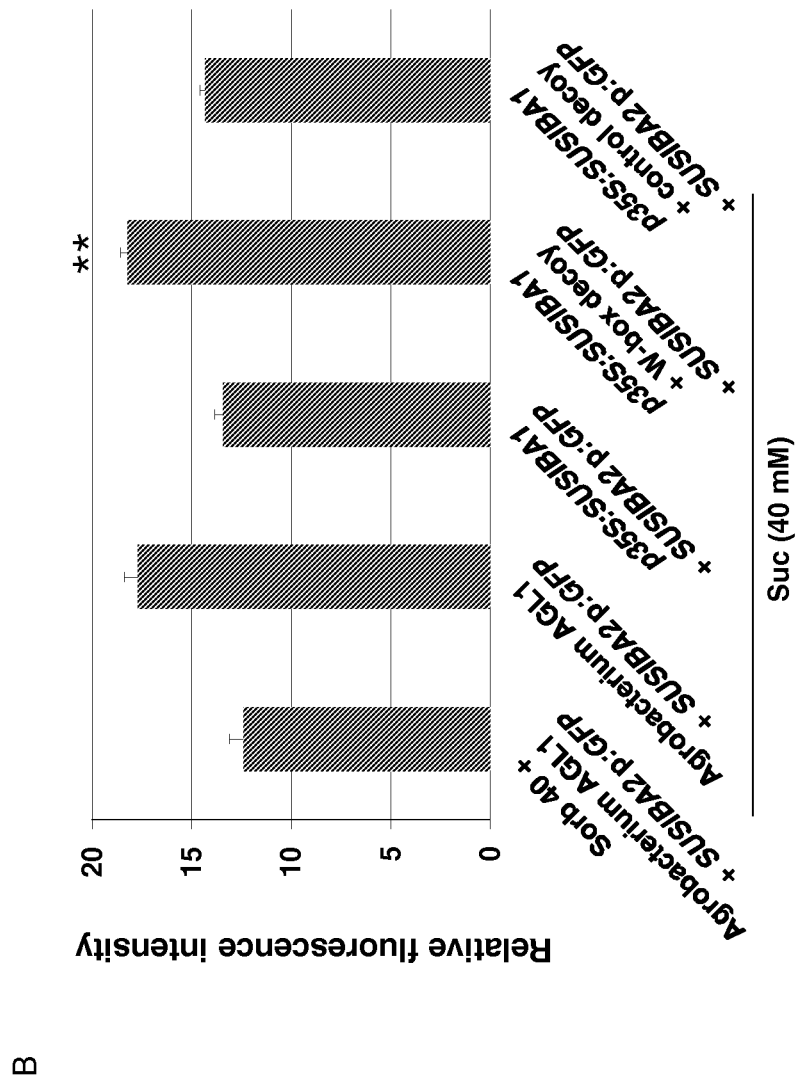
Figure 21:
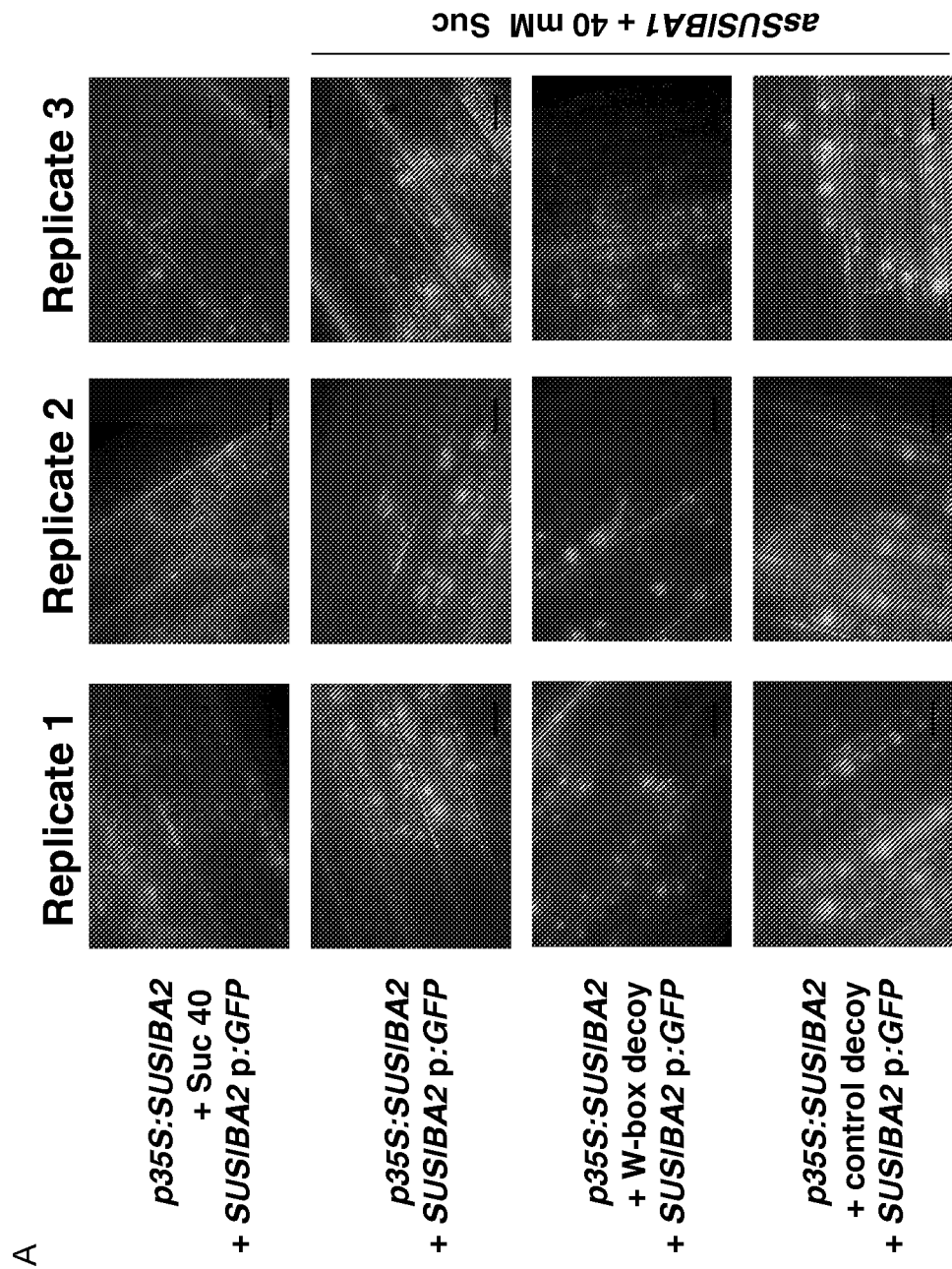
FIG. 21. Fluorescent analysis of the W-box role in SUSIBA1/SUSIBA2 self-promoting activity using the SUSIBA2 p:GFP construct when SUSIBA1 was inhibited. (A) The SUSIBA2 p:GFP construct was co-infiltrated with the combinations in FIG. 18C to monitor SUSIBA2 promoter activity. Three days after infiltration, fluorescence was examined under a microscope at a wave length of 460-500 nm. (B) Relative fluorescence intensity was quantified. Significant differences are analyzed statistically between p35S:SUSIBA2 and decoy oligoes, and indicated by asterisks (**p≤0.01). One-way ANOVA was used (Error bars show s.d.) Three independent experiments were performed (n=3). Bars=100 μm.
Figure 21:
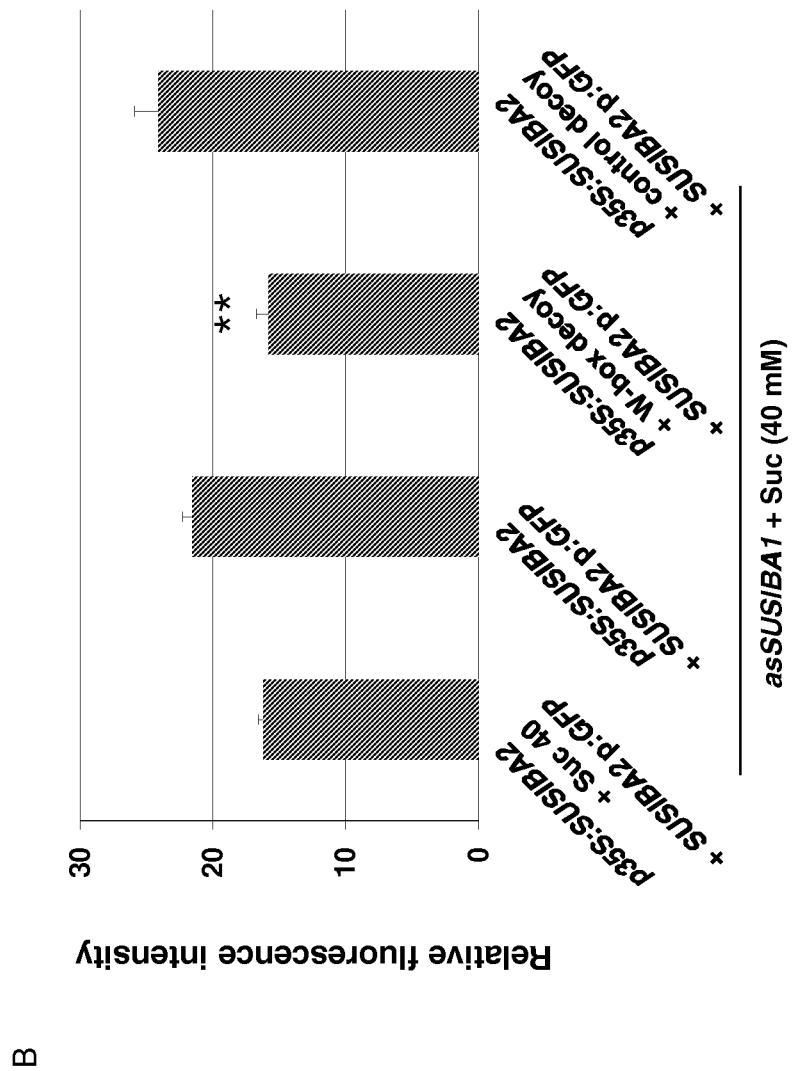
Figure 22:
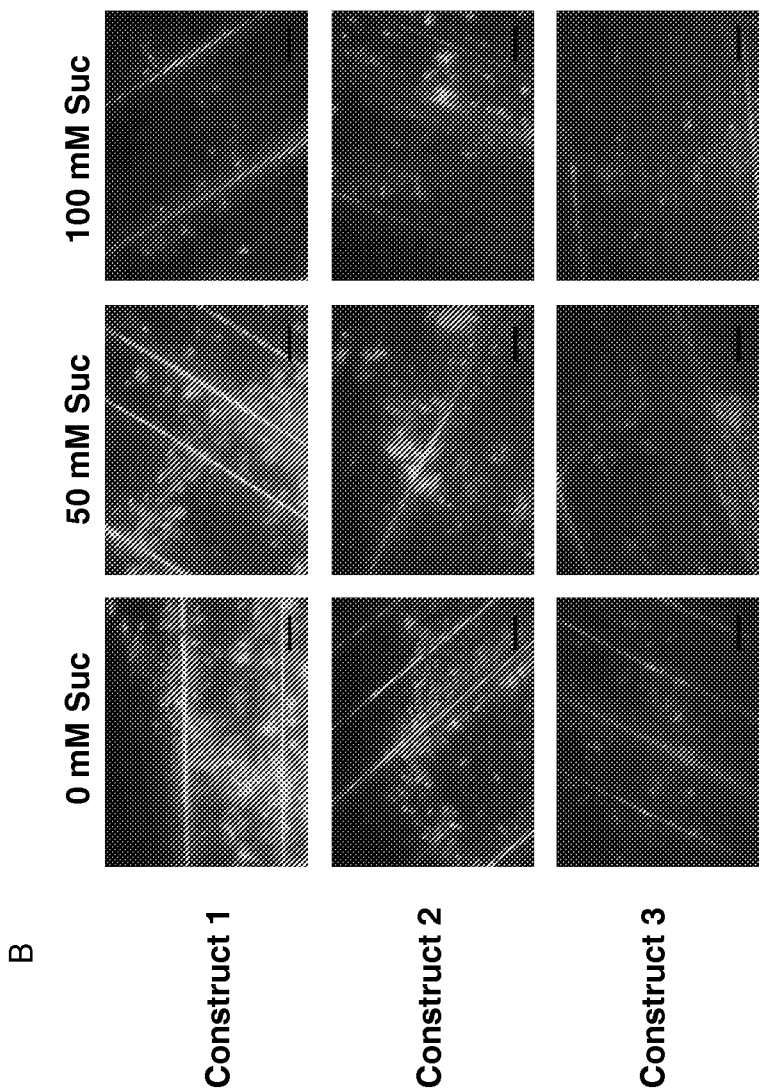
Figure 22:
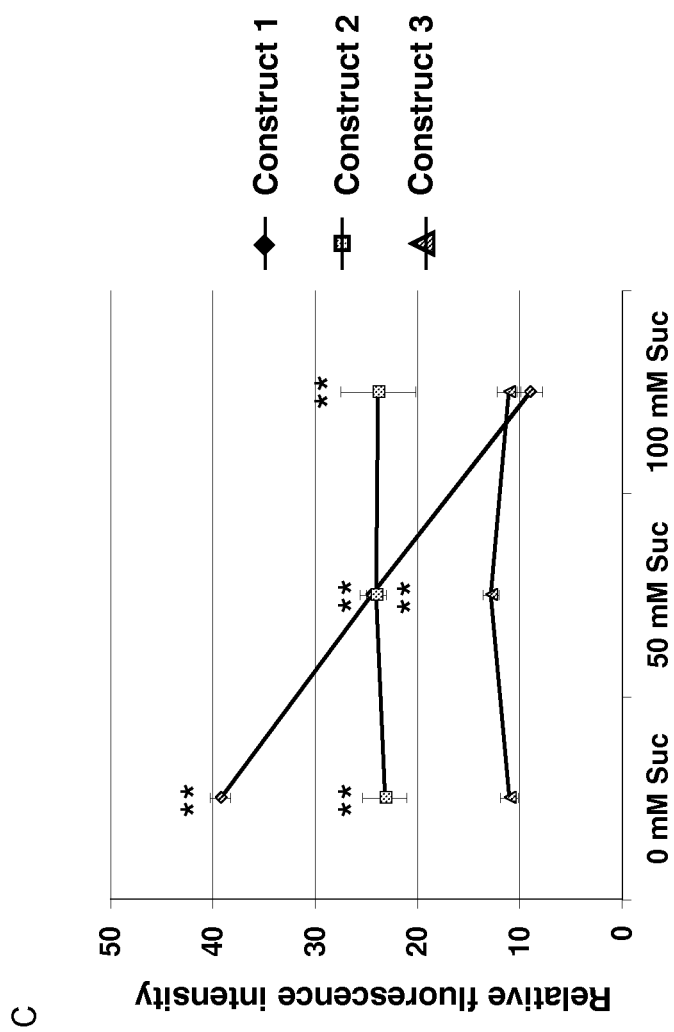

Competitive Binding by SUSIBA2 and SUSIBA1 to a W-Box in the SUSIBA2 Promoter Drives the Antagonistic System and SUSIBA2 Expression Identification of the antagonistic system prompted the question as to how the differential activity of the two alternative promoters and the antagonistic system is executed. This question was addressed by a suite of approaches, including promoter deletion, asODN inhibition, double-stranded decoy oligo TF trapping, overexpression by infiltration, DNA sequencing, and EMSA. When different lengths of the SUSIBA2 promoter were fused to the GFP reporter gene, and agroinfiltrated into barley leaves, the full-length promoter responded to sucrose concentrations as expected, whereas no or little response was found for the truncated promoter lacking 25% of the 5' end (FIGS. 16A-16O). This observation indicated that the sugar-responsive sequence is located in the distal 5'-end of the SUSIBA2 promoter. Co-infiltration of the full-length version of SUSIBA2 p:GFP with 35p:SUSIBA1 also virtually abolished the SUSIBA2 promoter activity (FIGS. 16B and 16C), suggesting that SUSIBA1 represses SUSIBA2 activity by binding to the far 5' region of the SUSIBA2 promoter. This notion is seemingly in disagreement with the results presented in FIGS. 11A, 11B, where asODN inhibition of SUSIBA1 did not change SUSIBA2 expression at 40 mM Suc. It was hypothesized that, at 40 mM Suc, SUSIBA1 expression is already decreased and any de-repression of SUSIBA2 activity by further decreasing the SUSIBA1 titer is not noticeable. Activation of SUSIBA2 expression, however, by asODN inhibition of SUSIBA1 at 25 mM Suc, the low side of the sucrose induction threshold for SUSIBA2 expression (25 mM/40 mM) (FIG. 17A) and at different Suc levels in the absence or presence of overexpressed SUSIBA1 (FIG. 17B) clearly suggested that SUSIBA1 acts as a repressor for SUSIBA2 expression. Interestingly, when SUSIBA1 was inhibited, supply/overexpression of SUSIBA2 could promote SUSIBA2 expression, suggesting that SUSIBA2/SUSIBA2 has self-promoting activity when SUSIBA1 is low or that the self-promoting activity is obstructed by SUSIBA1 repressive activity (FIGS. 17C, 19A, 19B). From the previous EMSA experiment (FIG. 8E to 8J), it was shown that SUSIBA1 could efficiently bind to W-box motifs. Search for W-boxes in the sugar-responsive distal 5'-end of the SUSIBA2 promoter revealed a W-box. Adopting the decoy oligo TF trapping technology, a decoy oligo covering the W-box and a control decoy oligo without any W-box randomly selected from the SUSIBA2 promoter were designed (FIG. 18A). When the decoy oligos were co-infiltrated with p35S:SUSIBA1, the W-box decoy oligo abolished SUSIBA1 repression of sugar-responsive SUSIBA2 expression (FIGS. 18B, 20A, 20B), implying that the W-box in the SUSIBA2 promoter are the cognate binding site for the SUSIBA1 repressor. W-boxes are also targets for SUSIBA2 activation of downstream genes. A hypothesis is that SUSIBA1 and SUSIBA2 compete for the W-box in the SUSIBA2 promoter. In support for this hypothesis, overexpression of SUSIBA2 at 40 mM Suc could enhance SUSIBA2 expression upon inhibition of SUSIBA1 (FIGS. 17C, 19A, 19B), and the W-box decoy oligo trapping targeting SUSIBA2 in a background of low SUSIBA1 expression dramatically reduced the positive action of SUSIBA2 on SUSIBA2 expression (FIGS. 18C, 18D, 21A, 21B). Low SUSIBA1 expression was achieved through a high Suc concentration (100 mM, FIG. 18D), or by asODN inhibition (FIGS. 17C, 18C, 19, A, 19B, 21A, 21B). It was observed that, at 100 mM Suc, infiltration of the p35S: SUSIBA2 construct did not significantly increase endogenous SUSIBA2 expression, analyzed by SUSIBA2 mRNA 5'-end specific primers covering only the endogenous SUSIBA2 but not the construct sequence, possibly due to redundancy in activation by high Suc concentration and exogenous introduction of SUSIBA2 (FIG. 18D).

Further evidence for the concept of W-box competition was provided by EMSA experiments demonstrating that with the SUSIBA2 W-box decoy oligo as a probe, SUSIBA1 could effectively prevent SUSIBA2's binding activity to the W-box (FIG. 18E).

Figures 18, 22:
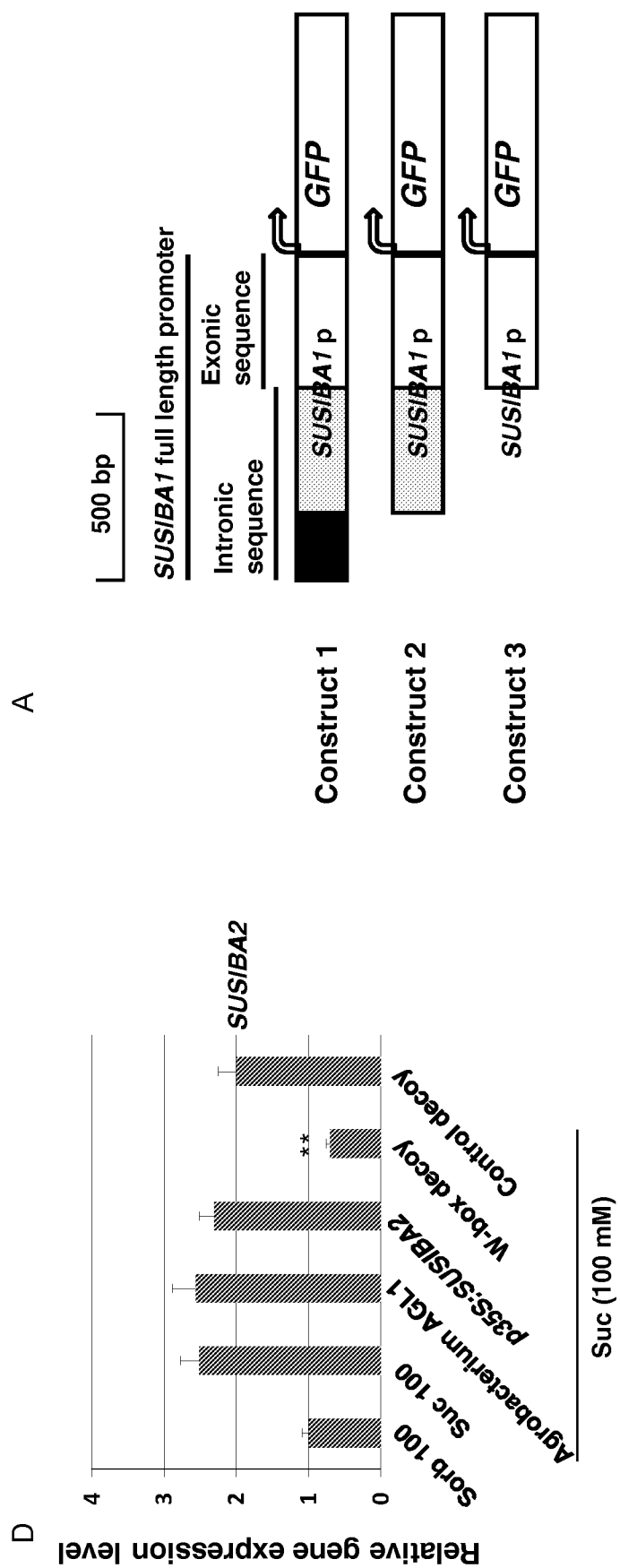
FIG. 22. Analysis of SUSIBA1 promoter activity. (A) Constructs of different lengths of the SUSIBA1 promoter for agroinfiltration in analysis of SUSIBA1 promoter activity. (B) SUSIBA1 promoter activity. The constructs were transformed into agrobacteria and infiltrated into barley leaves. Infiltrated barley leaves were incubated at different sucrose concentrations. Fluorescence was examined three days after infiltration under a microscope at a wave length of 460-500 nm. (C) Relative fluorescence intensity was quantified from triplicates. Significant differences between construct 1 and construct 3 and between construct 2 and construct 3 are statistically analyzed and indicated by asterisks (**p≤0.01). One-way ANOVA was used (Error bars show s.d.) Three independent experiments were performed (n=3). Bars=100 μm.
Figure 18:
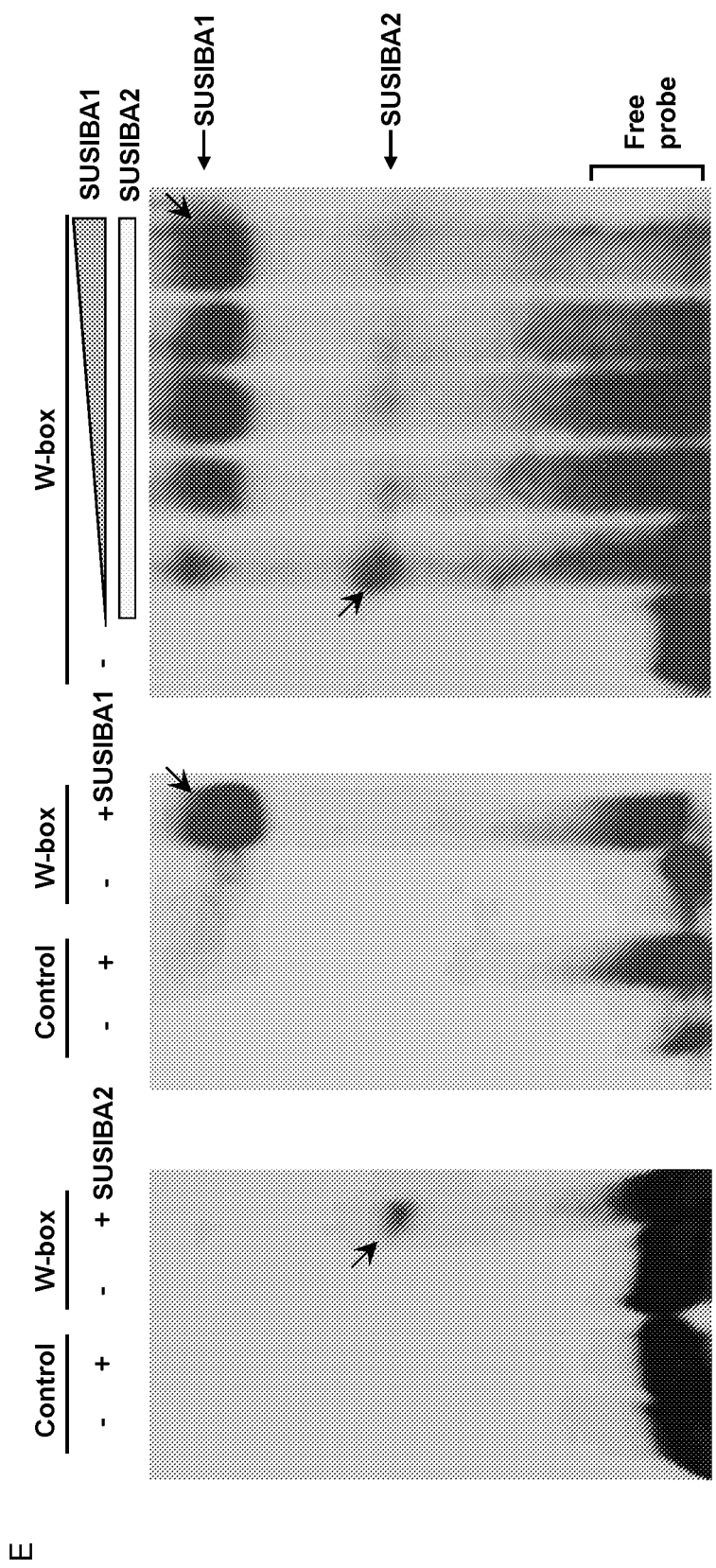
Figure 23:
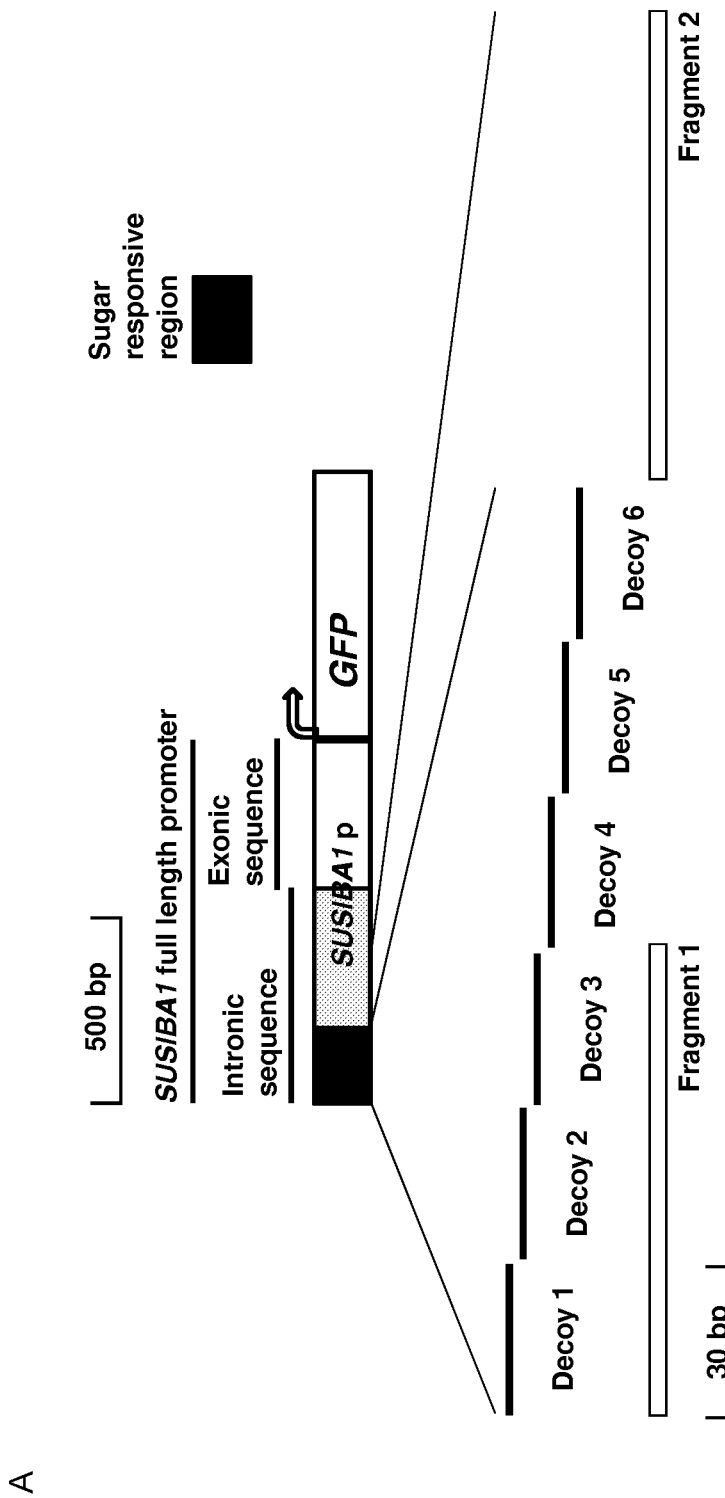
FIG. 23. Identification of a sugar-responsive cis sequence and the corresponding trans activity on the SUSIBA1 promoter. (A) Strategy for identification of sugar-responsive cis sequences and possible trans activity. The sugar-responsive region identified in the SUSIBA1 promoter was used for designing 6 decoy oligo sequences. One DNA fragment (Fragment 1) covering decoys 1-3 and a control DNA fragment (Fragment 2) covering a non-sugar-responsive region were generated by restriction enzymes, XbaI and BstXI for analysis. (B) Individual sequences of the 6 decoy oligoes (SEQ ID NO: 80-91). (C) Transcript levels of SUSIBA1 after infiltration with different decoy oligoes and incubation at different sucrose concentrations. (D) EMSA of nuclear protein extracts from leaves treated at different sugar concentrations. Fragments 1 and 2 (left panel) and decoy oligoes 2 and 3 (right panel) were used in EMSA analysis. EMSA was performed in the absence (−) or presence (+) of the nuclear protein extracts. The position of the free probe is indicated. Binding activity displayed as band shifts is indicated with arrows. Significant differences are indicated by asterisks (**p≤0.01) between decoy oligoes and H2O, 50 mM Suc or 100 mM Suc in (C). One-way ANOVA was used (Error bars show s.d.) Three independent experiments were performed for decoy oligo trapping and qPCR analysis (n=3).
Figure 23:
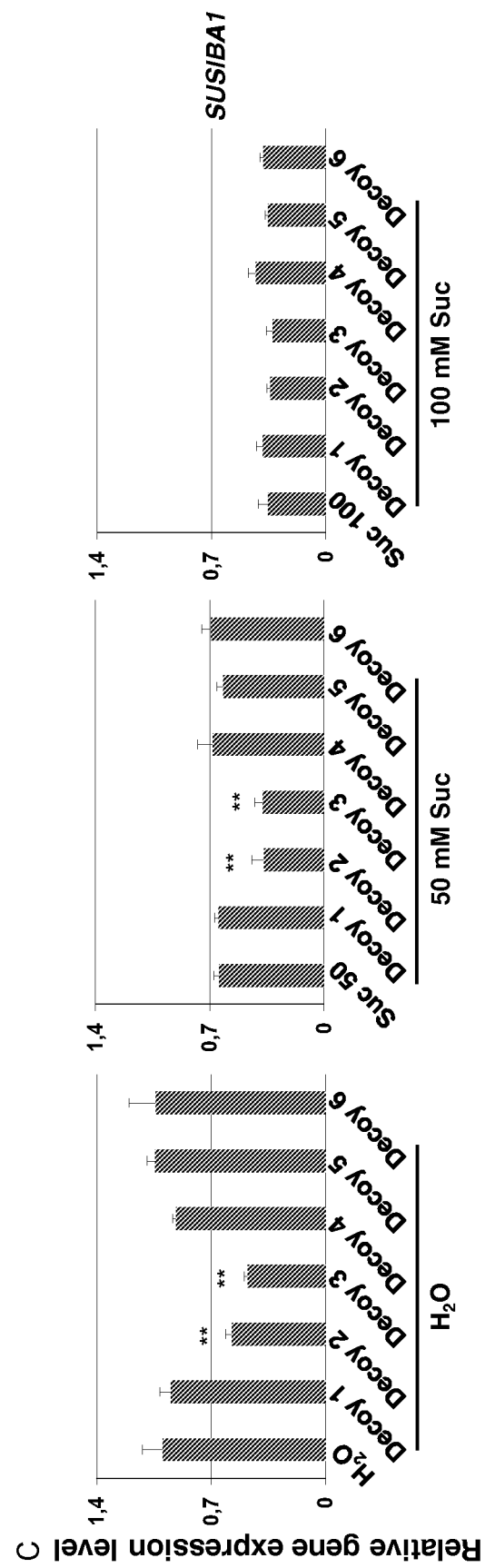
Figure 23:
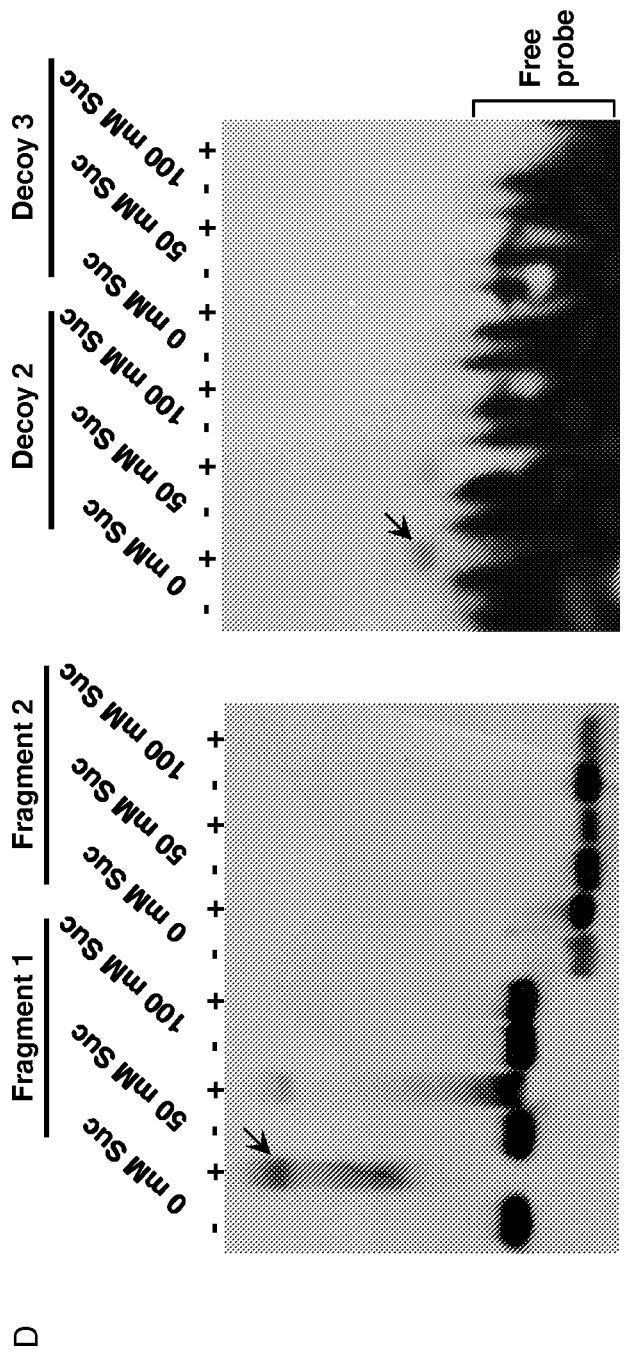
Figure 24:
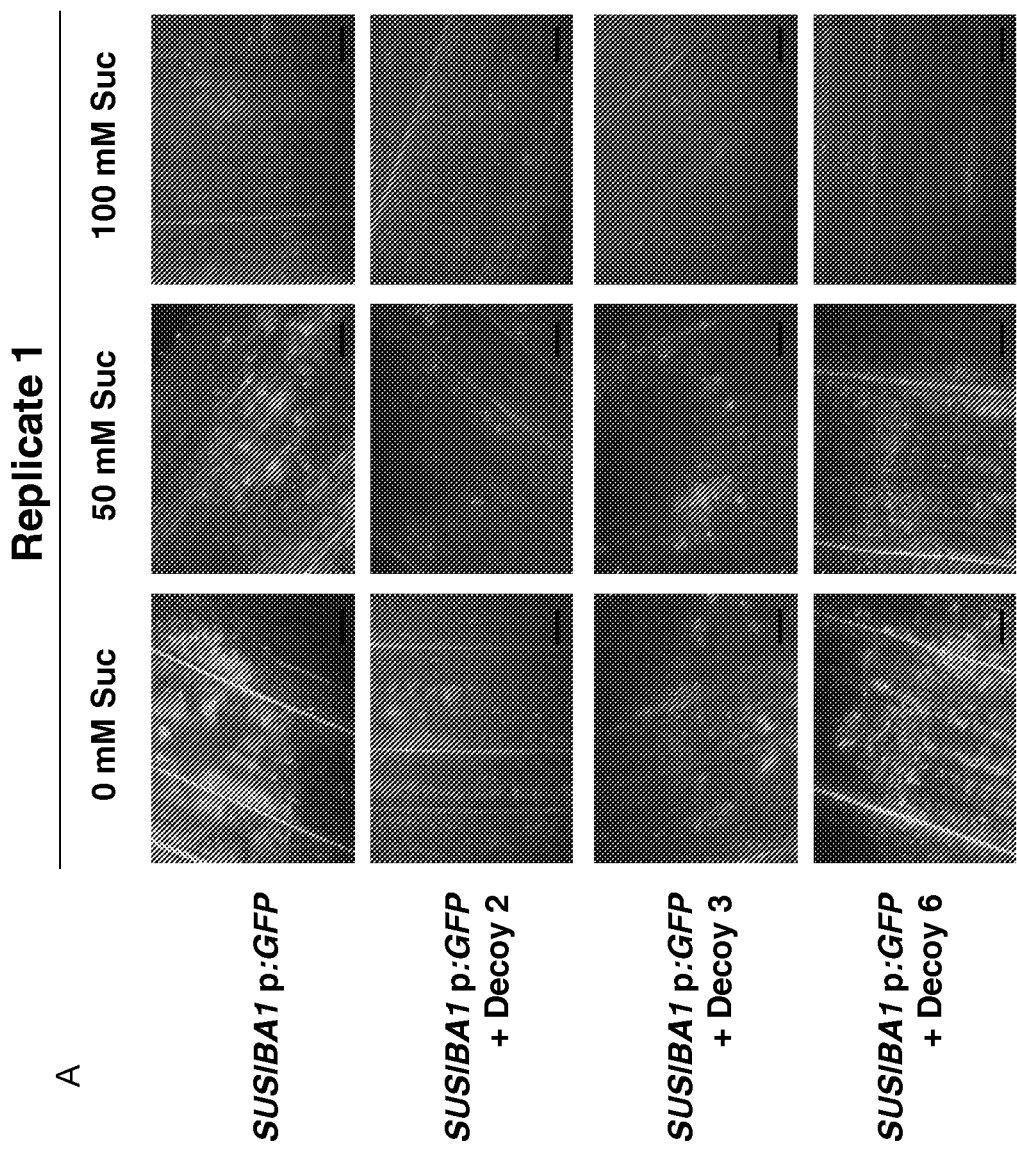
FIG. 24. Fluorescent analysis of impacts of decoy oligoes 2, 3 and 6 on SUSIBA1 sugar responsive activity using the SUSIBA1 p:GFP construct. (A-C) The SUSIBA1 p:GFP construct was co-infiltrated with decoy oligoes 2, 3 and 6 as in FIG. 23C to monitor SUSIBA1 promoter activity. Infiltrated leaves were incubated at different concentrations of Suc. Three days after infiltration and incubation, fluorescence was examined under a microscope at a wave length of 460-500 nm. (D) Relative fluorescence intensity was quantified. Significant differences are analyzed statistically and indicated by asterisks (**p≤0.01) for SUSIBA1 p:GFP, decoy 2 and decoy 6 compared with decoy 3. One-way ANOVA was used (Error bars show s.d.) Bars=100 μm.
Figure 24:
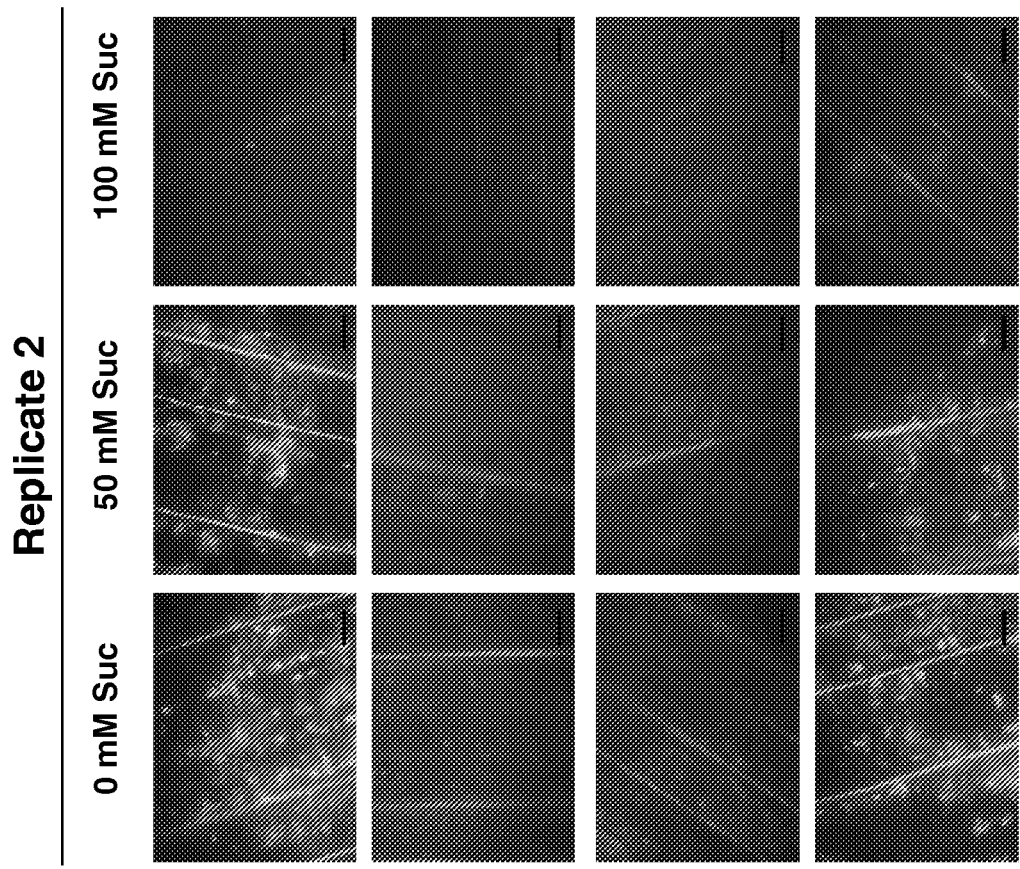
Figure 24:
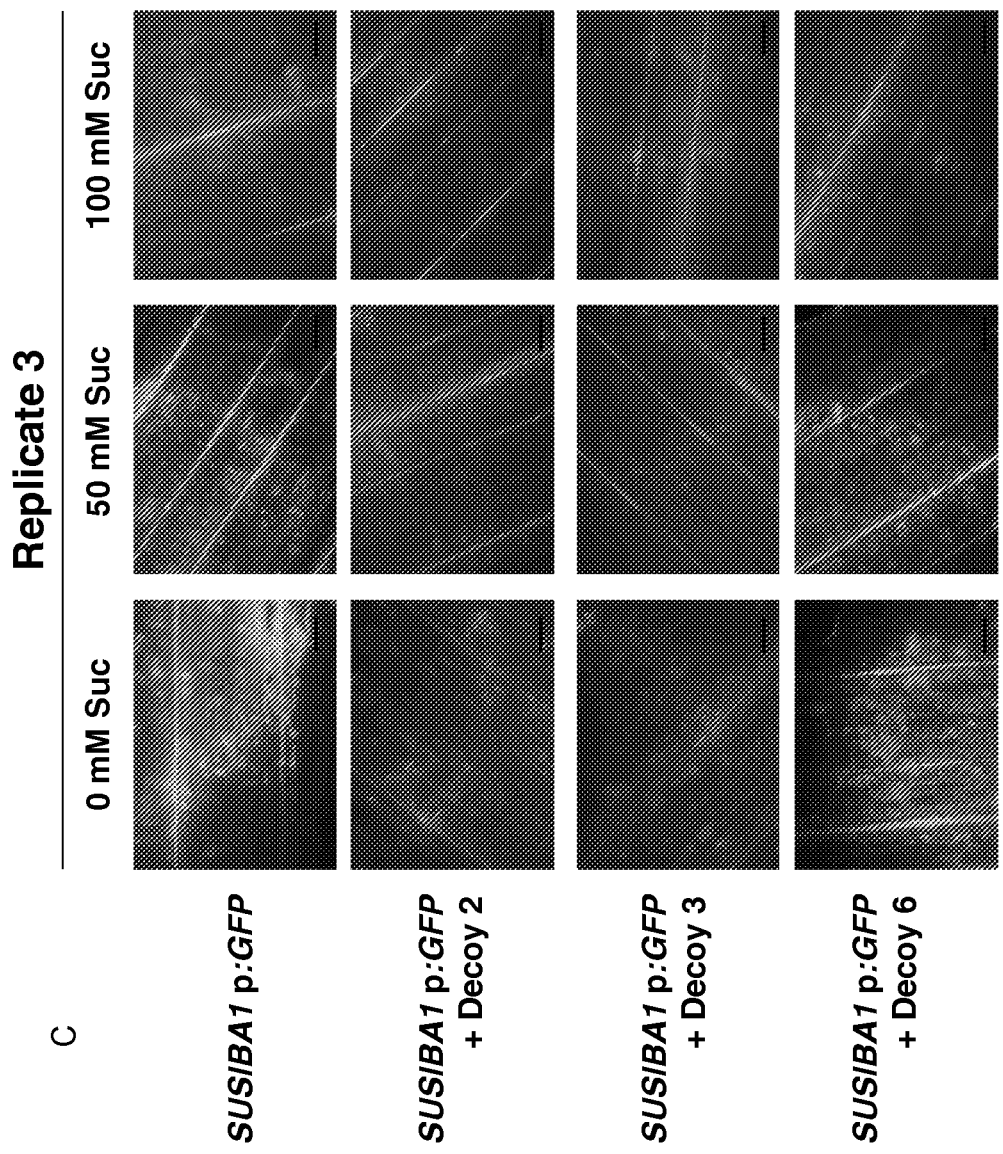
Figure 24:
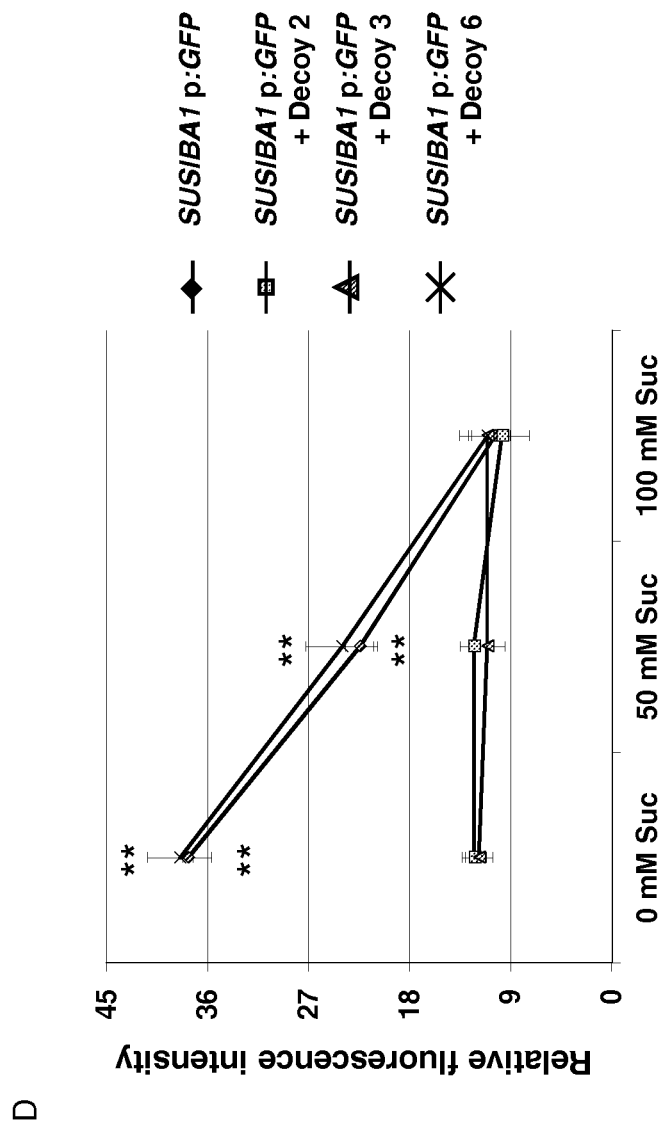

A Cis Sequence and Corresponding Trans Activity in the SUSIBA1 Promoter Constitute the Sugar Sensor in the Antagonistic System Given the discovered role of SUSIBA1 in controlling SUSIBA2 expression in a sugar-dependent manner, the mechanism by which SUSIBA1 senses sugar becomes critically important. To address this question, the same strategies were used as described above for SUSIBA2 to dissect the SUSIBA1 promoter. Promoter deletion experiments indicated that a sugar-responsive sequence should be located in the 177 bp-long 5'-end region of the SUSIBA1 promoter and deletion of this region fully abolished the sugar-responsive activity of the SUSIBA1 promoter (FIGS. 22A-22C). In addition, deletion of the entire intronic promoter sequence significantly reduced the overall promoter activity of SUSIBA1, which is in line with result presented in FIGS. 3A-3C. To narrow down the sugar-responsive element within the 177 bp-long region the decoy trapping strategy was used and the region was split up into 6 decoy oligos (FIGS. 23A and 23B). Following infiltration into barley leaves, decoys 2 and 3 could significantly reduce SUSIBA1 expression at low and moderate sugar levels, which are permissible for a SUSIBA1 expression background for analysis (FIGS. 23C, 24A, 24B). To analyze the corresponding trans factor involved in SUSIBA1's sugar-responsive activity, nuclear protein extracts from barley leaves treated at different Suc concentrations together with a DNA fragment covering decoys 2 and 3, a control fragment outside the 177 bp-long region (FIG. 23A), and decoys 2 and 3, were used in EMSA experiments (FIG. 23D). EMSA visualized trans factor activity that could bind to fragment 1 and decoy 2, but not to fragment 2 and decoy 3. The trans factor seemed to be a positive regulator as its activity correlated with SUSIBA1 expression. Detailed examination of the decoy 2 sequence revealed that it contains a TTATC motif that resembles an identified sugar-repressive element (SRE).

Figure 25:
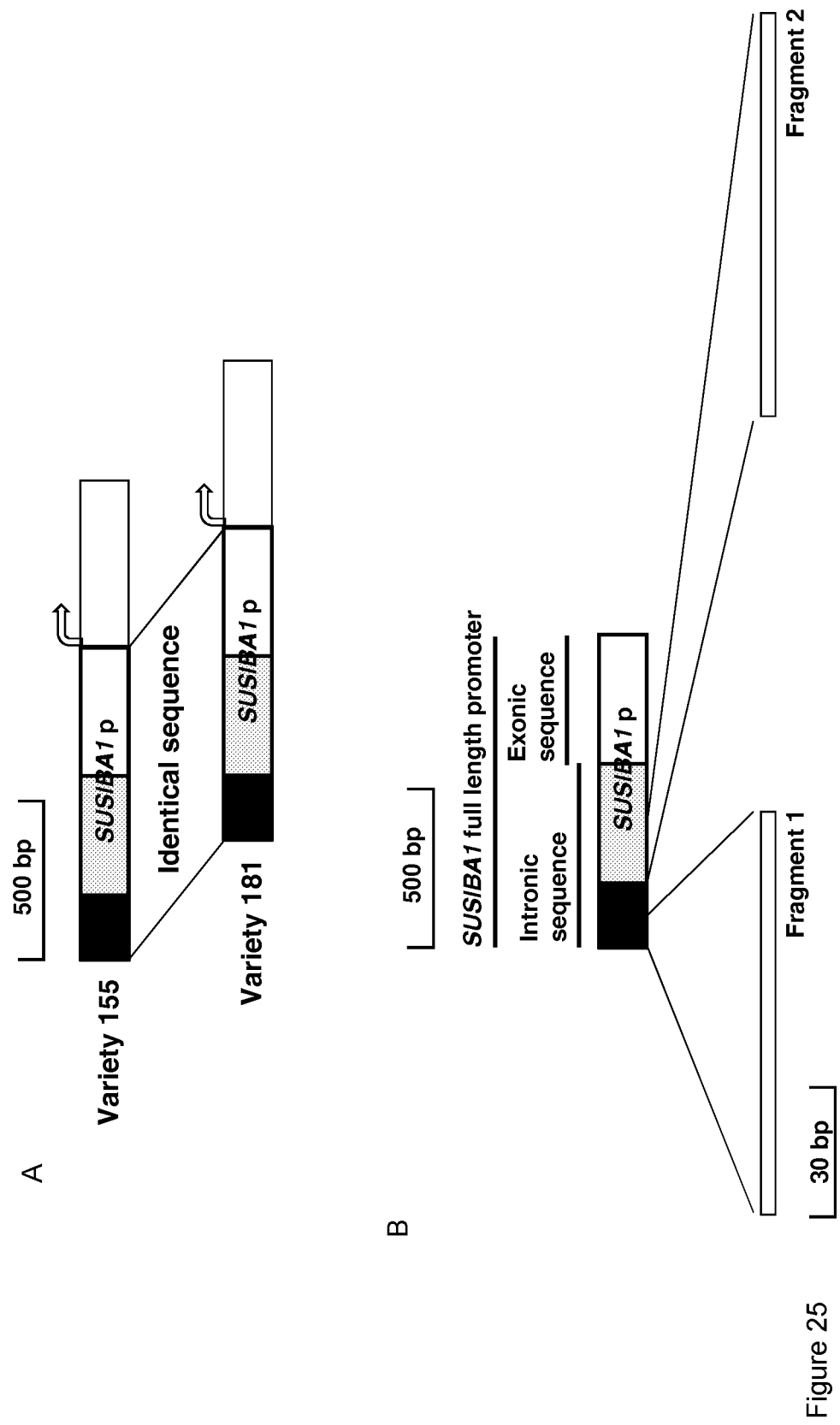
FIG. 25. Analysis of SUSIBA1 promoter sequences and the identified trans activity between high (variety 155) and low (variety 181) fructan varieties. (A) Schematic representation of the two sequenced SUSIBA1 promoter isolated by PCR from barley varieties 155 (high fructan content variety) and 181 (low fructan content variety). (B) A fragment (Fragment 1; see also FIG. 23A) from the sugar-responsive region containing the identified sugar-responsive cis sequence and a control fragment (Fragment 2; see also FIG. 23A) were used for EMSA analysis. (C) EMSA of nuclear protein extracts isolated from 9 daf seeds of the two varieties. EMSA was performed in the absence (−) or presence (+) of the nuclear protein extracts. The position of the free probe is indicated. Binding activity displayed as a band shift is indicated with an arrow.
Figure 25:
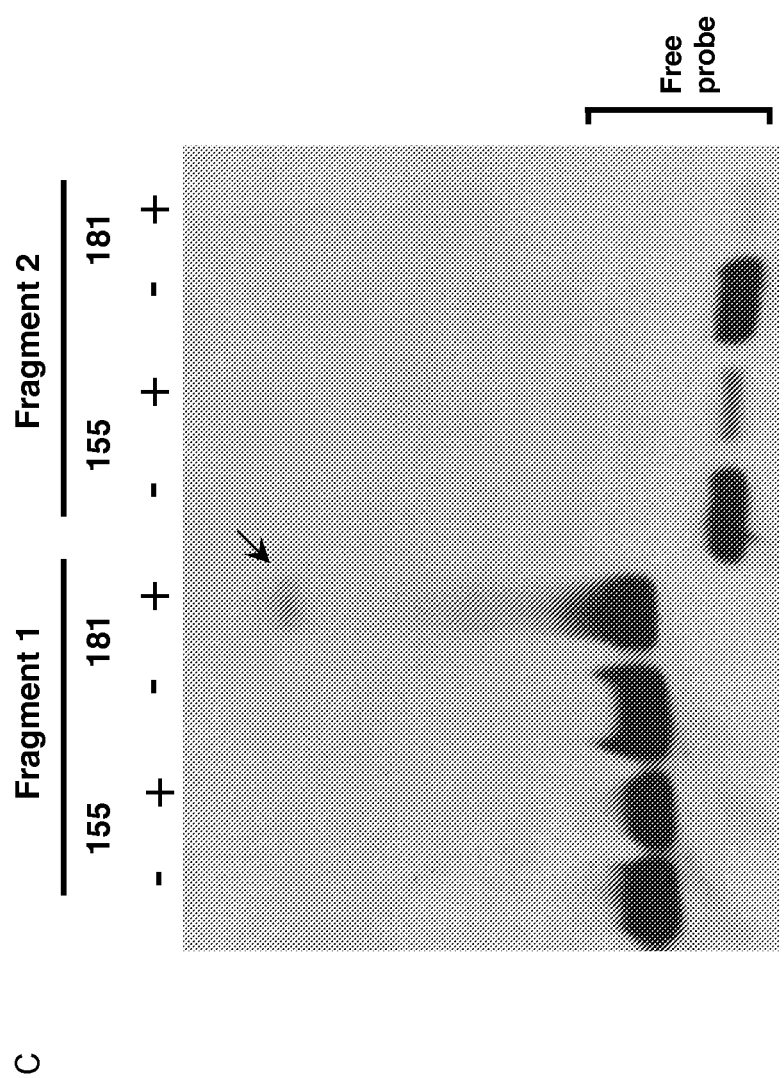

The importance of the SUSIBA1 177 bp-long 5' promoter sequence and the detected cognate trans factor in fructan synthesis was corroborated by EMSA experiments using two different barley genotypes, the high-fructan cultivar 155, and the low-fructan cultivar 181 (FIGS. 25A-25C). Sequencing data and EMSA results support the role of the trans factor activity as a determinant for fructan content in barley (FIGS. 25A-25C).

A molecular machinery that orchestrates the coordinated regulation of starch and fructan synthesis in barley has been demonstrated. This regulatory circuitry comprises two opposing functionalities (an antagonistic system) executed by the interlocking SUSIBA1 and SUSIBA2 TF genes (FIGS. 26A, 26B). At the core of the system, competitive binding of the two TFs to the W-box in the sugar-responsive region of the SUSIBA2 promoter, serves as an internal adaptive mechanism for autoregulation of the antagonistic system. The results suggest that the SUSIBA1/SUSIBA2 competitive binding as a whole in the system plays an important role in delaying starch synthesis to a higher sugar level than the sugar level required for fructan synthesis (FIGS. 4A, 4B). A higher sugar level generates a condition of less to no SUSIBA1 that allows for progressive expression and binding of SUSIBA2 to the W-box in promoting SUSIBA2 expression for upregulating starch synthesis. A trans factor is recruited as an activator to the intronic promoter element of the SUSIBA1 promoter and serves as the ultimate sugar sensor in the intricate sugar-signaling pathways of the system. The results also suggest that induction of the regulatory machinery for starch and fructan synthesis is triggered by cellular import of photosynthate (Suc) and mediated by Glc/Fru signaling, while T6P did not seem to be involved under the experimental conditions (FIGS. 6A-6D, 7A-7D). The possibility of a role of T6P in the regulation under conditions of higher sugar concentrations (i.e., >85 mM) and in the light cannot be excluded. The high starch accumulation in the Glc-treated (85 mM) samples (FIGS. 6A and 6B) might be ascribed to Glc being a central metabolite in the starch synthetic pathway. The dynamics of fructan metabolism in barley sink organs inferred herein (FIGS. 15A, 15B) may point to the need for balancing the pool sizes of Suc and hexoses in source and sink organs or for adjusting the osmotic pressure to control unloading of Suc in sink tissues.

Figure 27:
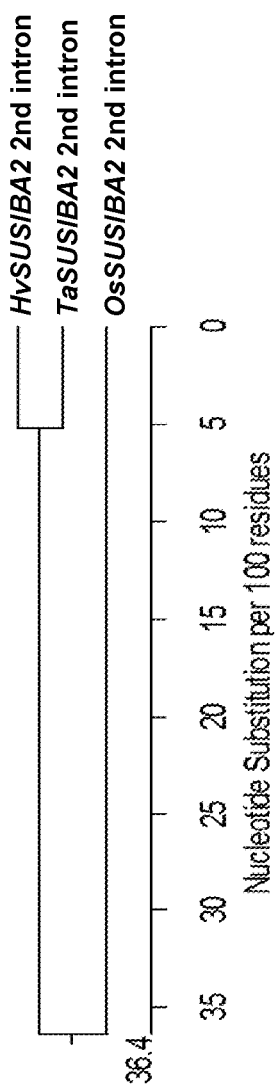
FIG. 27. Phylogenetic data analysis of the SUSIBA2 second introns (major portions of the SUSIBA1 promoters) from three crop species, barley, wheat and rice. Second intron sequences of barley SUSIBA2 (Genbank accession number AC269483 or KT290559), wheat SUSIBA2 orthologue (TaSUSIBA2, Scaffold TGACv1_scaffold_114535_2AS: 19,457-27,625 at http://ensembl.gramene.org/) and rice SUSIBA2 orthologue (OsSUSIBA2, GenBank accession number AP014963.1) were used for analysis by the program of DNASTAR Lasergene version 12.

The sugar-sensing competitive transcription factor binding model (FIGS. 26A, 26B) for controlling starch and fructan synthesis in temperate grasses proposed herein could be used in breeding programs through marker-assisted selection or transgenics for altering starch and fructan levels in, for instance, barley and wheat cultivars to suit specific food, feed, and industrial applications. Inhibition of the trans activity or deletion of the SUSIBA1 intronic promoter sequence via transgenics or genome editing technologies could potentially increase fructan and starch content simultaneously. Phylogenic data analysis indicates that the second intron sequences of SUSIBA2 or major portions of the SUSIBA1 promoters are conserved among three important crop species, barley, wheat and rice and particularly between barley and wheat (FIG. 27). The sugar-controlled SUSIBA1/SUSIBA2 antagonistic system may exist in the crop species for regulation of starch and other carbohydrate synthesis. Since rice does not accumulate fructan, what else carbohydrate than starch synthesis is regulated by the system in the species need to be illustrated.

The application of agro-infiltration as an investigative tool in monotcots, introduced herein, holds great promise for advancing the understanding of gene function in cereals and grasses. Also, as illustrated here, the combination of agro-infiltration, decoy oligo trapping and the asODN approach significantly increases the utility of the employed technologies in plant biology for analysis of gene and promoter functions.

An internal promoter (SUSIBA1 p) in a plant genome that results in expression of a protein with functions distinct from those of the product encoded by the harboring gene (SUSIBA2) can have significant implications for plant genomics, in that it affects the annotation of genes, prediction of gene function and products, and the interpretation of knockout phenotypes.

Long Barley Panicle is Associated with High SUSIBA2 Level and Short Panicle Associated with High SUSIBA1

Cereals are the most important food resources for human race and cereal yield is the most concerned issue in terms of the global food security. Cereal yield depends on several factors, such as panicle number, panicle size and thousand kernel weight. The panicle size is one of the key factors that determine cereal yield. It has previously been reported that a mutation in a gene encoding a repressor-type of transcription factor in barley result in six-rowed barley from two rowed. The six row barley has a theoretical yield-increase of three times more than the two rowed. However, what determines the cereal panicle length in the vertical dimension remains challenging to be illustrated.

Since SUSIBA2 can increase sink-strength in storage tissues, SUSIBA2 may increase panicle length with more grain number by directing more sucrose to the developing panicles during grain filling. More available sugars to the developing panicles, i.e., developing zygotes, can rescue already set seeds and prevent their abortion in developing panicles during grain filling. In the progenies of crossed barley varieties 155 (or SLU7) and 199 (or KVL1113), two types of barley panicles were generated, short (8-10 cm) and long (13-15 cm), see FIG. 31. Careful examination of gene expression in developing panicles around pollination, i.e., egg fertilization time, indicated that high expression of SUSIBA2 was always associated with the long panicle, lower panel in FIG. 32. The phenomenon raised immediately an important and intriguing question, whether SUSIBA2 is a genetic determiner in panicle length or not.

Through many years of investigation in the barley sugar signaling pathway, the barley SUSIBA2 gene was found to be located on chromosome 2. The SUSIBA2 locus employs two alternative promoters to produce two transcription factors SUSIBA1 and SUSIBA2, see FIGS. 26A, 26B. The SUSIBA1 promoter is located in the second intron and 5'-end of the third exon of SUSIBA2. Thus, SUSIBA1 is about the C-terminal half of SUSIBA2. SUSIBA1 is a repressor of SUSIBA2 and prevents SUSIBA2 self-activating expression. The SUSIBA1 and SUSIBA2 promoters respond to sugars differentially. When sugar level is low, an unidentified sugar-controlled actor-type protein complex promotes the SUSIBA1 expression. SUSIBA1 binds to the SUSIBA2 promoter. High expression of SUSIBA1 prevents the SUSIBA2 expression. When sugar is high, the sugar-controlled activating activity is reduced and the SUSIBA1 expression decreases. Reduction of the SUSIBA1 expression releases the SUSIBA2 expression progressively. When sugar is continuously high, less SUSIBA1 results in high expression of SUSIBA2. SUSIBA2 with an increasing level binds to its own gene promoter via competitive binding with SUSIBA1 and self-promotes its own expression for upregulating down-stream genes such as starch genes.

Materials and Methods

Plant Materials and Growth Conditions

Barley seeds of *Hordeum vulgare* varieties Golden Promise, SLU 7 (variety 155), and KVL 301 (variety 181) were obtained from the Nordic Gene Bank, the Swedish University of Agricultural Sciences (SLU) and the Royal Veterinary and Agricultural University (KVL), respectively. Golden Promise was grown in 16 h light at 22° C., 8 h dark at 18° C., 70% relative humidity with a light intensity of 400 μmol $m^{-2}$ $s^{-1}$, SLU 7 and KVL 301 at 24/16° C. and 18/10° C., respectively. Other growth conditions were similar to those previously described [6]. Barley development stages were monitored according to the Zadoks scale [18], or days after flowering (daf) for developing seeds. Second leaves from four-week old barley seedlings were used for sugar-induction, asODN inhibition and other experiments.

Oligonucleotides

Oligonucleotides used in this work are listed in Table 1. They were purchased from Sigma-Aldrich (St. Louis, Mo., USA).

Molecular Cloning and cDNA Library Screening

Plasmids containing GFP, BFP and GUS were obtained as described [1, 7]. *Arabidopsis* WRI1 was amplified from GenBank accession number NM_202701. All procedures for molecular cloning were as described [1, 2, 4, 8], 5'-RACE was performed according to Gene Race®core kit (Invitrogen, Carlsbad, Calif., USA) following the manufacturer's manual. cDNA library screening was carried out as described [1, 8].

Sucrose Induction and asODN Inhibition

Experiments with sucrose induction and asODN inhibition were as reported previously [1, 2, 4, 5, 9]. In brief, barley plants were kept in darkness for 24 h to deplete sugars and then used for the experiments. The second leaf from the top of 4-week-old seedlings was detached and incubated in various concentrations of sucrose with or without ODNs. For sucrose induction, water and sorbitol were used as controls. For asODN inhibition, sense ODNs were used as controls.

Agro-Infiltration

Agro-infiltration was performed according to a published protocol for dicots [10] with minor modifications. Seedlings of 4-week-old plants were kept in darkness for 24 h to deplete sugars. The second leaf from the top was infiltrated with construct-containing *agrobacterium* AGL1 suspended in different solutions to the same OD concentrations to optimize the agro-infiltration condition for an equal transformation efficiency as described [10]. After infiltration, leaves or plants were incubated in darkness with or without different solutions for another 48 h before qPCR analysis or 72 h before observation under UV-light and a microscope at wavelength 460-500 nm for GFP and 340-380 nm for BFP. Different sequences were fused to the reporter genes and transformed to agrobacteria and infiltrated into barley leaves.

Decoy Oligo Trapping Assay

Oligodeoxynucleotide decoys were generated by annealing oligonucleotides in 14 mM Tris-HCl, pH 8.0, and 7 mM MgCl2, followed by dilution to a working concentration of 25 μM for infiltration into barley leaves. For qPCR transcript analysis, the infiltrated areas were used for RNA isolation 48 h after infiltration. For fluorescence microscopy analysis, the infiltrated areas were used 72 h after infiltration.

Northern and Western Blot Analysis

Northern and Western blot analysis were performed as described [1]. cDNA of SUSIBA2 was used as a probe for Northern analysis and an antibody against barley 6-SFT, a kind gift from Dr. Martinez-Carrasco, was used for Western blot analysis. A typical whole profile of proteins stained with Coomassie and immune-reacted bands on the blot from the same amount of loading are shown in FIG. 6D. Western blot analysis for SUSIBA1 and SUSIBA2 was run on different blots instead of on the same blots due to the cross reaction of the antibody against the full-length of SUSIBA2 peptide to SUSIBA1 was weaker than to SUSIBA2.

qPCR Analysis

Quantitative real-time PCR (qPCR) was performed as described previously [2, 11]. Relative expression level of SUSIBA1 was calculated by subtraction of delta Ct value of SUSIBA1+2 to that of SUSIBA2, i.e., delta Ct value of SUSIBA1=delta Ct value of SUSIBA1+2−delta Ct value of SUSIBA2 using the same house-keeping gene (or reference gene).

Microscopy

Fluorescence microscopy and confocal microscopy were as described [2]. Relative fluorescence intensity was measured with the software ImageJ [19].

Nuclear Protein Isolation

Barley leaves were treated with 0 mM, 50 mM and 100 mM Suc for two days, and nuclear proteins were isolated as described previously [12]. Nuclear proteins from 9 daf seeds of varieties 155 and 181 were isolated following the same protocol.

EMSA

The electrophoretic mobility shift assay (EMSA) experiments were carried out according to as described previously [1, 12]. In brief, overexpressed SUSIBA1 and SUSIBA2 proteins were purified or barley nuclear proteins were isolated and used for EMSA. DNA fragment probes were end-labeled by [γ$^{32}$P]-ATP with PNK (T4 polynucleotide kinase). For oligo probes, one strand was end-labeled by [γ$^{32}$]-ATP with PNK and annealed with a complementary strand of oligo at 14 mM Tris (pH 8.0) and 7 mM MgCl2. Agarose gels were used for large DNA fragments and polyacrylamide gels for oligonucleotide fragments. For competitive assays, 0.2 μg of the overproduced SUSIBA2 was incubated with incremental additions of the overproduced SUSIBA1 with 0.0125, 0.025, 0.05, 0.1 and 0.2 μg to the binding reactions. Polyacrylamide gel of 6% was used and constant voltage of 160 V was applied.

Experimental Design, Statistical and Bioinformatic Analysis

Biological and technical triplicates were used except starch and fructan analysis, in which technical duplicates were used according to the manufacturer's protocols (Megazyme, Bray, Co. Wicklow, Ireland). The methods one-way ANOVA [13] and bioinformatics [11] were used for analysis. Phylogenetic tree was created by the program of DNASTAR lasergene version 12.

Determination of Fructan, Starch, Glc, Fm, and T6P

Fructan, starch and endogenous fructose and glucose were extracted and analyzed as described [2, 11] and according to protocols provided in kits from Megazyme (Bray, Co. Wicklow, Ireland). Endogenous trehalose 6-phosphate was isolated following exactly the protocol previously described [14] and analyzed by liquid chromatography-mass spectrometry (LC/MS) as previously described [15]. LC/MS analyses were performed on Agilent 1100 HPLC coupled to an Amazon Speed ETD ion trap mass spectrometer (Bruker Daltonics, Bremen, Germany). Separations were attempted on an Accucore-150-HILIC-Amide column (2.1×150 mm) with 2.6 μm size particles from Thermo Scientific (USA) at 25° C. The flow rate was maintained at 200 μl min$^{-1}$ and an injection volume of 20 μl was used for both the standard and the extracts. The mobile phases were as described [15]. The ion trap mass spectrometer was operated using Electro Spray Ionization (ESI) in the negative mode and mass spectra were acquired over a scan range of m/z 50-500.

Trehalose 6-Phosphate Synthase Assay

Trehalose 6-phosphate synthase assay was performed as previously described [16] except that the first reaction time and temperature were set for 120 min and 25° C., respectively. Enzyme activity is presented as a decrease in NADH absorbance at 340 nm per min in the second reaction.

TABLE 1 oligonucleotides

| Primer name | Gene name | SEQ ID NO | Primer sequence (5'→3') |
|---|---|---|---|
| ExtF | HvSUSIBA2 | 1 | AAGCTTGCTCCTGCTATGAGTGATCT |
| ExtR | | 2 | GTCGACTTCACAATTAGGATGTGTGCAC |
| In+ExtF | HvSUSIBA2 | 3 | AAGCTTGTACACAACCTTTAATTTTCTT |
| GFPF1 | GFP | 4 | GTCGACATGGTGAGCAAGGGCGAGGA |
| GFPR1 | | 5 | GAGCTCTTACTTGTACAGCTCGTCCATG |
| RandomF | GUS | 6 | AAGCTTAACTGCATCAGCCGATTATCAT |
| RandomR | | 7 | GTCGACGTGGTGGCTAGCTTGTTTGC |
| 35SF | 35S p | 8 | GAGCTCCATGGAGTCAAAGATTCAAATAG |
| 35SR | | 9 | GTCGACAGTCCCCCGTGTTCTCTCC |

TABLE 1-continued

| Primer name | Gene name | SEQ ID NO | Primer sequence (5'→3') |
|---|---|---|---|
| WRIF | AtWRI1 | 10 | GTCGACTCTCAGAGTTTAATGAAGAAGCG |
| WRIR | | 11 | CACGTGGGCAAAGACATTGATTATTC |
| p6-SFTF | Hv6-SFT p | 12 | GGGAGCTCTCCGTAGTAAAAGAAACAGG |
| p6-SFTR | | 13 | CGGAATTCTTTGTAGGCGTACGGTAGCGG |
| GFPF2 | GFP | 14 | CGGAATTCATGGTGAGCAAGGGCGAGGA |
| GFPR2 | | 15 | GGCACGTGTTACTTGTACAGCTCGTCCATG |
| SU1F1 | HvSUSIBA2 | 16 | GGGTCGACATGGTTGAGCCTGTTCCAGC |
| SU1R1 | | 17 | AACACGTGTCATGGACCCATGCCCAAGT |
| SU1R2 | | 18 | CGGAATTCTGGACCCATGACCAAGTTC |
| pSUSIBA2F | HvSUSIBA2 p | 19 | GGGAGCTCGAGGTAAAACCCTACATCCT |
| pSUSIBA2R | | 20 | TTAAGCTTTCTCATGTAGTAATCATACGGTGGG |
| BFPF | BFP | 21 | TTAAGCTTATGGTGAGCAAGGGCGAGGA |
| BFPR | | 22 | AACACGTGCTATTTGTACAGCTCGTCCATGC |
| pSu1TR1F | HvSUSIBA2 | 23 | GCAAGCTTTGTTGCCTCTCTTTTGTAAA |
| pSu1TR2F | HvSUSIBA2 | 24 | GCAAGCTTGGTAGAGTTTGAAGGAAGTA |
| pSu2F | HvSUSIBA2 p | 25 | GCAAGCTTGAGGTAAAACCCTACATCCT |
| pSu2TR1F | | 26 | GCAAGCTTCCCGCGACCCGAGGACCTCT |
| pSu2TR2F | | 27 | GCAAGCTTTGGCTATCTCTCTTTGTTGA |
| pSu2TRR | | 28 | AAACTAGTTCTCATGTAGTAATCATACG |
| GFPSpeIF | GFP | 29 | AAACTAGTATGGTGAGCAAGGGCGAGGA |
| Su2FXhoI | HvSUSIBA2 | 30 | AACTCGAGATGTCCCCCGCGCGGCTGCC |
| Su2RXhoI | | 31 | AACTCGAGTCATGGACCCATGACCAAGT |
| Su1AntiSense1 | HvSUSIBA1 | 32 | GCTATTCATCTGCTGCGG |
| Su1Sense1 | HvSUSIBA1 | 33 | CCGCAGCAGATGAATAGC |
| Su1AntiSense2 | HvSUSIBA1 | 34 | TCCTATTGGGCTGGGGCT |
| Su1AntiSense3 | HvSUSIBA1 | 35 | GCTCAACCATACCAGGCG |
| Su1AntiSense4 | HvSUSIBA1 | 36 | GTCTTCCACCTCCAGCAT |
| Su1AntiSense5 | HvSUSIBA1 | 37 | ACCAGCAGACTCCATTTT |
| Su2AntiSense1 | HvSUSIBA2 | 38 | CGCGGGGGACATGGCCTT |
| Su2Sense1 | HvSUSIBA2 | 39 | AAGGCCATGACCCCCGCG |
| Su12Rev1 | HvSUSIBA2 | 40 | TCAACCTCACTTACAGTTTG |
| Su12Rev2 | | 41 | GTGATGCTCTCTCAACATGC |
| SUSIBA1+2F | HvSUSIBA2 | 42 | TTGATCTTGGTGTTGGAATCA |
| SUSIBA1+2R | | 43 | CCCATGGTTTGCATTTGATA |
| SUSIBA2F | HvSUSIBA2 | 44 | TGAATGAAAACAGACCTCCC |
| SUSIBA2R | | 45 | ATGTACCAACTTCAGCAGGC |
| 6-SFTF | Hv6-SFT | 46 | GACGAACGGCACGACTACTA |

TABLE 1-continued oligonucleotides

| Primer name | Gene name | SEQ ID NO | Primer sequence (5'→3') |
|---|---|---|---|
| 6-SFTR |  | 47 | ATAGAAGGAGGTGGACGCAT |
| AtWRI1F | AtWRI1 | 48 | CGTGGTGGGAAGAGAGAGC |
| AtWRI1R |  | 49 | TGTTGATGAAGCAGAGTCAGTAGA |
| SBEIIbF | HvSBEIIb | 50 | AGACGAGGCGGGGTCAGTTG |
| SBEIIbR |  | 51 | TCCCCGCCGCGGAAACTGC |
| 1-FEHF | Hv1-FEH | 52 | GCGGTGGAGAGCTTCGGTG |
| 1-FEHR |  | 53 | GCGCTGAGCTGTGGCACC |
| 6-FEHF | Hv6-FEH | 54 | TGTACCCTGAGCACGCCG |
| 6-FEHR |  | 55 | GCCAGCCTCCATGCTTCG |
| TPSF | HvTPS-like | 56 | AACGGACGGGTCAGTCATCG |
| TPSR |  | 57 | CCACCAGGCCCTTGCTCACG |
| UbiquitinF | HvUbiquitin | 58 | GCCAAGAAGCGCAAGAAGAAGA |
| UbiquitinR |  | 59 | GGTCGAAGTGGTTGGCCATGA |
| QSUSIBA2UTRF | HvSUSIBA2 | 60 | GCGGGCGCGAGGTACAAGGC |
| QSUSIBA2UTRR |  | 61 | AGTTGGTGAGGAGCACGGGG |
| SP8aF | Hv6-SFT p | 62 | CTGTACTGTGTTTTTAGCCT |
| SP8aR |  | 63 | GACATGACACAAAAATCGGA |
| SUREaF |  | 64 | CACACATGGCACGCCAAAAC |
| SUREaR |  | 65 | GTGTGTACCGTGCGGTTTTG |
| W-boxF |  | 66 | TTATTTTGACCATATATACG |
| W-boxR |  | 67 | AATAAAACTGGTATATATGC |
| SP8aMF |  | 68 | CTGTAAAAAAAATTTAGCCT |
| SP8aMR |  | 69 | GACATTTTTTTAAATCGGA |
| W-boxMF |  | 70 | TTATTAAAAAAATATATACG |
| W-boxMR |  | 71 | AATAATTTTTTTATATATGC |
| SUREaM1F |  | 72 | CAAAAATGGCACGCCAAAAC |
| SUREaM1R |  | 73 | GTTTTTTCCGTGCGGTTTTG |
| SUREaM2F |  | 74 | CACACAAAAAACGCCAAAAC |
| SUREaM2R |  | 75 | GTGTGTTTTTTGCGGTTTTG |
| SUREaM3F |  | 76 | CACACATGGCAAAAAAAAAC |
| SUREaM3R |  | 77 | GTGTGTACCGTTTTTTTTTG |
| SUREaM4F |  | 78 | CAAAAAAAAAAAAAAAAAAC |
| SUREaM4R |  | 79 | GTTTTTTTTTTTTTTTTTTG |
| pSU1 Decoy1S | HvSUSIBA2 | 80 | GTACACAACCTTTAATTTTCTTTTCTG |
| pSU1 Decoy1AS |  | 81 | CATGTGTTGGAAATTAAAAGAAAAGAC |
| pSU1 Decoy2S |  | 82 | TGTCCTATAGAGATTAATGCACTTTATCTT |
| pSU1 Decoy2AS |  | 83 | ACAGGATATCTCTAATTACGTGAAATAGAA |

TABLE 1-continued oligonucleotides

| Primer name | Gene name | SEQ ID NO | Primer sequence (5'→3') |
|---|---|---|---|
| pSU1 Decoy3S | | 84 | GCAGAACATTAAGATGAAATTTAAGCATTT |
| pSU1 Decoy3AS | | 85 | CGTCTTGTAATTCTACTTTAAATTCGTAAA |
| pSU1 Decoy4S | | 86 | TGTTTCTAGATGACCCTGCAACTTTTTTG |
| pSU1 Decoy4AS | | 87 | ACAAAGATCTACTGGGACGTTGAAAAAAAC |
| pSU1 Decoy5S | | 88 | GCCTTTATTGTGCATATTATATAATTTGGC |
| pSU1 Decoy5AS | | 89 | CGGAAATAACACGTATAATATATTAAACCG |
| pSU1 Decoy6S | | 90 | CAGGTTCTTGAATTGTTGCATAATTCATAA |
| pSU1 Decoy6AS | | 91 | GTCCAAGAACTTAACAACGTATTAAGTATT |
| pSU2 W-boxS | HvSUSIBA2 p | 108 | TAGGTCGTCAATTTGACTTATATAAAATAT |
| pSU2 W-boxAS | | 109 | ATATTTTATATAAGTCAAATTGACGACCTA |
| pSU2 Decoy1S | | 110 | GCTTCATCAACGTATCCGCACGTTACACGG |
| pSU2 Decoy1AS | | 111 | CCGTGTAACGTGCGGATACGTTGATGAAGC |

Materials and Methods

Barley Varieties 253 barley varieties have been collected. Among them, 12 varieties were characterized in detail in different analyses [22]. From the 12 varieties, four varieties (155, 199, 224 and 235) were selected for crossbreeding in this study for high seed fructan barley.

Plant Cultivation

The modern phytrotons at SLU were used for plant cultivation as previously described herein and in [22].

Molecular Biology

The sequences of SUSIBA 1 and SUSIBA 2 were used as DNA probes and antibodies against SUSIBA1 and SUSIBA 2, SBEIIb and 6-SFT [1] were used as protein probes for screening progenies after crossing. Other experiments such as qPCR, Western blot, microscopy and etc. were carried out as previously described herein.

Carbohydrate Analysis

Fructan and β-glucan analysis was performed according to published protocols [11, 20, 21, 22].

Barley Crossbreeding

Screening of genetic variations of SUSIBA1 expression levels among barley varieties resulted in a number of lines with different expression levels of SUSIBA1. Among them, varieties 155 and 199 were the varieties with low expression of SUSIBA1 and were selected for crossing with varieties 224 and 235, in which SUSIBA1 expression was high and fructan hydrolytic activity was low. This crossing of varieties was performed to test whether the low SUSIBA1 expression and low fructan hydrolytic activity could be inherited to progenies. The varieties were cultivated in a phytotron and used for crossbreeding following a crossbreeding technique as previously described [23]. The progeny lines after crossing were used for various analyses in screening.

Results

Figure 33:
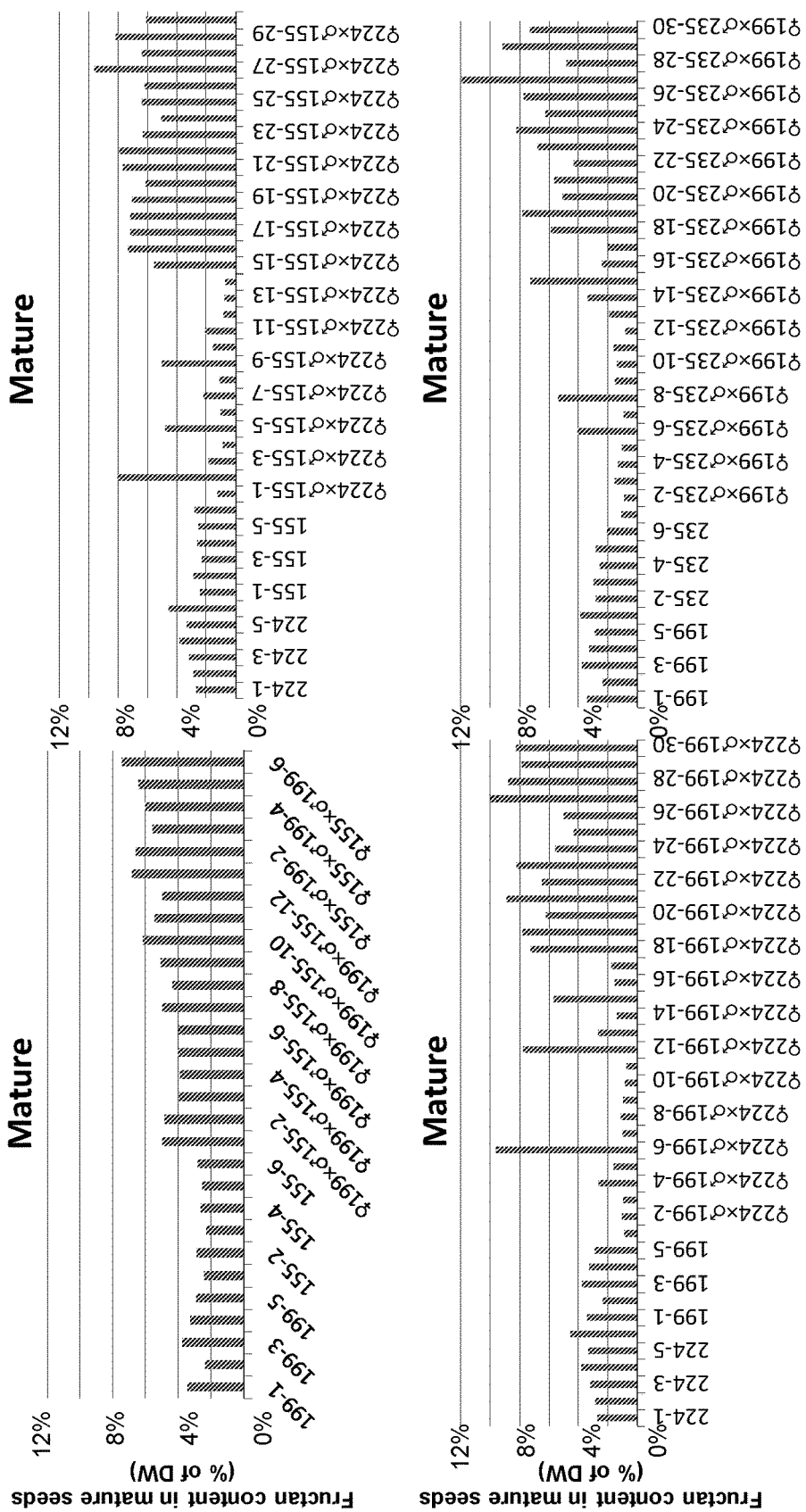
FIG. 33. Individual plant fructan content in $F_2$ progenies. Different numbers (up to 30 seeds) of progeny seeds were applied to fructan content analysis. Five or six of parent seeds from 155, 199, 224 and 235 were used as controls. Individual seed fructan content varied a lot in the progeny seeds. The highest fructan content over 10% per dry weight (DW) was recorded for ♀199×♂235-plant 27 and near 10% for ♀224×♂155-plant 27, ♀224×♂199-plant 6, and ♀224×♂199-plant 27. Phenotypic traits of round seeds and flat seeds in the progenies associated with low and high fructan content were preliminarily observed.
Figure 34:
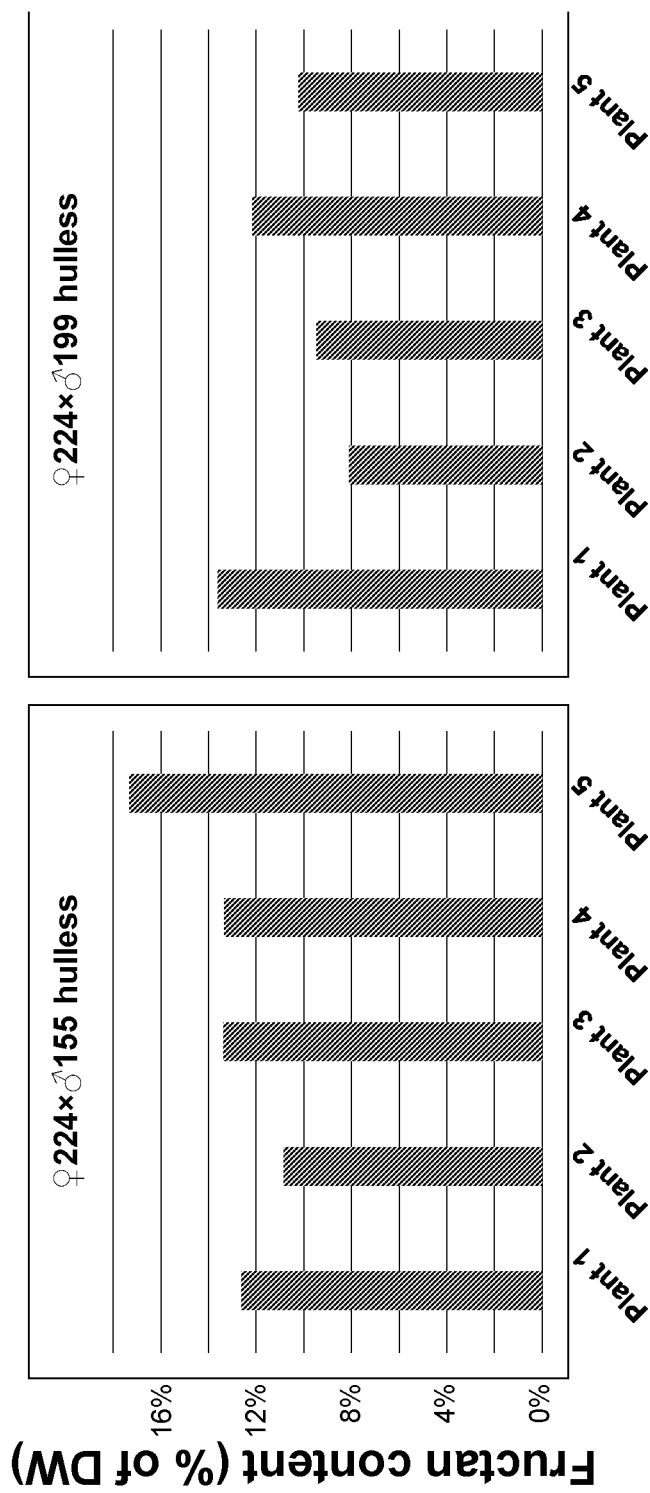
FIG. 34. Fructan content in the homozygous $F_4$ progenies of ♀224×♂155 hulless (naked) and ♀224×♂199 hulless (the two highest fructan lines in phytotron). The highest fructan content (over 13%) was associated with the line of ♀224×♂155 hulless in the phytotron conditions.
Figure 35:
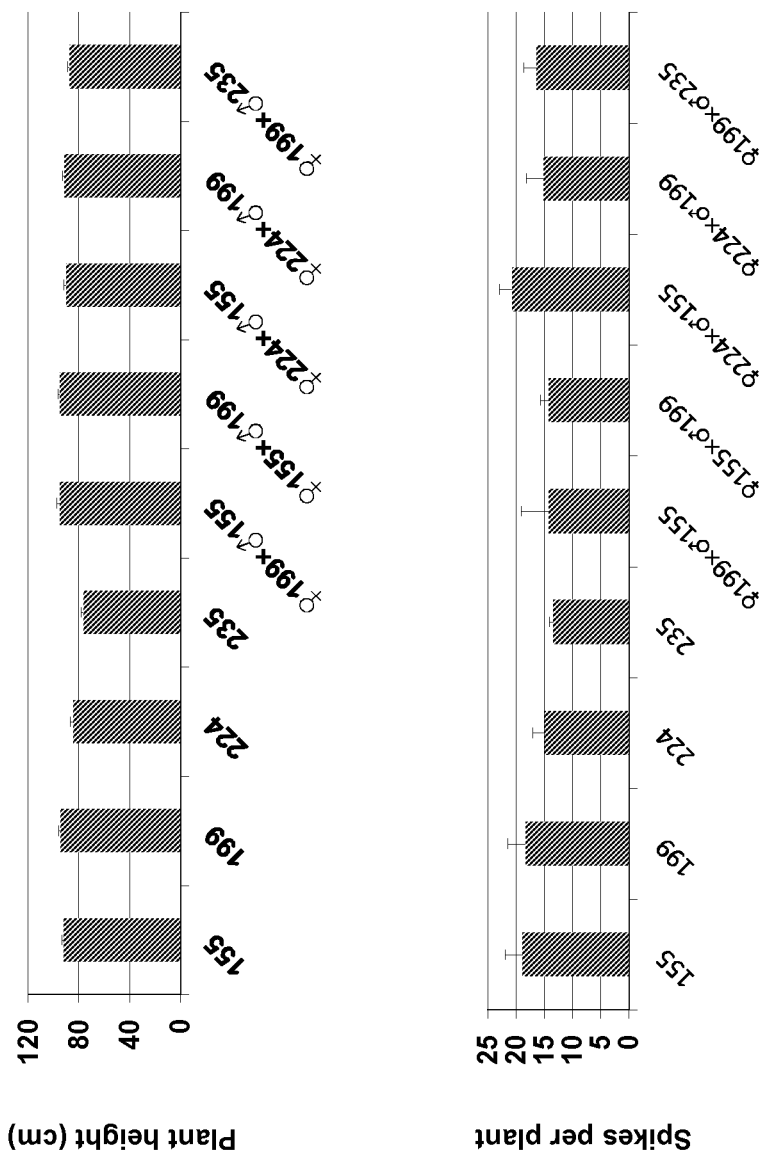
FIG. 35. Phenotypic traits of plant height, spikes per plant, grains per plant and thousand kernel weight in parents and $F_2$ progenies.
Figure 35:
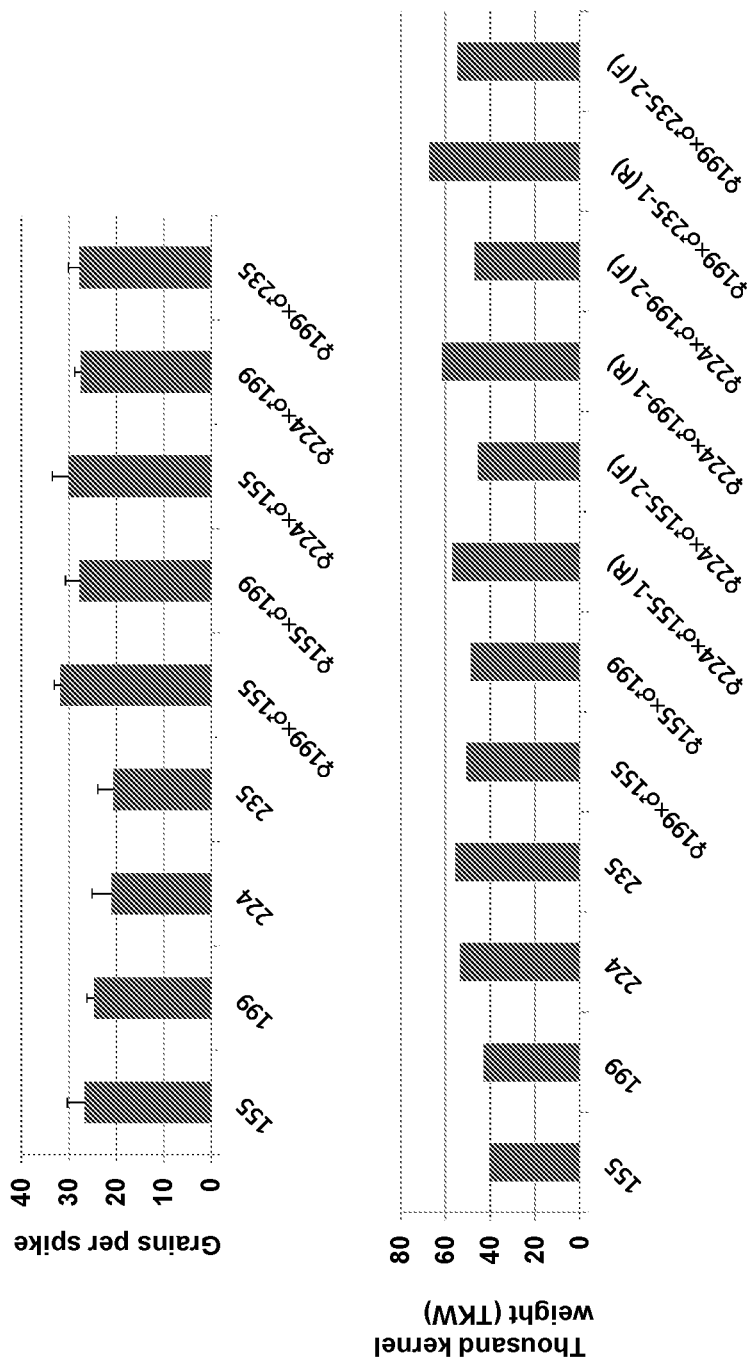
Figure 36:
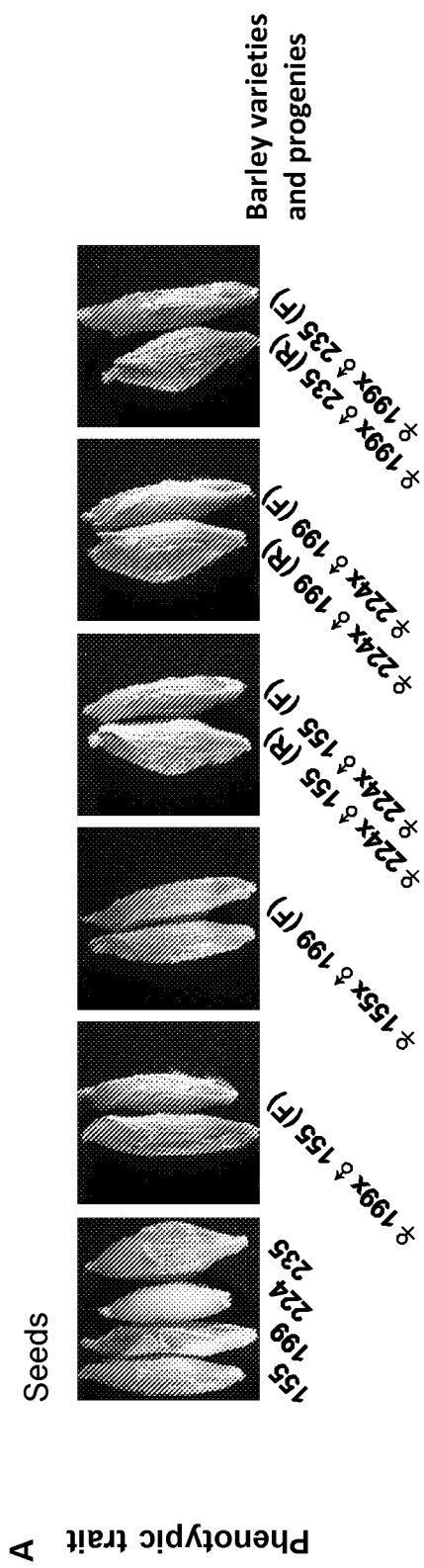
FIG. 36. Average content of seed fructan and beta-glucan in the round and flat seeds of $F_2$ progenies. A. Phenotypic traits of parent seeds, round progeny seeds (R) and flat progeny seeds (F). B. Average fructan content in the round and flat seeds of $F_2$ progenies. C. Average beta-glucan content in the round and flat seeds of F2 progenies. High fructan and bet-glucan content was associated with the traits of flat seeds and a strong correlation between fructan and beta-glucan content was observed in all progenies.
Figure 36:
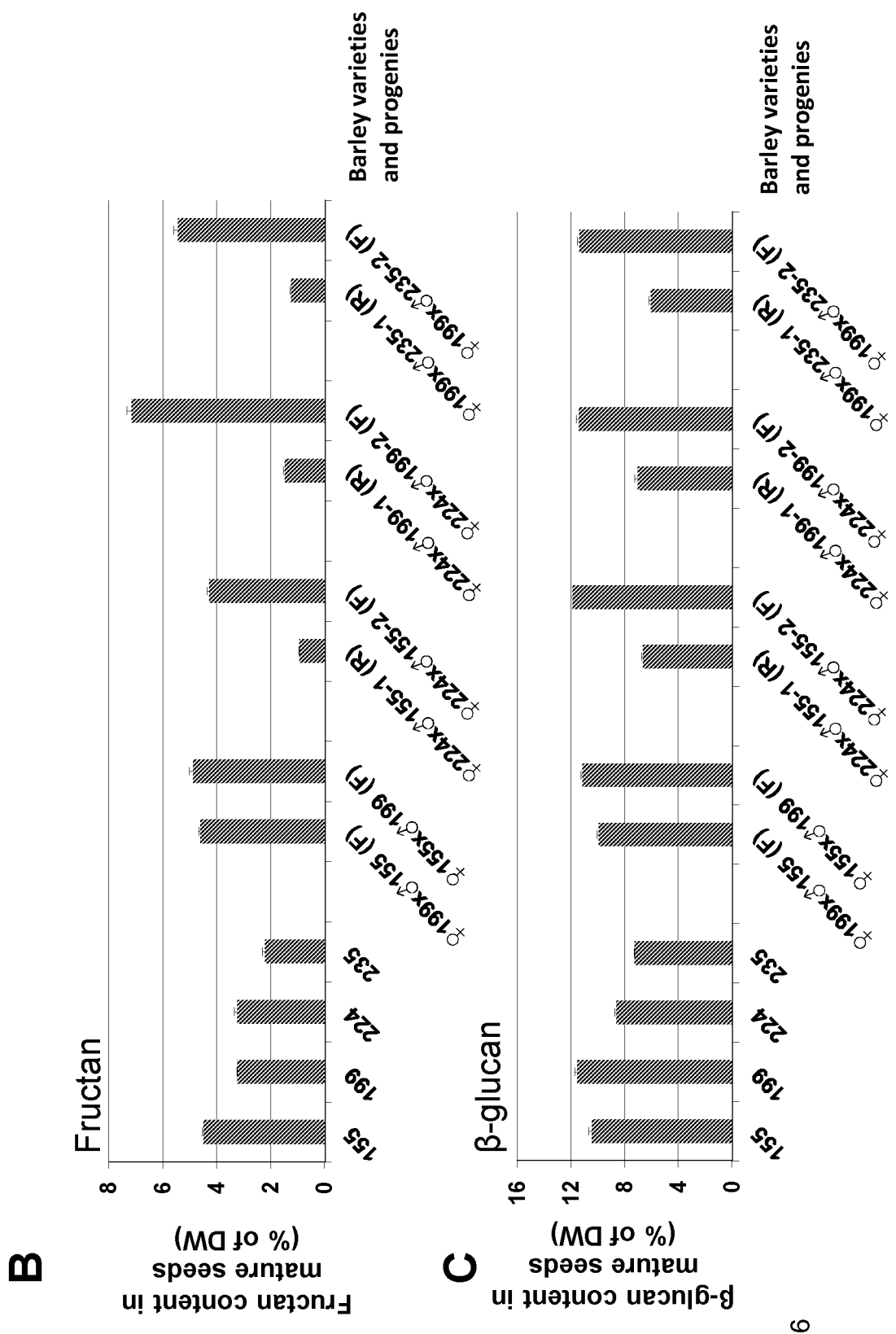

The yin-yang system was used as a molecular marker to follow fructan synthetic activity, and two hydrolytic enzyme genes, 1-FEH and 6-FEH, were used as marker genes to monitor fructan hydrolytic activity during barley seed development. The focus was on a high synthetic activity at an early stage (9 days after flowering) and a low hydrolytic activity at a late stage (22 days after flowering). From the 12 barley varieties, two varieties (varieties 155 and 199) that had a high synthetic activity at the early stage and two varieties (224 and 235) that showed a low hydrolytic activity at the late stage were identified. These four varieties were used for crossbreeding to increase seed fructan content. The concept was to combine the high synthetic activity with the low hydrolytic activity for increasing fructan accumulation during seed development. In the F₁ progenies after crossing, five progenies with relatively high fructan content were selected to follow the segregation of fructan content traits. The five progenies were ♀199×♂155, ♀155×♂199, ♀224×♂155, ♀224×♂199 and ♀199×♂235. During seed development, the selected progenies accumulated more and more fructan through developmental stages, especially at the late stages 22 days after flowering and in the mature seeds (FIG. 33) indicating that the low hydrolytic activity in varieties 224 and 235 had been introduced into the progenies, which led to a higher accumulation compared with the parents 155 and 199. It was observed that when the progenies were in homozygotes, the lines of ♀224×♂155 hulless (naked), ♀224×♂199 hulless (naked) produced the highest seed fructan content with individual plant fructan content up to over 13% per dry weight (DW) without affecting thousand kernel weight (TKW) (FIGS. 34 and 35). During screening, two types of seeds were observed, round and flat seeds in the progenies (FIG. 36A). When the average seed fructan content was measured, the high fructan content was associated with the flat seed phenotype (FIGS. 36B, 36C). Interestingly, the high fructan content in the flat seeds correlated strongly with high β-glucan content, implying that the yin-yang system may control the β-glucan synthesis (FIG. 36).

Also other traits related to yield were investigated. Importantly, the high seed fructan and β-glucan content in the flat seeds did not affect the traits: plant height, spike numbers, grain numbers and TKW, even with a slight increase of TKW when compared with variety 155 (FIG. 35).

Figure 32:
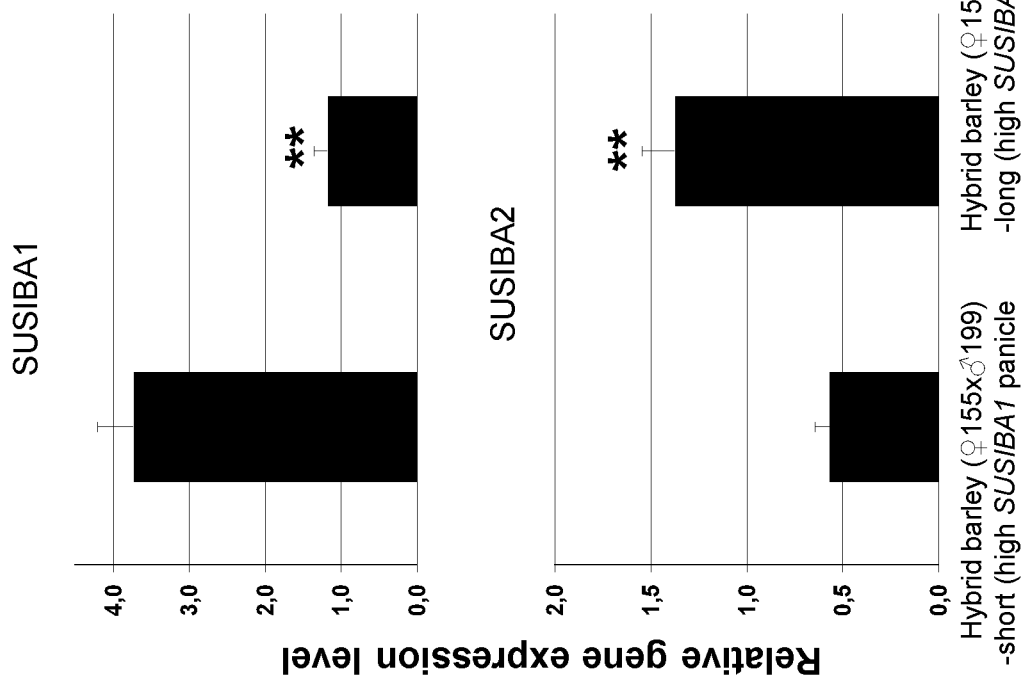
FIG. 32. Relative expression level of SUSIBA1 and SUSIBA2 in short (left) and long (right) developing panicles at 2 days before flowering. Statistical differences between short and long panicles are indicated by **($P<0.01$).
Figure 31:
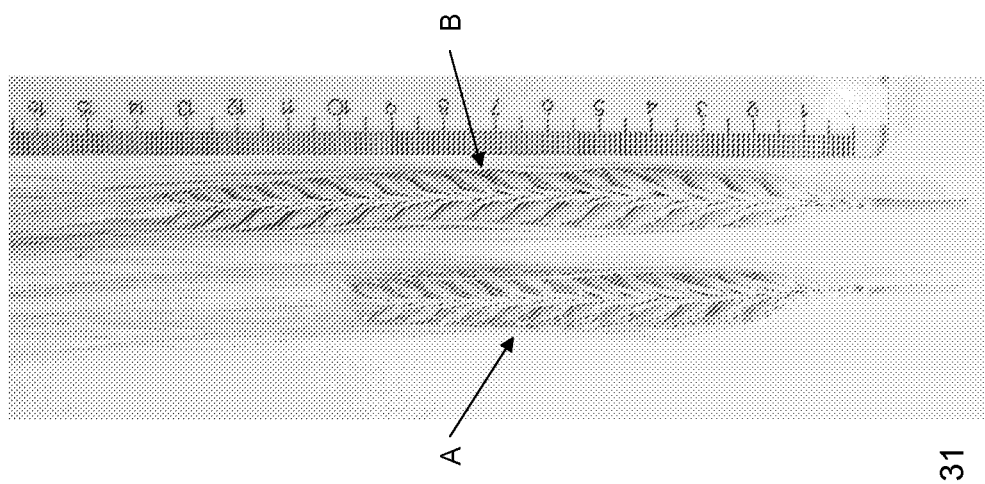
FIG. 31. Long barley panicle is associated with high SUSIBA2 level and short panicle is associated with high SUSIBA1. The figure illustrates short-type (A) and long-type (B) barley panicles in progenies of hybrid barley of varieties SLU7 (155) and KVL1113 (199).

In the progenies of crossed barley varieties 155 and 199, two types of barley panicles were observed, short (8-10 cm) and long (13-15 cm) (FIG. 31). Careful examination of gene expression in the developing panicles around pollination (egg fertilization time) indicated that high expression of SUSIBA2 and low expression of SUSIBA1 were always associated with the long panicles (FIG. 32). It is hypothesized that SUSIBA2 may be a genetic determiner in the panicle length and the yin-yang system may regulate barley panicle length. The hypothesis is based on the function of SUSIBA2 and that SUSIBA2 can increase sink-strength in storage tissues and may increase panicle length with more grain number by directing more sucrose to the developing panicles during grain filling. As also suggested in [24], more available sugars to the developing panicles containing developing zygotes can rescue already set seeds and prevent their abortion in developing panicles during grain filling.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

1. Sun et al., *Plant Cell* 2003, 15: 2076-2092
2. Sun et al., *Plant J.* 2005, 44: 128-138
3. Su et al., *Nature* 2015, 523: 602-606
4. Sun et al., *Plant J.* 2007, 52: 1192-1198
5. Xie et al., *Plant J.* 2014, 77: 954-961
6. Nalawade et al., *Appl. Energy* 2012, 91: 405-411
7. McCluskey, *Adv. Appl. MicrobioL* 2003, 52: 245-262
8. Sun et al., *Plant Physiol.* 1998, 118: 37-49
9. Sun et al., *Plant Signal. Behav.* 2008, 3: 328-330
10. Wood et al., *Plant Biotechnolol. J.* 2009, 7: 914-924
11. Zhang et al., *BMC Plant Biol.* 2012, 12: 230
12. Sun et al., *Plant Mol. Biol.* 1999, 40: 431-443
13. Liu et al., *Nat. Med.* 2014, 20: 272-282
14. Lunn et al., *Biochem J.* 2006, 397: 139-148
15. Antonio et al., *Rapid Commun. Mass Spectrom.* 2008, 22: 1399-1407
16. De Smet et al., *Microbiology* 2000, 146: 199-208
17. U.S. patent application no. 2006/0191037
18. Zadoks et al., *Weed Res* 1974, 14: 415-421
19. Collins, *Biotechniques* 2007, 43: 25-30
20. McCleary and Codd, *J Sci Food Agric* 1991, 55: 303-312
21. McCleary et al., *J AOAC International* 2000, 83: 356-364
22. Nemeth et al., *Food Nutr Sci* 2014, 5: 581-589
23. Poehlman and Sleper, Breeding Field Crops, Fourth Edition (Ames, Iowa: Iowa State University Press) 1995
24. Tuncel and Okita, *Plant Sci* 2013, 211: 52-60

The invention claimed is:

1. A plant material comprising a genomic nucleotide sequence encoding a sugar signaling in barley 2 (SUSIBA2) transcription factor, wherein said plant material is a barley plant material, or encoding a SUSIBA2-like. transcription factor, wherein said plant material is a. rice plant material or a. wheat plant material, wherein said SUSIBA2or SUSIBA2-like transcription factor is under transcriptional control of a promoter active in said plant material, wherein said genomic nucleotide sequence encoding said SUSIBA2or SUSIBA2-like. transcription factor in said barley plant material, rice plant material, or wheat plant material lacks at least a portion of, respectively, (i) a sugar-responsive activation region as defined in SEQ ID NO: 92 of a SUSIBA1 promoter (SUSIBA1) present in an intron of a wild-type version of said. genomic nucleotide sequence in said barley plant material, (ii) a sugar-responsive activation region as defined in SEQ ID NO: 93 of a SUSIBA1-like, promoter (SUSIBA1) present in an intron of a wild-type version of said genomic nucleotide sequence in said rice plant material, or (iii) a sugar-responsive activation region as defined in SEQ ID NO: 112 of a SUSIBA1-like p present in intron of a wild-type version of said genomic nucleotide sequence in said wheat plant material, and wherein binding of a trans activation factor to said sugar-responsive activation region induces expression of SUSIBA1encoding SUSIBA1transcription factor in a wild-type version of said barley plant material or SUSIBA1-like encoding SUSIBA1-like transcription factor in a wild-type version of said rice plant material or wheat plant material.

2. The plant material according to claim 1, wherein said at least a portion of said sugar-responsive activation region of SUSIBA1p or SUSIBA1-like p of said wild-type version is deleted from said wild-type version of said genomic nucleotide sequence encoding said SUSIBA2or SUSIBA2-like transcription factor to provide the genomic nucleotide sequence.

3. The plant material according to claim 2, wherein said at least a portion of said sugar-responsive activation region of SUSIBA1p or SUSIBA1-like p of said wild-type version is deleted by clustered regularly interspaced short palindromic repeat, (CRISPR)/CRISPR associated protein 9 (Cas9) mediated deletion.

4. The plant material according to claim 1, wherein said genomic nucleotide sequence encoding said SUSIBA2 or SUSIBA2-like transcription factor is a genomic endogenous nucleotide sequence encoding said SUSIBA2 or SUSIBA2-like transcription factor.

5. The plant material according to claim 1, wherein said genomic nucleotide sequence encoding said SUSIBA2 transcription factor lacks at least a portion of a sugar repressive region as defined in SEQ ID NO: 94 of said SUSIBA1 p present in said intron of a wild-type version of said genomic nucleotide sequence encoding said SUSIBA2 transcription factor, or wherein said genomic nucleotide sequence encoding said SUSIBA2-like transcription factor lacks at least a portion of a sugar repressive region as defined in SEQ ID NO: 95 or SEQ ID NO: 113 of said SUSIBA1-like p present in said intron of a wild-type version of said genomic nucleotide sequence encoding said SUSIBA2-like transcription factor in said rice plant material or said wheat plant material, respectively.

6. The plant material according to claim 1, wherein said genomic nucleotide sequence encoding said SUSIBA2or SUSIBA2-like transcription factors lacks an intronic portion of said SUSIBA1 p or SUSIBA1-like p of a wild-type version of said genomic nucleotide sequence.

7. The plant material according to claim 1, wherein said genomic nucleotide sequence encoding said SUSIBA2 or SUSIBA2-like transcription factor lacks intron 2 of a wild-type version of said genomic nucleotide sequence encoding said SUSIBA2 or SUSIBA2-like transcription factor.

8. The plant material according to claim 1, wherein said plant material is selected from a group consisting of a rice plant, a rice plant cell and a rice seed.

9. The plant material according to claim 8, wherein said SUSIBA2-like transcription factor has an amino acid sequence according to SEQ ID NO: 105.

10. The plant material according to claim 1, wherein said plant material is selected from the group consisting of a plant, a plant cell and a seed.

\* \* \* \* \*

UNITED STATES PATENT AND TRADEMARK OFFICE
CERTIFICATE OF CORRECTION

Page 1 of 2

PATENT NO. : 11,466,060 B2
APPLICATION NO. : 16/497989
DATED : October 11, 2022
INVENTOR(S) : Chuanxin Sun et al.

It is certified that error appears in the above-identified patent and that said Letters Patent is hereby corrected as shown below:

In the Claims

Claim 1, Column 91, Line 38, after "a" delete ".".

Claim 1, Column 91, Line 39, after "a" delete ".".

Claim 1, Column 91, Line 40, change "SUSIBA2or" to --SUSIBA2 or--.

Claim 1, Column 91, Line 44, change "SUSIBA2or" to --SUSIBA2 or--.

Claim 1, Column 91, Line 48, change "(SUSIBA1 promoter (SUSIBA1))" to --(*SUSIBA1* promoter (*SUSIBA1*-p*))*--.

Claim 1, Column 91, Line 53, change "SUSIBA1-like," to --*SUSIBA1*-like--.

Claim 1, Column 91, Line 54, change "(SUSIBA1)" to --(*SUSIBA1*-like p)--.

Claim 1, Column 91, Line 58, change "(SUSIBA1-like p)" to --(*SUSIBA1*-like p)--.

Claim 1, Column 91, Line 59, add --an-- before "intron".

Claim 1, Column 91, Line 61, change "trans" to --*trans*--.

Claim 1, Column 91, Line 63, change "SUSIBA1encoding SUSIBA1transcription" to --*SUSIBA1* encoding SUSIBA1 transcription--.

Claim 1, Column 91, Line 65, change "(SUSIBA1-like)" to --(*SUSIBA1*-like)--.

Claim 2, Column 92, Line 35, change "SUSIBA1p or SUSIBA1-like" to --*SUSIBA1* p or *SUSIBA1*-like--.

Signed and Sealed this
Twenty-fourth Day of January, 2023

Katherine Kelly Vidal
*Director of the United States Patent and Trademark Office*

CERTIFICATE OF CORRECTION (continued)
U.S. Pat. No. 11,466,060 B2

Claim 2, Column 92, Line 37, change "SUSIBA2or" to --SUSIBA2 or--.

Claim 3, Column 92, Line 42, change "SUSIBA1p or SUSIBA1-like" to --*SUSIBA1* p or *SUSIBA1*-like--.

Claim 5, Column 92, Line 54, change "SUSIBA1" to --*SUSIBA1*--.

Claim 5, Column 92, Line 60, change "SUSIBA1" to --*SUSIBA1*--.

Claim 6, Column 92, Line 66, change "SUSIBA2or" to --SUSIBA2 or--.

Claim 6, Column 93, Line 1, change "SUSIBA1 p or SUSIBA1-like" to --*SUSIBA1* p or *SUSIBA1*-like--.